(12) United States Patent
Kim et al.

(10) Patent No.: US 12,256,634 B2
(45) Date of Patent: Mar. 18, 2025

(54) ARYLAMINE COMPOUND, LIGHT-EMITTING DEVICE INCLUDING THE SAME, AND ELECTRONIC APPARATUS INCLUDING THE LIGHT-EMITTING DEVICE

(71) Applicant: Samsung Display Co., Ltd., Yongin-si (KR)

(72) Inventors: Dongjun Kim, Yongin-si (KR); Hankyu Pak, Yongin-si (KR); Minji Kim, Yongin-si (KR); Eunjae Jeong, Yongin-si (KR); Sohee Jo, Yongin-si (KR); Sanghyun Han, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 740 days.

(21) Appl. No.: 17/445,459

(22) Filed: Aug. 19, 2021

(65) Prior Publication Data

US 2022/0069227 A1    Mar. 3, 2022

(30) Foreign Application Priority Data

Sep. 2, 2020   (KR) .................. 10-2020-0111683
Dec. 21, 2020  (KR) .................. 10-2020-0179923

(51) Int. Cl.
| | |
|---|---|
| *H10K 50/15* | (2023.01) |
| *C07D 209/88* | (2006.01) |
| *C09K 11/06* | (2006.01) |
| *H10K 50/17* | (2023.01) |
| *H10K 85/60* | (2023.01) |

(52) U.S. Cl.
CPC ........ *H10K 85/636* (2023.02); *C07D 209/88* (2013.01); *C09K 11/06* (2013.01); *H10K 85/633* (2023.02); *C07B 2200/05* (2013.01); *C09K 2211/1018* (2013.01); *H10K 50/15* (2023.02); *H10K 50/17* (2023.02); *H10K 85/615* (2023.02); *H10K 85/626* (2023.02); *H10K 85/6572* (2023.02)

(58) Field of Classification Search
None
See application file for complete search history.

(56) References Cited

U.S. PATENT DOCUMENTS

| | | | |
|---|---|---|---|
| 4,720,432 | A  | 1/1988  | VanSlyke et al. |
| 5,061,569 | A  | 10/1991 | VanSlyke et al. |
| 6,242,115 | B1 | 6/2001  | Thomson et al. |
| 8,298,684 | B2 | 10/2012 | Kwang et al. |
| 8,394,511 | B2 | 3/2013  | Hwang et al. |

(Continued)

FOREIGN PATENT DOCUMENTS

| | | |
|---|---|---|
| EP | 2 093 271 A1 | 8/2009 |
| JP | 11-144873 A  | 5/1999 |

(Continued)

*Primary Examiner* — Tae H Yoon
(74) *Attorney, Agent, or Firm* — Womble Bond Dickinson (US) LLP

(57) ABSTRACT

Provided are an arylamine compound including a phenyl-naphthyl linker substituted with at least one deuterium and an amine group substituted with at least one carbazole group, a light-emitting device including the arylamine compound, and an electronic apparatus including the light-emitting device. The arylamine compound is the same as described in the present specification.

15 Claims, 3 Drawing Sheets

(56) References Cited

U.S. PATENT DOCUMENTS

| | | | |
|---|---|---|---|
| 9,991,446 B2* | 6/2018 | Bae | H10K 85/626 |
| 2010/0032656 A1* | 2/2010 | Kwang | H10K 85/636 |
| | | | 257/E51.027 |
| 2019/0334096 A1 | 10/2019 | Kim et al. | |
| 2020/0152884 A1 | 5/2020 | Hwang et al. | |

FOREIGN PATENT DOCUMENTS

| | | |
|---|---|---|
| JP | 2000-302756 A | 10/2000 |
| JP | 2003-133075 A | 5/2003 |
| JP | 2004-79265 A | 3/2004 |
| JP | 2006-151979 A | 6/2006 |
| JP | 4477803 B2 | 6/2010 |
| KR | 10-2008-0038606 A | 5/2008 |
| KR | 10-2009-0120699 A | 11/2009 |
| KR | 10-2010-0006072 A | 1/2010 |
| KR | 10-2010-0008947 A | 1/2010 |
| KR | 10-2014-0091496 A | 7/2014 |
| KR | 10-2014-0142923 A | 12/2014 |
| KR | 10-2015-0051662 A | 5/2015 |
| KR | 10-2018-0021028 A | 2/2018 |
| KR | 10-2019-0125560 A | 11/2019 |

* cited by examiner

ARYLAMINE COMPOUND, LIGHT-EMITTING DEVICE INCLUDING THE SAME, AND ELECTRONIC APPARATUS INCLUDING THE LIGHT-EMITTING DEVICE

CROSS-REFERENCE TO RELATED APPLICATION

This application claims priority to Korean Patent Application No. 10-2020-0111683, filed on Sep. 2, 2020 and No. 10-2020-0179923, filed on Dec. 21, 2020, in the Korean Intellectual Property Office, the entire contents of each of which are hereby incorporated by reference.

BACKGROUND

1. Field

One or more embodiments of the present disclosure relate to an arylamine compound, a light-emitting device including the same, and an electronic apparatus including the light-emitting device.

2. Description of Related Art

Organic light-emitting devices (OLEDs) are self-emission devices that, as compared with other devices of the art, have wide viewing angles, high contrast ratios, short response times, and excellent characteristics in terms of luminance, driving voltage, and response speed, and produce full-color images.

OLEDs may include a first electrode on a substrate, and a hole transport region, an emission layer, an electron transport region, and a second electrode sequentially stacked on the first electrode. Holes provided from the first electrode move toward the emission layer through the hole transport region, and electrons provided from the second electrode move toward the emission layer through the electron transport region. Carriers, such as holes and electrons, recombine in the emission layer to produce excitons. These excitons transition from an excited state to a ground state to thereby generate light.

SUMMARY

One or more embodiments of the present disclosure include an arylamine compound, a light-emitting device including the same, and an electronic apparatus including the light-emitting device.

Additional aspects of embodiments will be set forth in part in the description which follows and, in part, will be apparent from the description, or may be learned by practice of the presented embodiments of the disclosure.

According to one or more embodiments, an arylamine compound includes a phenyl-naphthyl linker substituted with at least one deuterium and an amine group substituted with a carbazole group.

The arylamine compound may be represented by Formula 1:

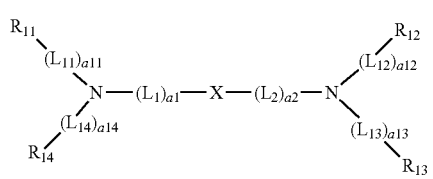

Formula 1

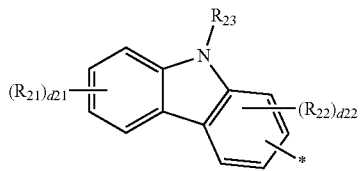

Formula 2

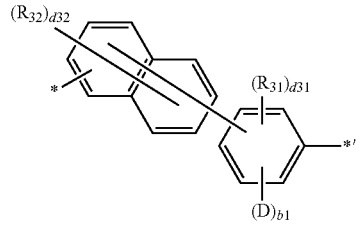

Formula 3 wherein, in Formula 1, $L_1$, $L_2$, and $L_{11}$ to $L_{14}$ may each independently be selected from a single bond, a $C_5$-$C_{60}$ carbocyclic group unsubstituted or substituted with at least one $R_{10a}$, and a $C_1$-$C_{60}$ heterocyclic group unsubstituted or substituted with at least one $R_{10a}$, a1, a2, and a11 to a14 may each independently be an integer from 1 to 3, $R_{11}$ to $R_{14}$ may each independently be selected from a group represented by Formula 2, a $C_1$-$C_{60}$ alkyl group unsubstituted or substituted with at least one $R_{10a}$, a $C_5$-$C_{30}$ carbocyclic group unsubstituted or substituted with at least one $R_{10a}$, and a $C_2$-$C_{30}$ heterocyclic group unsubstituted or substituted with at least one $R_{10a}$, wherein at least one of $R_{11}$ to $R_{14}$ may be a group represented by Formula 2, X may be a linking group represented by Formula 3, $R_{21}$ to $R_{23}$, $R_{31}$, and $R_{32}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), d21 may be an integer from 1 to 4,
d22 may be an integer from 1 to 3,
d31 may be an integer from 0 to 3,
d32 may be an integer from 1 to 6,
* in Formula 2 indicates a binding site to a neighboring atom,
D in Formula 3 may be deuterium,
b1 may be an integer from 1 to 4,
the sum of d31 and b1 may be 4,
* and *' each indicate a binding site to a neighboring atom,
$R_{10a}$ may be:
deuterium, —F, —Cl, —Br, —I, a hydroxyl group, a cyano group, or a nitro group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof, or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be hydrogen, deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

According to one or more embodiments, an organic light-emitting device includes a first electrode, a second electrode, and an interlayer between the first electrode and the second electrode and including an emission layer, wherein the interlayer includes an arylamine compound including a phenyl-naphthyl linker substituted with at least one deuterium and an amine group substituted with a carbazolyl group.

According to one or more embodiments, an electronic apparatus includes the light-emitting device.

BRIEF DESCRIPTION OF THE DRAWINGS

The above and other aspects and features of certain embodiments of the disclosure will be more apparent from the following description taken in conjunction with the accompanying drawings, in which.

DETAILED DESCRIPTION

Figure 1:
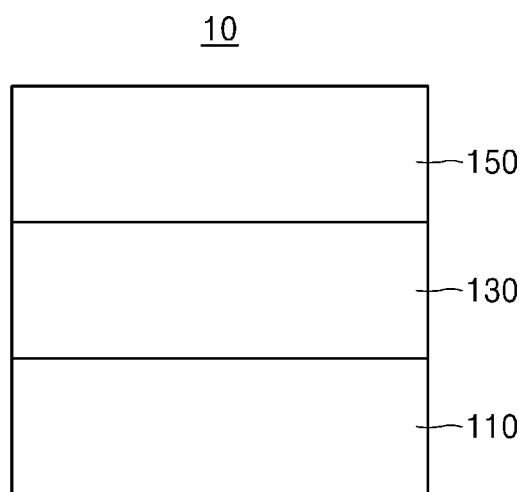
FIG. 1 is a schematic cross-sectional view of a light-emitting device according to an embodiment.

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of embodiments of the present description. As used herein, the term "and/or" includes any and all combinations of one or more of the associated listed items. Throughout the disclosure, the expression "at least one of a, b or c" indicates only a, only b, only c, both a and b, both a and c, both b and c, all of a, b, and c, or variations thereof.

An aspect of embodiments of the present disclosure provides an arylamine compound including a phenyl-naphthyl linker substituted with at least one deuterium and an amine group substituted with a carbazole group.

In an embodiment, a phenyl group of the phenyl-naphthyl linker may be substituted with at least one deuterium.

In an embodiment, the arylamine compound may be represented by Formula 1:

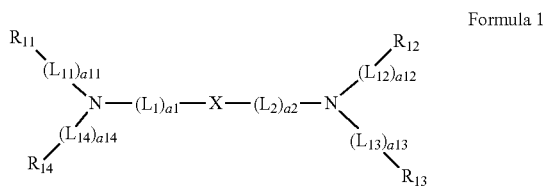

Formula 1

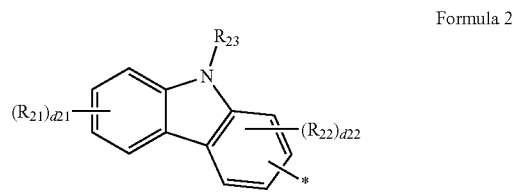

Formula 2

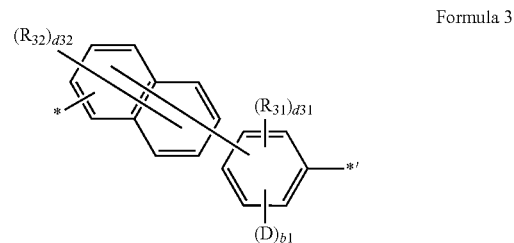

Formula 3 wherein, in Formula 1, $L_1$, $L_2$, and $L_{11}$ to $L_{14}$ may each independently be selected from a single bond, a $C_5$-$C_{60}$ carbocyclic group unsubstituted or substituted with at least one $R_{10a}$, and a $C_1$-$C_{60}$ heterocyclic group unsubstituted or substituted with at least one $R_{10a}$.

In an embodiment, a1, a2, and a11 to a14 may each independently be an integer from 1 to 3.

In an embodiment, $L_1$, $L_2$, and $L_{11}$ to $L_{14}$ may each independently be:

a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-a fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$.

Here, $R_{10a}$ may be understood according to the description provided elsewhere herein.

In one or more embodiments, $L_1$, $L_2$, and $L_{11}$ to $L_{14}$ may each independently be selected from:

a single bond and groups represented by Formulae 10-1 to 10-41:

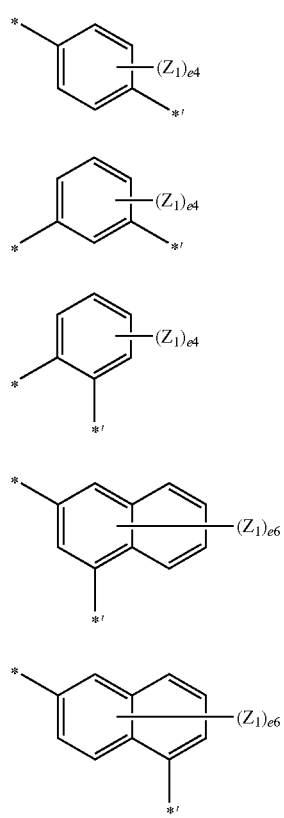

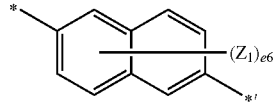

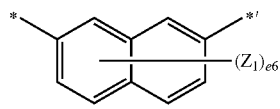

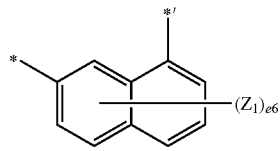

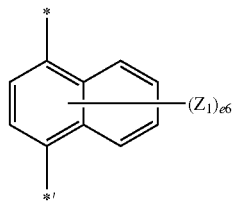

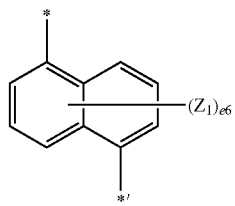

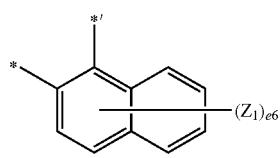

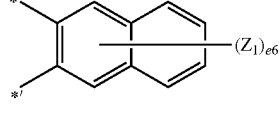

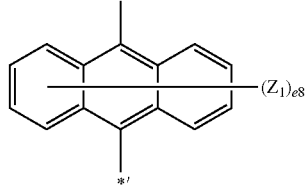

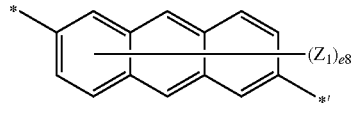

10-15
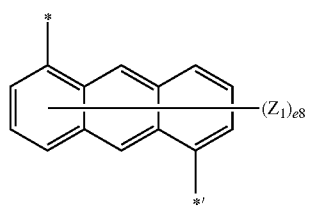
10-16
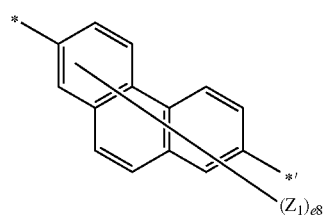
10-17
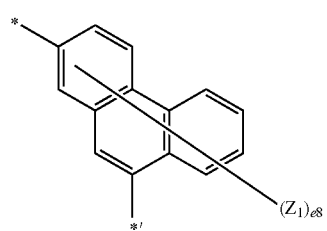
10-18
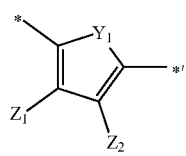
10-19
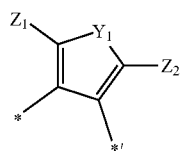
10-20
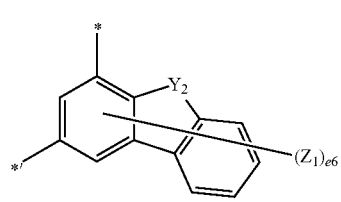
10-21
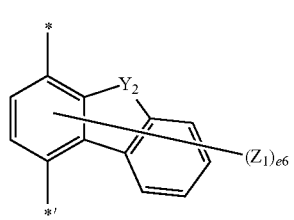
10-22
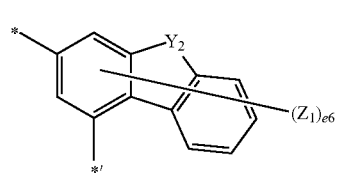
10-23
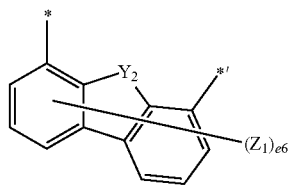
10-24
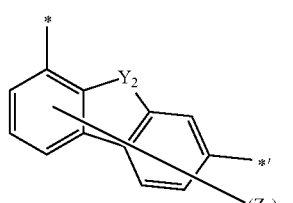
10-25
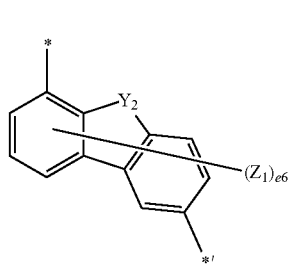
10-26
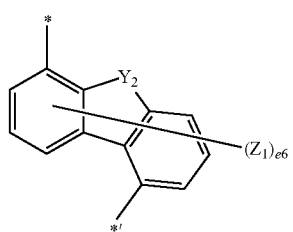
10-27
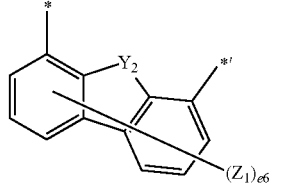
10-28
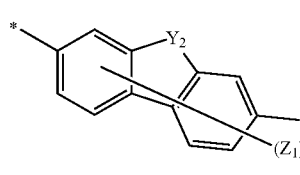
10-29
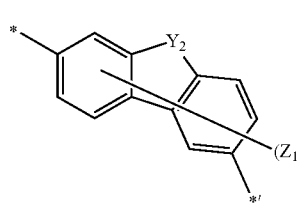

10-30 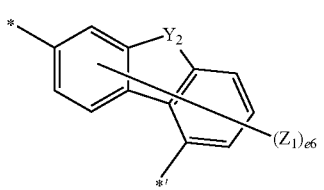
10-31 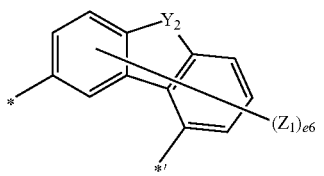
10-32 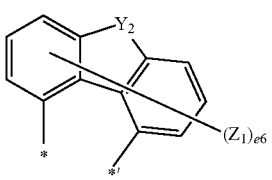
10-33 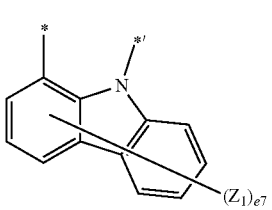
10-34 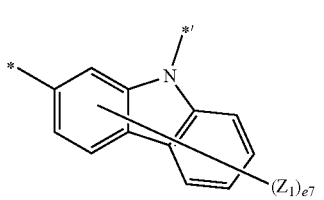
10-35 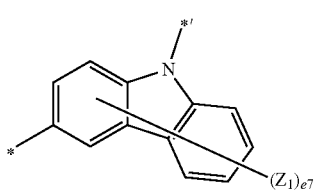
10-36 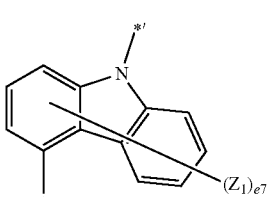
10-37 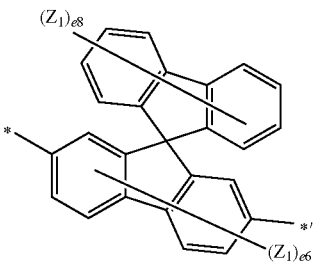
10-38 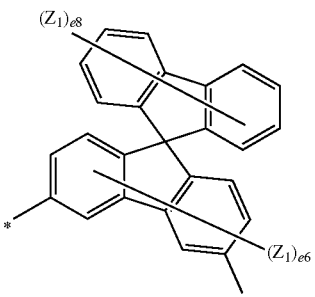
10-39 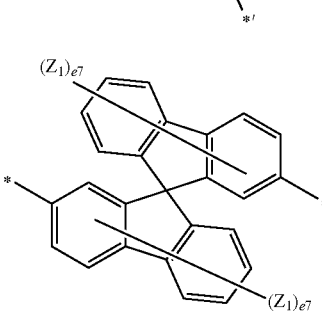
10-40 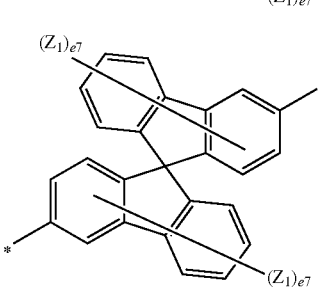
10-41 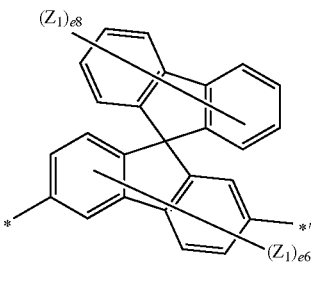
wherein, in Formulae 10-1 to 10-41,
$Y_1$ may be selected from O and S,
$Y_2$ may be selected from O, S, N($Z_3$), and C($Z_3$)($Z_4$),
$Z_1$ to $Z_4$ may each be the same as described in connection with $R_{21}$,
e4 may be an integer from 1 to 4,
e6 may be an integer from 1 to 6,
e7 may be an integer from 1 to 7,
e8 may be an integer from 1 to 8, and

* and *' each indicate a binding site to a neighboring atom.

In one or more embodiments, $L_1$ and $L_2$ may each be a single bond, and a1 and a2 may each be 1.

In one or more embodiments, a11 to a14 may each independently be 0 or 1.

In an embodiment, $R_{11}$ to $R_{14}$ may each independently be selected from a group represented by Formula 2, a $C_1$-$C_{60}$ alkyl group unsubstituted or substituted with at least one $R_{10a}$, a $C_5$-$C_{30}$ carbocyclic group unsubstituted or substituted with at least one $R_{10a}$, and a $C_2$-$C_{30}$ heterocyclic group unsubstituted or substituted with at least one $R_{10a}$, wherein at least one of $R_n$ to $R_{14}$ may be a group represented by Formula 2.

In one or more embodiments, $R_{11}$ to $R_{14}$ may each independently be: a group represented by Formula 2; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, a naphthacenyl group, a picenyl group, a hexacenyl group, a pentaphenyl group, a rubicenyl group, a coronenyl group, an ovalenyl group, a naphthopyrrolyl group, a naphthofuranyl group, a naphthothiophenyl group, a naphthosilolyl group, a benzofurocarbazolyl group, a benzothienocarbazolyl group, a benzosilolocarbazolyl group, a triindolophenyl group, a pyrrolophenanthrenyl group, a furanophenanthrenelenyl group, a thienophenanthrenyl group, a benzonaphthofuranyl group, a benzonaphthothiophenyl group, an (indolo)phenanthrenyl group, a (benzofurano)phenanthrenyl group, and a (benzothieno)phenanthrenyl group, each unsubstituted or substituted with at least one selected from deuterium, —F, —Cl, —Br, —I, cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, a naphthacenyl group, a picenyl group, a hexacenyl group, a pentaphenyl group, a rubicenyl group, a coronenyl group, an ovalenyl group, a naphthopyrrolyl group, a naphthofuranyl group, a naphthothiophenyl group, a naphthosilolyl group, a benzofurocarbazolyl group, a benzothienocarbazolyl group, a benzosilolocarbazolyl group, a triindolophenyl group, a pyrrolophenanthrenyl group, a furanophenanthrenelenyl group, a thienophenanthrenyl group, a benzonaphthofuranyl group, a benzonaphthothiophenyl group, an (indolo)phenanthrenyl group, a (benzofurano)phenanthrenyl group, and a (benzothieno)phenanthrenyl group, wherein at least one of $R_{11}$ to $R_{14}$ may be a group represented by Formula 2.

In an embodiment, Formula 2 may be represented by one of Formulae 2-1 to 2-4:

Formula 2-1

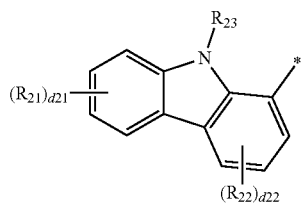

Formula 2-2

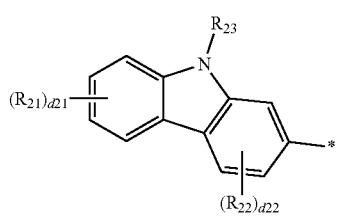

Formula 2-3

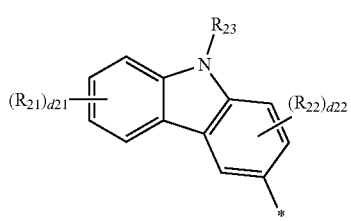

Formula 2-4

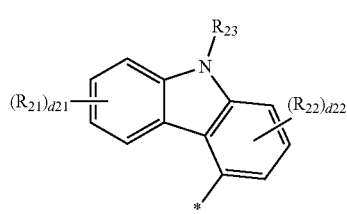

wherein, in Formulae 2-1 to 2-4, $R_{21}$ to $R_{23}$ and d21 to d23 may each be each the same as described elsewhere herein, and * indicates a binding site to a neighboring atom.

In an embodiment, $R_{11}$ may be a group represented by Formula 2;

$R_{12}$ may be a group represented by Formula 2;

$R_{11}$ and $R_{12}$ may each be a group represented by Formula 2;

$R_{11}$ and $R_{14}$ may each be a group represented by Formula 2;

$R_{11}$, $R_{12}$, and $R_{14}$ may each be a group represented by Formula 2;

$R_{11}$, $R_{12}$, and $R_{13}$ may each be a group represented by Formula 2; or $R_{11}$, $R_{12}$, $R_{13}$, and $R_{14}$ may each be a group represented by Formula 2.

In one or more embodiments, $R_{11}$ may be a group represented by Formula 2; or $R_{12}$ may be a group represented by Formula 2.

In an embodiment, X may be a linking group represented by Formula 3.

In an embodiment, Formula 3 may be represented by one of Formulae 3-1 to 3-14:

3-1

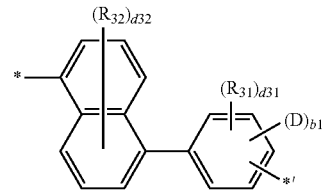

3-2

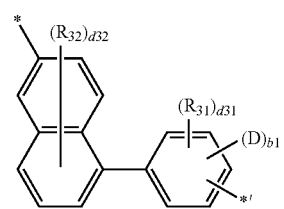

3-3

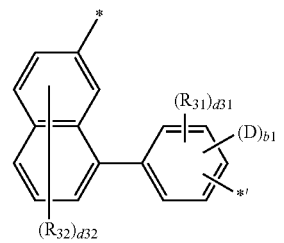

3-4

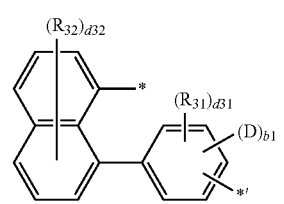

3-5

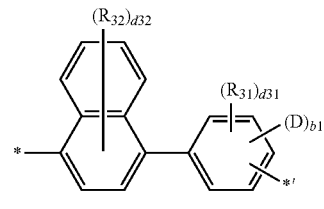

3-6

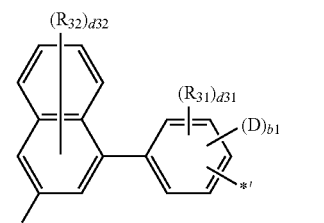

3-7

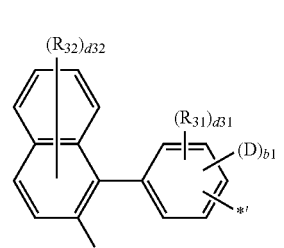

3-8 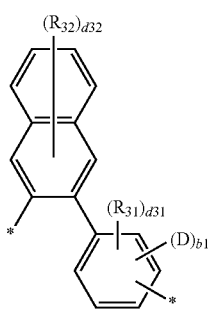
3-9 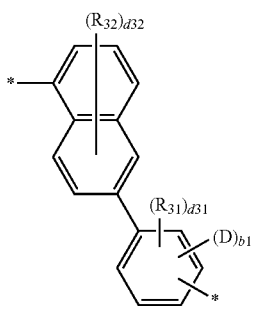
3-13 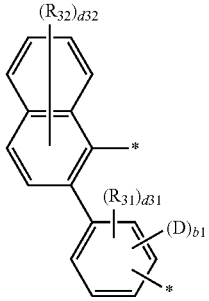
3-14
3-10 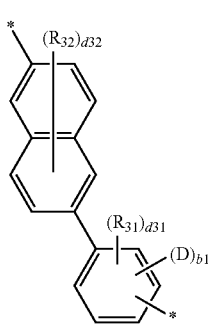
3-11 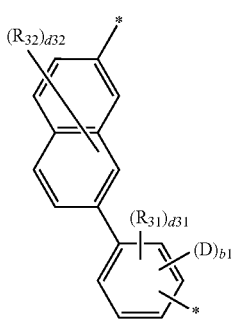
3-12 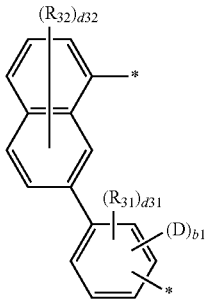
wherein, in Formulae 3-1 to 3-14, $R_{31}$, $R_{32}$, d31, d32, and b1 may each be the same as described elsewhere herein, and * and *' each indicate a binding site to a neighboring atom.
In one or more embodiments, Formula 3 may be represented by one of Formulae 4-1 to 4-14:
4-1 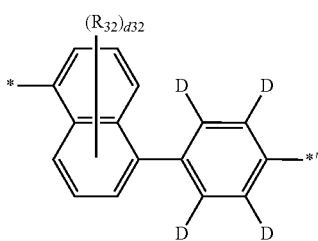
4-2 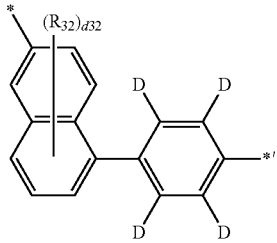
4-3 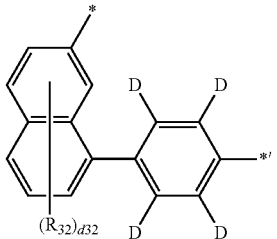
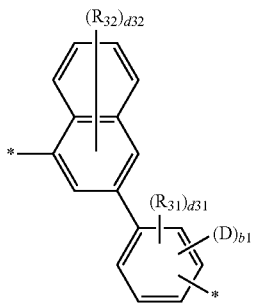

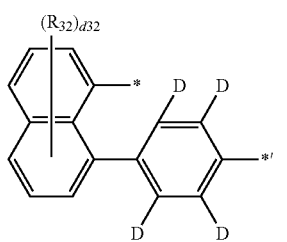
4-4
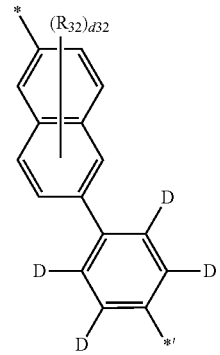
4-9
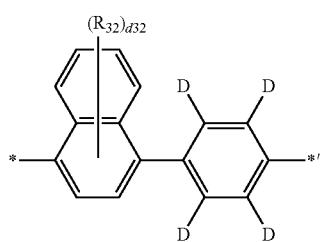
4-5
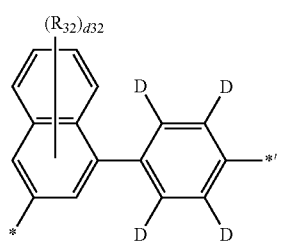
4-6
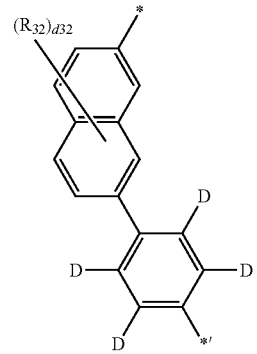
4-10
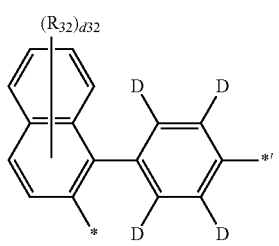
4-7
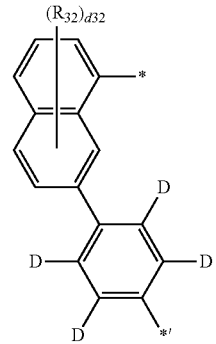
4-11
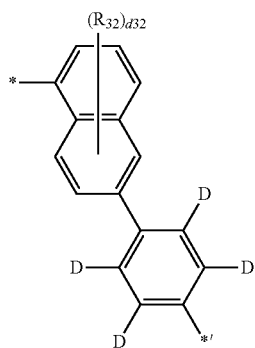
4-8
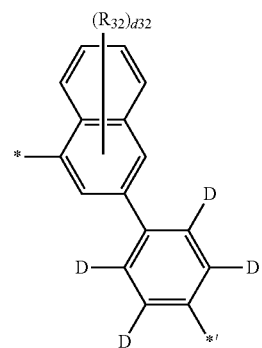
4-12

-continued 4-13

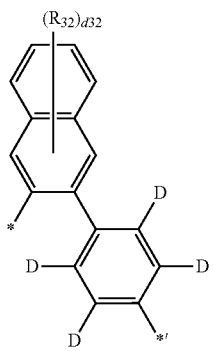

4-14 wherein, in Formulae 4-1 to 4-14, $R_{32}$ and d32 may each be the same as described elsewhere herein, and * and *' each indicate a binding site to a neighboring atom.

In an embodiment, $R_{21}$ to $R_{23}$, $R_{31}$, and $R_{32}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(=O)($Q_0$), —S(=O)$_2$($Q_1$), or —P(=O)($Q_1$)($Q_2$).

In one or more embodiments, $R_{21}$ to $R_{23}$, $R_{31}$, and $R_{32}$ may each independently be:
hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazino group, a hydrazono group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, and a pyrimidinyl group;
a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, and an azadibenzosilolyl group, each unsubstituted or substituted with at least one of deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, an azadibenzosilolyl group, —Si($Q_{31}$)($Q_{32}$)($Q_{33}$), —N($Q_{31}$)($Q_{32}$), —B($Q_{31}$)($Q_{32}$), —P($Q_{31}$)($Q_{32}$), —C(=O)($Q_{31}$), —S(=O)$_2$($Q_{31}$), and —P(=O)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), and $Q_1$ to $Q_3$ and $Q_{31}$ to $Q_{33}$ may each independently be selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, and a triazinyl group, each unsubstituted or substituted with at least one selected from deuterium, a $C_1$-$C_{10}$ alkyl group, a phenyl group, a biphenyl group, a pyridinyl group, a pyrimidinyl group, a pyridazinyl group, a pyrazinyl group, and a triazinyl group.

In one or more embodiments, $R_{21}$ to $R_{23}$, $R_{31}$, and $R_{32}$ may each independently be:

hydrogen, deuterium, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —CD$_3$, —CD$_2$H, —CDH$_2$, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, and a naphthyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an isoindolyl group, an indolyl group, an indazolyl group, a purinyl group, a carbazolyl group, a benzofuranyl group, a benzothiophenyl group, a dibenzofuranyl group, a dibenzothiophenyl group, a benzocarbazolyl group, and a dibenzocarbazolyl group, each unsubstituted or substituted with at least one selected from deuterium, —CD$_3$, —CD$_2$H, —CDH$_2$, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an isoindolyl group, an indolyl group, an indazolyl group, a purinyl group, a carbazolyl group, a benzofuranyl group, a benzothiophenyl group, a dibenzofuranyl group, a dibenzothiophenyl group, a benzocarbazolyl group, a dibenzocarbazolyl group, —Si($Q_{31}$)($Q_{32}$)($Q_{33}$), —N($Q_{31}$)($Q_{32}$), and —B($Q_{31}$)($Q_{32}$); and —Si($Q_1$)($Q_2$)($Q_3$), —N($Q_1$)($Q_2$), and —B($Q_1$)($Q_2$), and $Q_1$ to $Q_3$ and $Q_{31}$ to $Q_{33}$ may each independently be selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each unsubstituted or substituted with at least one selected from deuterium, a $C_1$-$C_{10}$ alkyl group, a phenyl group, and a biphenyl group, d21 may be an integer from 1 to 4, d22 may be an integer from 1 to 3, d31 may be an integer from 0 to 3, d32 may be an integer from 1 to 6,

* in Formula 2 indicates a binding site to a neighboring atom,

D in Formula 3 may be deuterium, b1 may be an integer from 1 to 4 (or 1 to 3), the sum of d31 and b1 may be 4, and

* and *' each indicate a binding site to a neighboring atom.

In an embodiment, b1 in Formula 3 may be 3 or 4. For example, b1 in Formula 3 may be 3, d31 may be 1, and $R_{31}$ may be deuterium.

In an embodiment, $R_{10a}$ may be:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In an embodiment, Formula 1 may be represented by Formula 1-1 or 1-2:

Formula 1-1
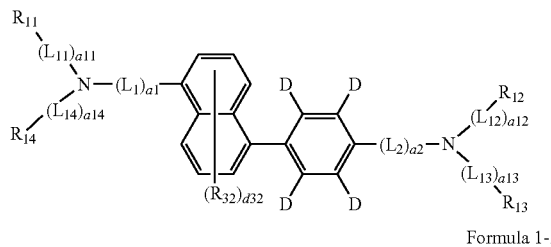
Formula 1-2
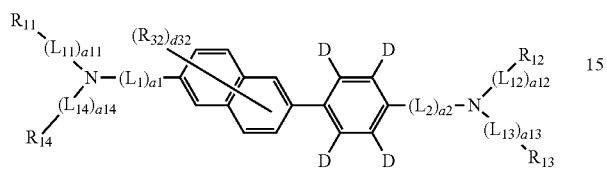
wherein, in Formulae 1-1 and 1-2, $L_1$, $L_2$, $L_{11}$ to $L_{14}$, a1, a2, a11 to a14, $R_{11}$ to $R_{14}$, $R_{32}$, and d32 may each be the same as described elsewhere herein.
In an embodiment, the arylamine compound may be selected from Compounds 1 to 228, but embodiments of the present disclosure are not limited thereto:
1
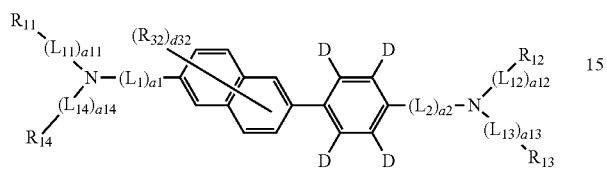
2
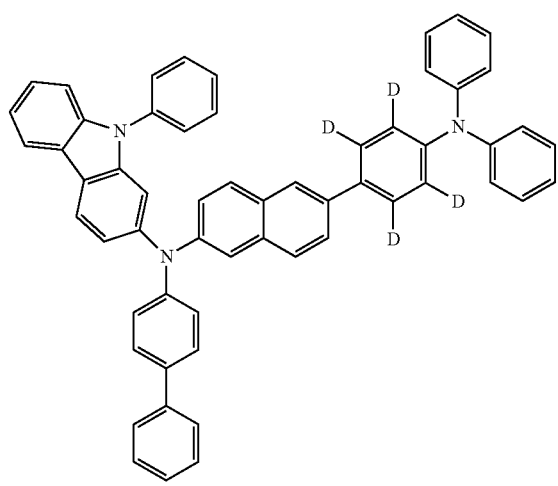
3
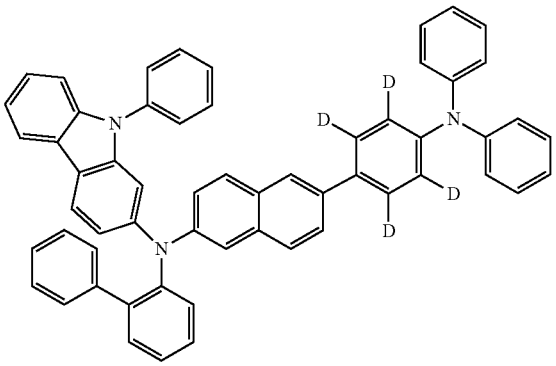
4
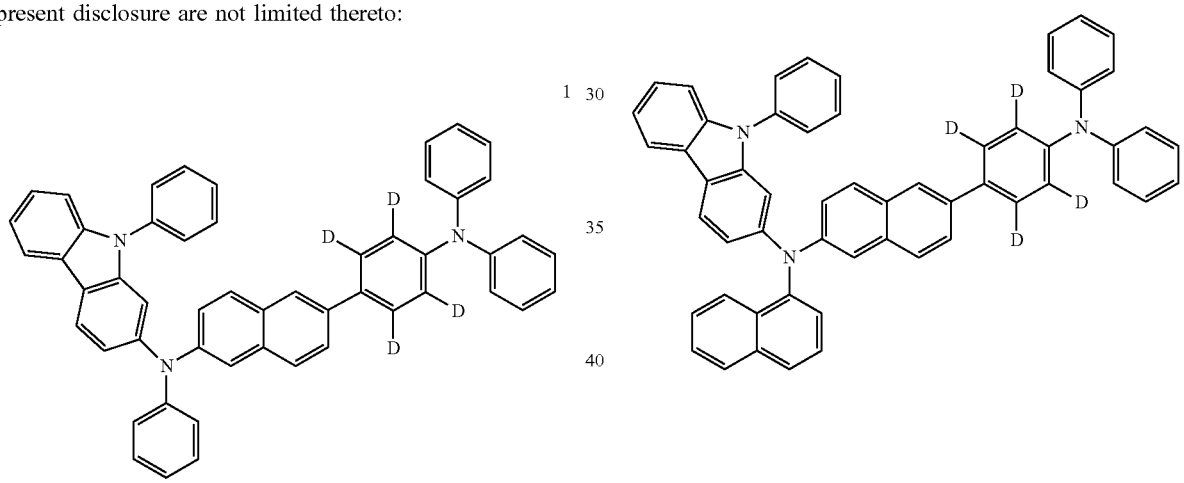
5
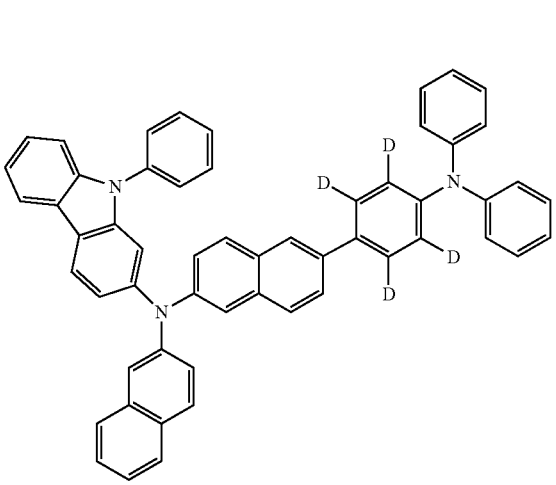

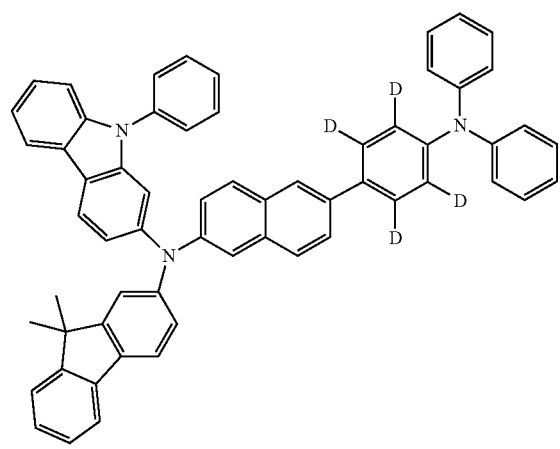
6
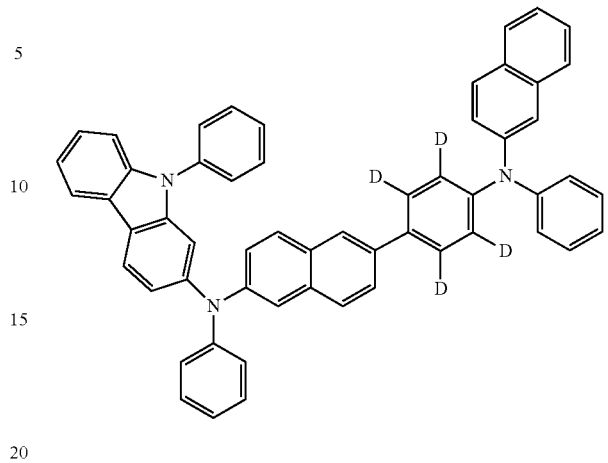
9
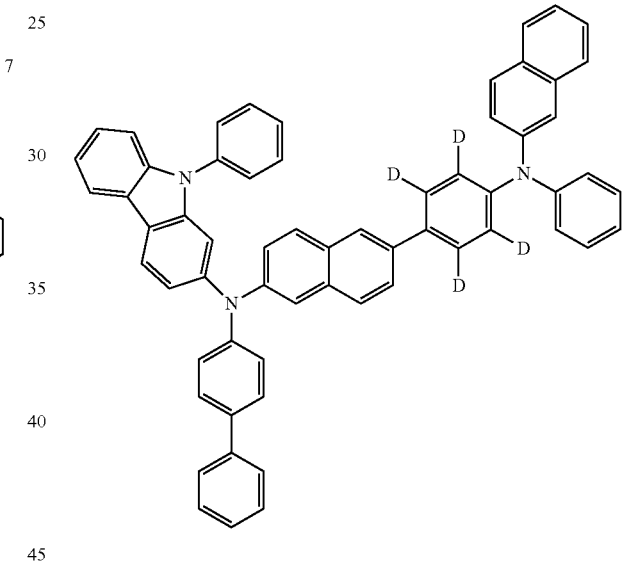
10
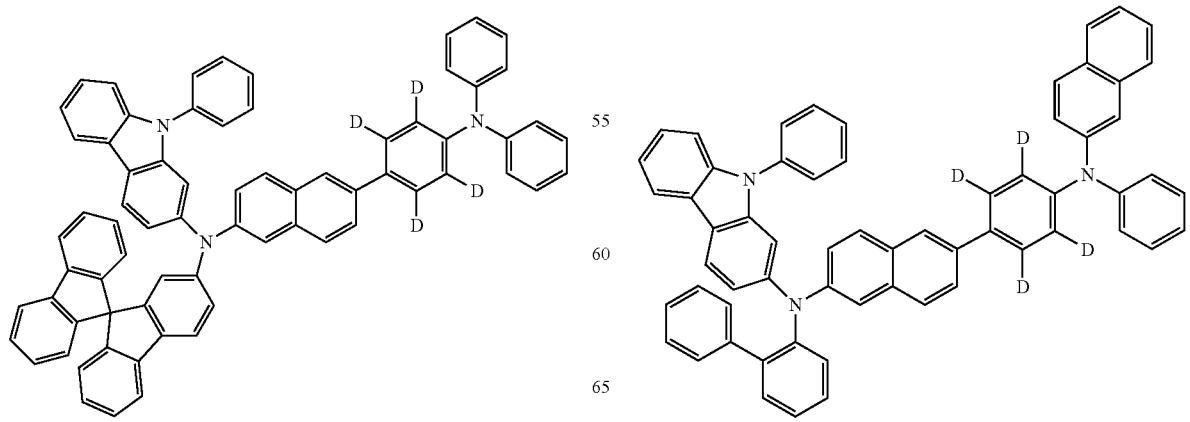

12
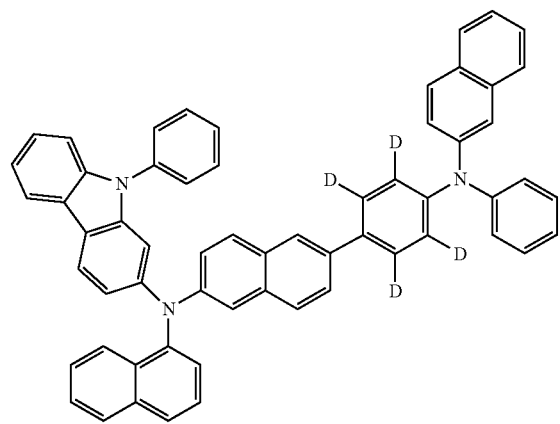
13
15
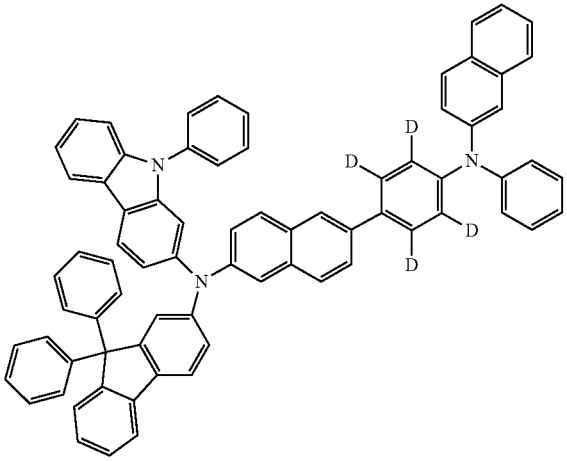
16
14
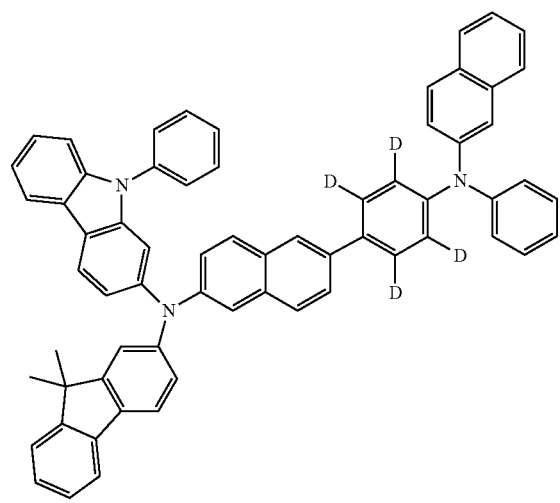
17
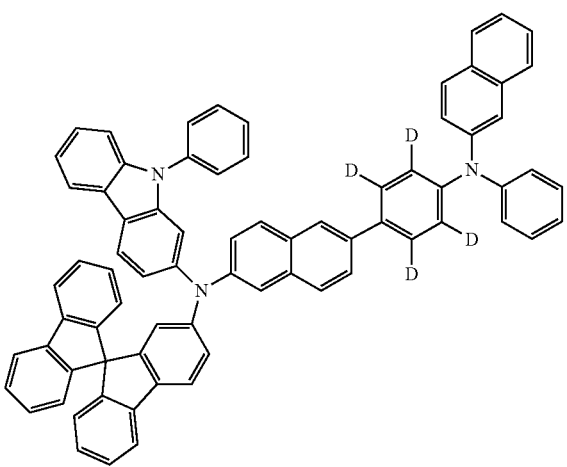

18
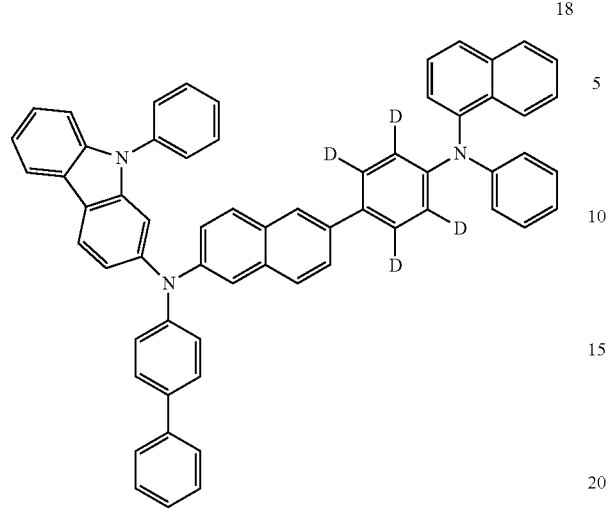
21
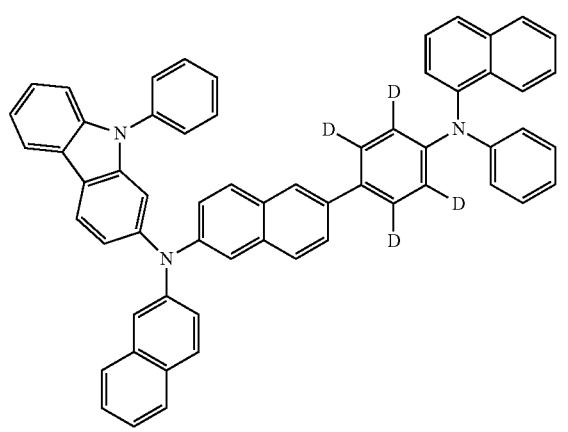
19
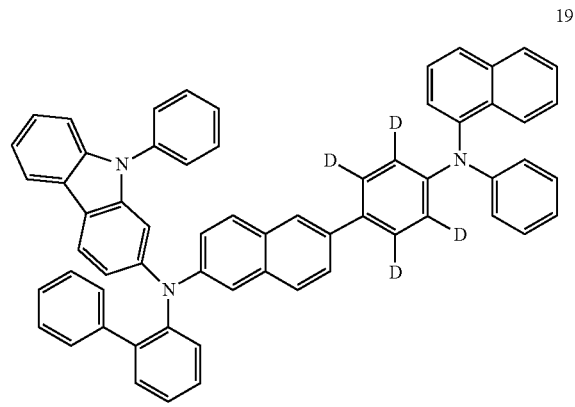
22
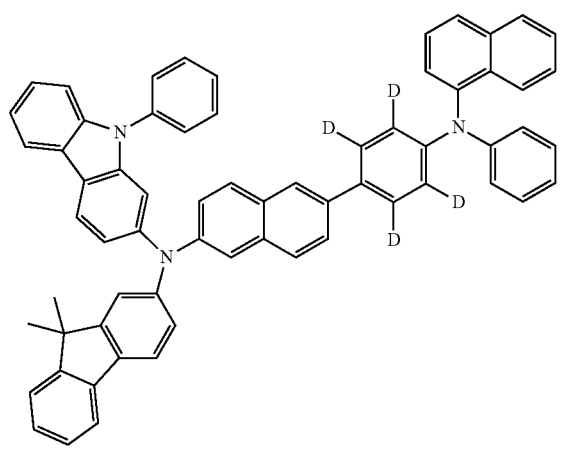
20
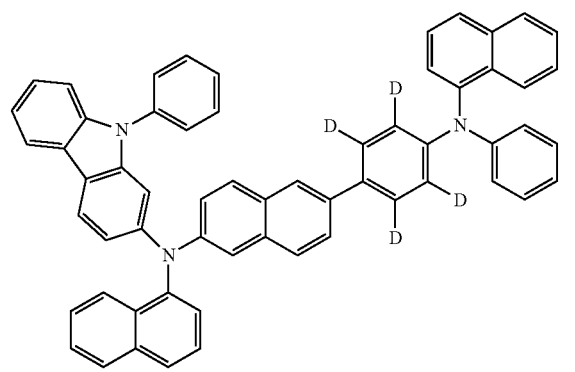
23
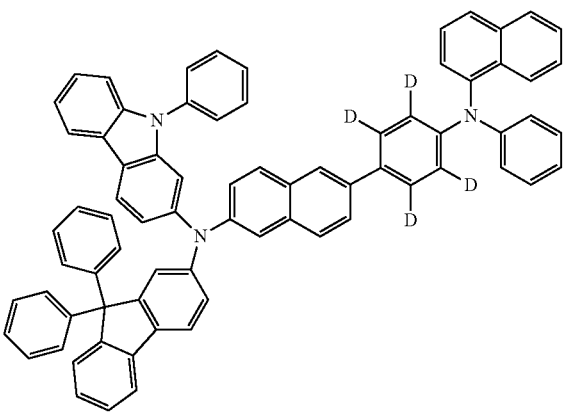

24
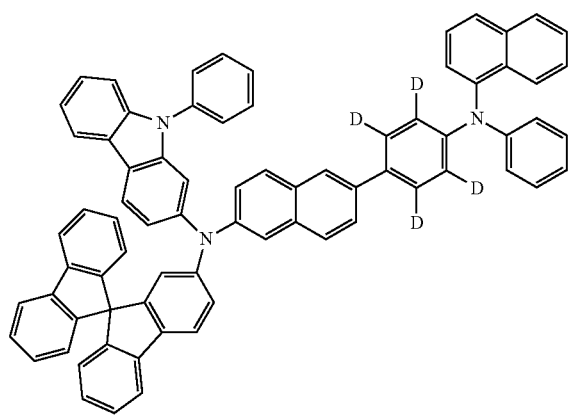
25
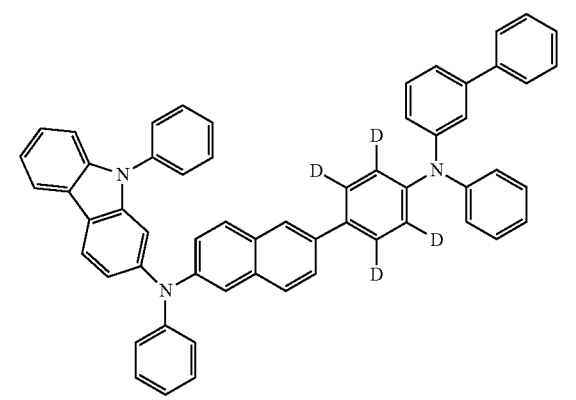
26
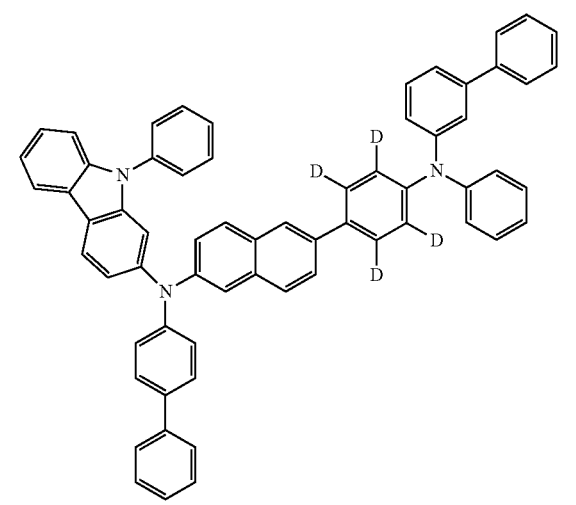
27
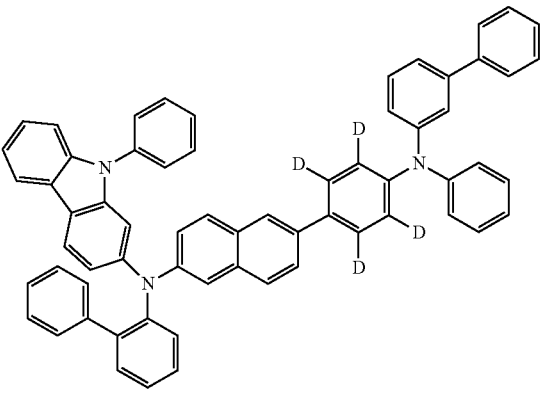
28
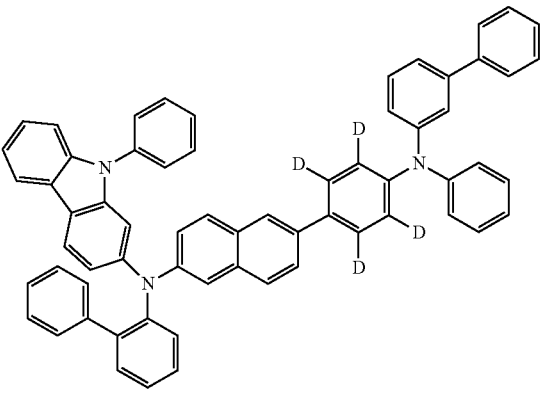
29
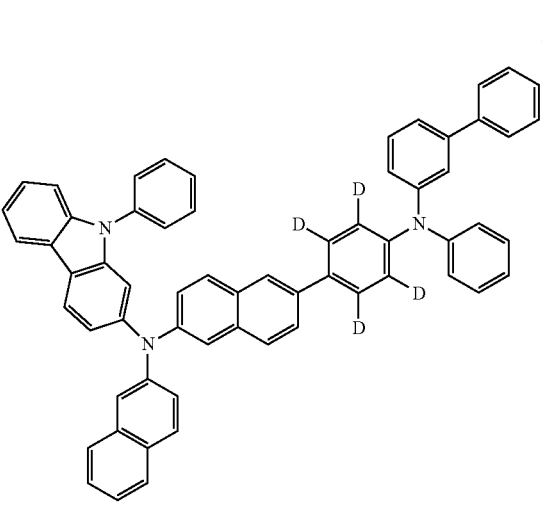

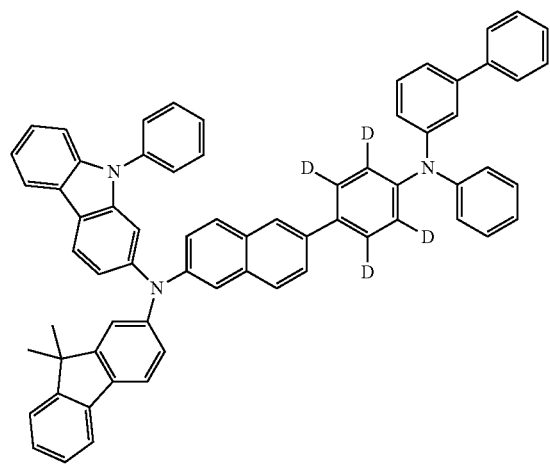
30
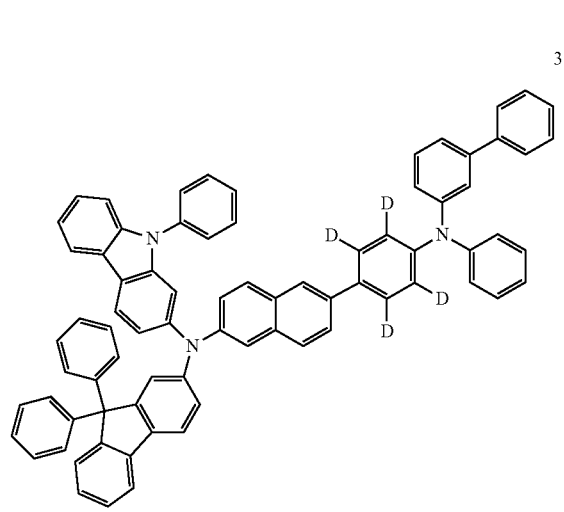
31
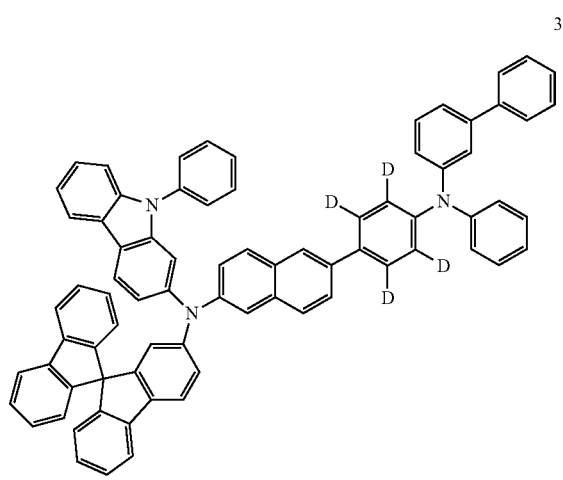
32
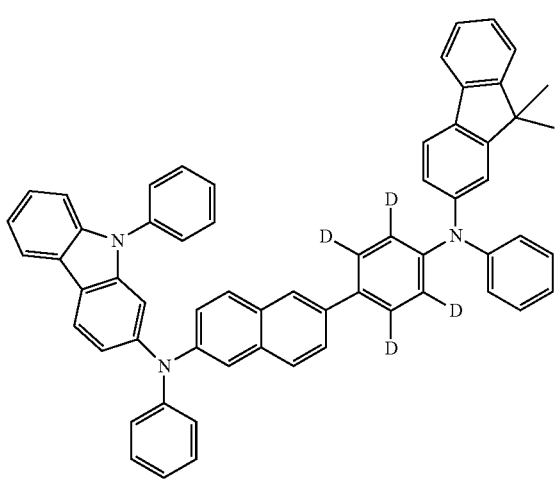
33
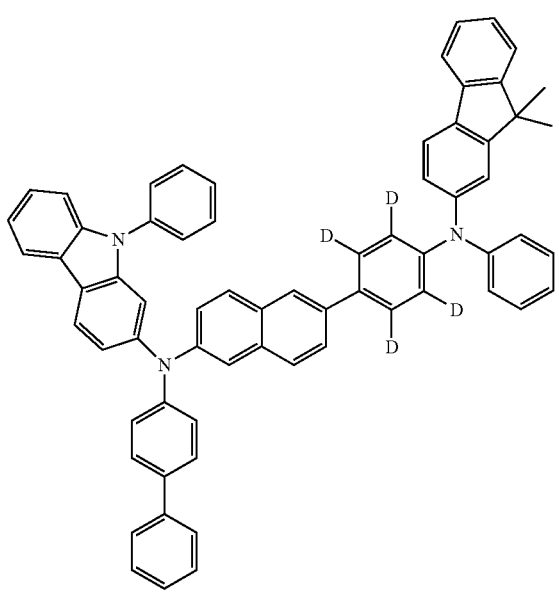
34

35
-continued
36
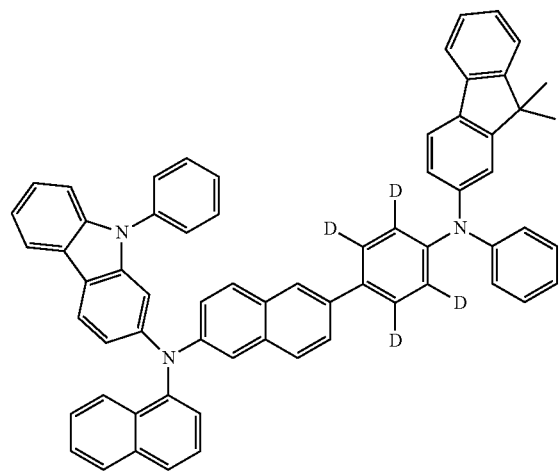
37
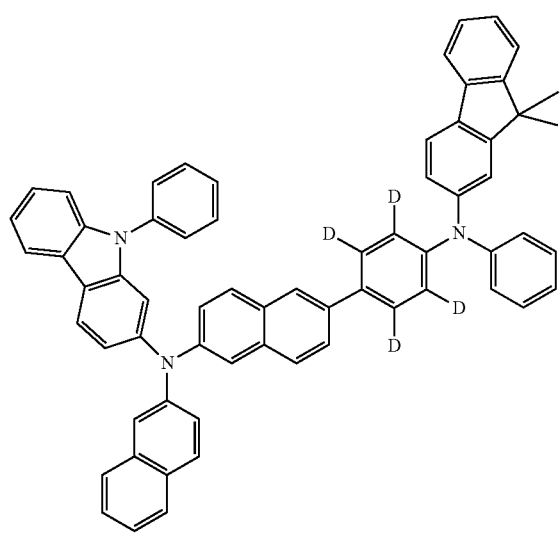
38
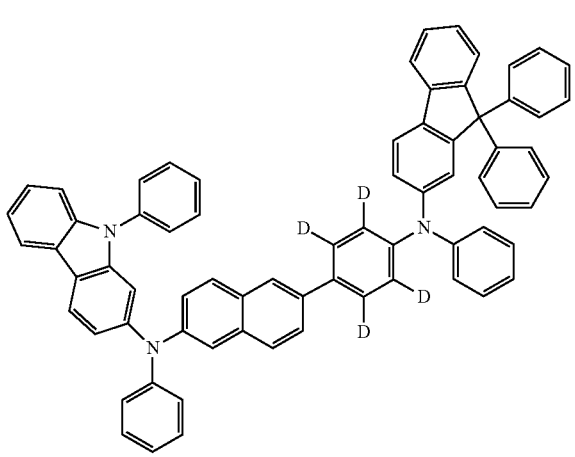
36
-continued
39
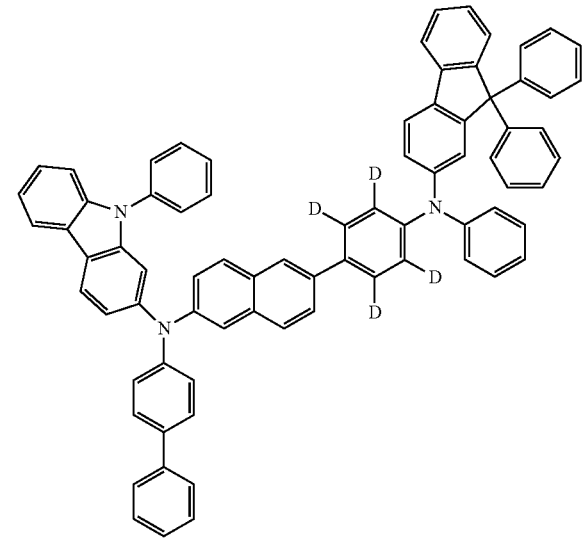
40
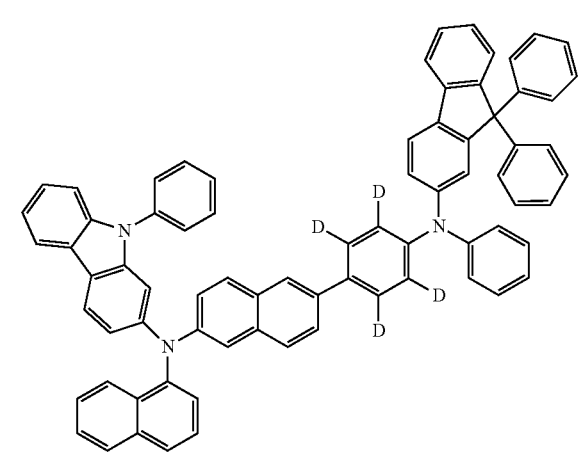
41

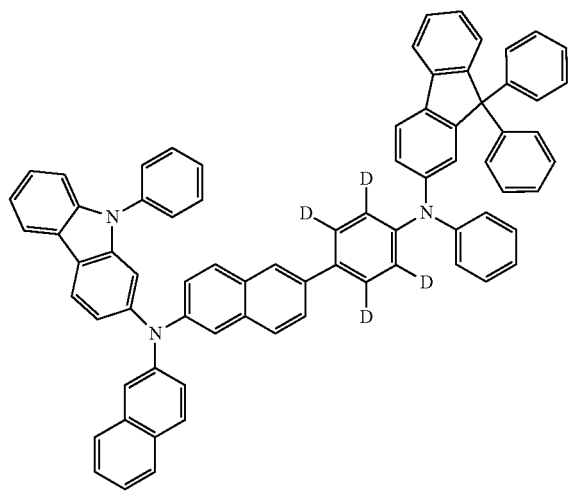
42
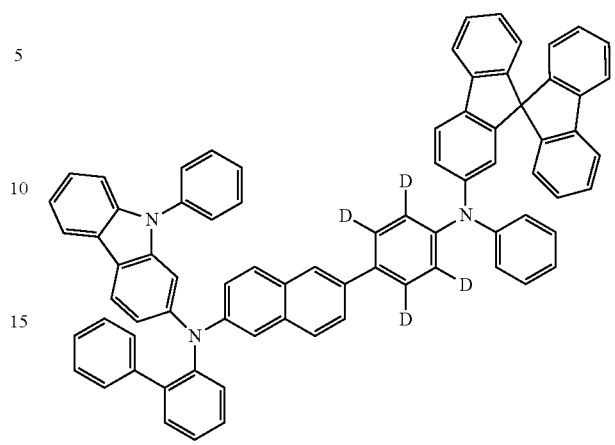
45
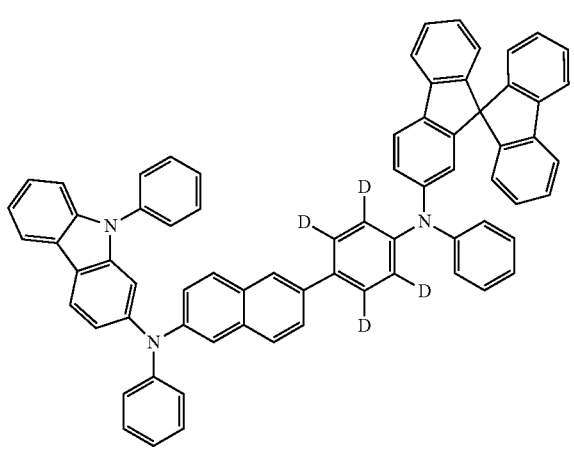
43
46
44
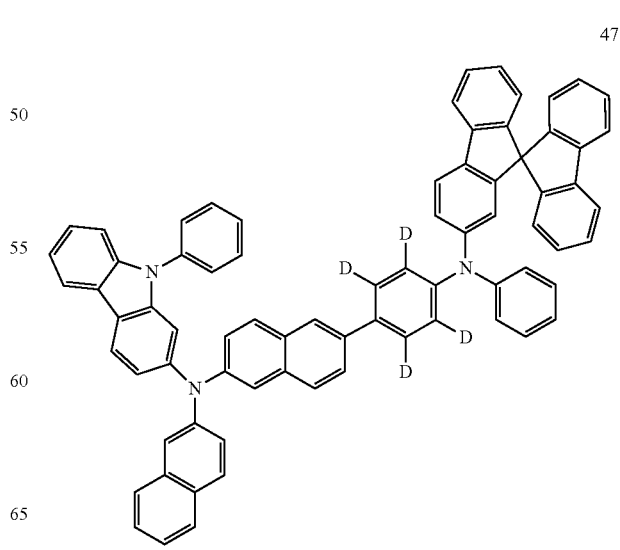
47

48
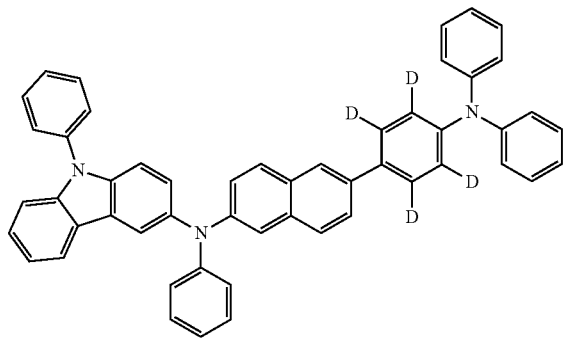
49
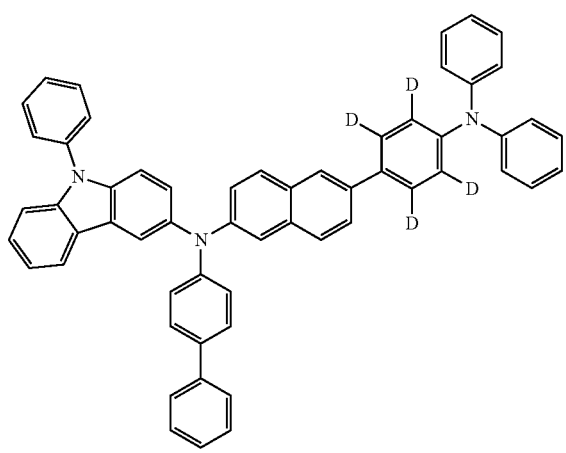
50
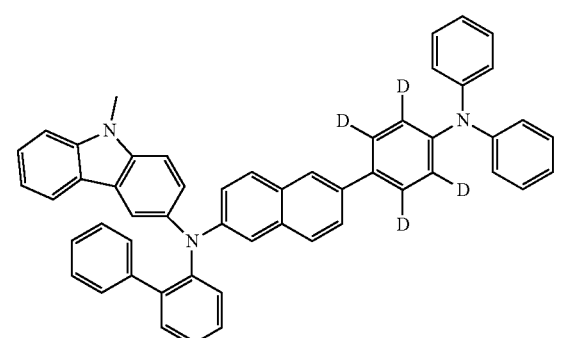
51
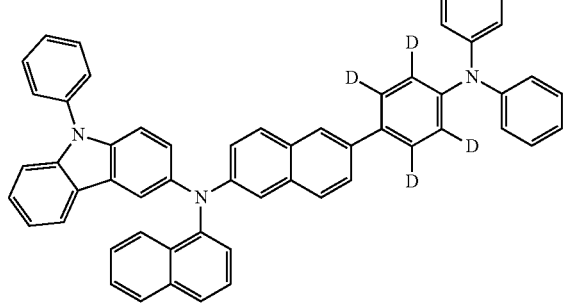
52
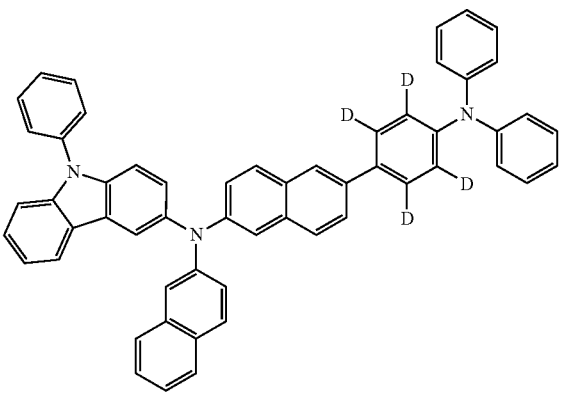
53
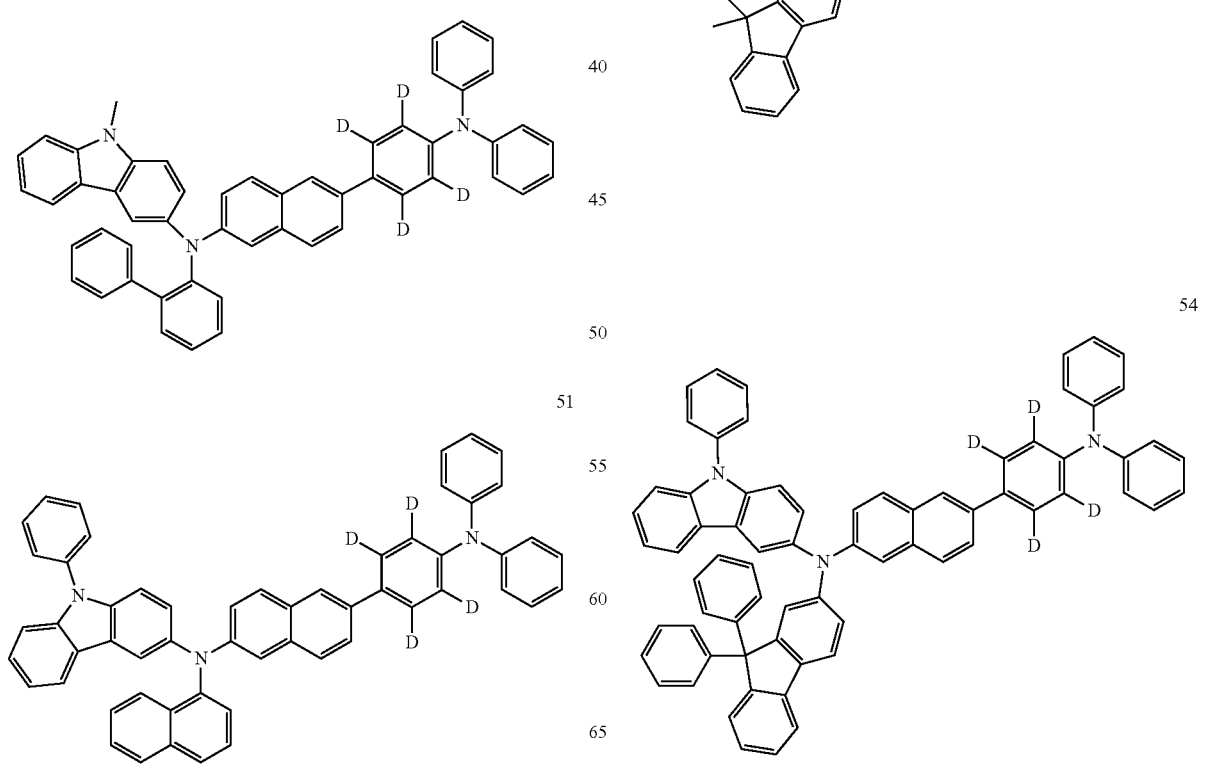
54

55
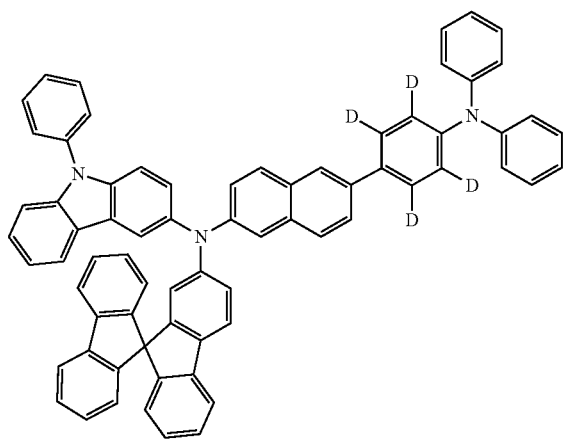
56
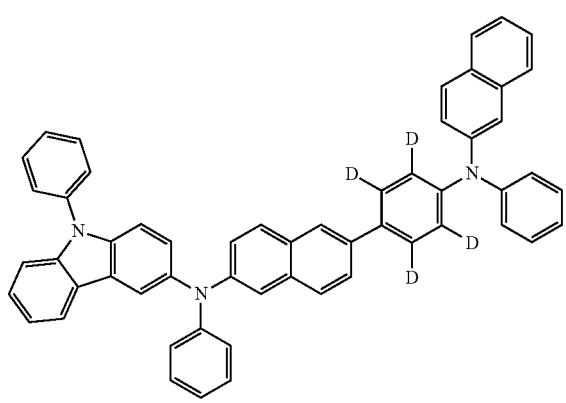
57
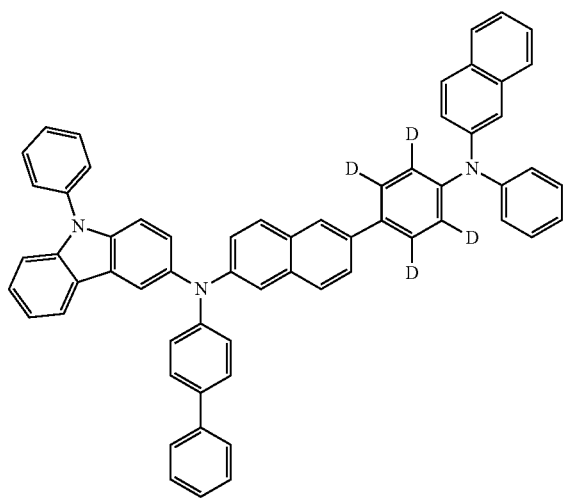
58
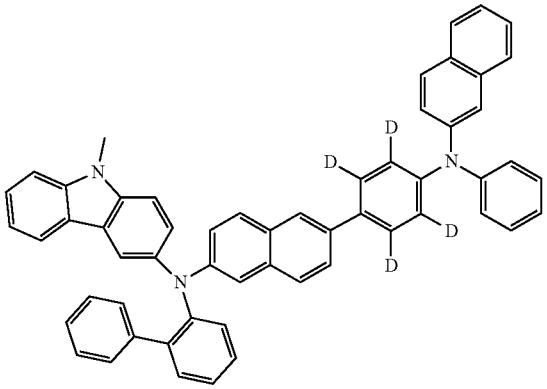
59
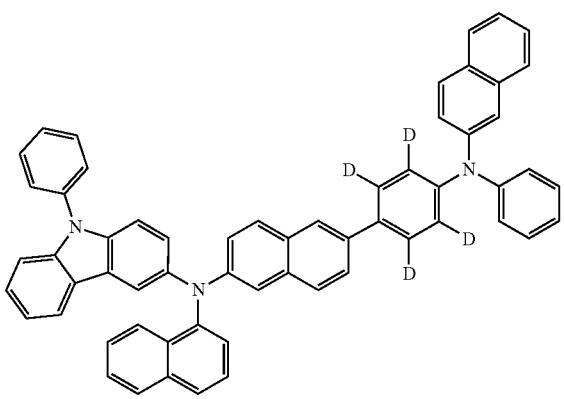
60
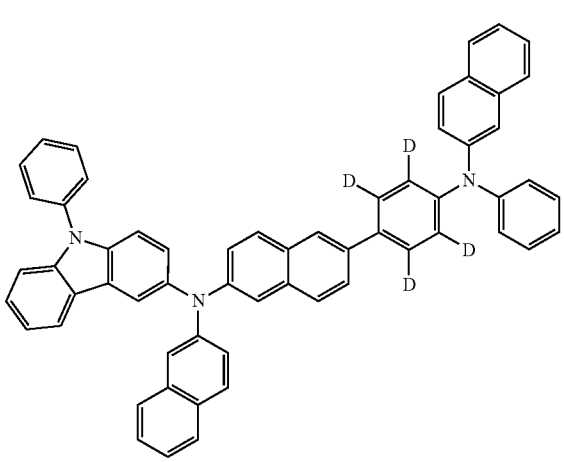

61
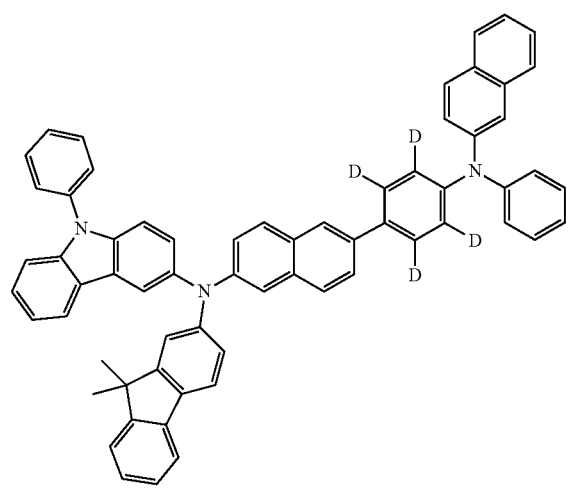
62
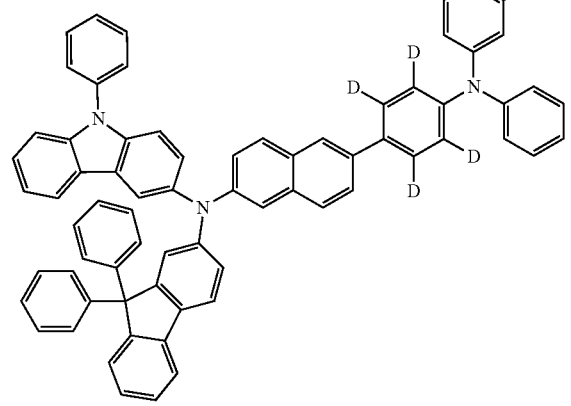
63
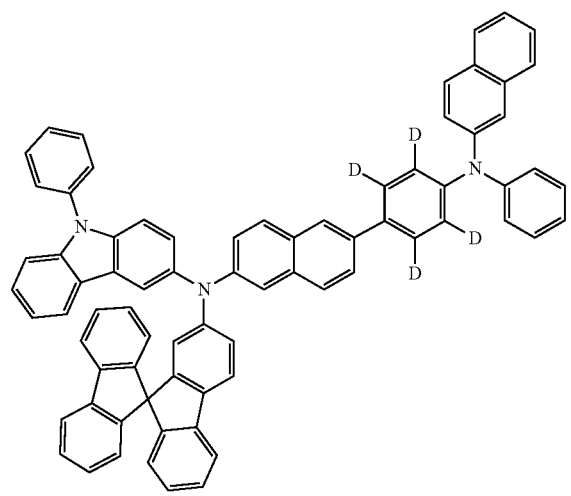
64
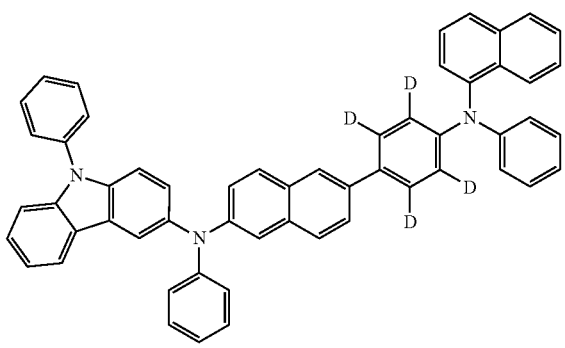
65
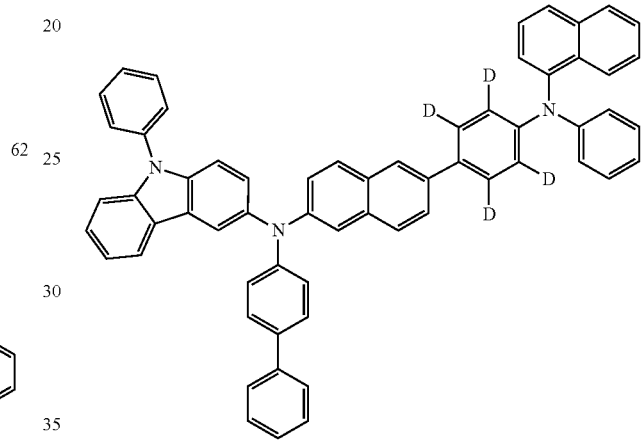
66
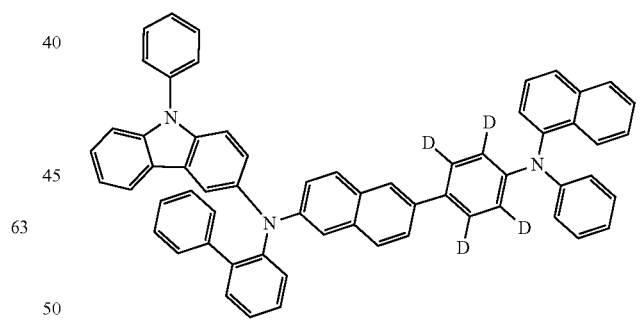
67
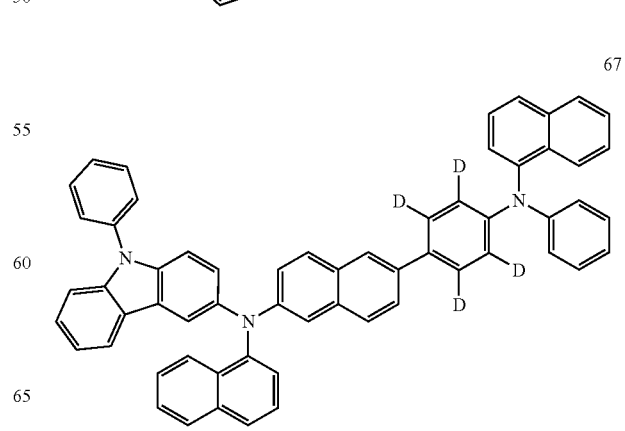

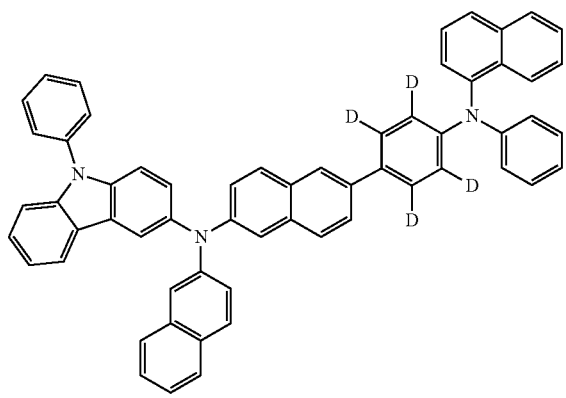
68
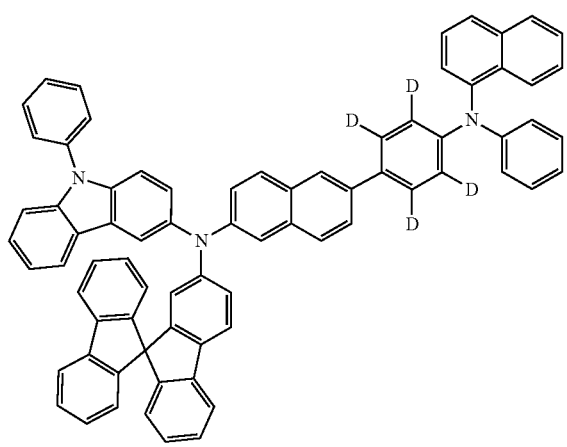
71
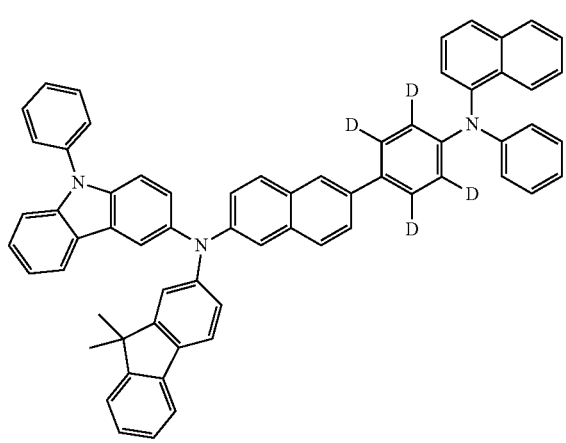
69
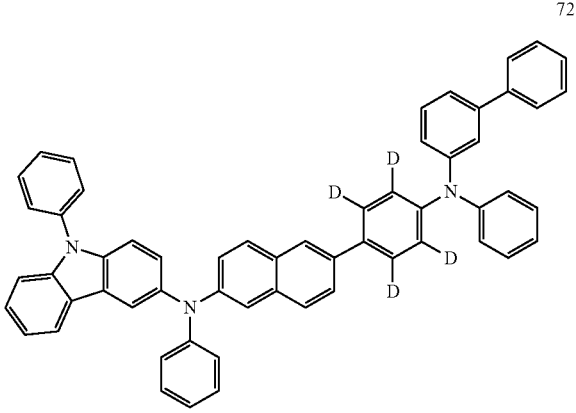
72
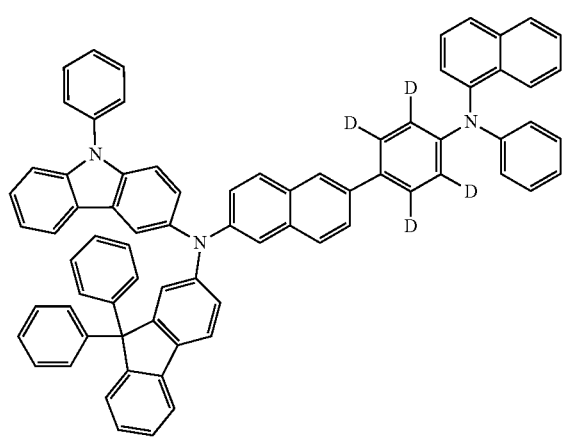
70
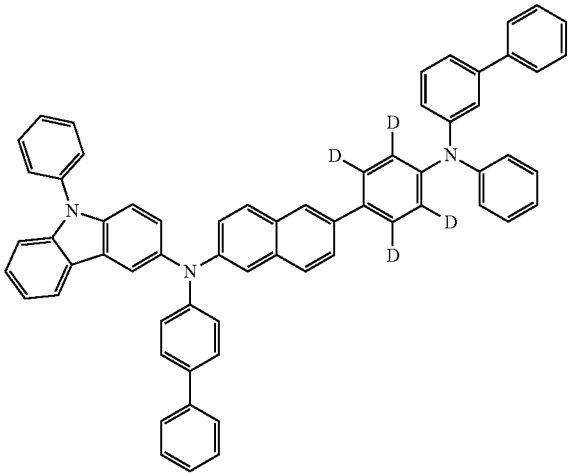
73

74
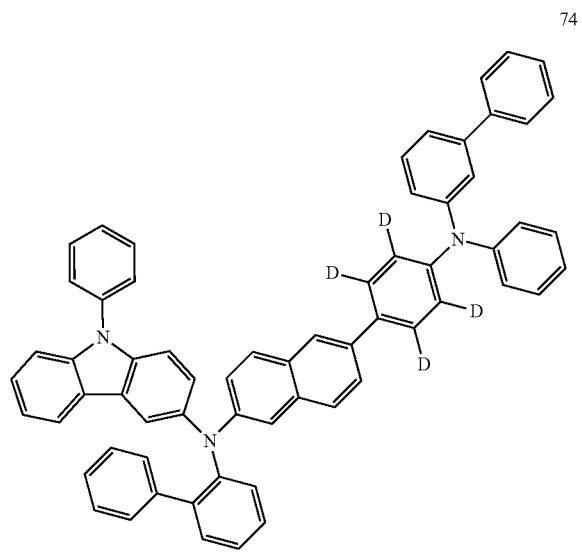
75
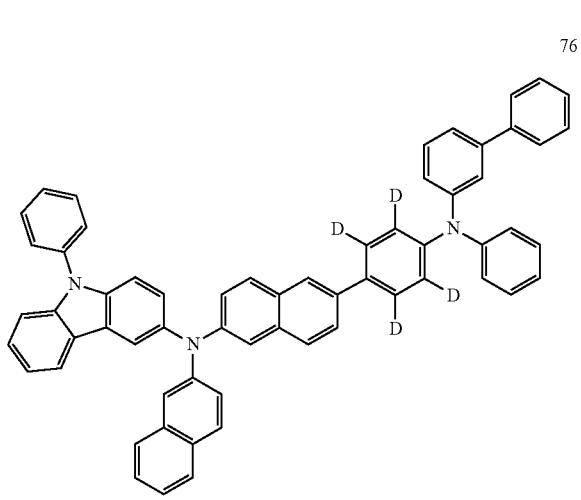
76
77
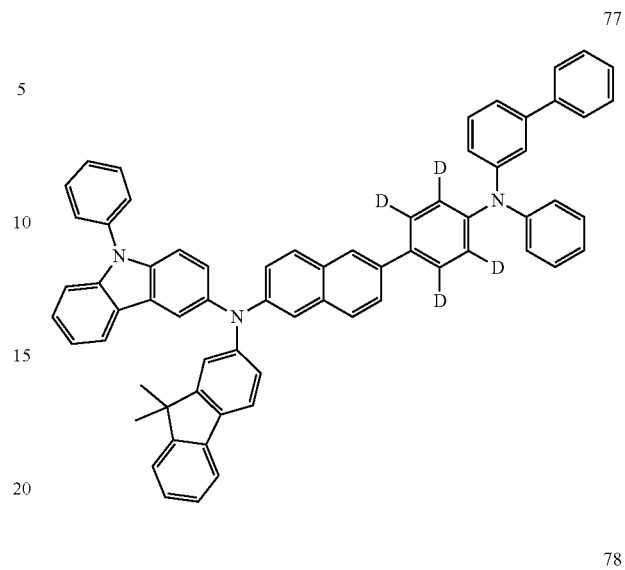
78
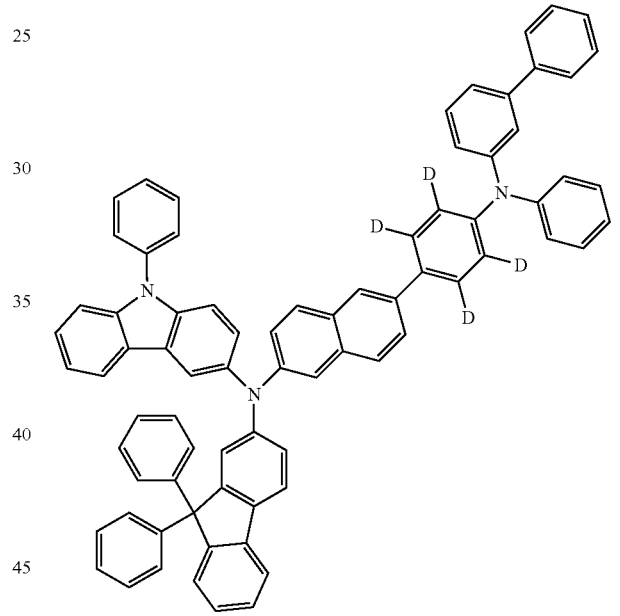
79
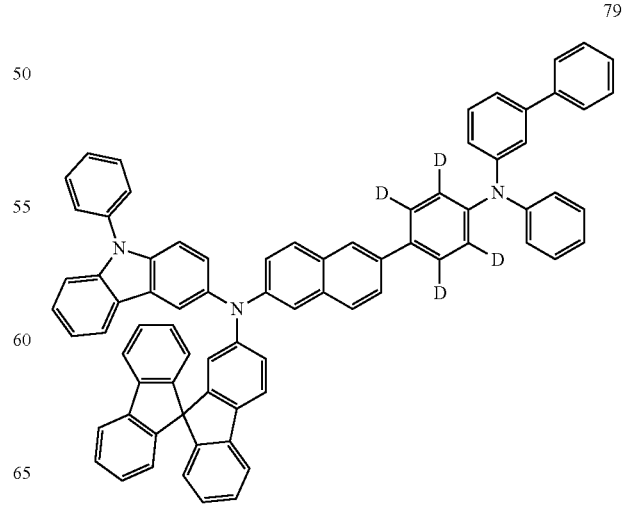

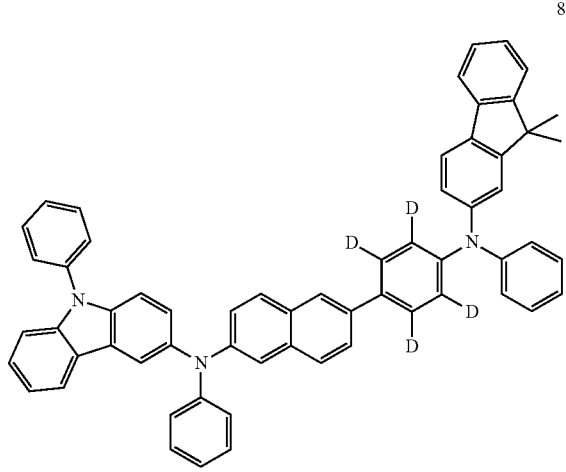
80
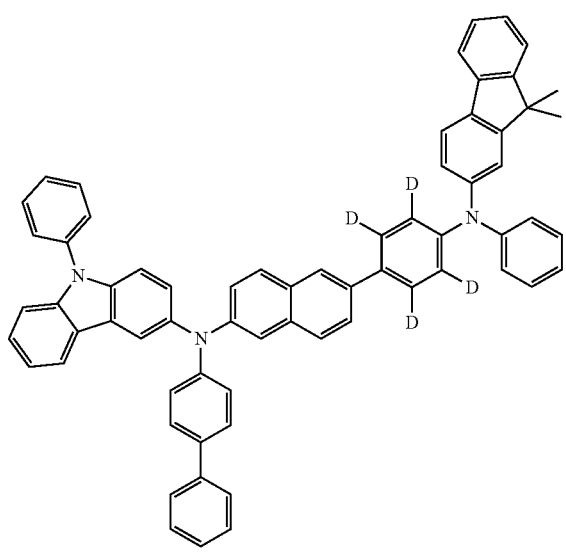
81
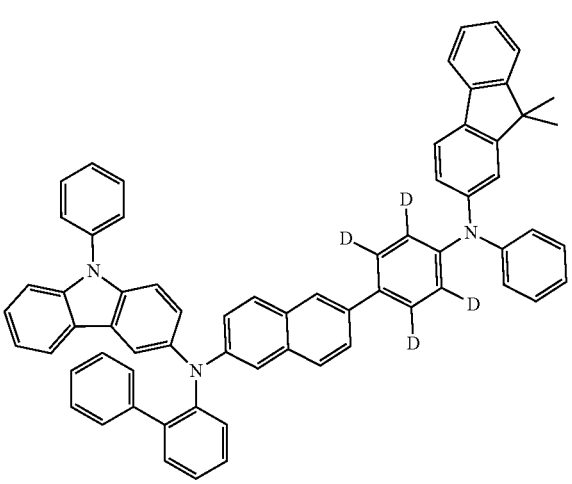
82
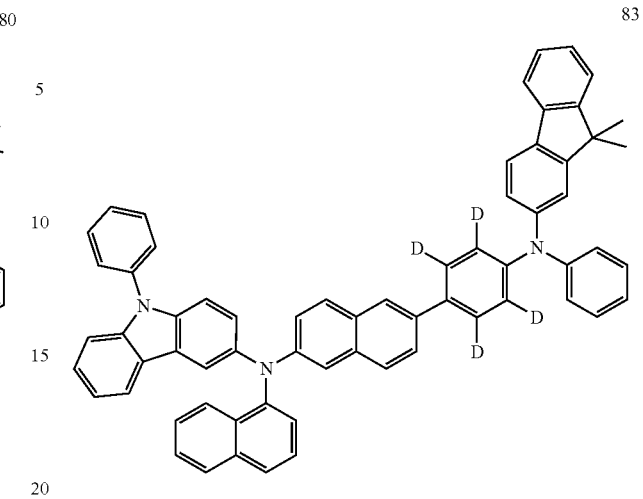
83
84
85

86
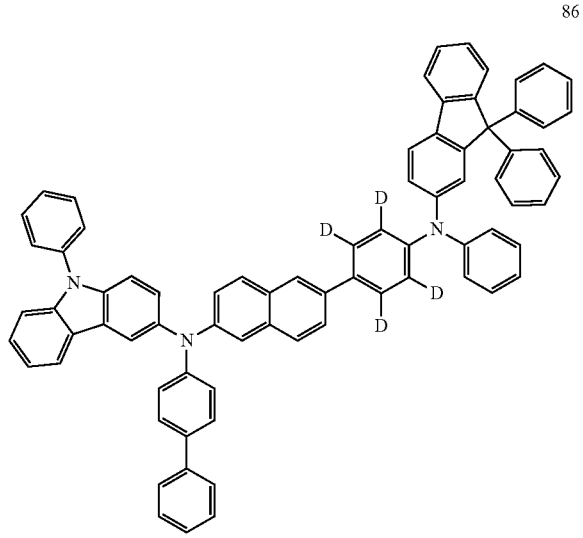
87
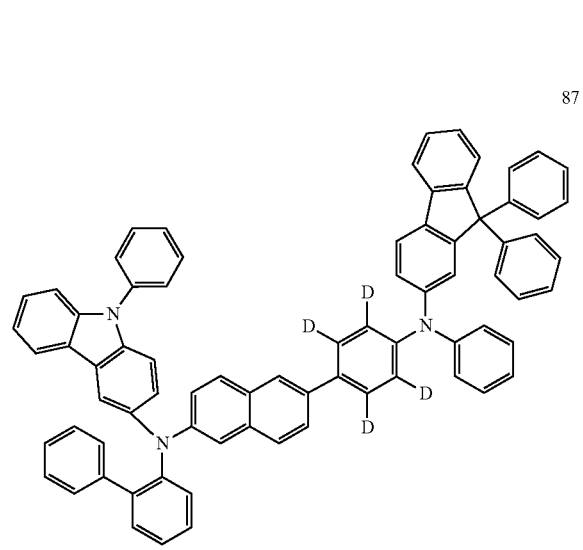
88
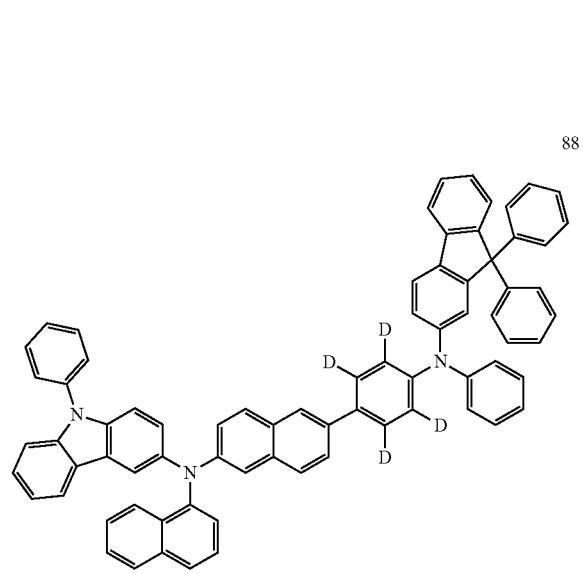
89
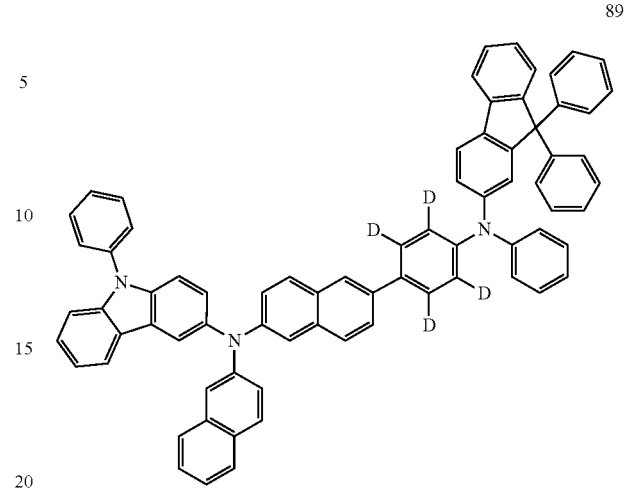
90
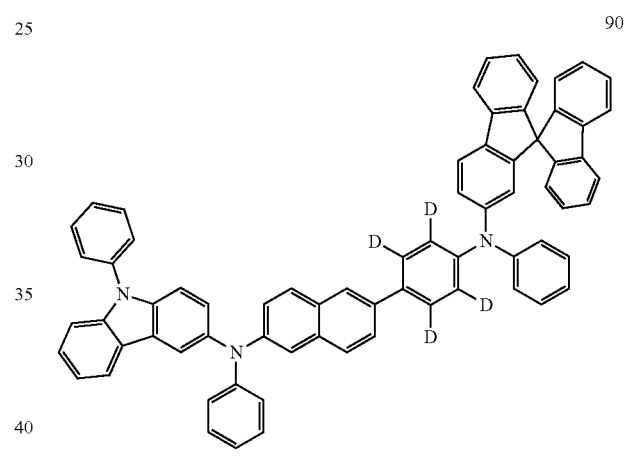
91
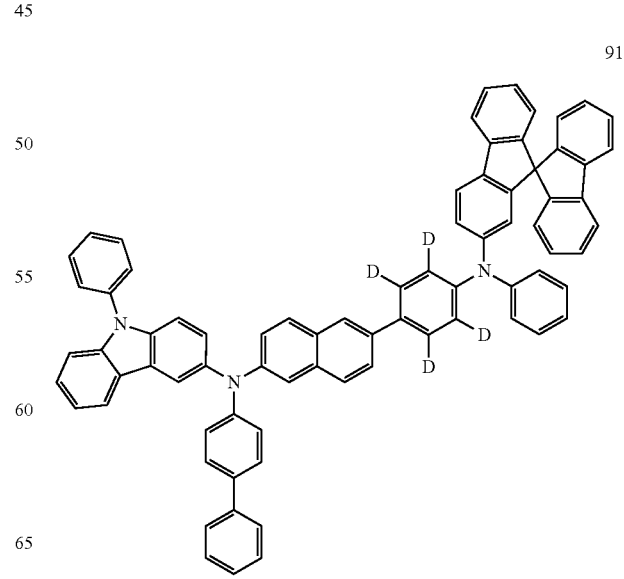

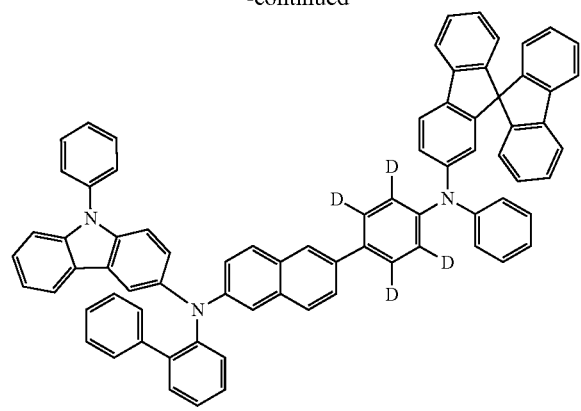
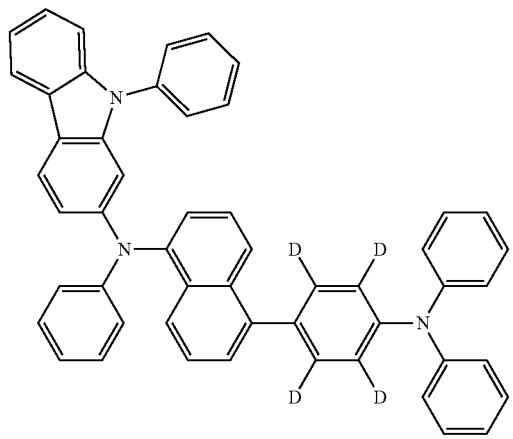
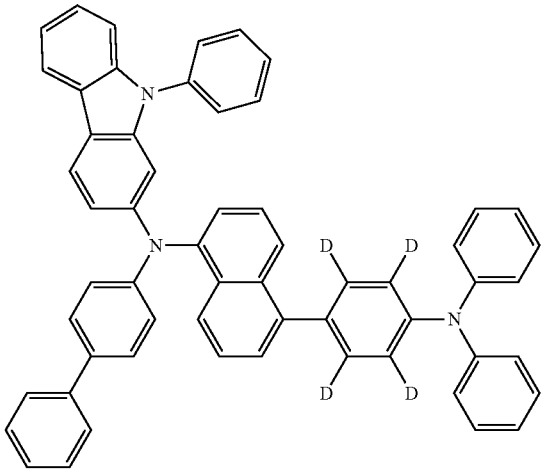
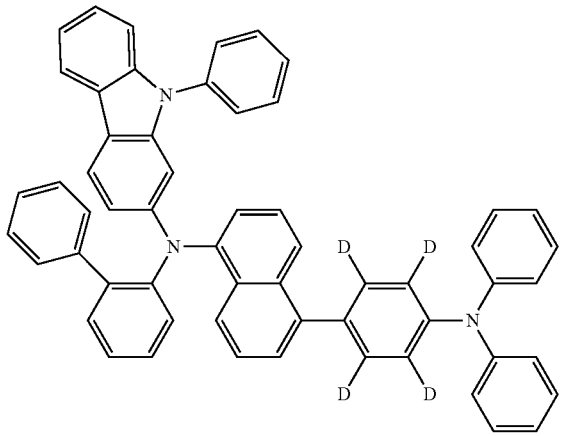

98
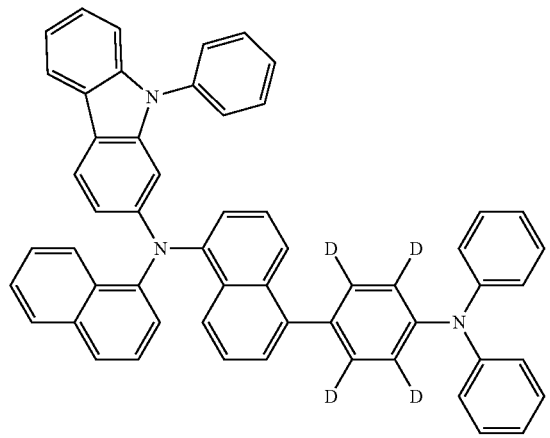
99
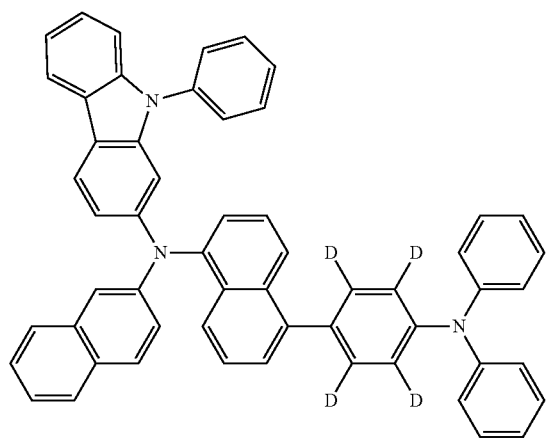
100
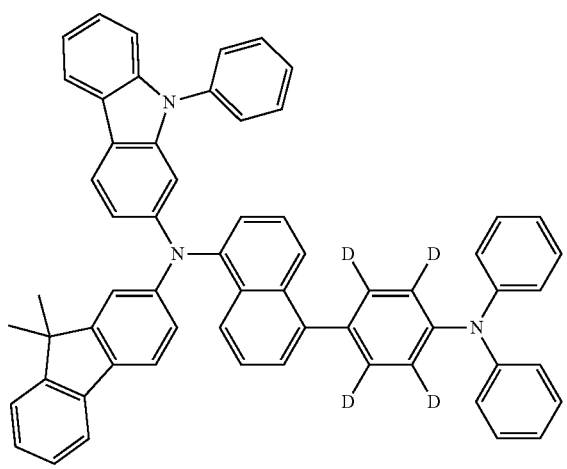
101
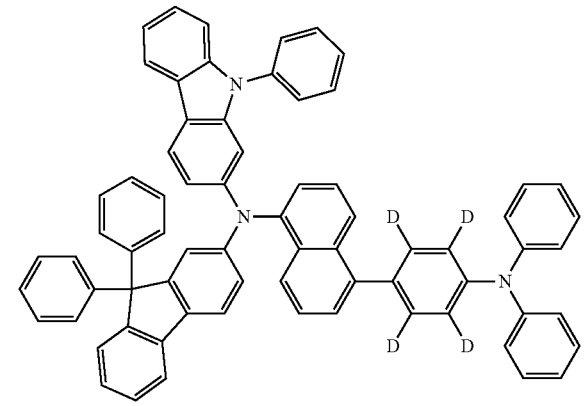
102
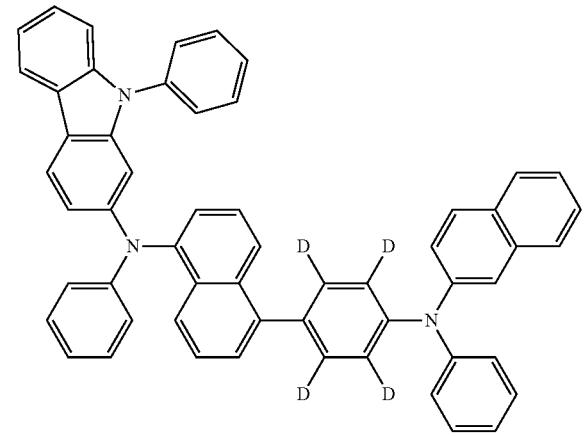
103

104
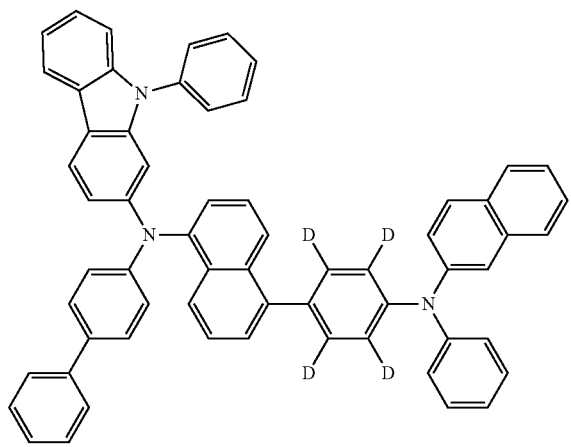
105
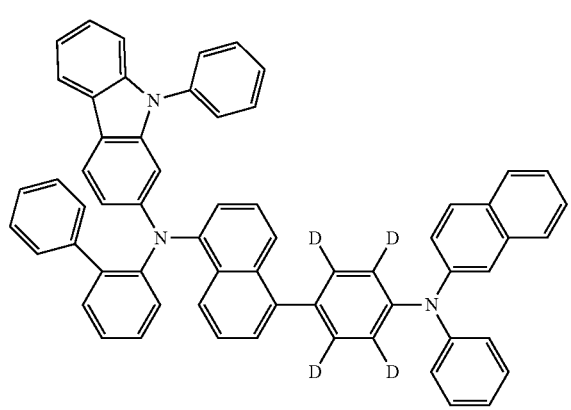
106
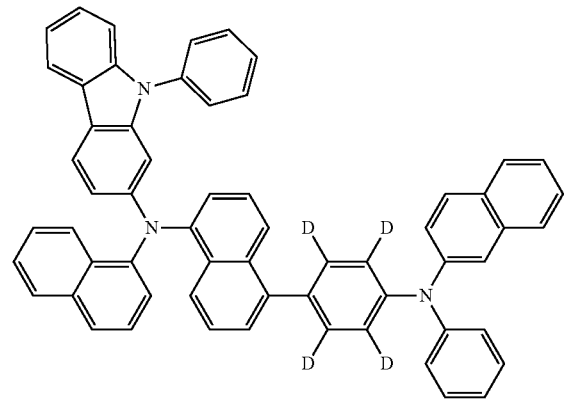
107
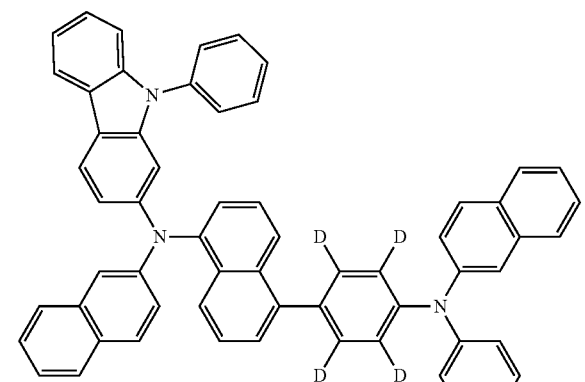
108
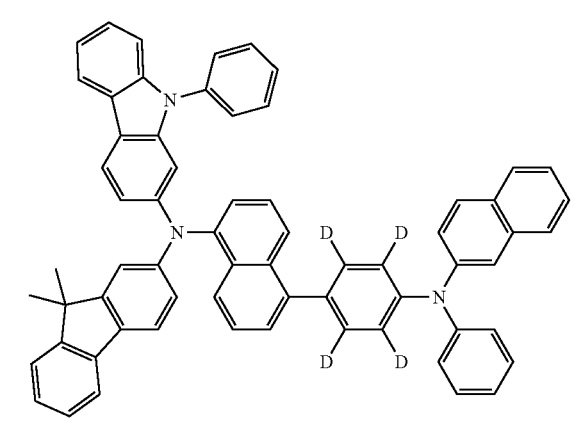
109
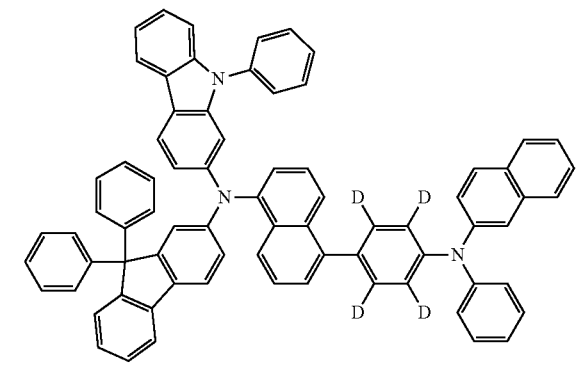
110
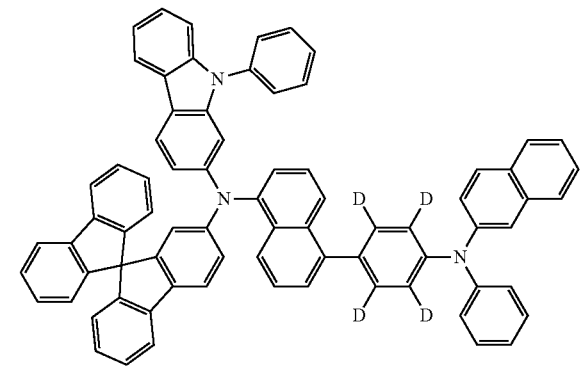

111
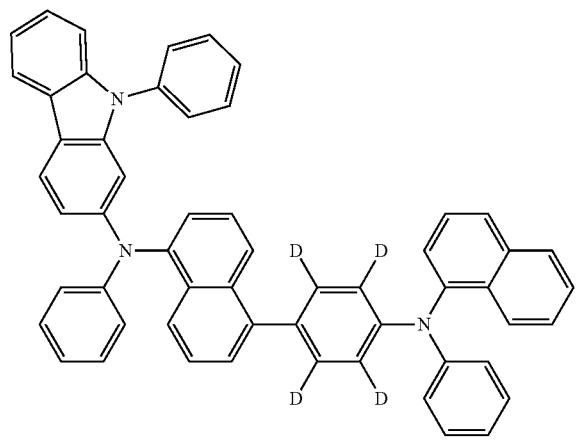
112
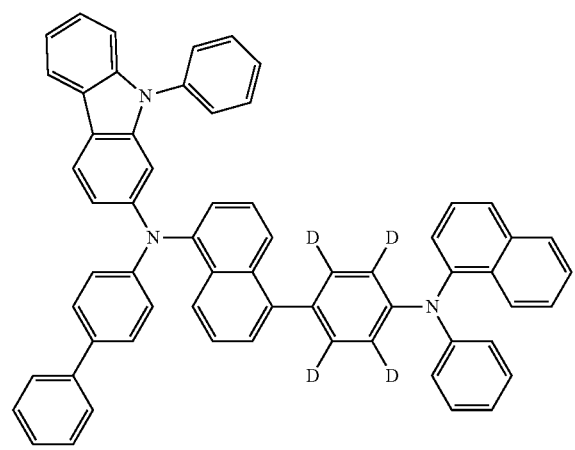
113
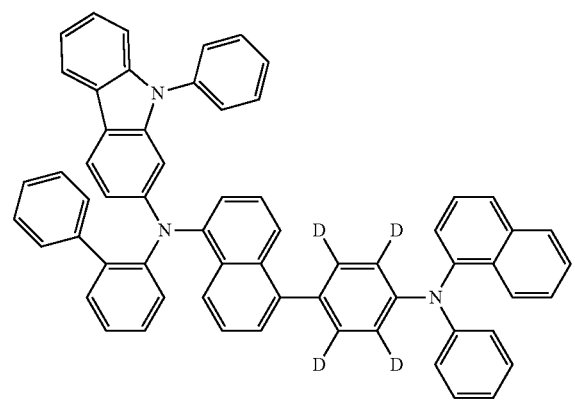
114
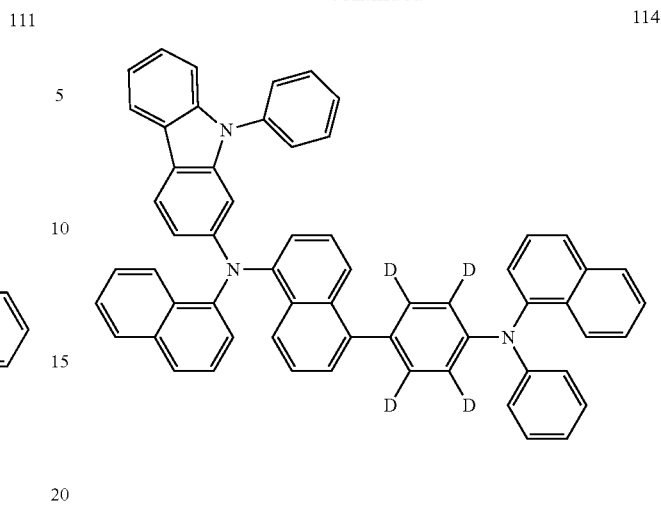
115
116
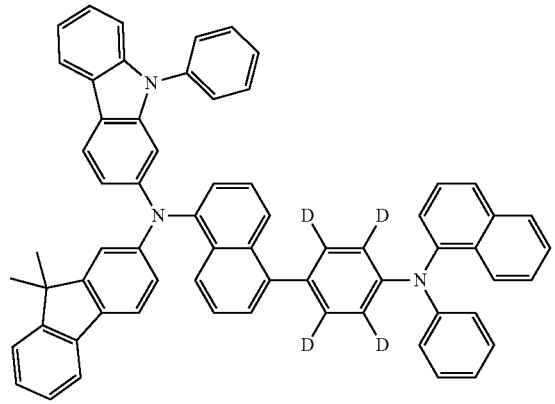

117
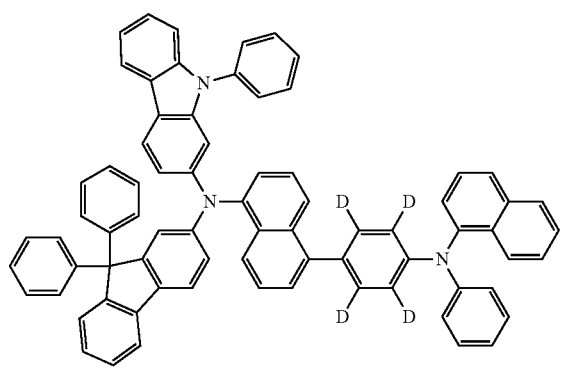
118
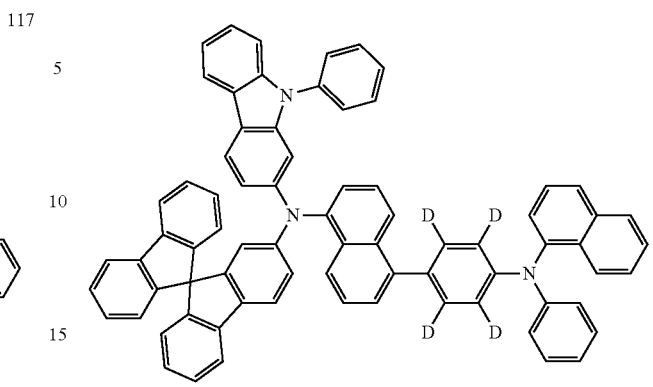
119
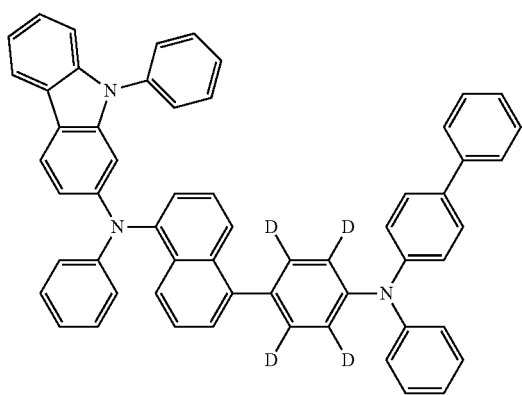
120
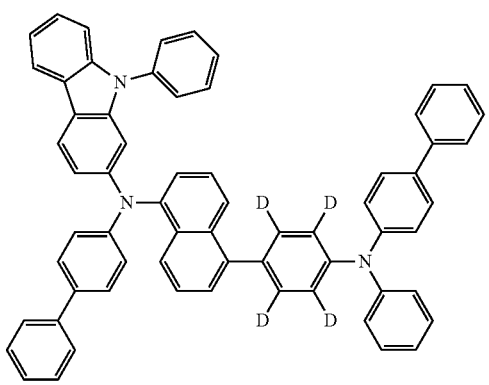
121
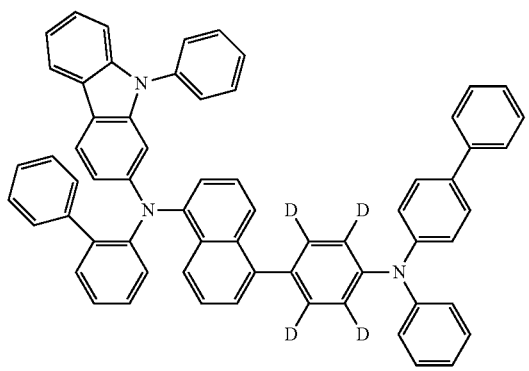
122
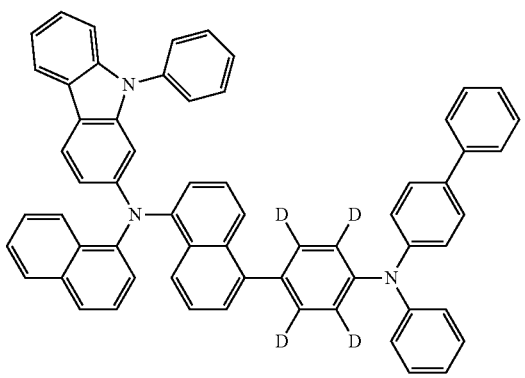
123
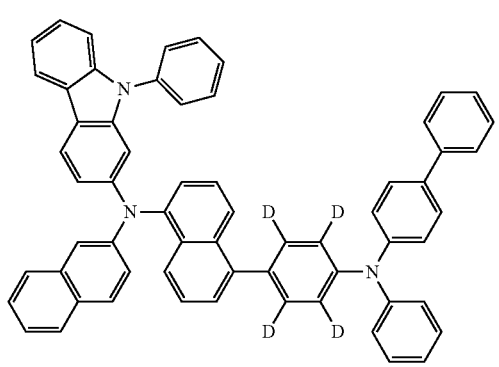
124
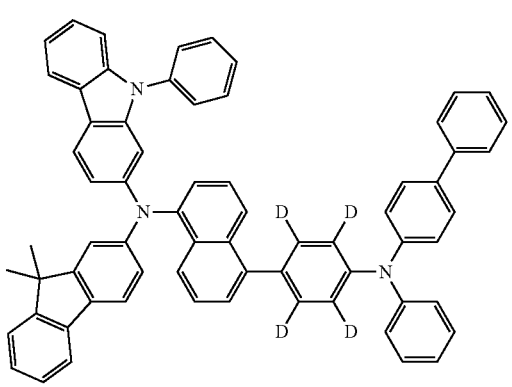

-continued
125
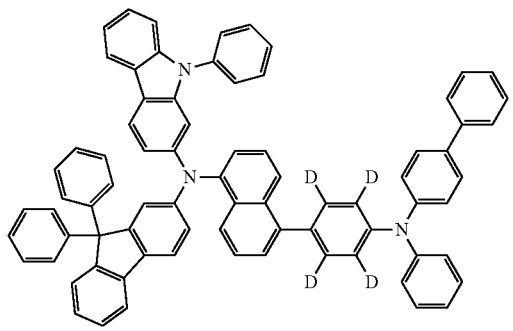
126
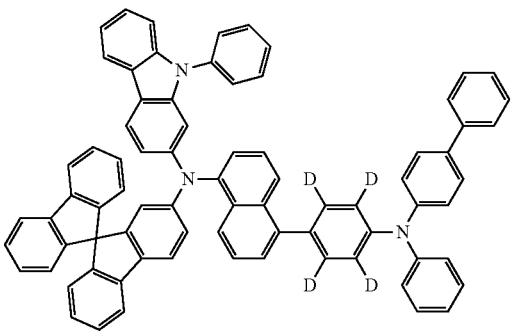
127
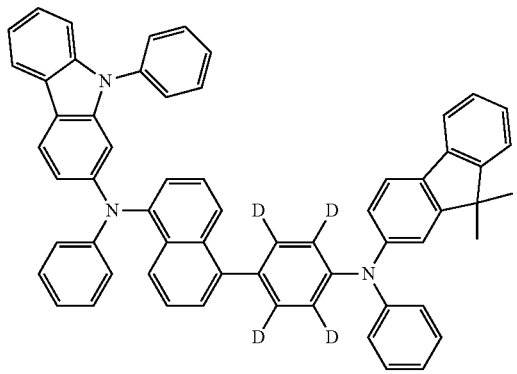
128
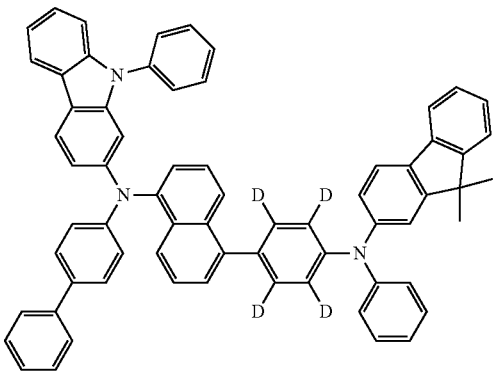
129
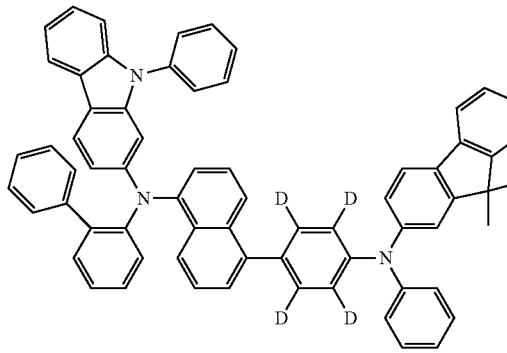
130
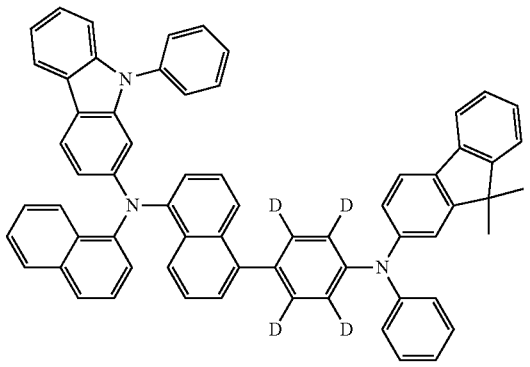
131
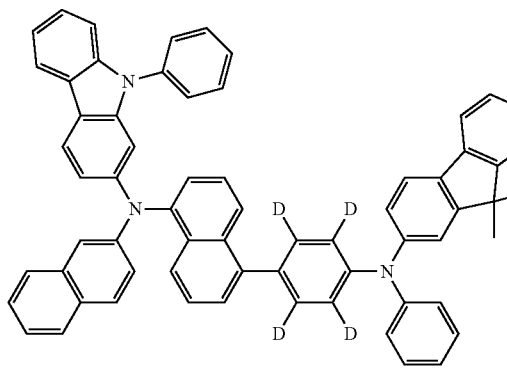
132
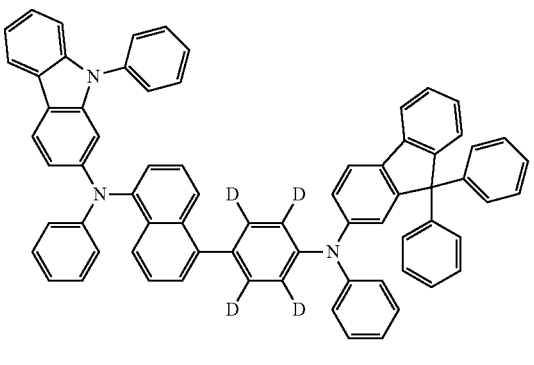

-continued
133
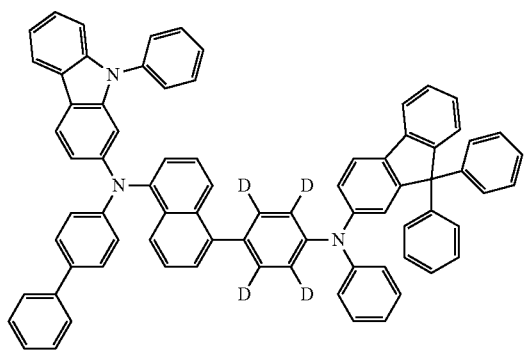
134
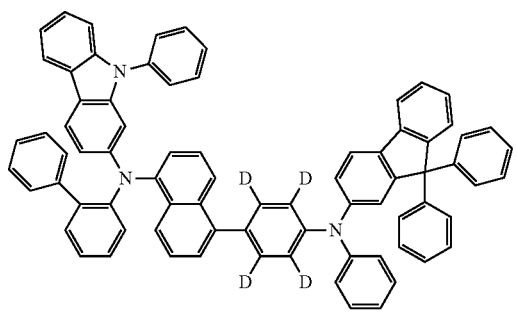
135
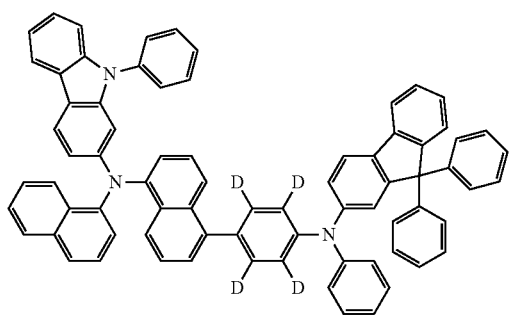
136
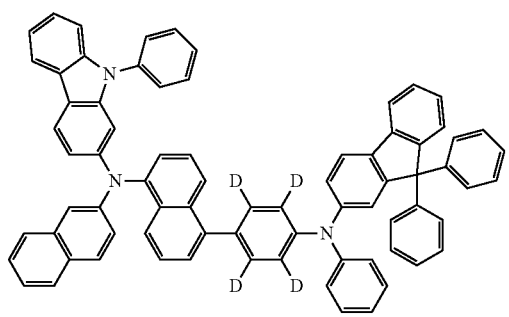
137
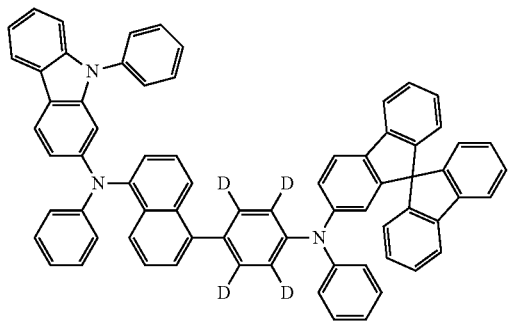
138
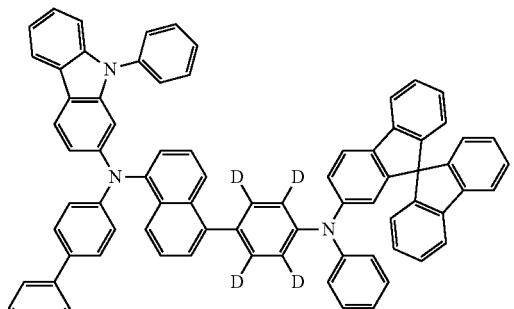
139
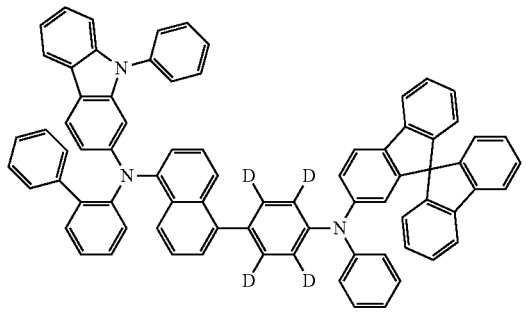
140
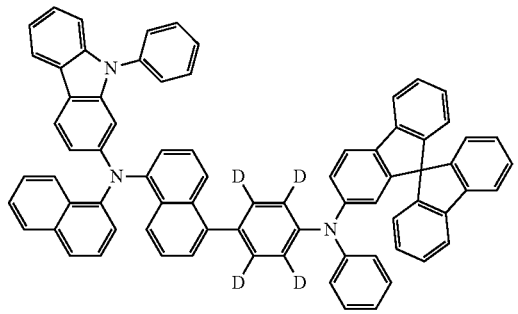

141
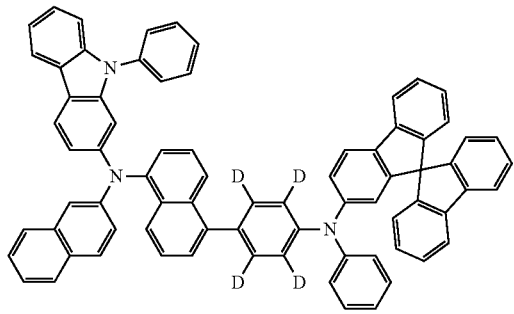
142
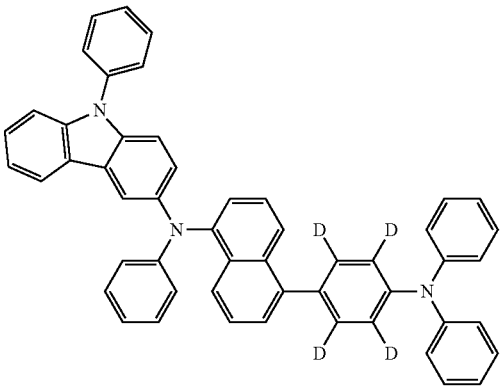
143
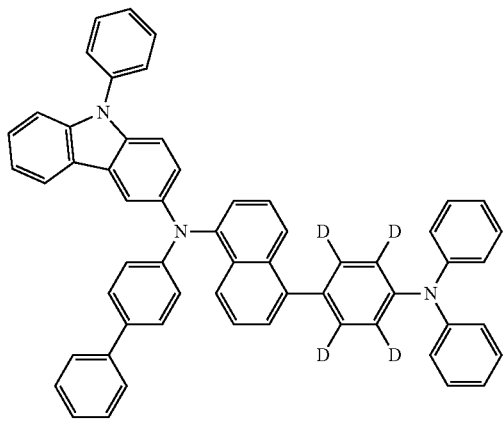
144
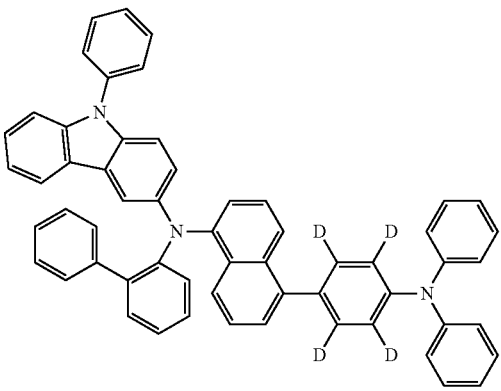
145
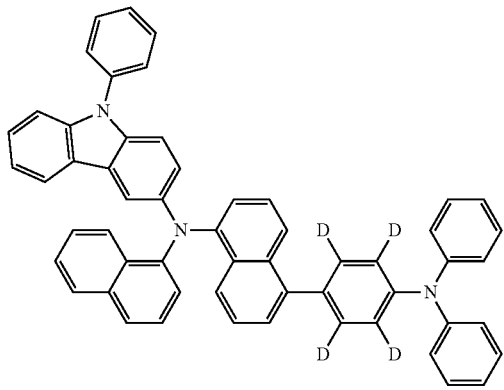
146
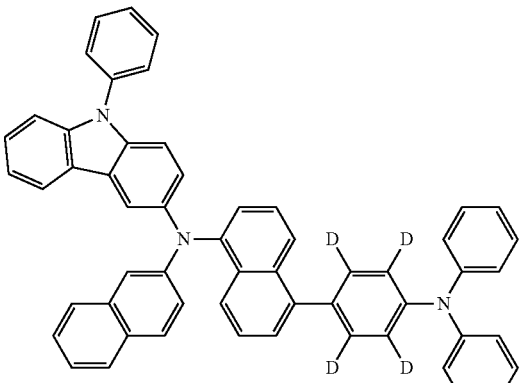
147
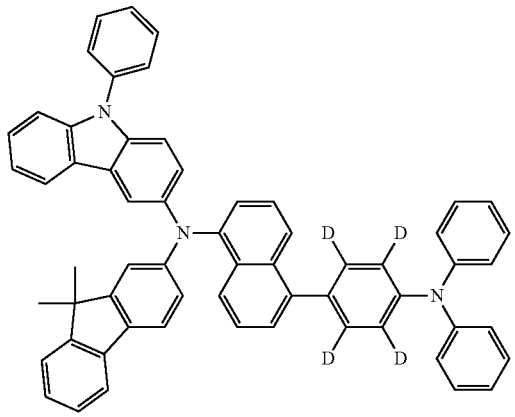
148
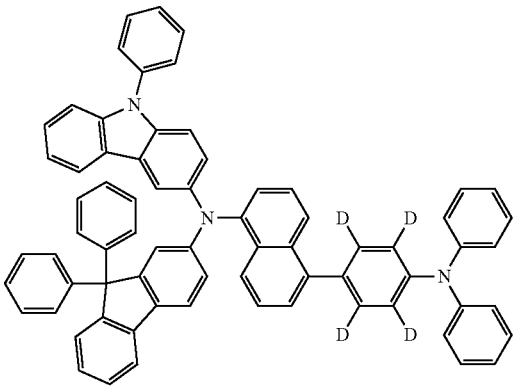

-continued
149
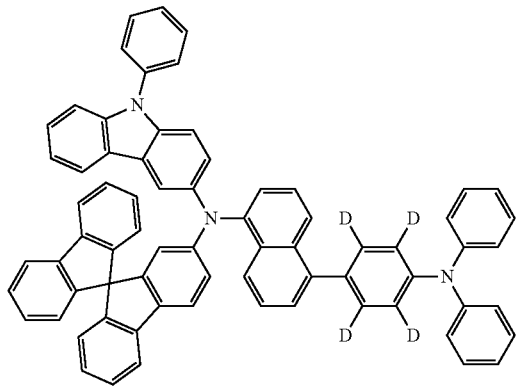
150
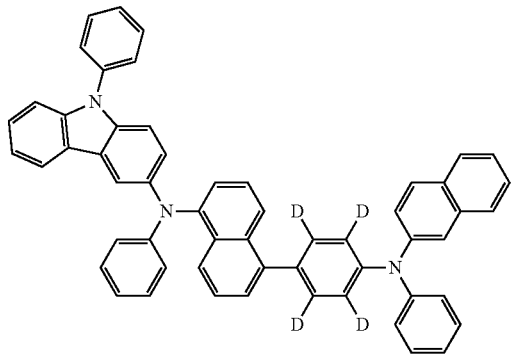
151
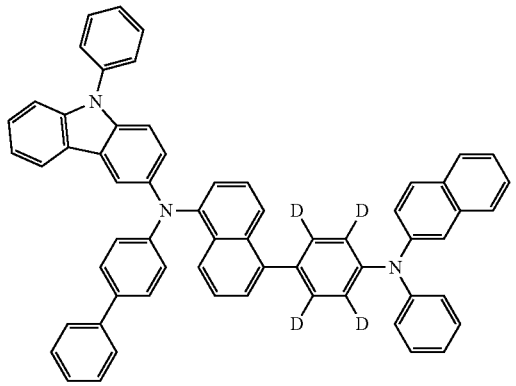
152
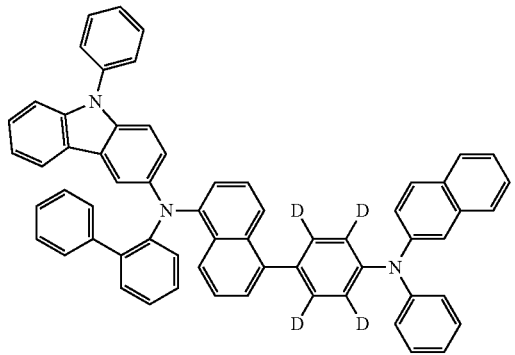
153
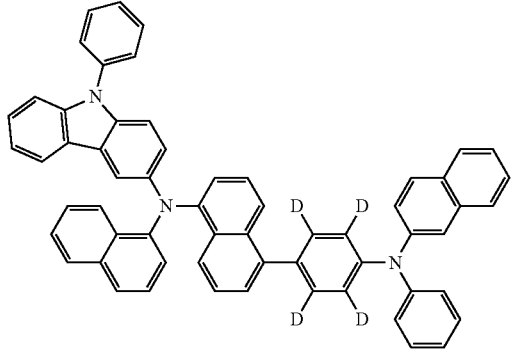
154
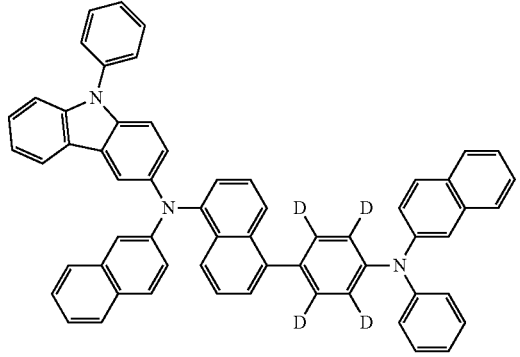
155
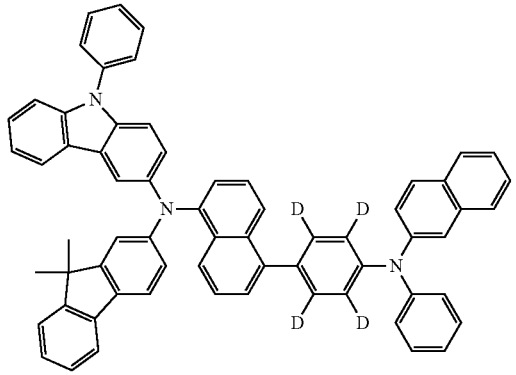
156
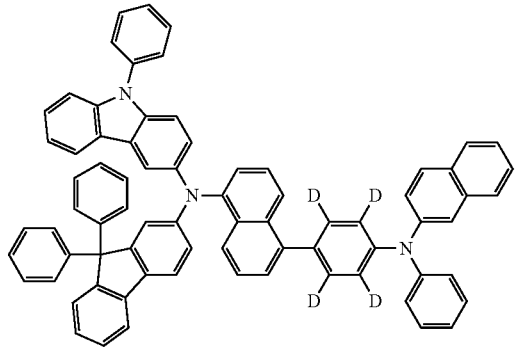

-continued
157
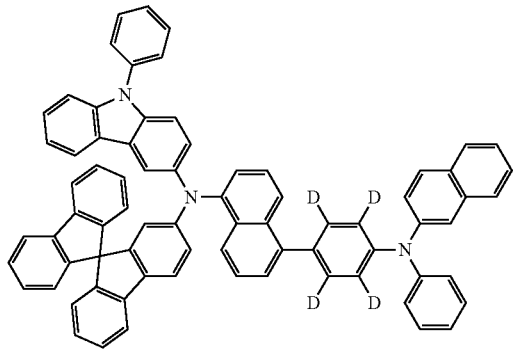
158
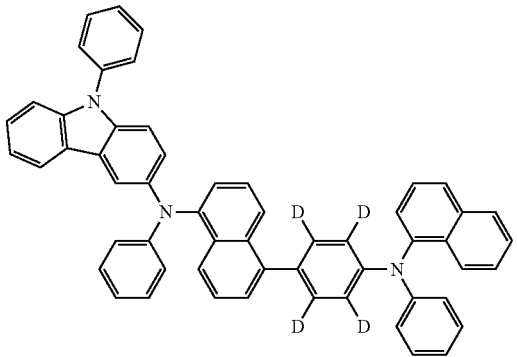
159
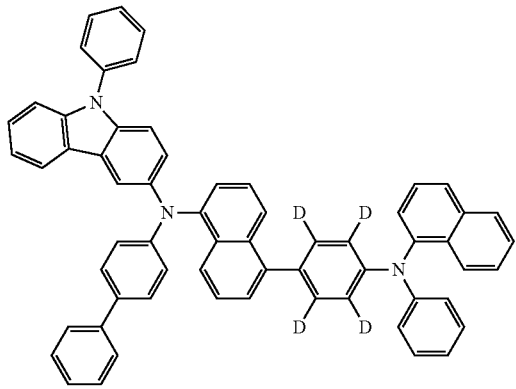
160
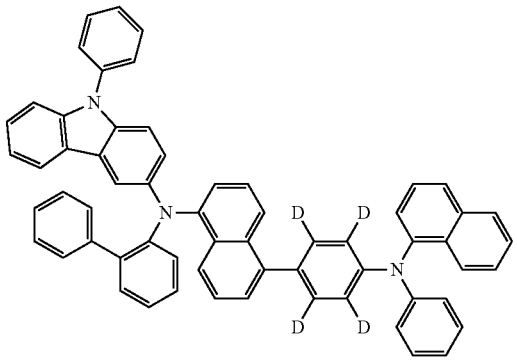
161
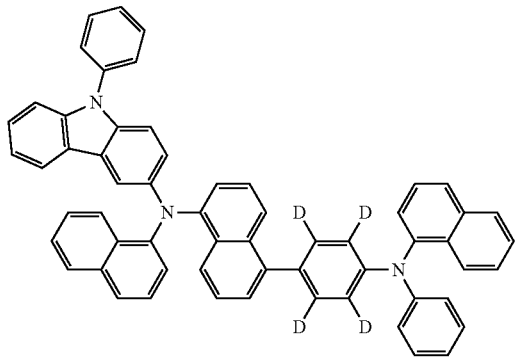
162
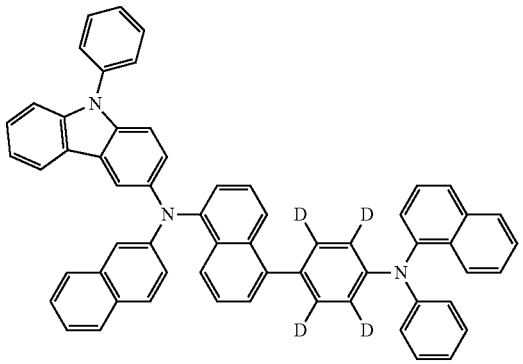
163
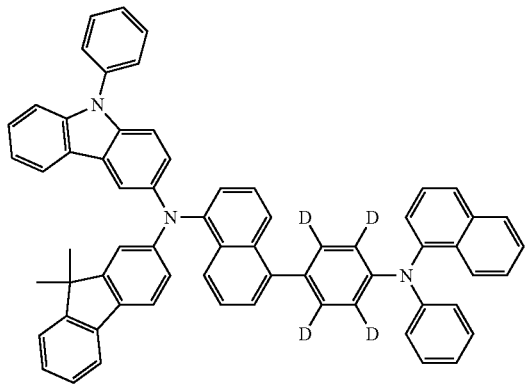
164
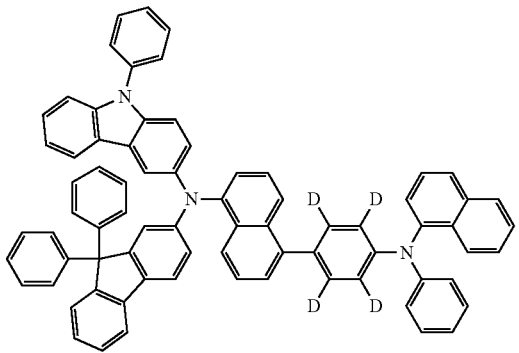

-continued
165
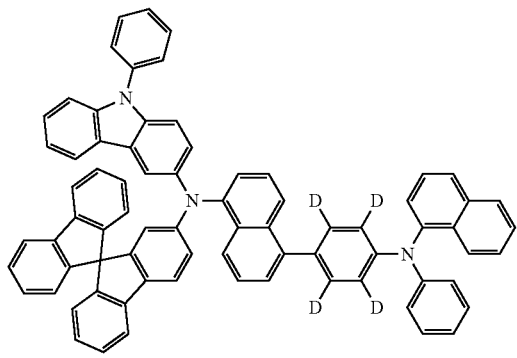
166
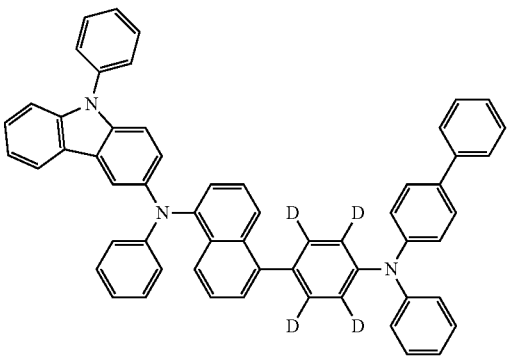
167
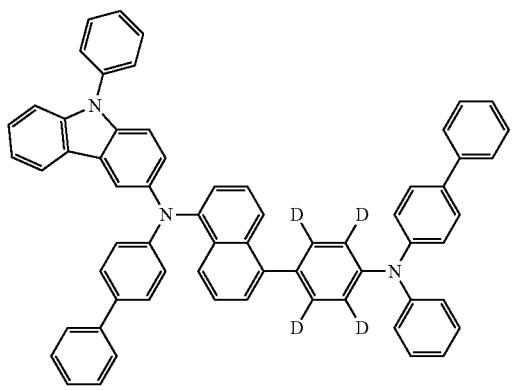
168
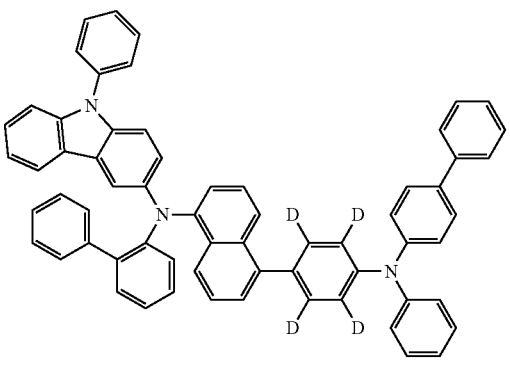
169
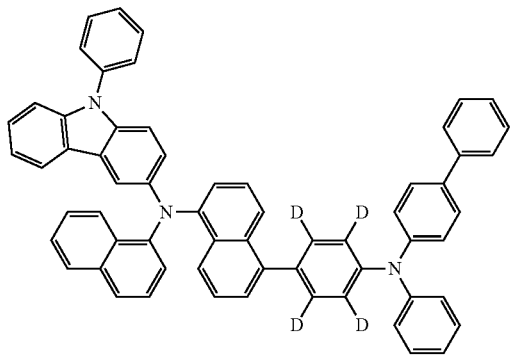
170
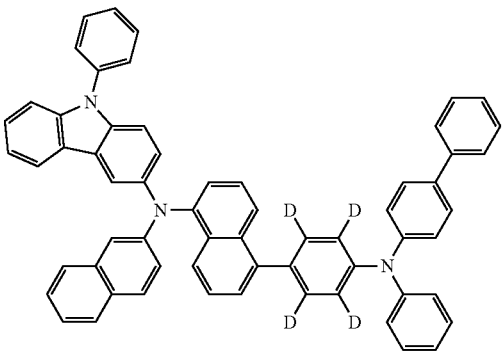
171
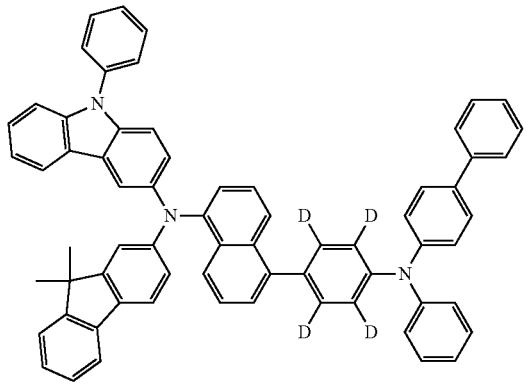
172
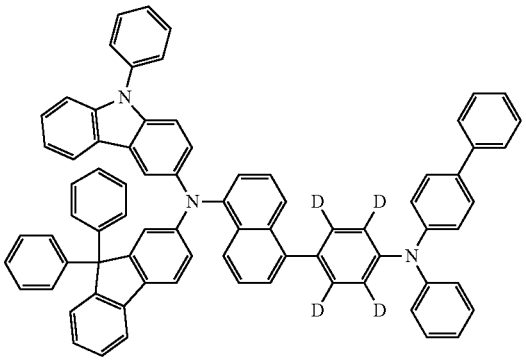

-continued
173
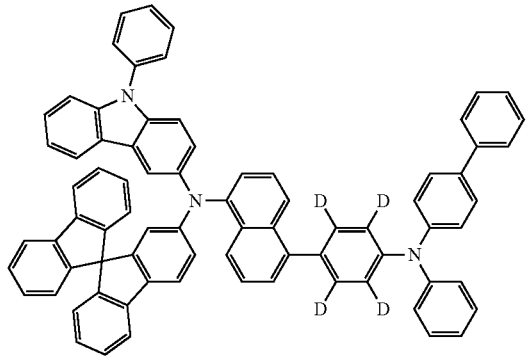
174
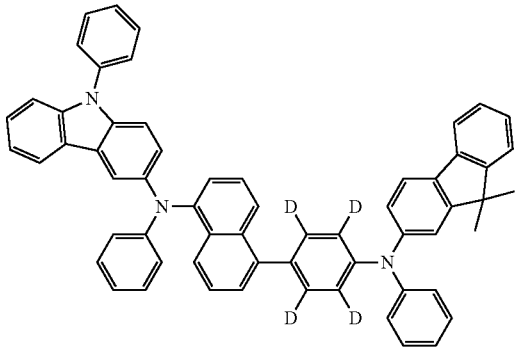
175
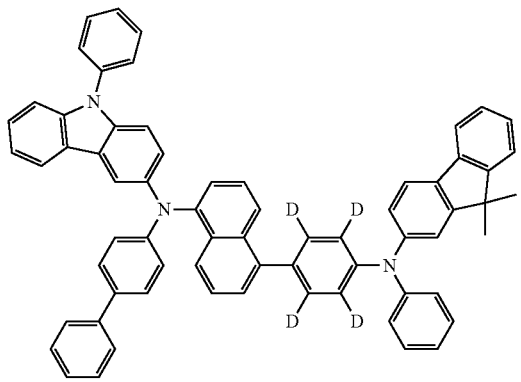
176
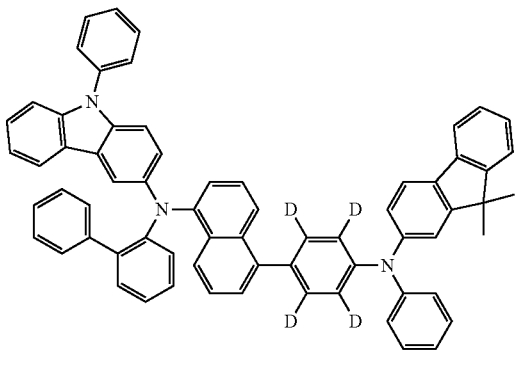
177
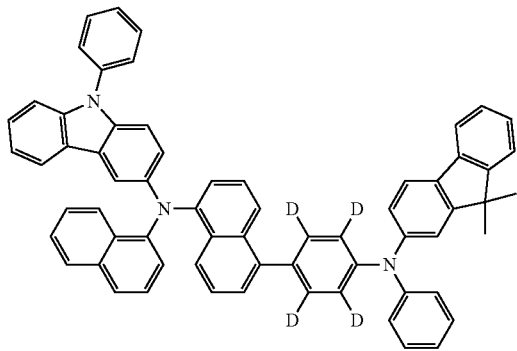
178
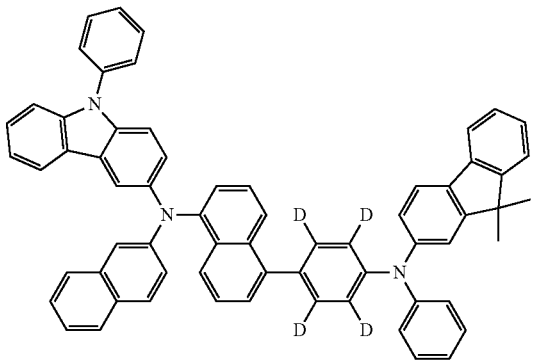
179
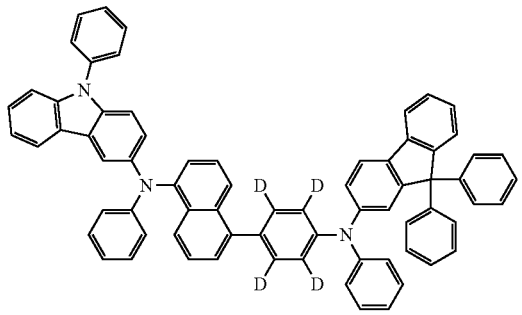
180
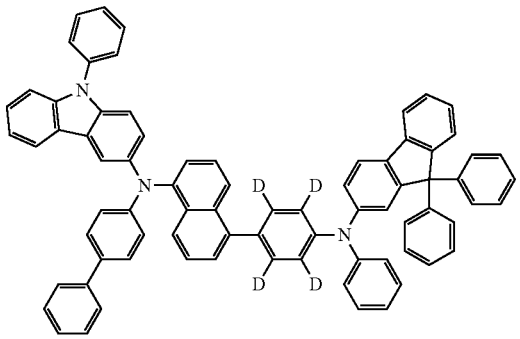

-continued
181
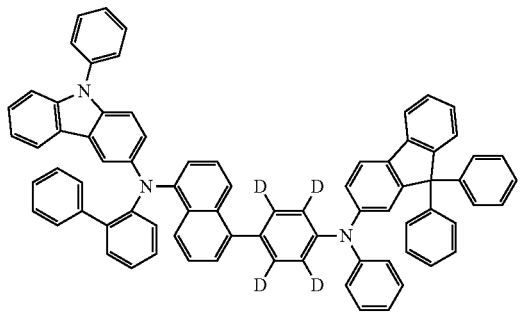
182
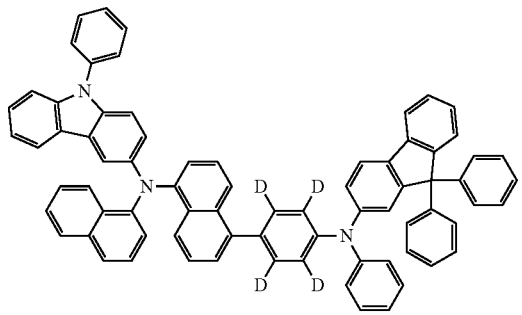
183
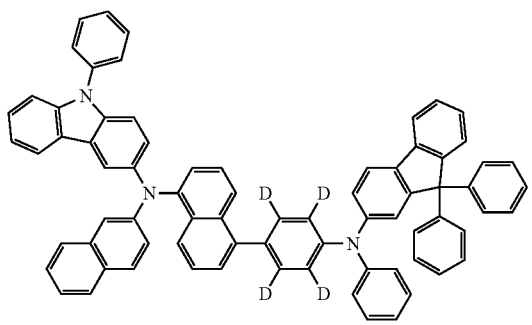
184
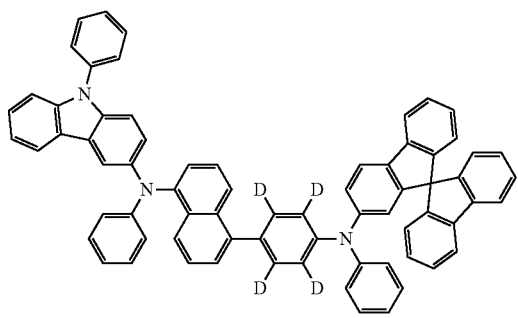
185
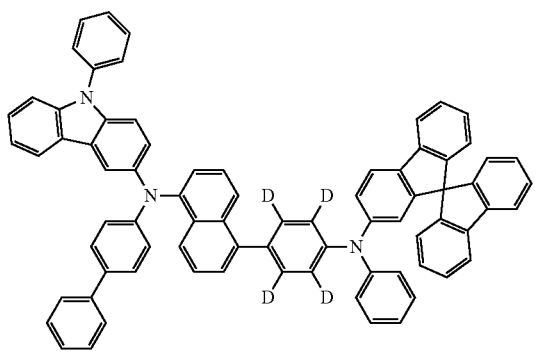
186
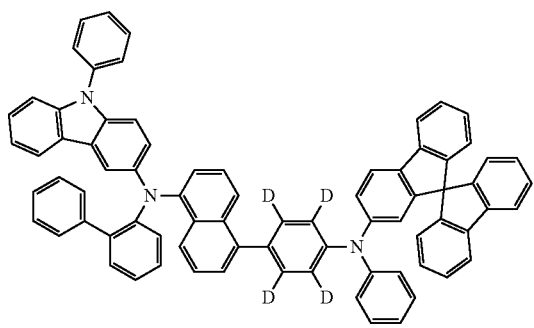
187
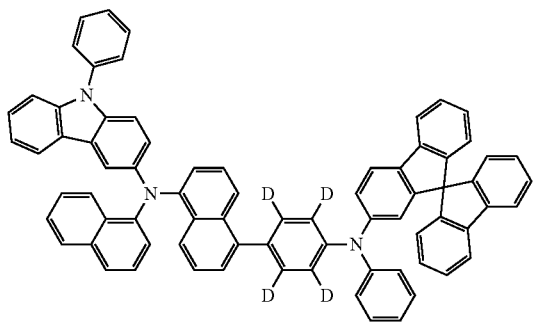
188
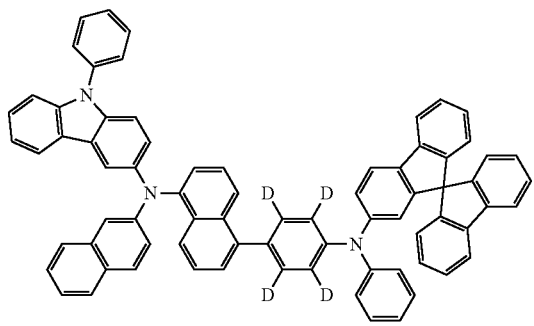

-continued
189
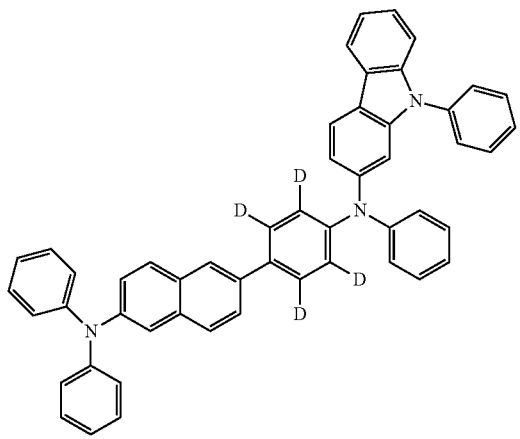
190
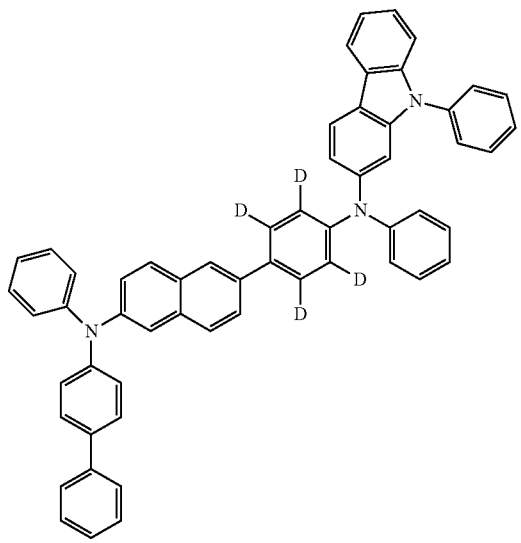
191
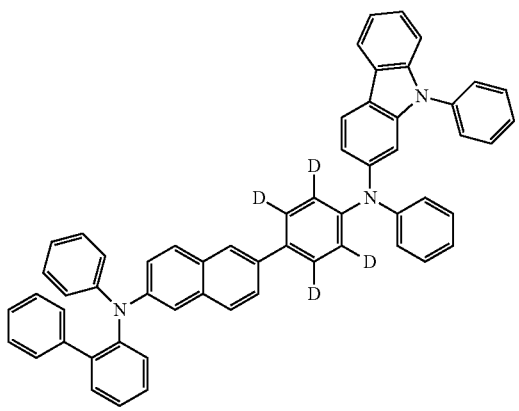
192
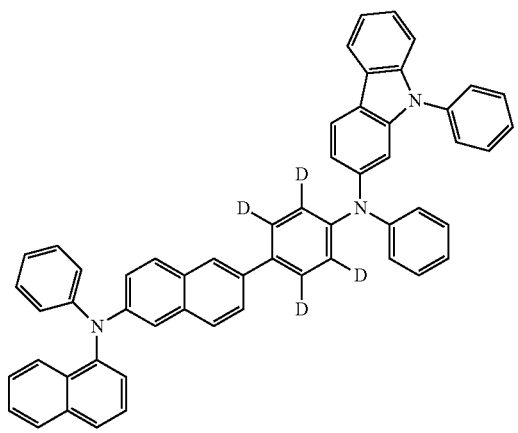
193
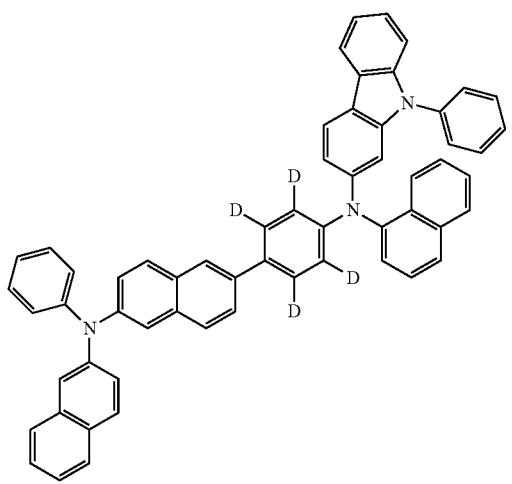
194
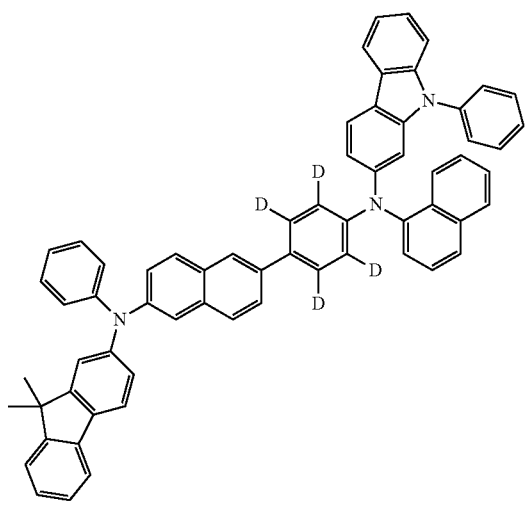

-continued
195
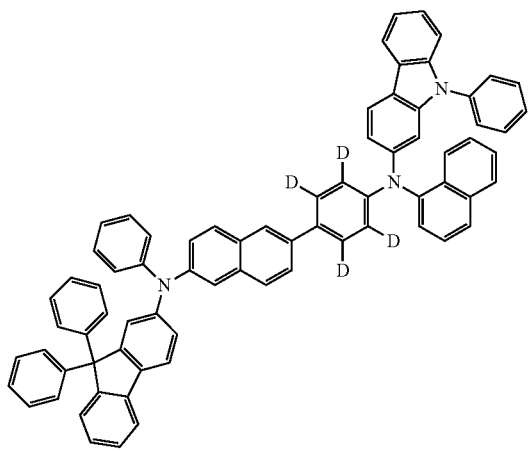
196
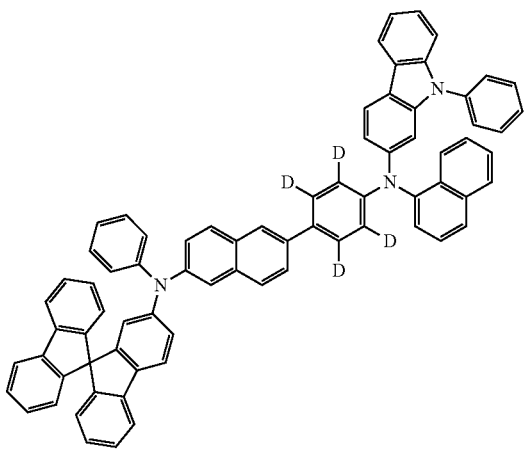
197
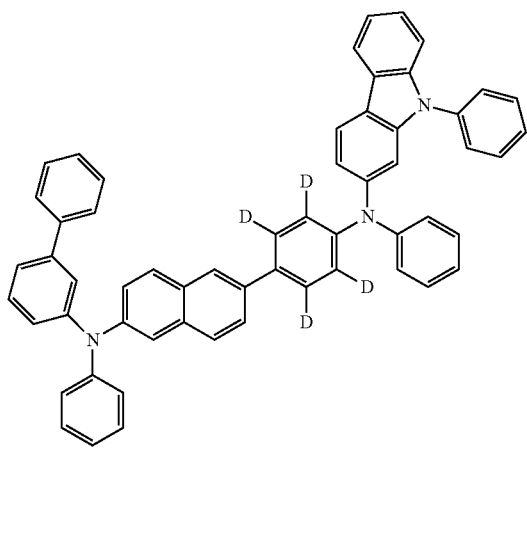
198
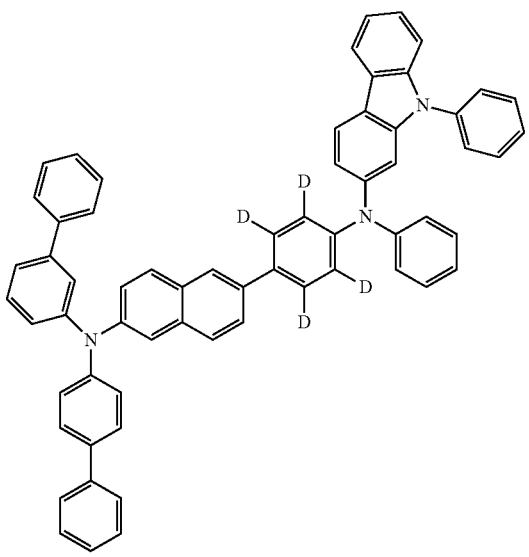
199
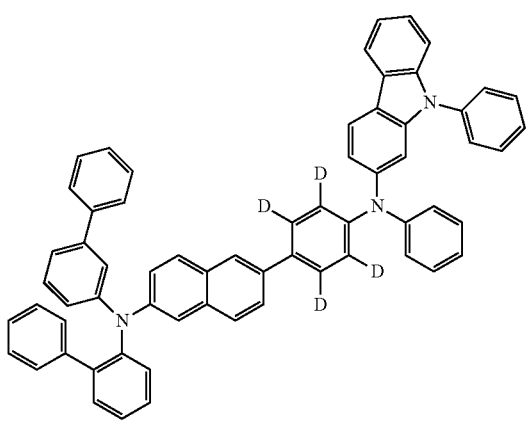
200
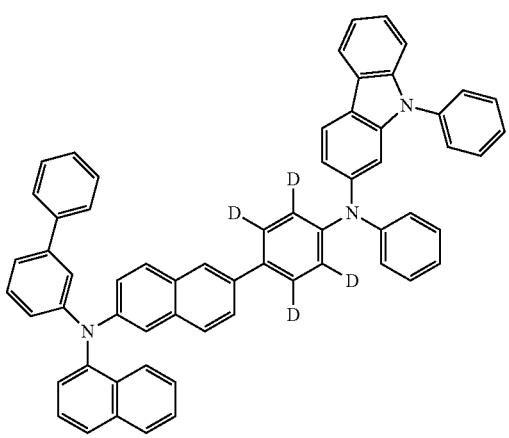

-continued
201
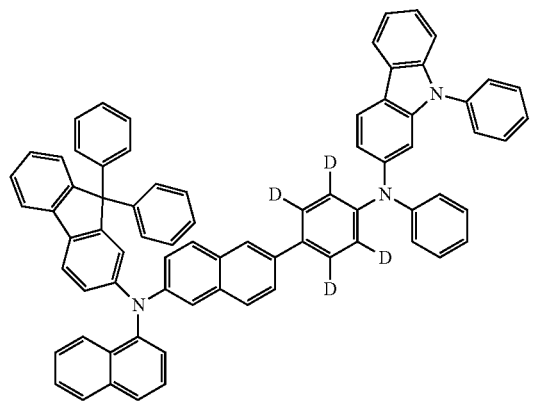
202
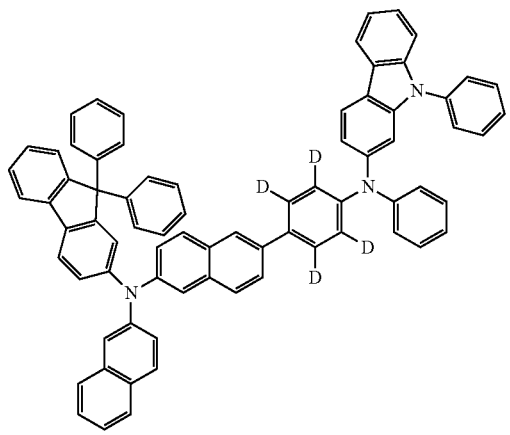
203
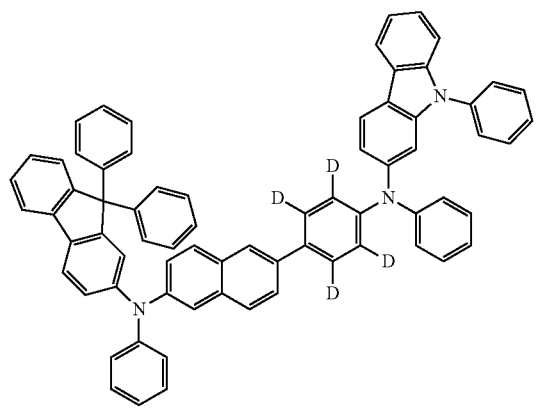
204
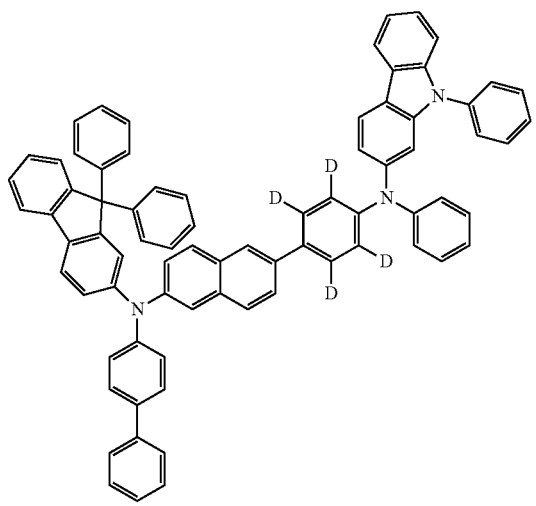
205
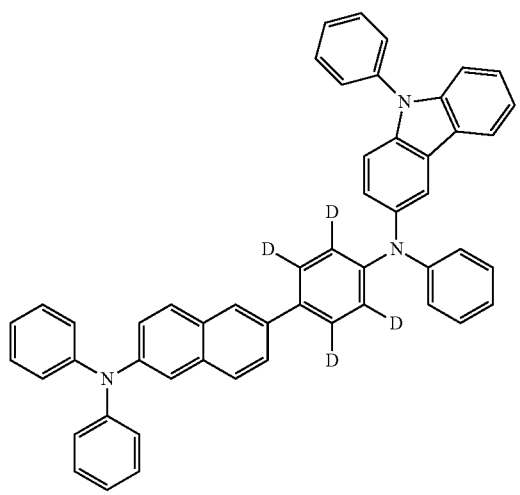
206
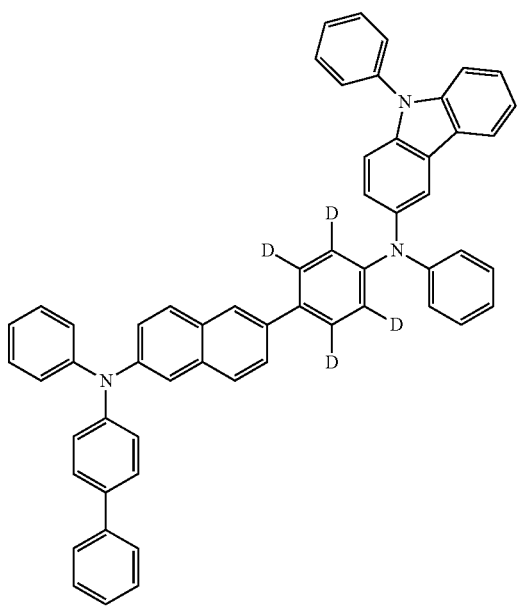

-continued
207
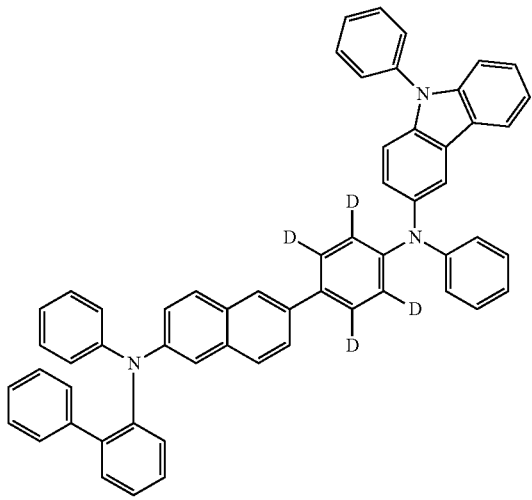
208
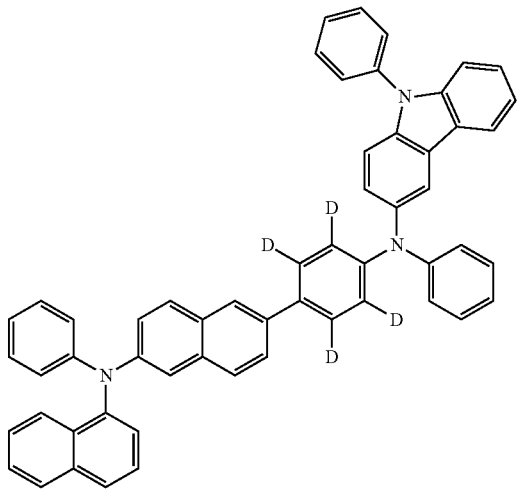
209
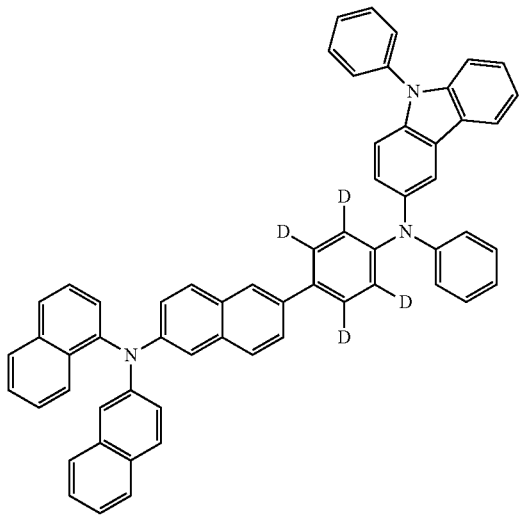
210
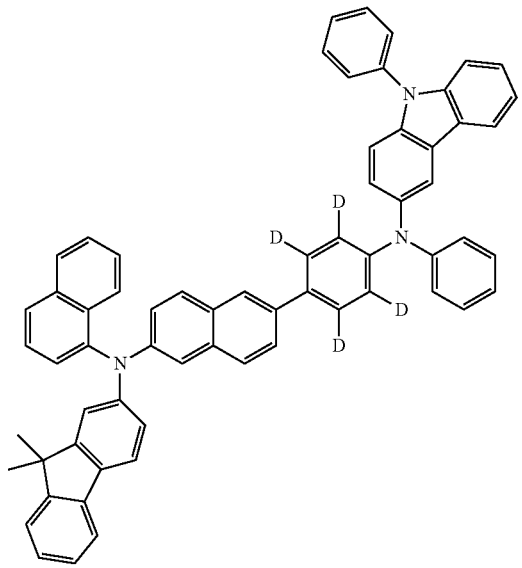
211
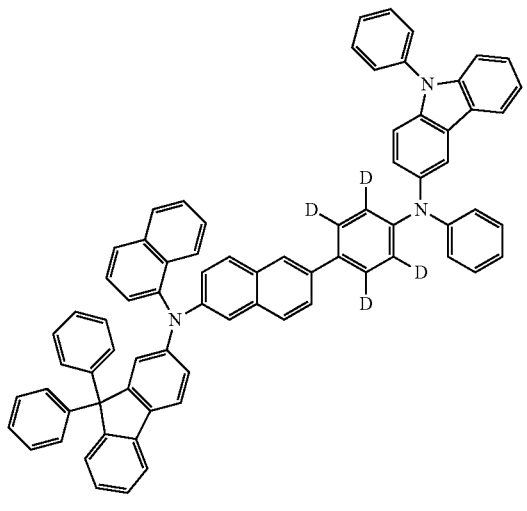
212
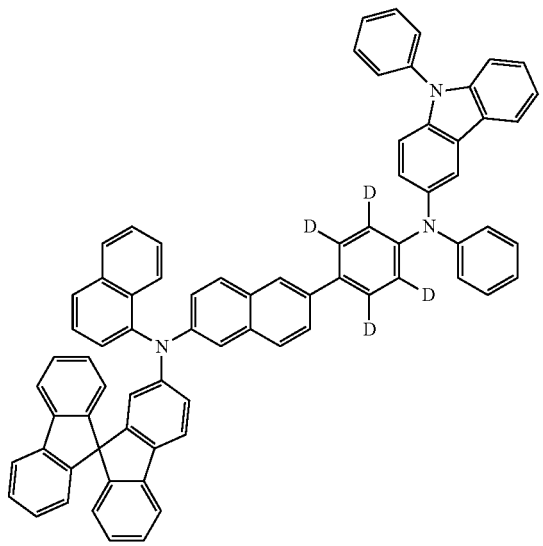

-continued
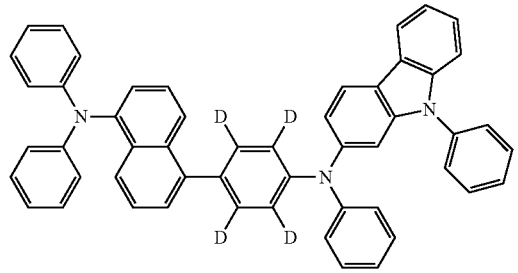
213
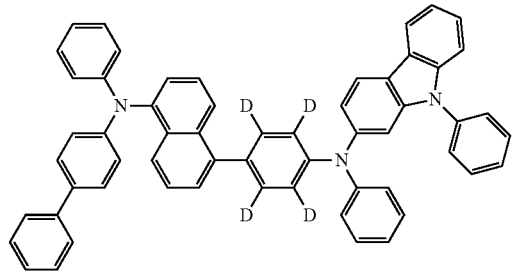
214
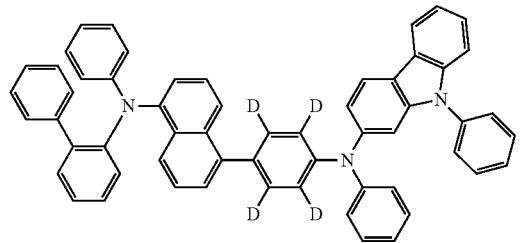
215
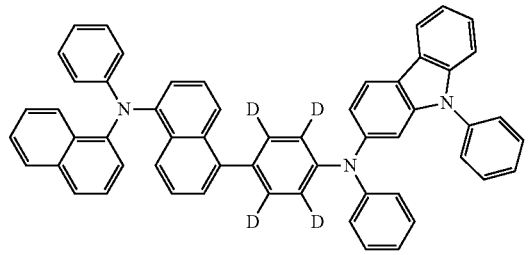
216
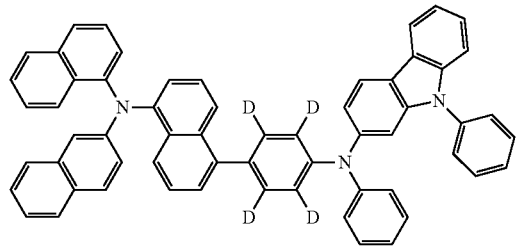
217
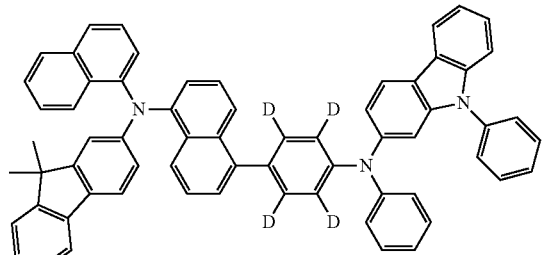
218
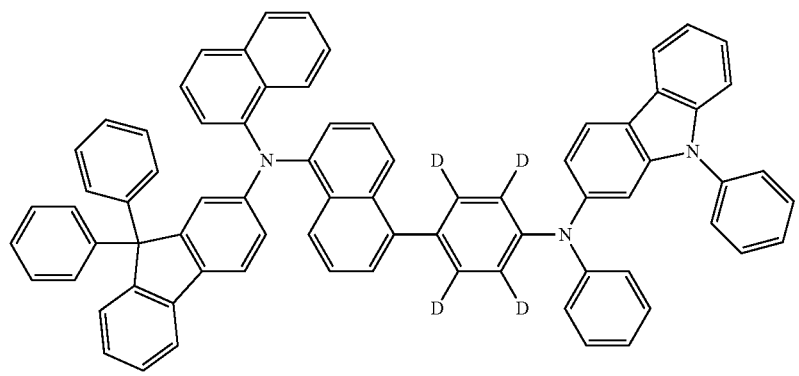
219
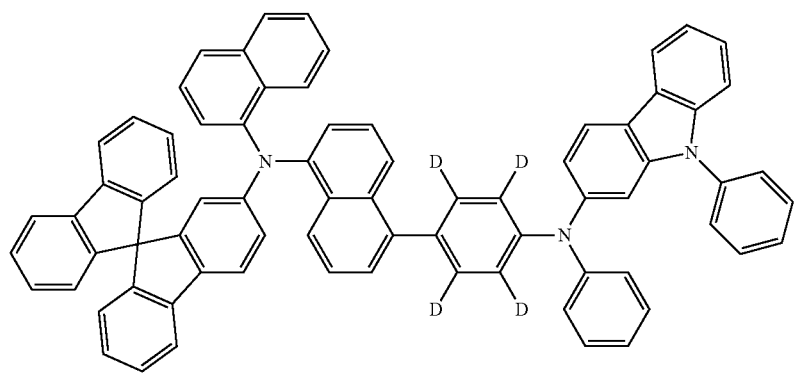
220

221 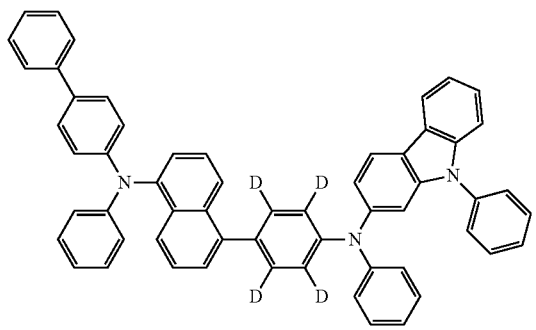

222 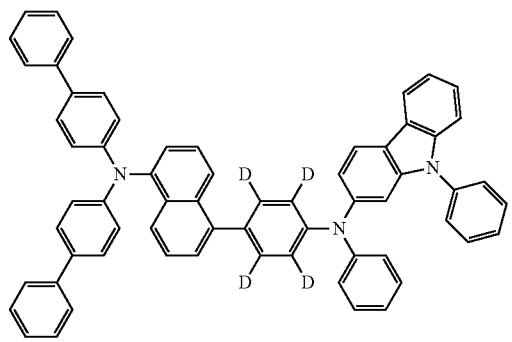

223 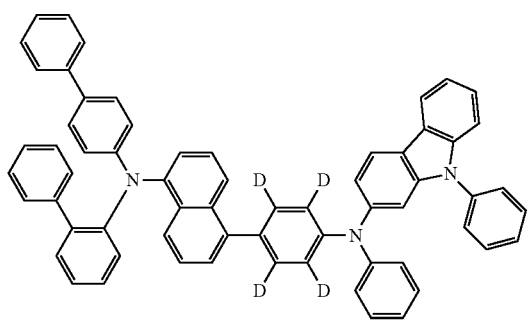

224 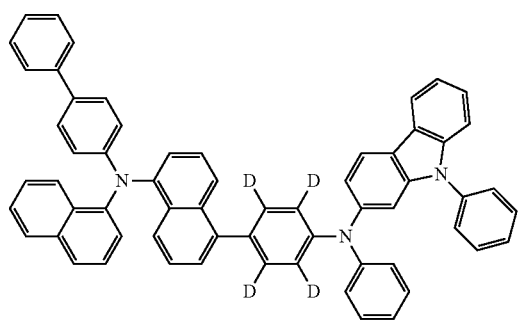

225 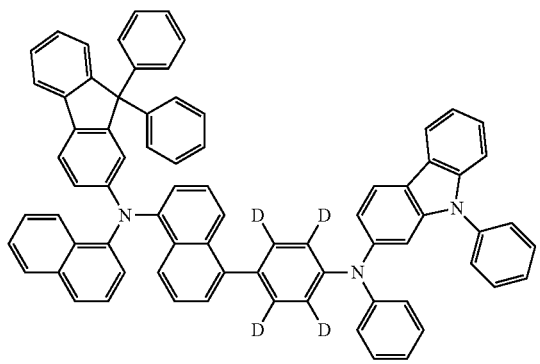

226 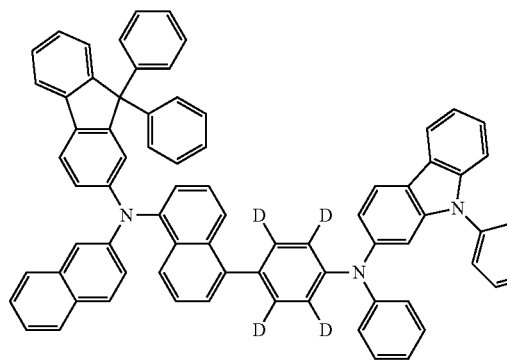

227 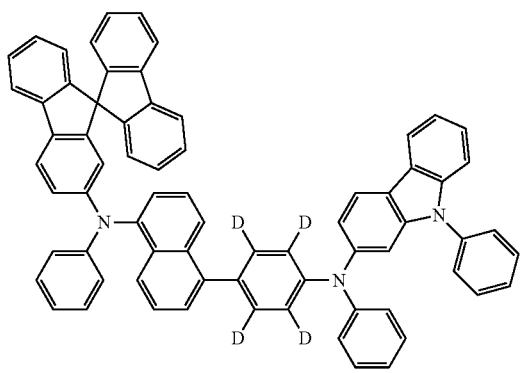

228 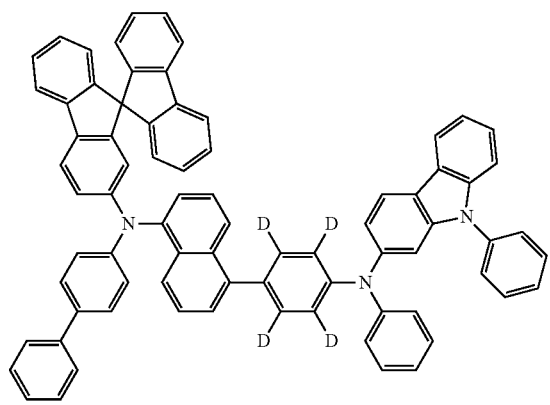

The arylamine compound represented by Formula 1 may include an amine group substituted with a group represented by Formula 2 and a phenyl-naphthyl linker substituted with at least one deuterium.

By including the amine group substituted with the group represented by Formula 2, the arylamine compound represented by Formula 1 may have a high glass transition temperature (Tg) and/or a high melting point, resulting in high resistance in high temperature environments and high resistance against Joule heat generated during luminescence inside the interlayer, between layers, or between the interlayer and a metal electrode. In this regard, a light-emitting device including the arylamine compound may have high durability during storage and driving of the device.

In addition, the arylamine compound represented by Formula 1 may include a phenyl-naphthyl linker substituted with at least one deuterium. Accordingly, when the arylamine compound is used as a hole transport material in a light-emitting device, characteristics of high mobility (e.g., high hole mobility) and long lifespan of the light-emitting device may be obtained.

Therefore, an electronic device, e.g., an organic light-emitting device, using the arylamine compound represented by Formula 1 may have a low driving voltage, high maximum quantum efficiency, high efficiency, and a long lifespan.

Synthesis methods of the arylamine compound represented by Formula 1 may be recognizable by one of ordinary skill in the art by referring to Examples provided below.

At least one of the arylamine compounds represented by Formula 1 may be used between a pair of electrodes of the light-emitting device. In an embodiment, the arylamine compound may be included in an emission layer. In one or more embodiments, the arylamine compound represented by Formula 1 may be used as a material for forming a capping layer, which is outside of a pair of electrodes in the light-emitting device.

Another aspect of embodiments of the present disclosure provides a light-emitting device including: a first electrode; a second electrode; and an interlayer between the first electrode and the second electrode and including an emission layer, In the light-emitting device, the interlayer may include an arylamine compound including a phenyl-naphthyl linker substituted with at least one deuterium and an amine group substituted with a carbazole group.

The expression "(an interlayer) includes at least one of arylamine compounds," as used herein, may include a case in which "(an interlayer) includes identical arylamine compounds represented by Formula 1" and a case in which "(an interlayer) includes two or more different arylamine compounds represented by Formula 1."

In an embodiment, the interlayer may include, as the arylamine compound, only Compound 1. In this embodiment, Compound 1 may be included in the emission layer of the light-emitting device. In one or more embodiments, the interlayer may include, as the arylamine compound, Compound 1 and Compound 2. In this embodiment, Compound 1 and Compound 2 may be included in the same layer (for example, both Compound 1 and Compound 2 may be included in an emission layer) or in different layers (for example, Compound 1 may be included in an emission layer, and Compound 2 may be included in an electron transport layer).

In an embodiment, a phenyl group of the phenyl-naphthyl linker may be substituted with at least one deuterium.

In an embodiment, the first electrode may be an anode, the second electrode may be a cathode,
the interlayer may further include a hole transport region between the emission layer and the second electrode, and
the hole transport region may include the arylamine compound.

In an embodiment, the hole transport region may include at least one selected from a hole injection layer and a hole transport layer, and the at least one selected from the hole injection layer and the hole transport layer may include the arylamine compound.

Another aspect of embodiments of the present disclosure provides an electronic apparatus including the light-emitting device.

In an embodiment, the electronic apparatus may further include a thin-film transistor,
wherein the thin-film transistor may include a source electrode and a drain electrode, and
the first electrode of the light-emitting device may be electrically coupled to the source electrode or the drain electrode of the thin-film transistor.

The term "an interlayer," as used herein, refers to a single layer and/or a plurality of layers between the first electrode and the second electrode of the light-emitting device. A material included in the "interlayer" is not limited to an organic material. For example, the interlayer may include an inorganic material.

For example, the light-emitting device may have i) a structure including a first electrode, an interlayer, a second electrode, and a second capping layer which are sequentially stacked in this stated order, ii) a structure including a first capping layer, a first electrode, an interlayer, and a second electrode which are sequentially stacked in this stated order, or iii) a structure including a first capping layer, a first electrode, an interlayer, a second electrode, and a second capping layer which are sequentially stacked in this stated order, wherein at least one of the first capping layer and the second capping layer may include the arylamine compound.

Description of FIG. 1

FIG. 1 is a schematic cross-sectional view of a light-emitting device 10 according to an embodiment. The light-emitting device 10 includes a first electrode 110, an interlayer 130, and a second electrode 150.

Hereinafter, the structure of the light-emitting device 10 according to an embodiment and a method of manufacturing the light-emitting device 10 will be described in connection with FIG. 1.

First Electrode 110

In FIG. 1, a substrate may be additionally under the first electrode 110 or above the second electrode 150. In an embodiment, the substrate may be a glass substrate and/or a plastic substrate. In one or more embodiments, the substrate may be a flexible substrate, and for example, the substrate may include plastics having excellent heat resistance and durability, such as polyimide, polyethylene terephthalate (PET), polycarbonate, polyethylene naphthalate, polyarylate (PAR), polyetherimide, or any combination thereof.

The first electrode 110 may be formed by, for example, depositing and/or sputtering a material for forming the first electrode 110 on the substrate. When the first electrode 110 is an anode, a high work function material that can easily inject holes may be used as the material for forming the first electrode 110.

The first electrode 110 may be a reflective electrode, a semi-transmissive electrode, or a transmissive electrode. In an embodiment, when the first electrode 110 is a transmissive electrode, the material for forming the first electrode 110 may include indium tin oxide (ITO), indium zinc oxide (IZO), tin oxide ($SnO_2$), zinc oxide (ZnO), or any combination thereof. In one or more embodiments, when the first electrode 110 is a semi-transmissive electrode or a reflective electrode, the material for forming the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combination thereof.

The first electrode 110 may have a single-layered structure including (e.g., consisting of) a single layer or a multi-layered structure including a plurality of layers. For example, the first electrode 110 may have a three-layered structure of ITO/Ag/ITO.

Interlayer 130

The interlayer 130 may be on the first electrode 110. The interlayer 130 includes an emission layer.

The interlayer 130 may further include a hole transport region between the first electrode 110 and the emission layer and an electron transport region between the emission layer and the second electrode 150.

The interlayer 130 may further include metal-containing compounds such as organometallic compounds, inorganic materials such as quantum dots, and/or the like, in addition to various suitable organic materials.

The interlayer 130 may include, i) two or more emitting units sequentially stacked between the first electrode 110 and the second electrode 150 and ii) a charge generation layer between the two emitting units. When the interlayer 130 includes the emitting unit and the charge generation layer as described above, the light-emitting device 10 may be a tandem light-emitting device.

Hole Transport Region in Interlayer 130

The hole transport region may have: i) a single-layered structure including (e.g., consisting of) a single layer including (e.g., consisting of) a single material, ii) a single-layered structure including (e.g., consisting of) a single layer including (e.g., consisting of) a plurality of different materials, or iii) a multi-layered structure including a plurality of layers including different materials.

The hole transport region may include a hole injection layer, a hole transport layer, an emission auxiliary layer, an electron blocking layer, or any combination thereof.

For example, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, layers are stacked sequentially on the first electrode 110.

The hole transport region may include a compound represented by Formula 201, a compound represented by Formula 202, or any combination thereof:

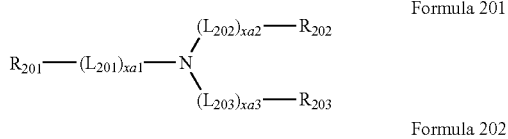

Formula 201

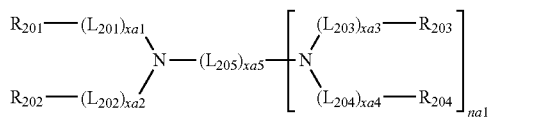

Formula 202 wherein, in Formulae 201 and 202,
$L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other via a single bond, a $C_1$-$C_5$ alkylene group unsubstituted or substituted with at least one $R_{10a}$ or a $C_2$-$C_5$ alkenylene group unsubstituted or substituted with at least one $R_{10a}$ to form a $C_8$-$C_{60}$ polycyclic group unsubstituted or substituted with at least one $R_{10a}$ (for example, a carbazole group and/or the like) (for example, see Compound HT16), $R_{203}$ and $R_{204}$ may optionally be linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

For example, Formulae 201 and 202 may each include at least one of groups represented by Formulae CY201 to CY717:

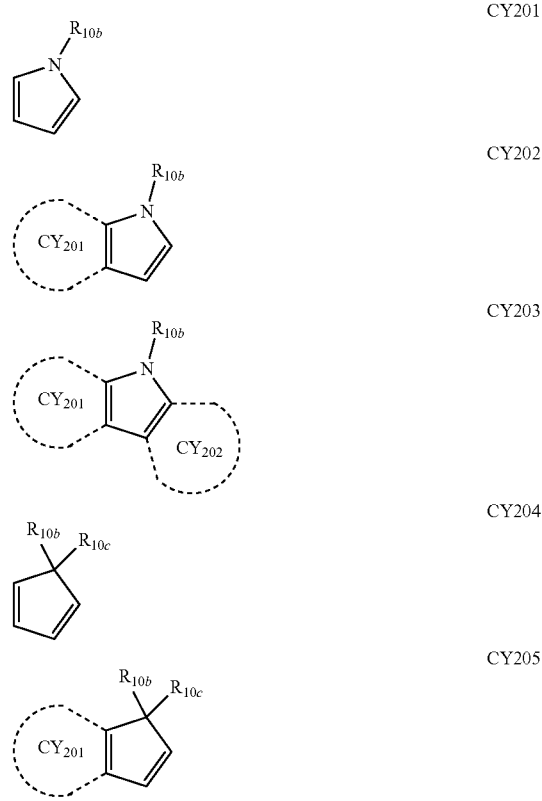

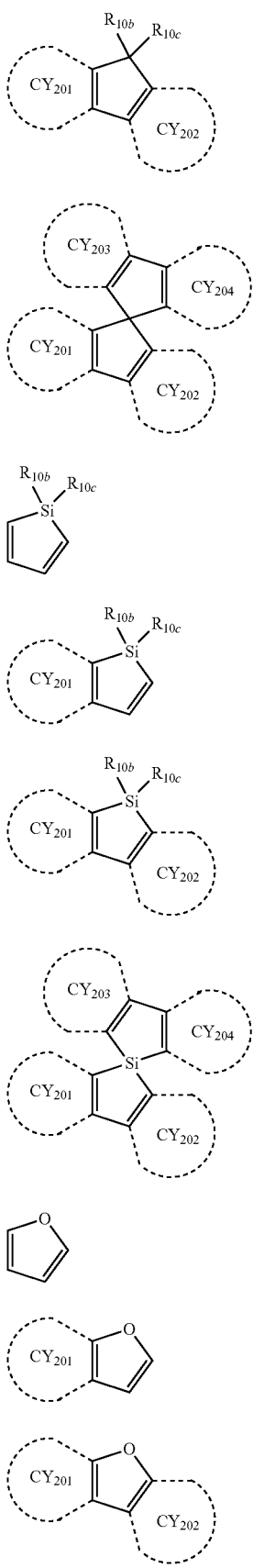

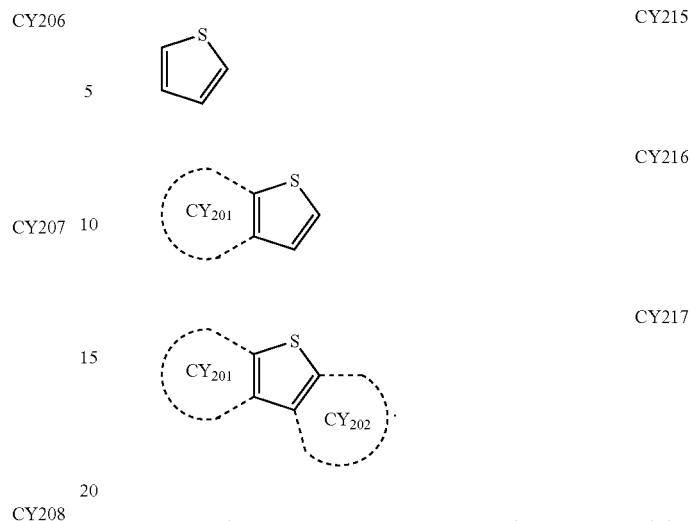

In Formulae CY201 to CY217, $R_{10b}$ and $R_{10c}$ may each be the same as described in connection with $R_{10a}$, ring $CY_{201}$ to ring $CY_{204}$ may each independently be a $C_3$-$C_{20}$carbocyclic group or a $C_1$-$C_{20}$ heterocyclic group, and at least one hydrogen in Formula CY201 to CY217 may be unsubstituted or substituted with at least one $R_{10a}$ described herein.

In an embodiment, ring $CY_{201}$ to ring $CY_{204}$ in Formulae CY201 to CY217 may each independently be a benzene group, a naphthalene group, a phenanthrene group, or an anthracene group.

In one or more embodiments, Formulae 201 and 202 may each include at least one of the groups represented by Formulae CY201 to CY203.

In one or more embodiments, Formula 201 may include at least one of the groups represented by Formulae CY201 to CY203 and at least one of the groups represented by Formulae CY204 to CY217.

In one or more embodiments, in Formula 201, xa1 may be 1, $R_{201}$ may be a group represented by one of Formulae CY201 to CY203, xa2 may be 0, and $R_{202}$ may be a group represented by one of Formulae CY204 to CY207.

In one or more embodiments, each of Formulae 201 and 202 may not include the groups represented by Formulae CY201 to CY203.

In one or more embodiments, each of Formulae 201 and 202 may not include the groups represented by Formulae CY201 to CY203, and may include at least one of the groups represented by Formulae CY204 to CY217.

In one or more embodiments, each of Formulae 201 and 202 may not include the groups represented by Formulae CY201 to CY217.

For example, the hole transport region may include one of Compounds HT1 to HT44, m-MTDATA, TDATA, 2-TNATA, NPB(NPD), β-NPB, TPD, Spiro-TPD, Spiro-NPB, methylated-NPB, TAPC, FIMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

| 97 | 98 |
|---|---|
| HT1 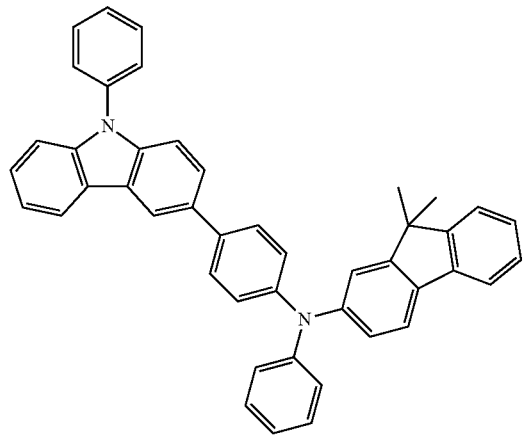 | HT2 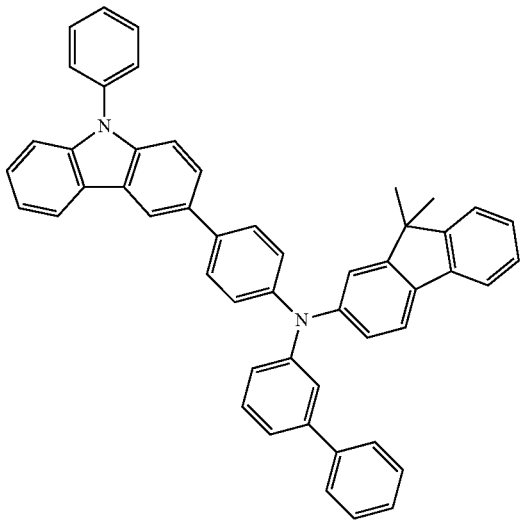 |
| HT3 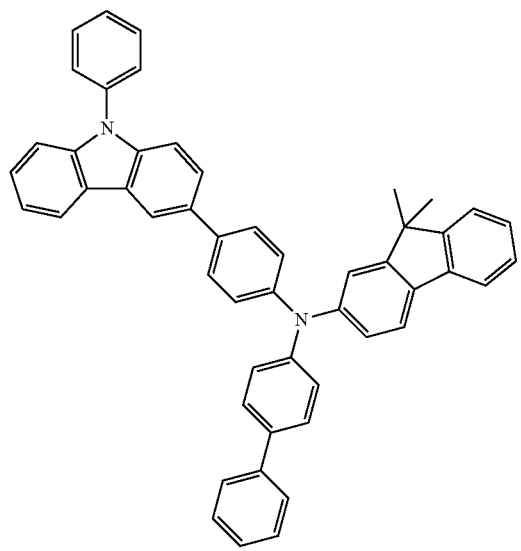 | HT4 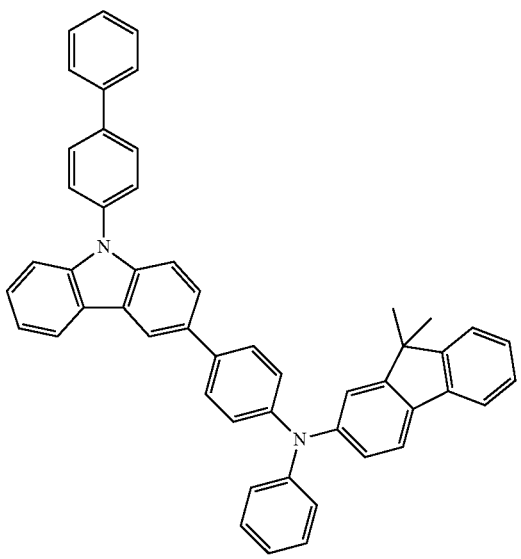 |
| HT5 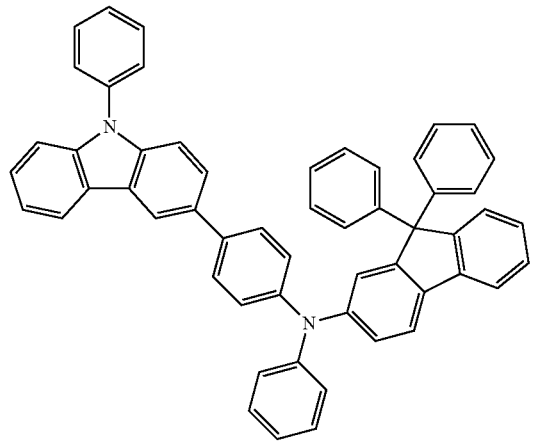 | HT6 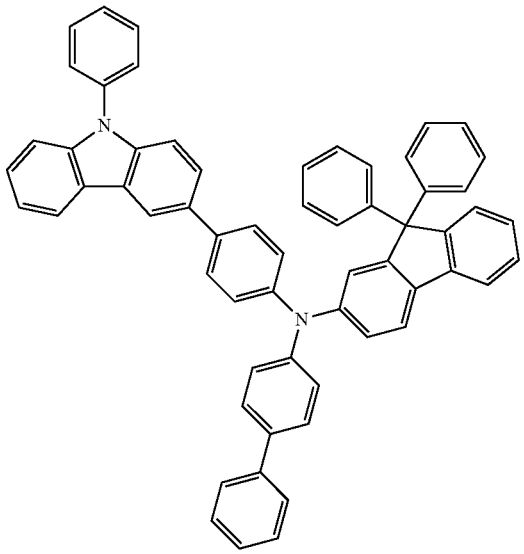 |

-continued
HT7
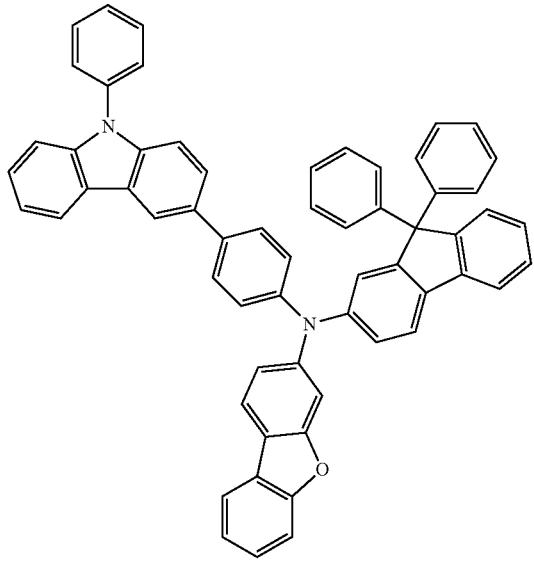
HT8
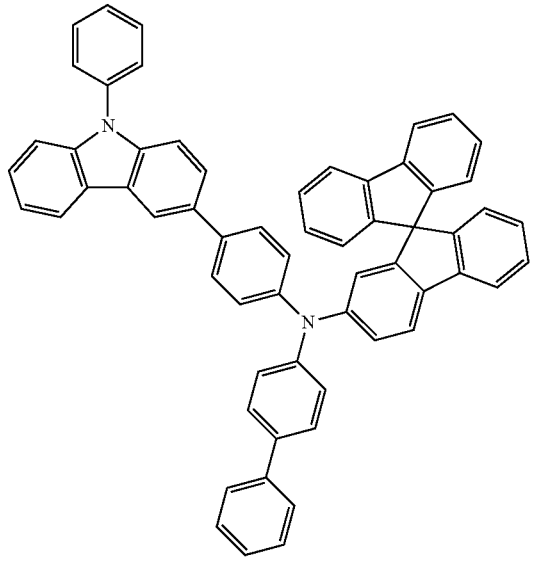
HT9
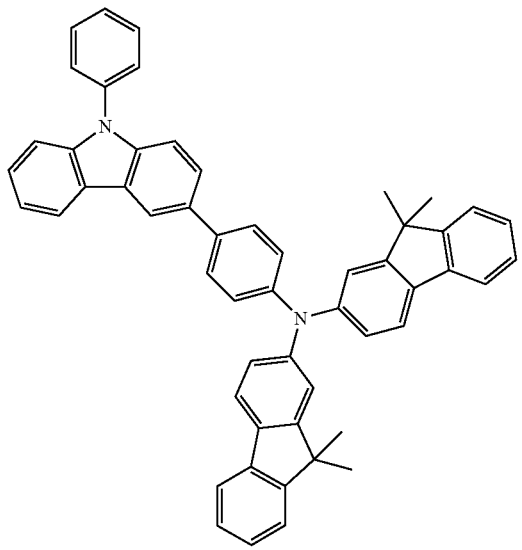
HT10
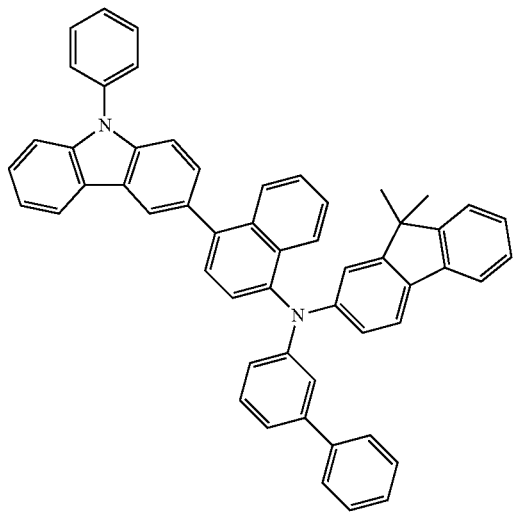
HT11
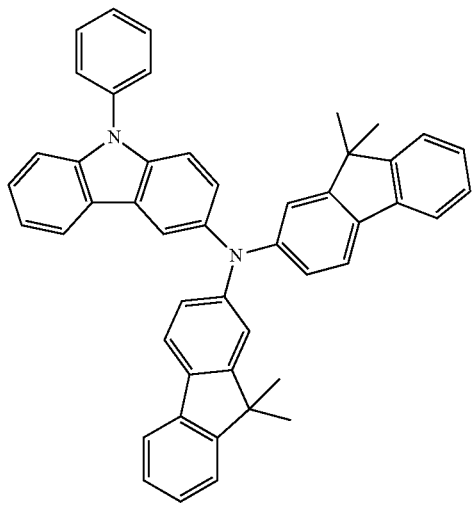
HT12
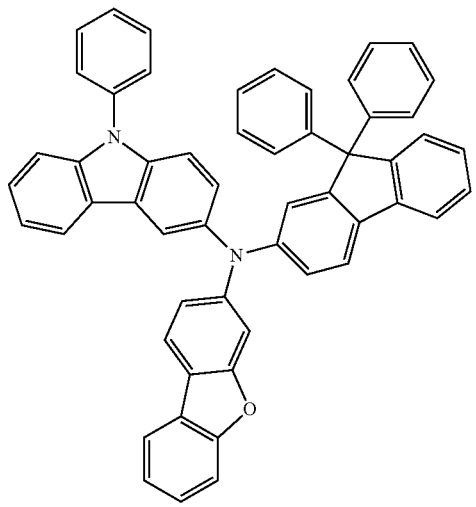

-continued
HT13
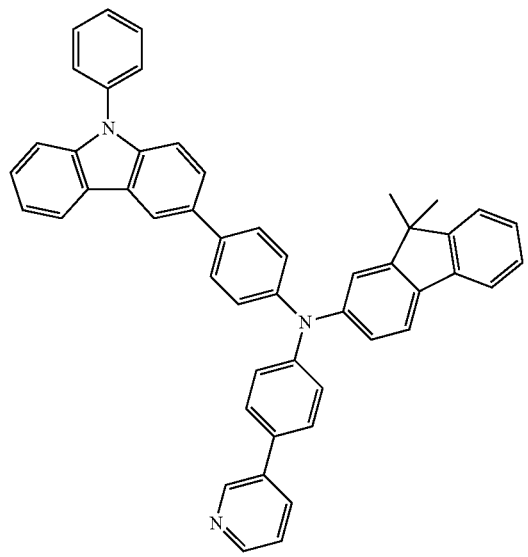
HT14
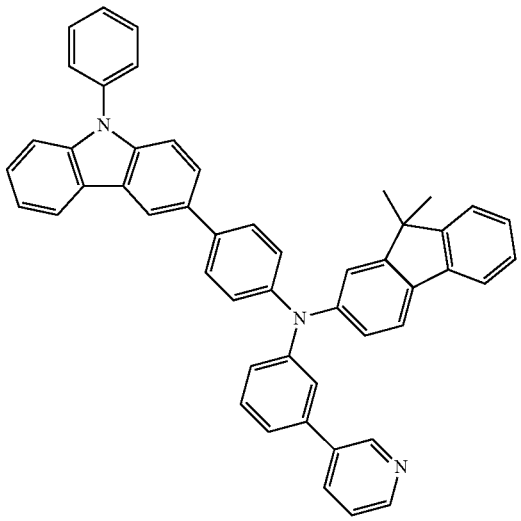
HT15
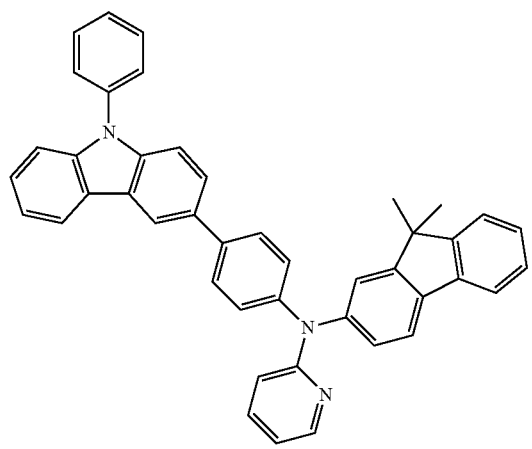
HT16
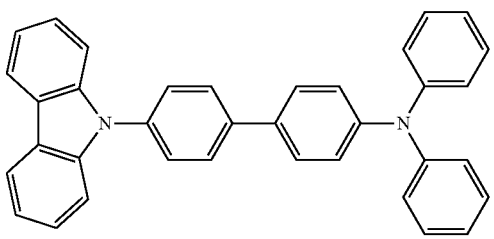
HT17
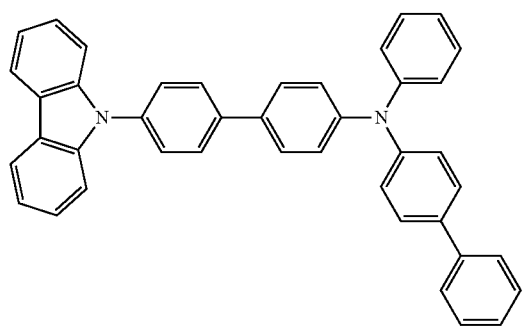
HT18
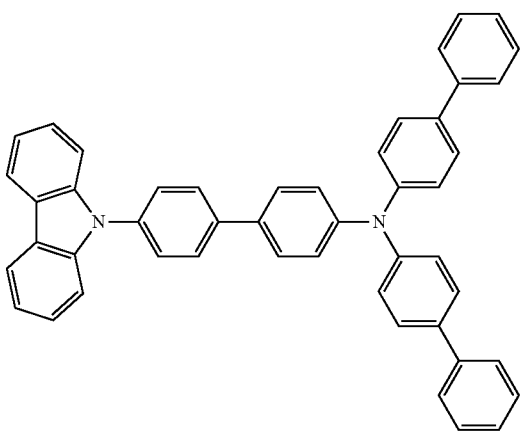

-continued
HT19
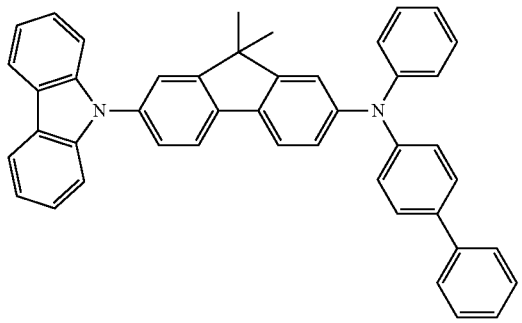
HT20
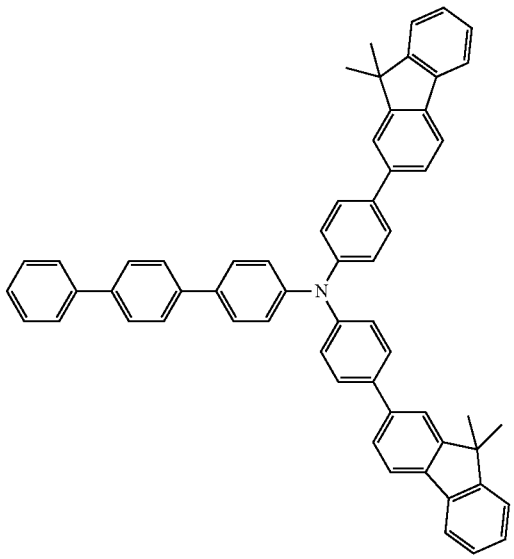
HT21
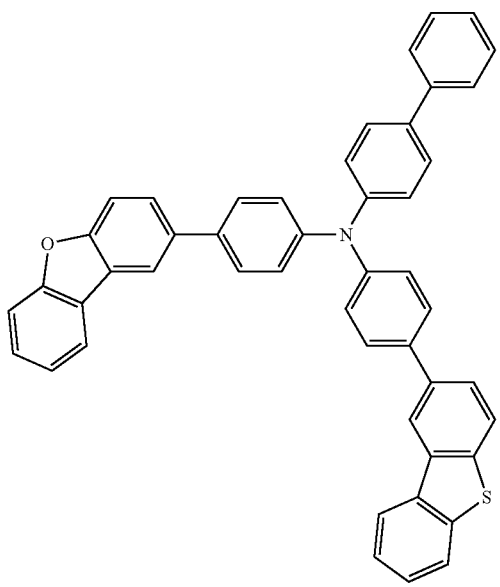
HT22
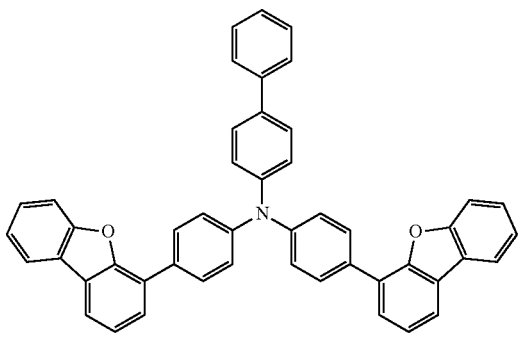
HT23
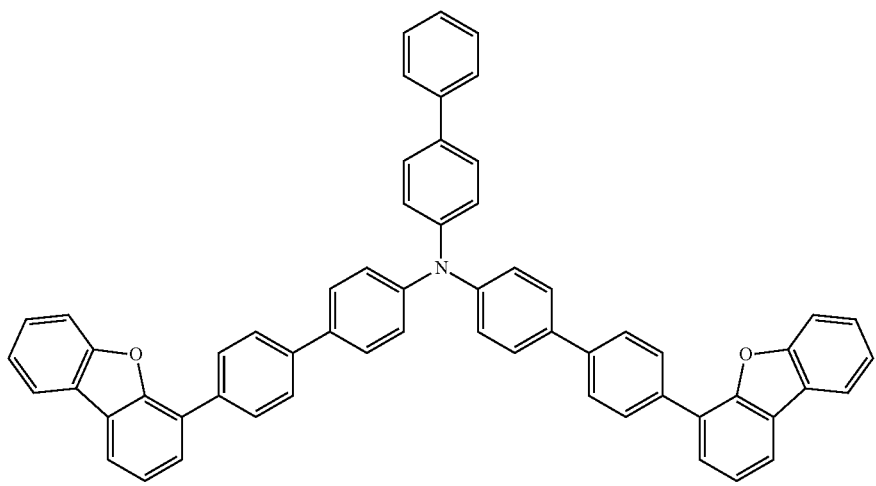

-continued
HT24
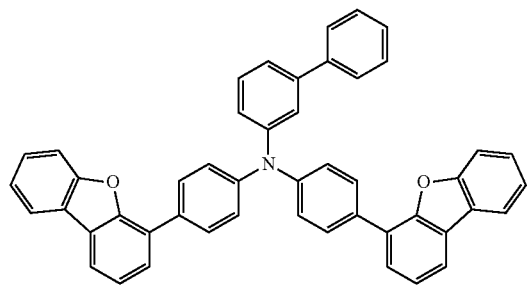
HT25
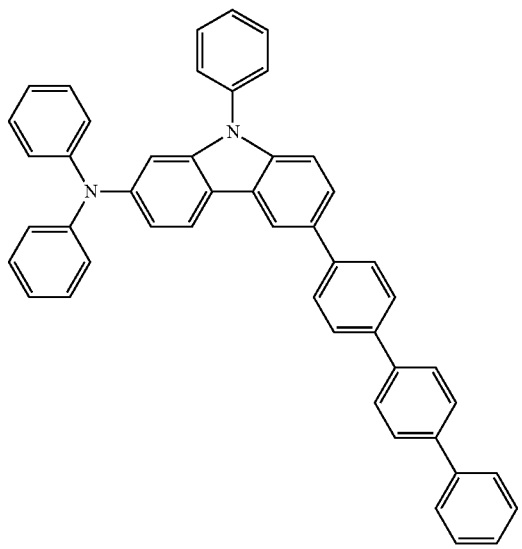
HT26
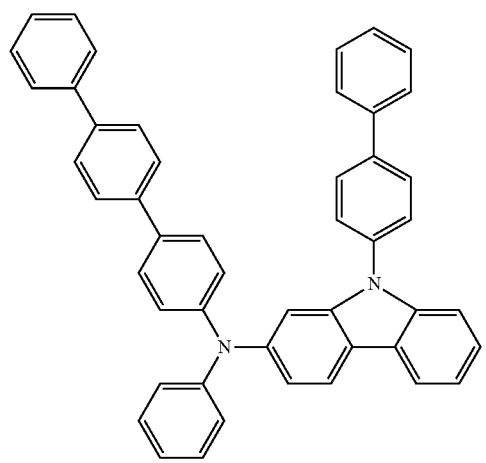
HT27
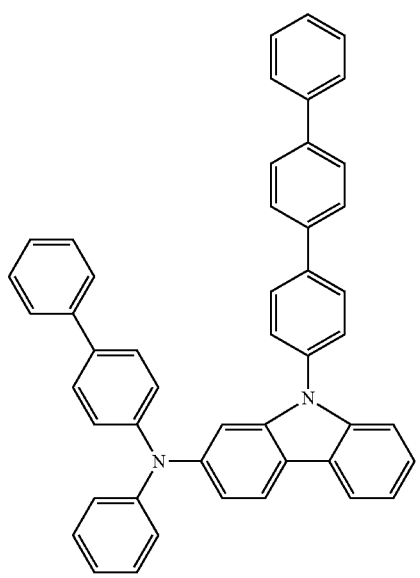
HT28
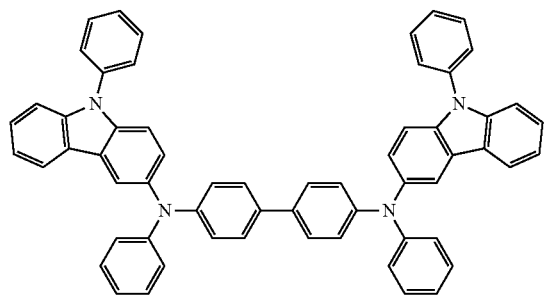
HT29
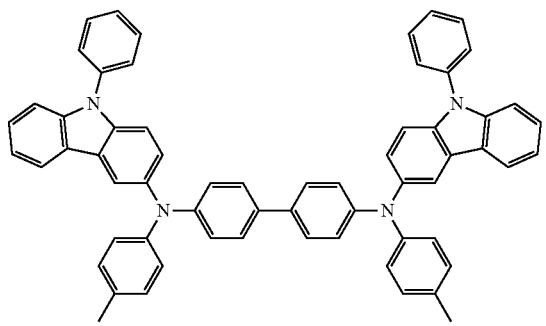

-continued
HT30
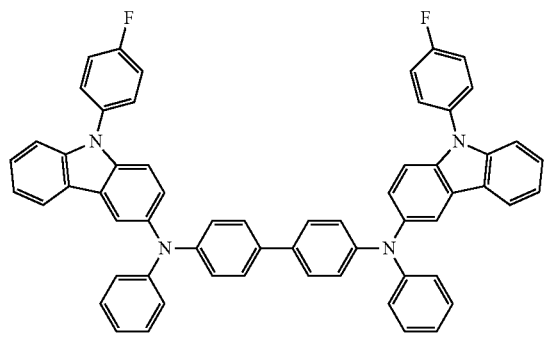
HT31
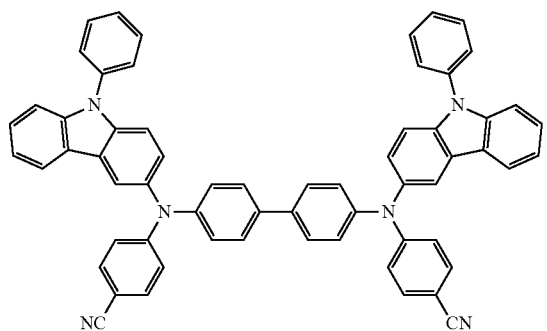
HT32
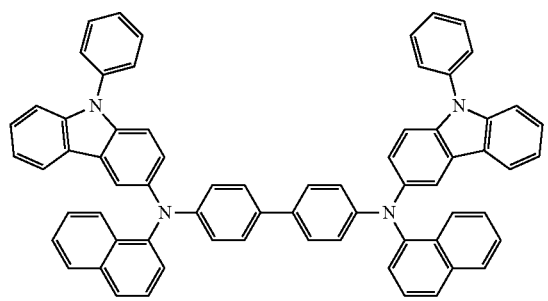
HT33
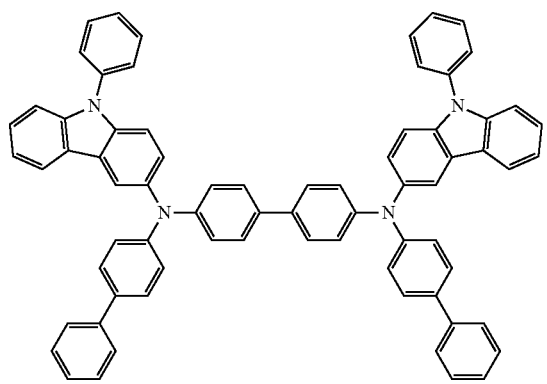
HT34
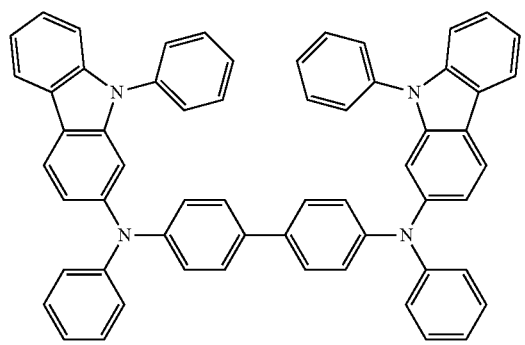
HT35
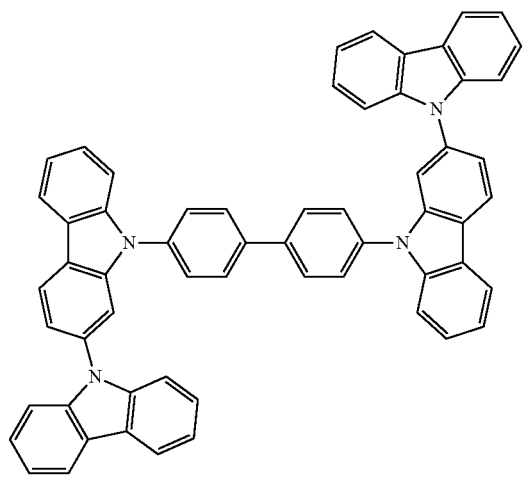

-continued
HT36
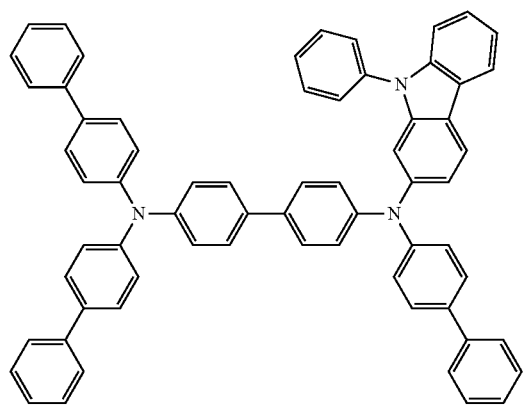
HT37
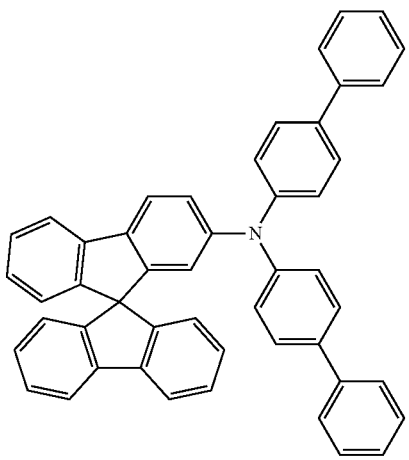
HT38
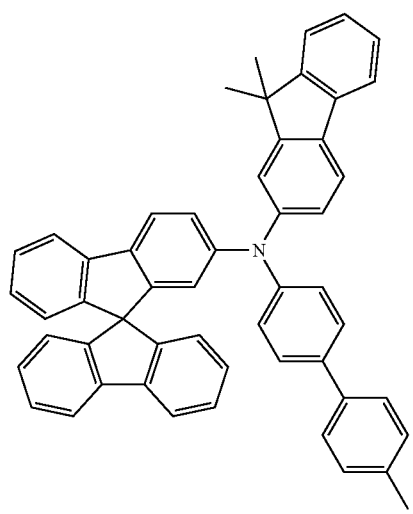
HT39
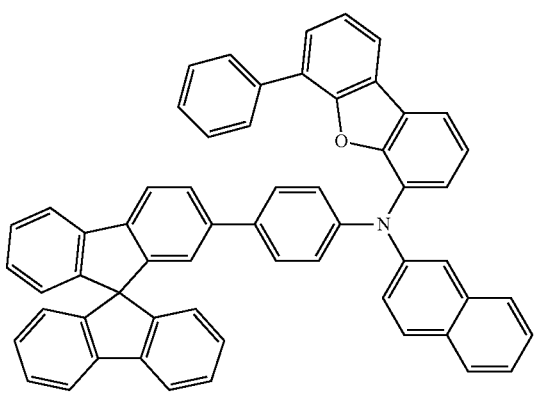
HT40
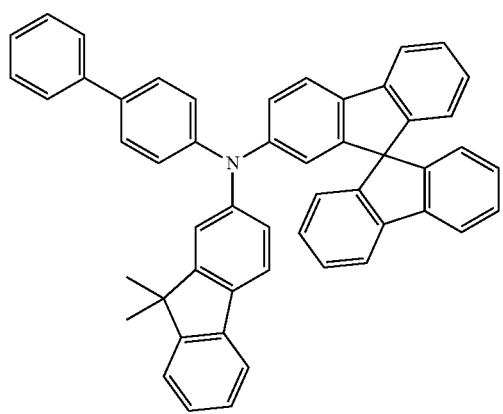
HT41
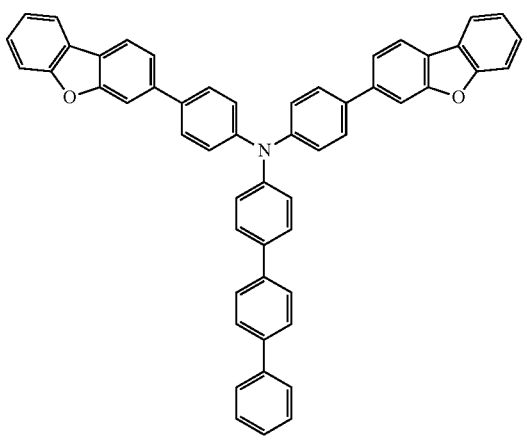

HT42
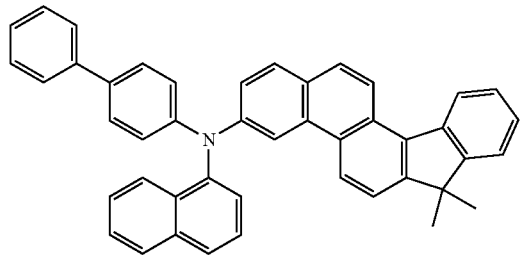
HT43
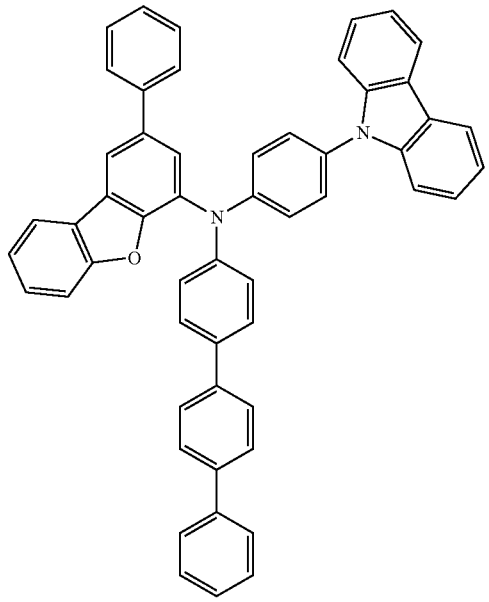
HT44
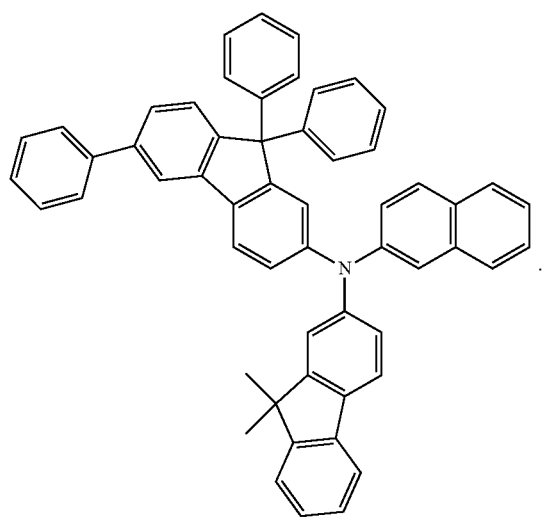

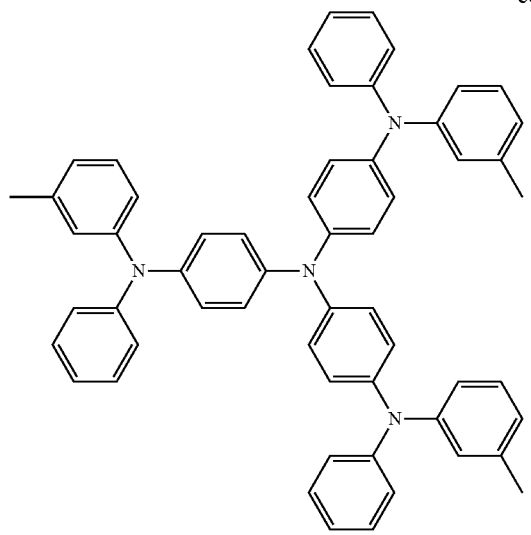
m-MTDATA
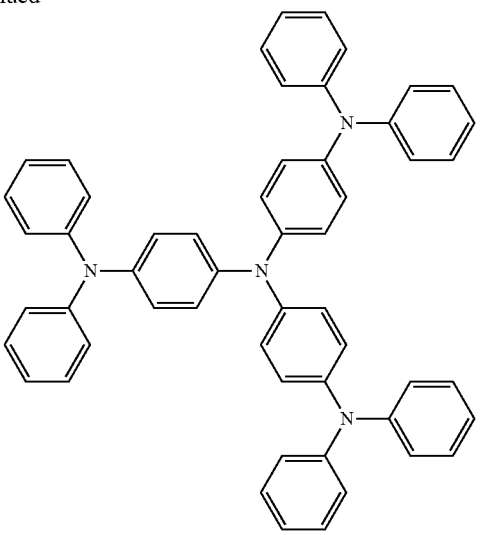
TDATA
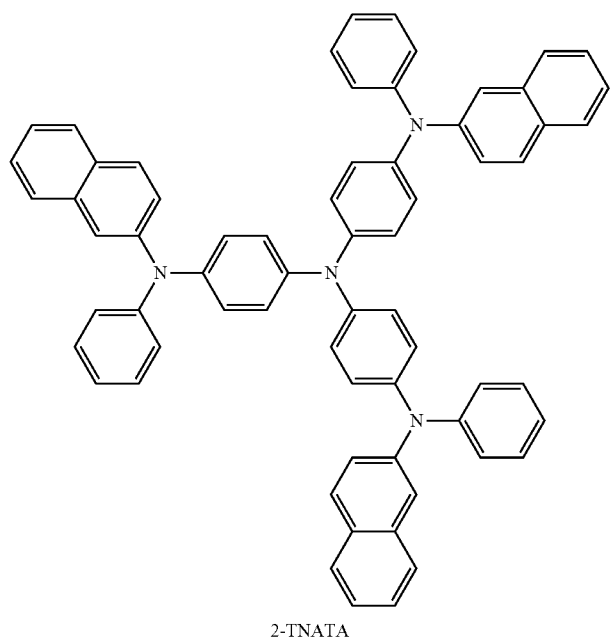
2-TNATA
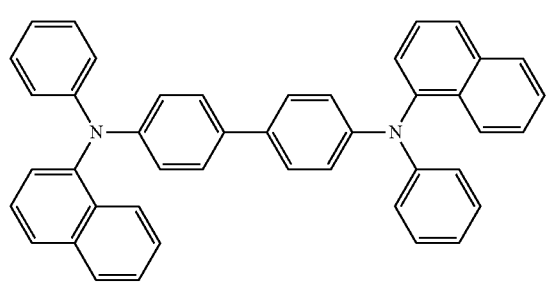
NPB

-continued
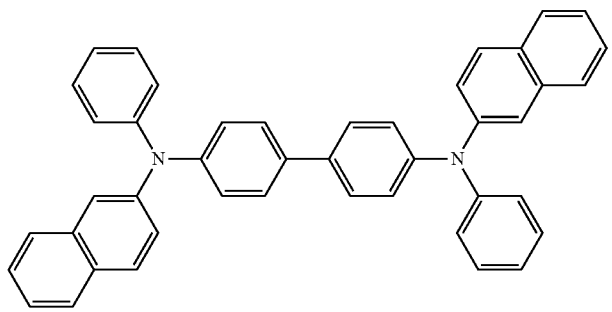
β-NPB
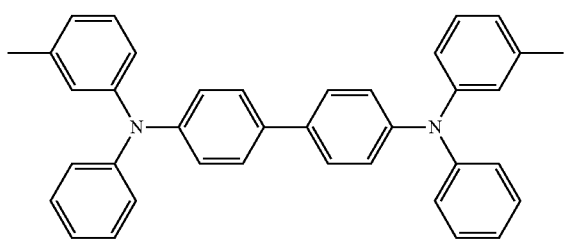
TPD
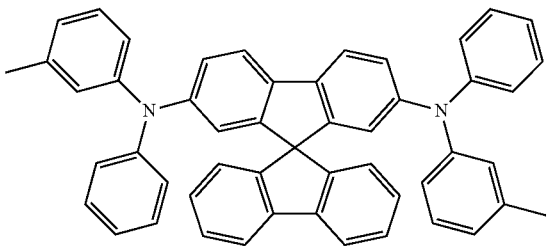
Spiro-TPD
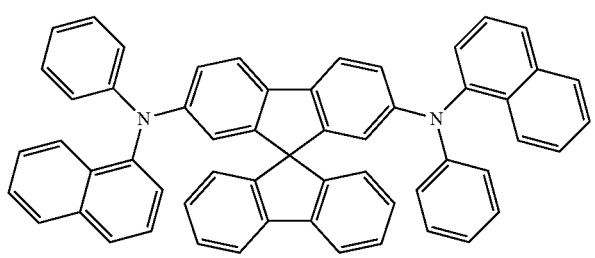
Spiro-NPB
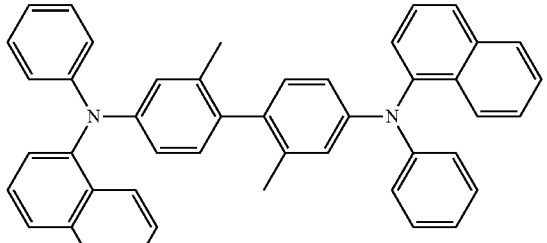
methylated-NPB
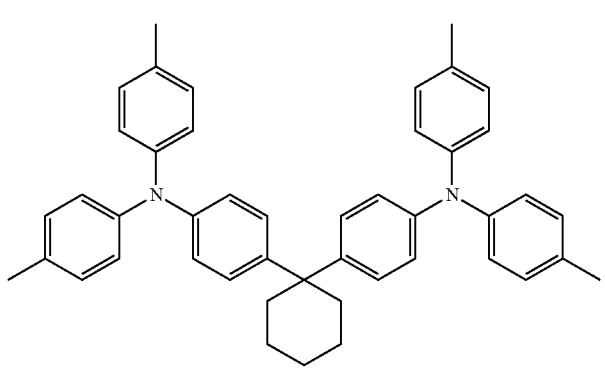
TAPC
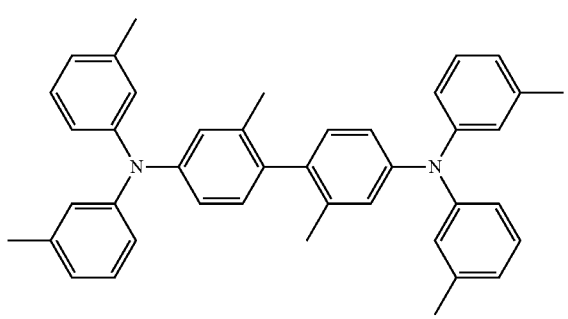
HMTPD A thickness of the hole transport region may be in a range of about 50 Å to about 10,000 Å, for example, about 100 Å to about 4,000 Å. When the hole transport region includes a hole injection layer, a hole transport layer, or any combination thereof, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of light emitted by the emission layer, and the electron blocking layer may block or reduce the flow of electrons from the electron transport region. The emission auxiliary layer and the electron blocking layer may include the materials as described above.

P-Dopant

The hole transport region may further include, in addition to these materials, a charge-generation material for the improvement of conductive properties (e.g., electrically conductive properties). The charge-generation material may be uniformly or non-uniformly dispersed in the hole transport region (for example, in the form of a single layer including (e.g., consisting of) a charge-generation material).

The charge-generation material may be, for example, a p-dopant.

In an embodiment, a lowest unoccupied molecular orbital (LUMO) energy level of the p-dopant may be equal to or less than $-3.5$ eV.

In an embodiment, the p-dopant may include a quinone derivative, a cyano group-containing compound, a compound containing element EL1 and element EL2, or any combination thereof.

Examples of the quinone derivative are TCNQ and F4-TCNQ.

Examples of the cyano group-containing compound are HAT-CN and a compound represented by Formula 221:

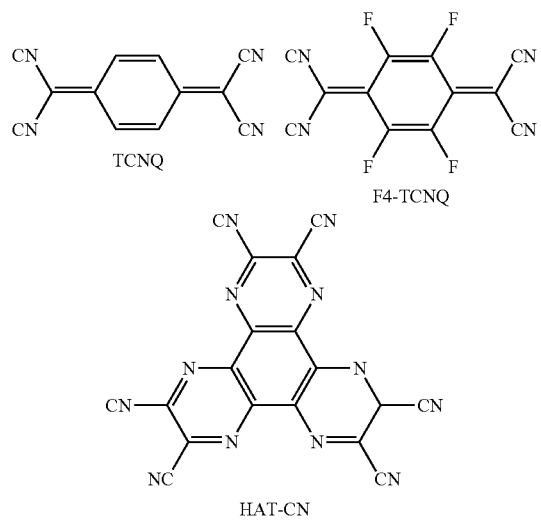

TCNQ

F4-TCNQ

HAT-CN

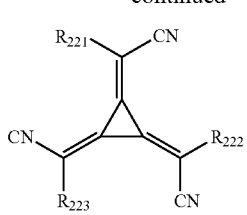

Formula 221 wherein, in Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with: a cyano group; —F; —Cl; —Br; —I; a $C_1$-$C_{20}$ alkyl group substituted with a cyano group, —F, —Cl, —Br, —I, or any combination thereof; or any combination thereof.

Regarding the compound containing element EL1 and element EL2, element EL1 may be metal, metalloid, or a combination thereof, and element EL2 may be a non-metal, metalloid, or a combination thereof.

Examples of the metal include: an alkali metal (for example, lithium (Li), sodium (Na), potassium (K), rubidium (Rb), cesium (Cs), and/or the like); alkaline earth metal (for example, beryllium (Be), magnesium (Mg), calcium (Ca), strontium (Sr), barium (Ba), and/or the like); transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (To), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), and/or the like); post-transition metals (for example, zinc (Zn), indium (In), tin (Sn), and/or the like); and lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), ruthenium (Lu), and/or the like).

Examples of the metalloid include silicon (Si), antimony (Sb), and tellurium (Te).

Examples of the non-metal include oxygen (O) and halogen (for example, F, Cl, Br, I, etc.).

Examples of the compound containing element EL1 and element EL2 include metal oxide, metal halide (for example, metal fluoride, metal chloride, metal bromide, and/or metal iodide), metalloid halide (for example, metalloid fluoride, metalloid chloride, metalloid bromide, and/or metalloid iodide), metal telluride, and any combination thereof.

Examples of the metal oxide include tungsten oxide (for example, WO, $W_2O_3$, $WO_2$, $WO_3$, and/or $W_2O_5$), vanadium oxide (for example, VO, $V_2O_3$, $VO_2$, and/or $V_2O_5$), molybdenum oxide (MoO, $Mo_2O_3$, $MoO_2$, $MoO_3$, and/or $Mo_2O_5$), and rhenium oxide (for example, $ReO_3$).

Examples of the metal halide include alkali metal halide, alkaline earth metal halide, transition metal halide, post-transition metal halide, and lanthanide metal halide.

Examples of the alkali metal halide include LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide include titanium halide (for example, $TiF_4$, $TiCl_4$, $TiBr_4$, and/or $TiI_4$), zirconium halide (for example, $ZrF_4$, $ZrCl_4$, $ZrBr_4$, and/or $ZrI_4$), hafnium halide (for example, $HfF_4$, $HfCl_4$, $HfBr_4$, and/or $HfI_4$), vanadium halide (for example, $VF_3$, $VCl_3$, $VBr_3$, and/or $VI_3$), niobium halide (for example, $NbF_3$, $NbCl_3$, $NbBr_3$, and/or $NbI_3$), tantalum halide (for example, $TaF_3$, $TaCl_3$, $TaBr_3$, and/or $TaI_3$), chromium halide (for example, $CrF_3$, $CrCl_3$, $CrBr_3$, and/or $CrI_3$), molybdenum halide (for example, $MoF_3$, $MoCl_3$, $MoBr_3$, and/or $MoI_3$), tungsten halide (for example, $WF_3$, $WCl_3$, $WBr_3$, and/or $WI_3$), manganese halide (for example, $MnF_2$, $MnCl_2$, $MnBr_2$, and/or $MnI_2$), technetium halide (for example, $TcF_2$, $TcCl_2$, $TcBr_2$, and/or $TcI_2$), rhenium halide (for example, $ReF_2$, $ReCl_2$, $ReBr_2$, and/or $ReI_2$), iron halide (for example, $FeF_2$, $FeCl_2$, $FeBr_2$, and/or $FeI_2$), ruthenium halide (for example, $RuF_2$, $RuCl_2$, $RuBr_2$, and/or $RuI_2$), osmium halide (for example, $OsF_2$, $OsCl_2$, $OsBr_2$, and/or $OsI_2$), cobalt halide (for example, $CoF_2$, $CoCl_2$, $CoBr_2$, and/or $CoI_2$), rhodium halide (for example, $RhF_2$, $RhCl_2$, $RhBr_2$, and/or $RhI_2$), iridium halide (for example, $IrF_2$, $IrCl_2$, $IrBr_2$, and/or $IrI_2$), nickel halide (for example, $NiF_2$, $NiCl_2$, $NiBr_2$, and/or $NiI_2$), palladium halide (for example, $PdF_2$, $PdCl_2$, $PdBr_2$, and/or $PdI_2$), platinum halide (for example, $PtF_2$, $PtCl_2$, $PtBr_2$, and/or $PtI_2$), copper halide (for example, $CuF$, $CuCl$, $CuBr$, and/or $CuI$), silver halide (for example, $AgF$, $AgCl$, $AgBr$, and/or $AgI$), and gold halide (for example, $AuF$, $AuCl$, $AuBr$, and/or $AuI$).

Examples of the post-transition metal halide include zinc halide (for example, $ZnF_2$, $ZnCl_2$, $ZnBr_2$, and/or $ZnI_2$), indium halide (for example, $InI_3$), and tin halide (for example, $SnI_2$).

Examples of the lanthanide metal halide include $YbF$, $YbF_2$, $YbF_3$, $SmF_3$, $YbCl$, $YbCl_2$, $YbCl_3SmCl_3$, $YbBr$, $YbBr_2$, $YbBr_3SmBr_3$, $YbI$, $YbI_2$, $YbI_3$, and $SmI_3$.

Examples of the metalloid halide include antimony halide (for example, $SbCl_5$).

Examples of the metal telluride include an alkali metal telluride (for example, $Li_2Te$, $Na_2Te$, $K_2Te$, $Rb_2Te$, and/or $Cs_2Te$), alkaline earth metal telluride (for example, $BeTe$, $MgTe$, $CaTe$, $SrTe$, and/or $BaTe$), transition metal telluride (for example, $TiTe_2$, $ZrTe_2$, $FlfTe_2$, $V_2Te_3$, $Nb_2Te_3$, $Ta_2Te_3$, $Cr_2Te_3$, $Mo_2Te_3$, $W_2Te_3$, $MnTe$, $TcTe$, $ReTe$, $FeTe$, $RuTe$, $OsTe$, $CoTe$, $RhTe$, $IrTe$, $NiTe$, $PdTe$, $PtTe$, $Cu_2Te$, $CuTe$, $Ag_2Te$, $AgTe$, and/or $Au_2Te$), post-transition metal telluride (for example, $ZnTe$), and lanthanide metal telluride (for example, $LaTe$, $CeTe$, $PrTe$, $NdTe$, $PmTe$, $EuTe$, $GdTe$, $TbTe$, $DyTe$, $HoTe$, $ErTe$, $TmTe$, $YbTe$, and/or $LuTe$).

Emission Layer in Interlayer 130

In an embodiment, when the light-emitting device 10 is a full-color light-emitting device, the emission layer may be patterned into a red emission layer, a green emission layer, and/or a blue emission layer, according to a subpixel. In one or more embodiments, the emission layer may have a stacked structure of two or more layers of a red emission layer, a green emission layer, and a blue emission layer, in which the two or more layers contact (e.g., physically contact) each other or are separated from each other. In one or more embodiments, the emission layer may include two or more materials of a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

An amount of the dopant in the emission layer may be in a range of about 0.01 parts by weight to about 15 parts by weight based on 100 parts by weight of the host.

In one or more embodiments, the emission layer may include a quantum dot.

In one or more embodiments, the emission layer may include a delayed fluorescence material. The delayed fluorescence material may act as a host or a dopant in the emission layer.

A thickness of the emission layer may be in a range of about 100 Å to about 1,000 Å, for example, about 200 Å to about 600 Å. When the thickness of the emission layer is within these ranges, excellent luminescence characteristics may be exhibited without a substantial increase in driving voltage.

Host

In an embodiment, the host may include a compound represented by Formula 301:

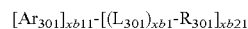   Formula 301 wherein, in Formula 301,

Ar$_{301}$ and L$_{301}$ may each independently be a C$_3$-C$_{60}$carbocyclic group unsubstituted or substituted with at least one R$_{10a}$ or a C$_1$-C$_{60}$ heterocyclic group unsubstituted or substituted with at least one R$_{10a}$, xb11 may be 1, 2, or 3, xb1 may be an integer from 0 to 5, R$_{301}$ may be hydrogen, deuterium, —F, —Cl, —Br, —I, a hydroxyl group, a cyano group, a nitro group, a C$_1$-C$_{60}$ alkyl group unsubstituted or substituted with at least one R$_{10a}$, a C$_2$-C$_{60}$ alkenyl group unsubstituted or substituted with at least one R$_{10a}$, a C$_2$-C$_{60}$alkynyl group unsubstituted or substituted with at least one R$_{10a}$, a C$_1$-C$_{60}$alkoxy group unsubstituted or substituted with at least one R$_{10a}$, a C$_3$-C$_{60}$carbocyclic group unsubstituted or substituted with at least one R$_{10a}$, a C$_1$-C$_{60}$ heterocyclic group unsubstituted or substituted with at least one R$_{10a}$, —Si(Q$_{301}$)(Q$_{302}$)(Q$_{303}$), —N(Q$_{301}$)(Q$_{302}$), —B(Q$_{301}$)(Q$_{302}$), —C(=O)(Q$_{301}$), —S(=O)$_2$(Q$_{301}$), or —P(=O)(Q$_{301}$)(Q$_{302}$), xb21 may be an integer from 1 to 5, and Q$_{301}$ to Q$_{303}$ may each be the same as described in connection with Q$_1$.

In one or more embodiments, when xb11 in Formula 301 is 2 or more, two or more of Ar$_{301}$(s) may be linked to each other via a single bond.

In one or more embodiments, the host may include a compound represented by Formula 301-1, a compound represented by Formula 301-2, or any combination thereof:

Formula 301-1

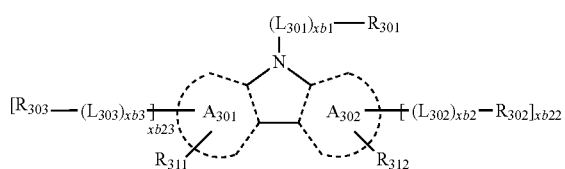

Formula 301-2

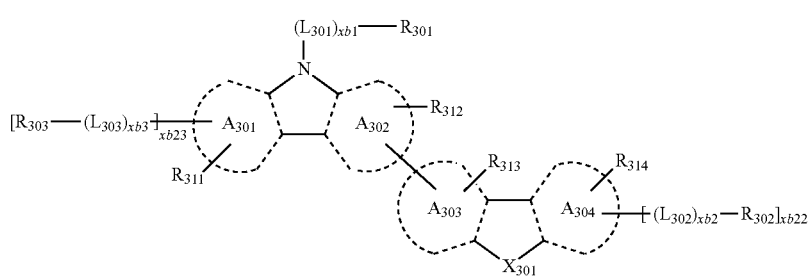

wherein, in Formulae 301-1 and 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-[($L_{304}$)$_{xb4}$-$R_{304}$], C($R_{304}$)($R_{305}$), or Si($R_{304}$)($R_{305}$), xb22 and xb23 may each independently be 0, 1, or 2, $L_{301}$, xb1, and $R_{301}$ may each be the same as described above, $L_{302}$ to $L_{304}$ may each independently be the same as described in connection with $L_{301}$, xb2 to xb4 may each independently be the same as described in connection with xb1, and $R_{302}$ to $R_{305}$ and $R_{311}$ to $R_{314}$ may each be the same as described in connection with $R_{301}$.

In one or more embodiments, the host may include an alkaline earth metal complex. In one or more embodiments, the host may include a Be complex (for example, Compound H55), a Mg complex, a Zn complex, or any combination thereof.

In one or more embodiments, the host may include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP) or any combination thereof:

H1

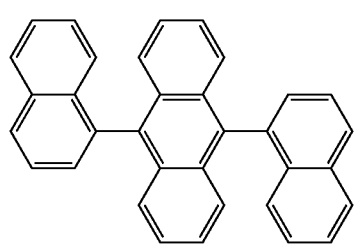

-continued

H2

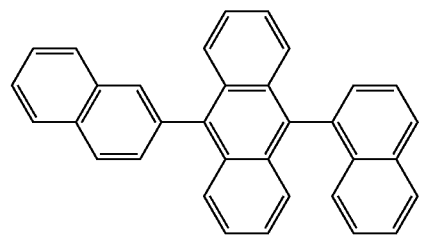

H3

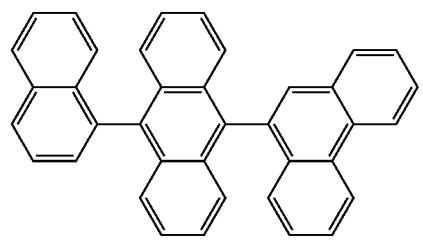

H4

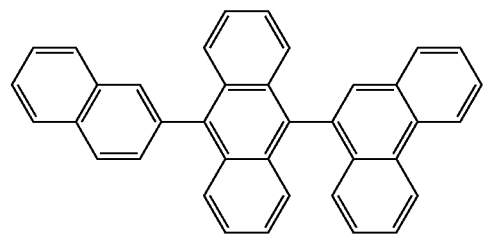

H5

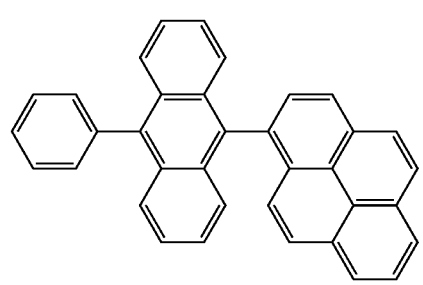

H6
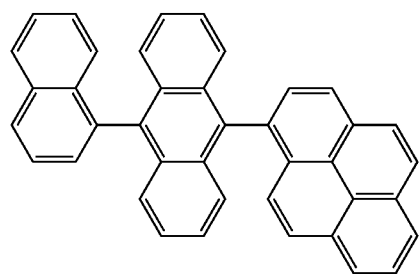
H7
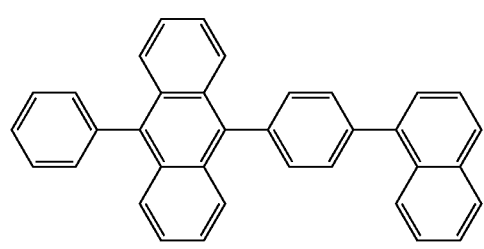
H8
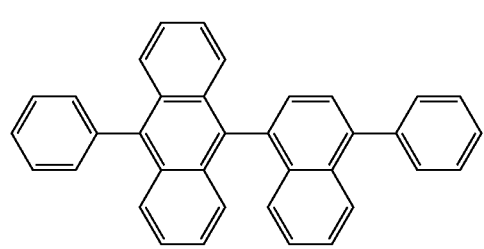
H9
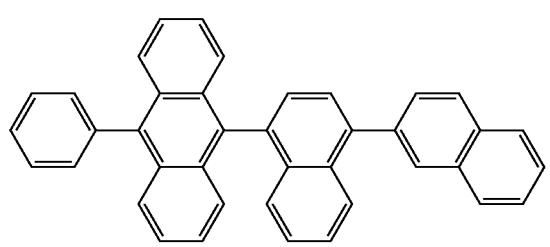
H10
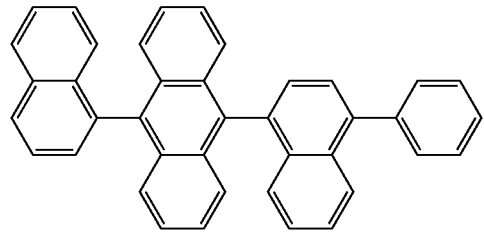
H11
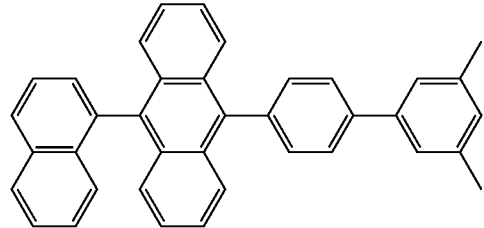
H12
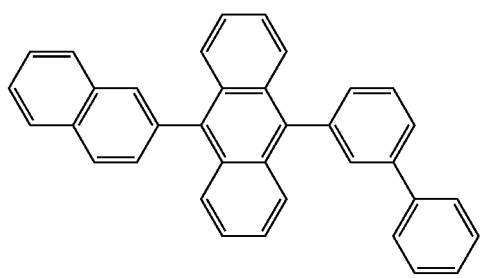
H13
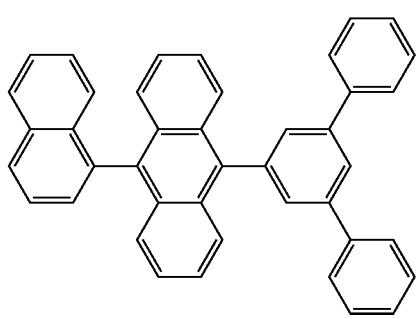
H14
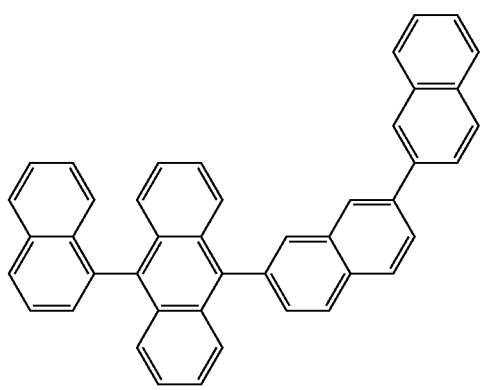
H15
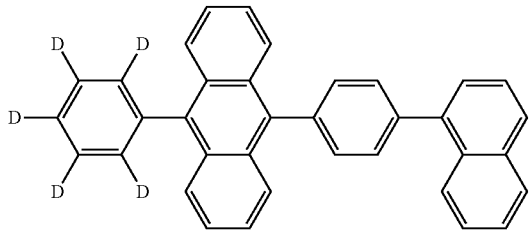
H16
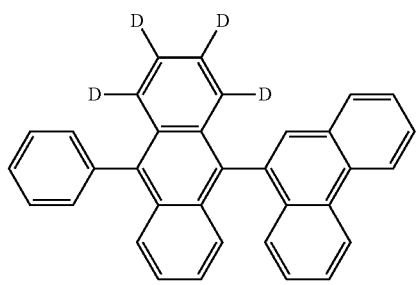

H17
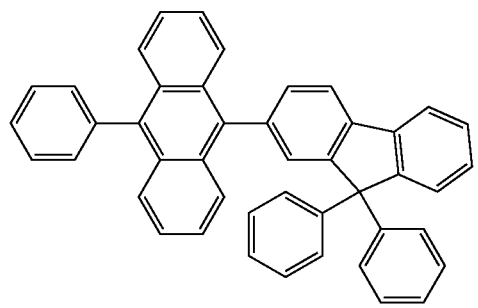
H18
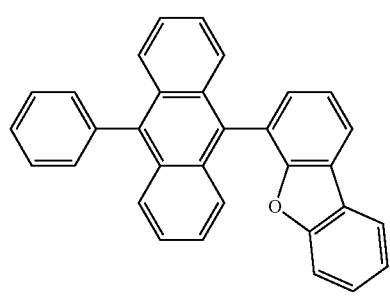
H19
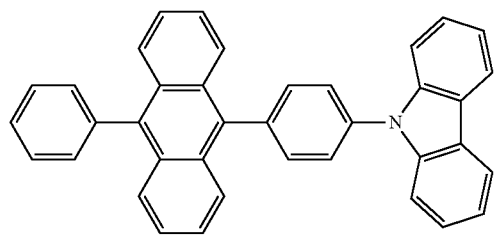
H20
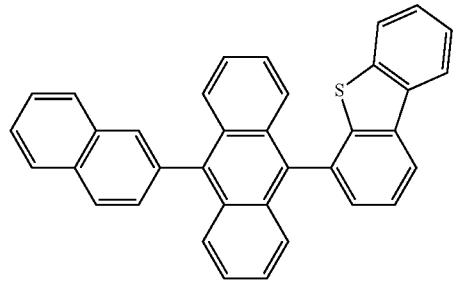
H21
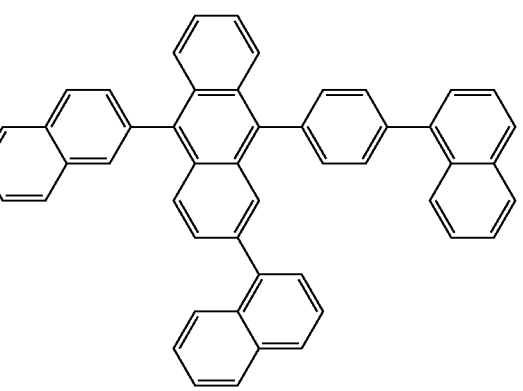
H22
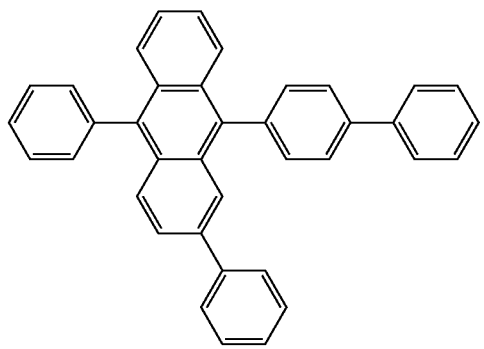
H23
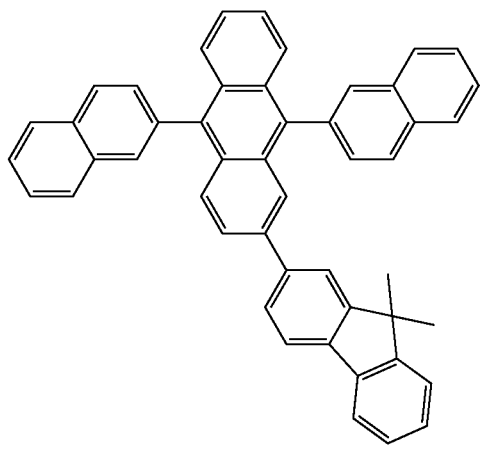
H24
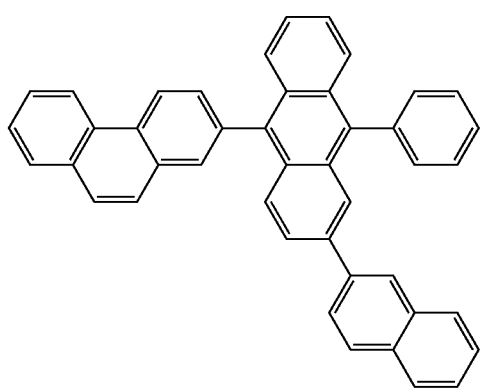

127
-continued
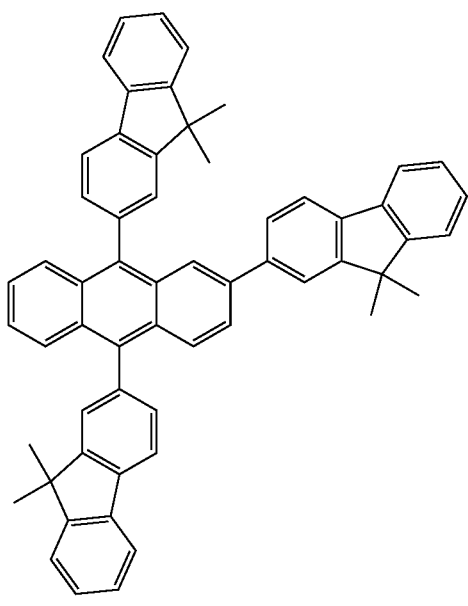
128
-continued
H25
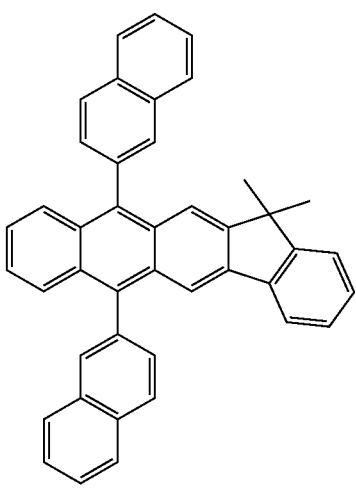
H27
H28
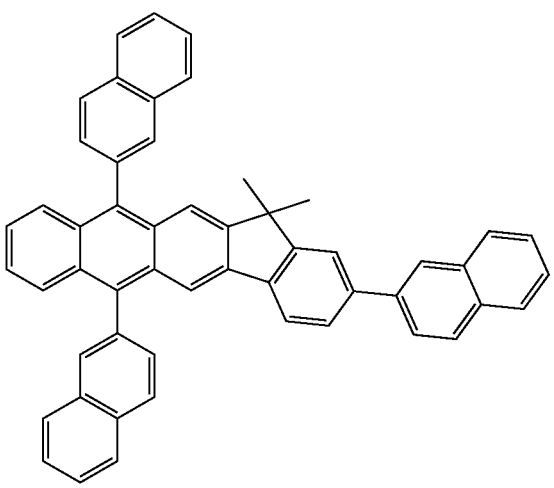
H26
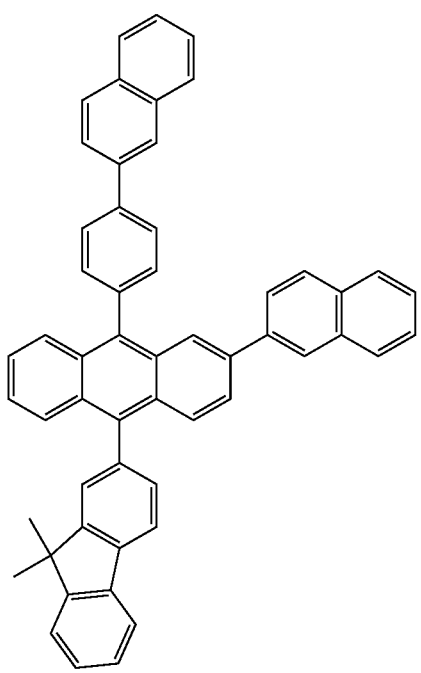
H29
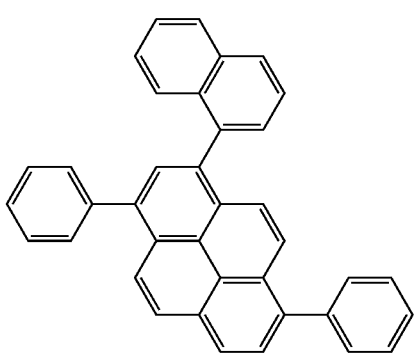

-continued
H30
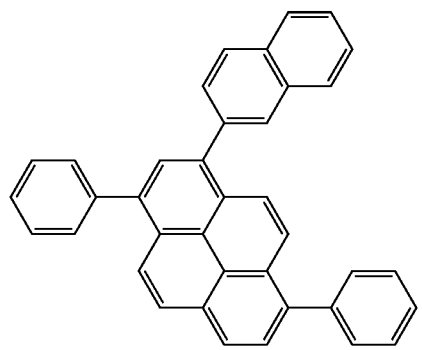
H31
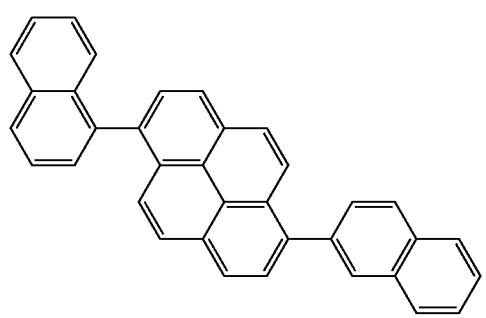
H32
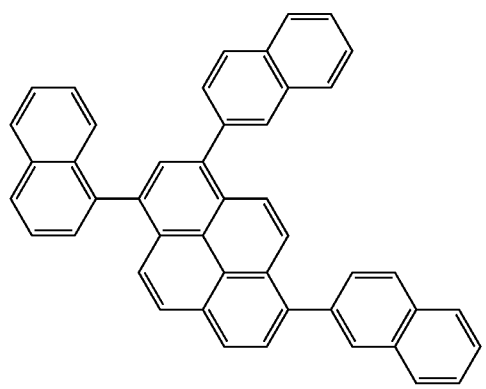
H33
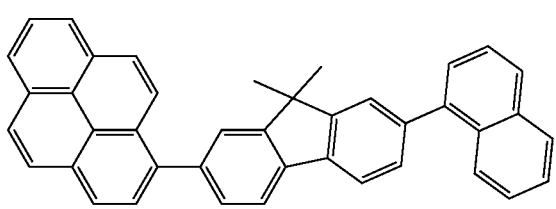
H34
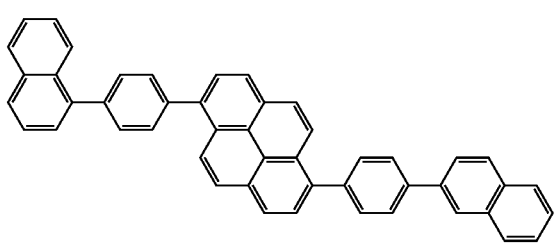
-continued
H35
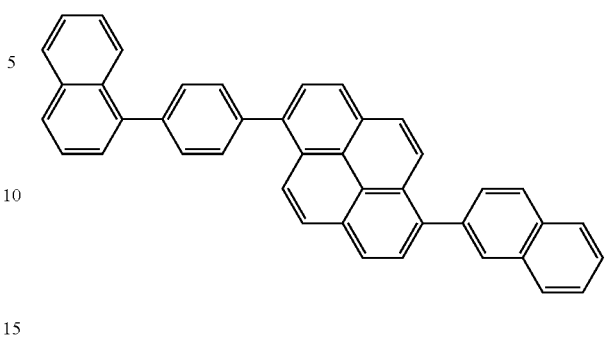
H36
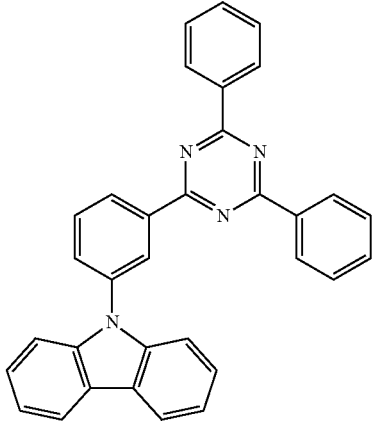
H37
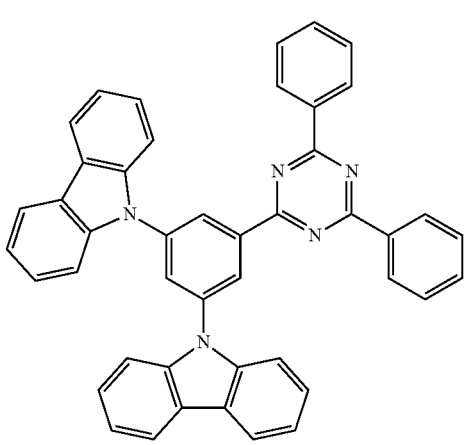
H38
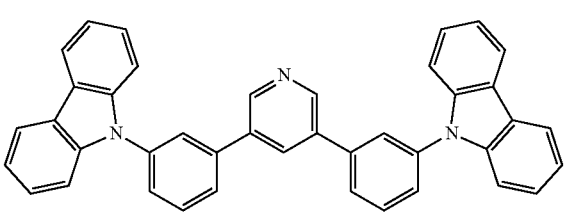

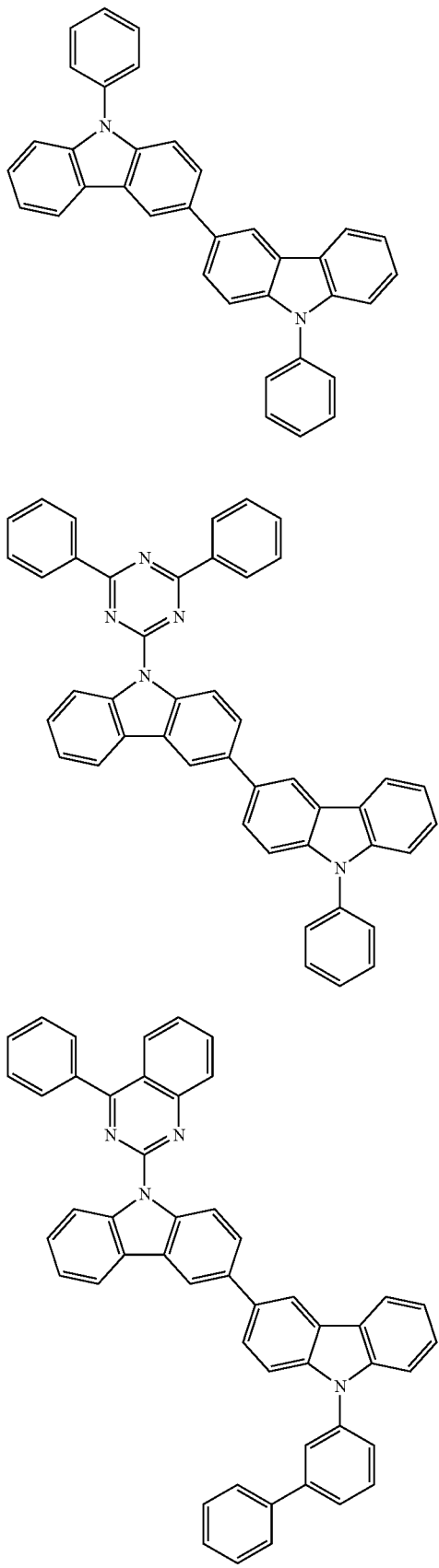
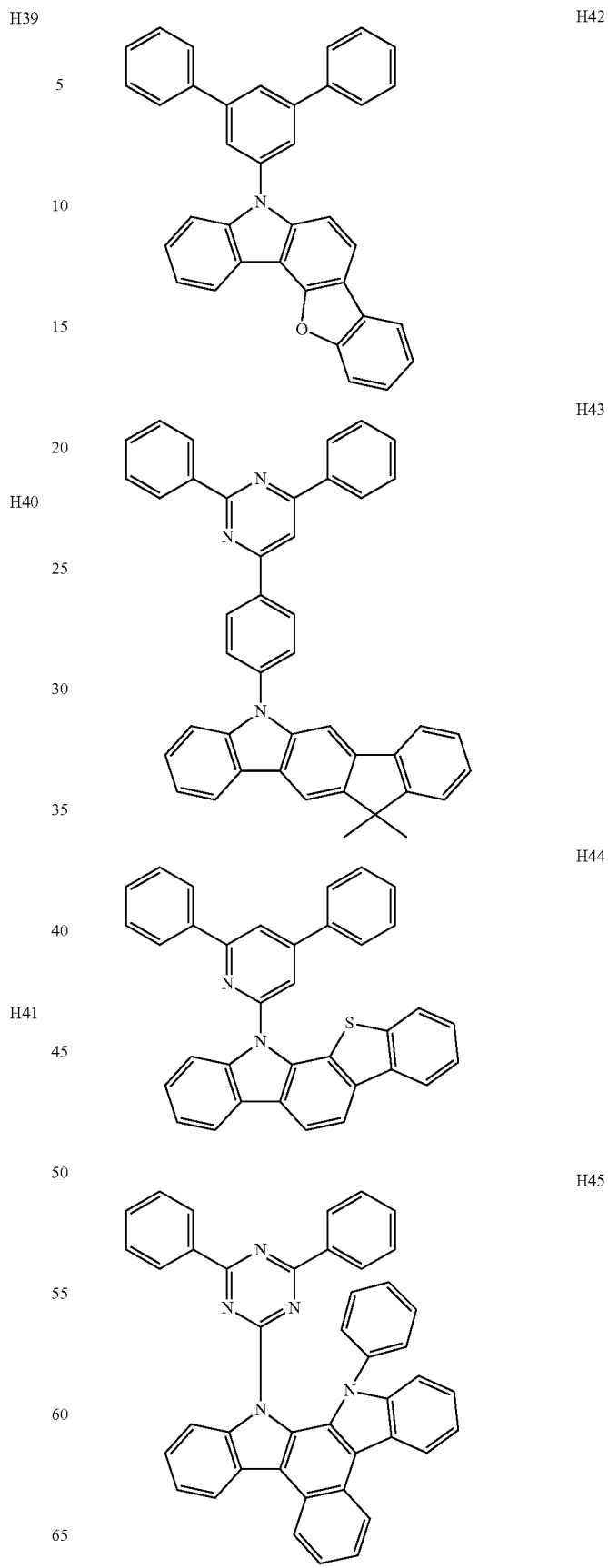

H46
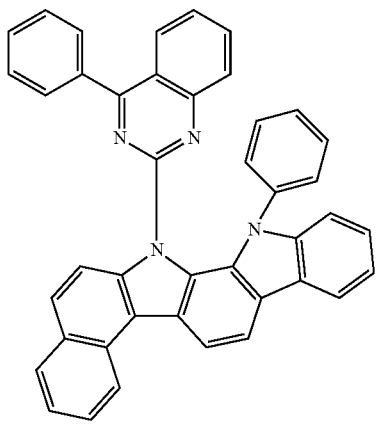
H52
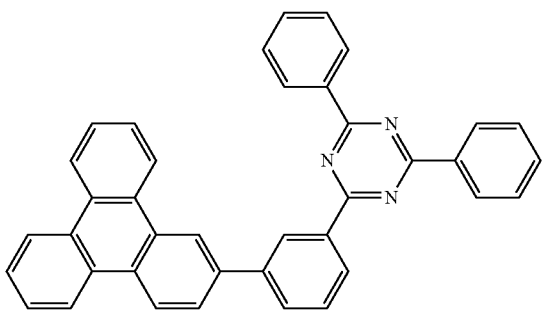
H47
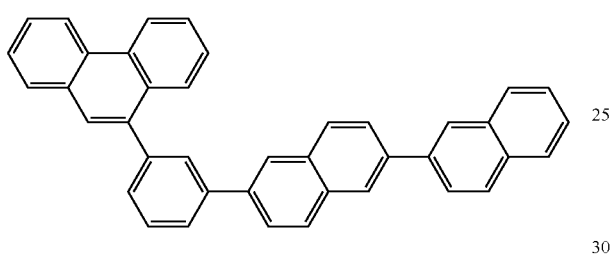
H53
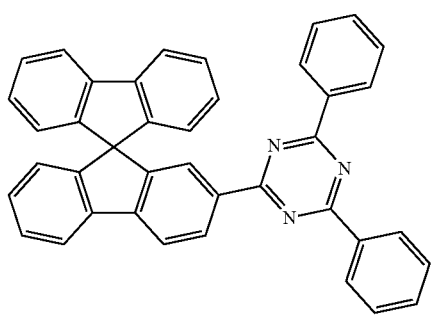
H48
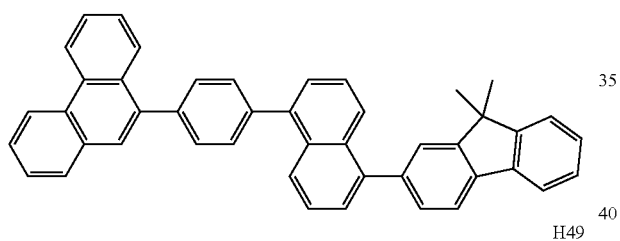
H49
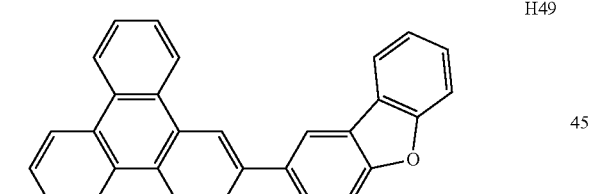
H54
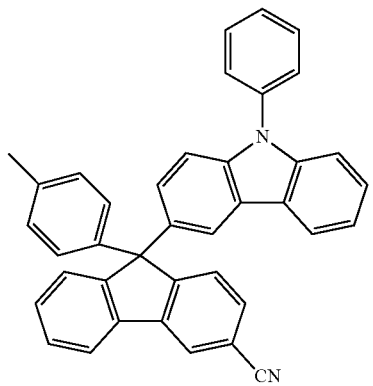
H50
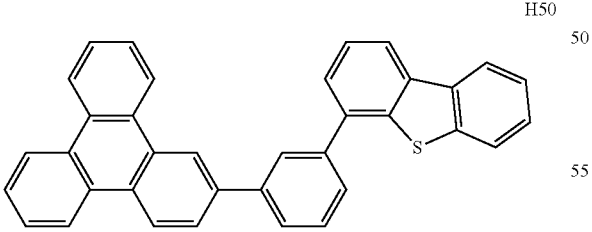
H51
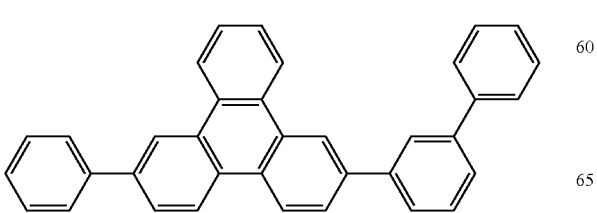
H55
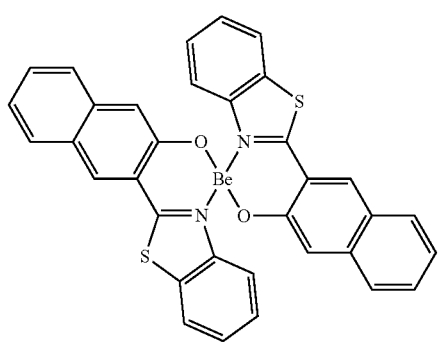

H56
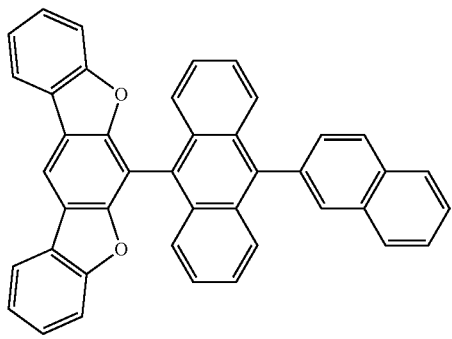
H57
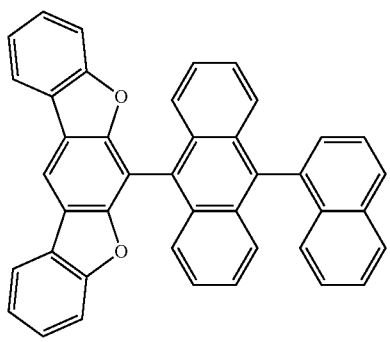
H58
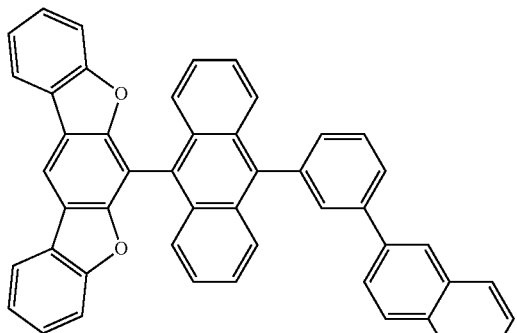
H59
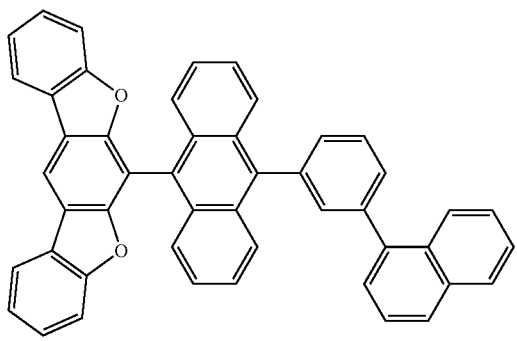
H60
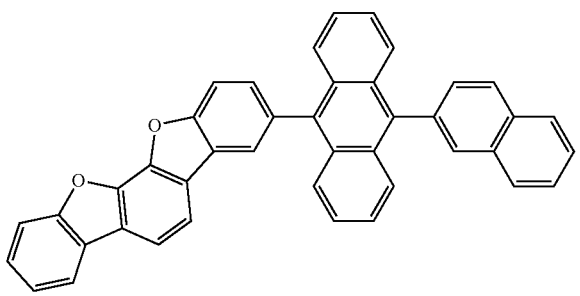
H61
H62
H63
H64
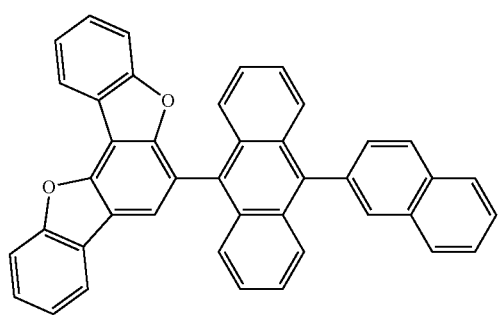

H65
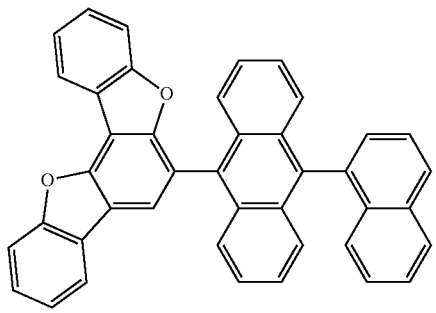
H66
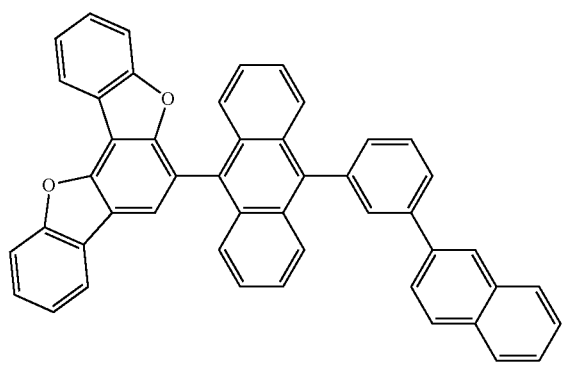
H67
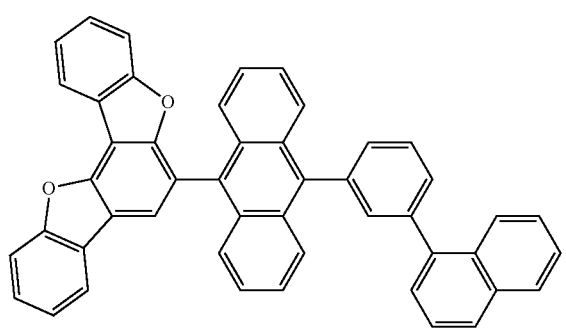
H68
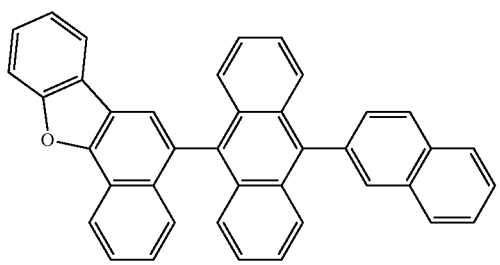
H69
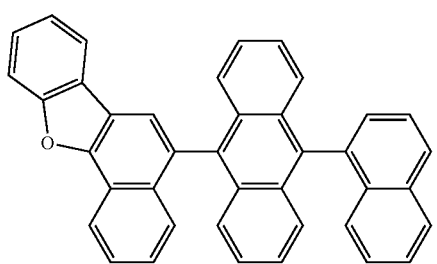
H70
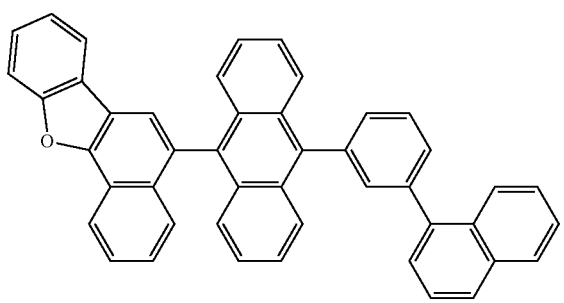
H71
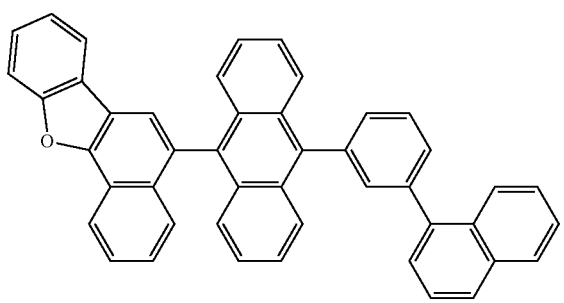
H72
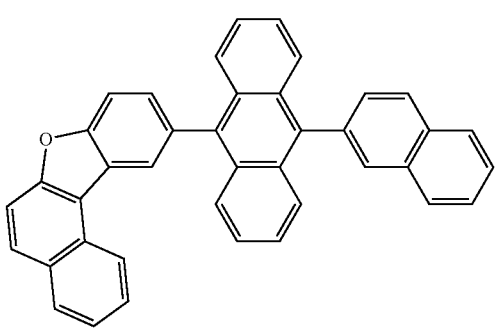
H73
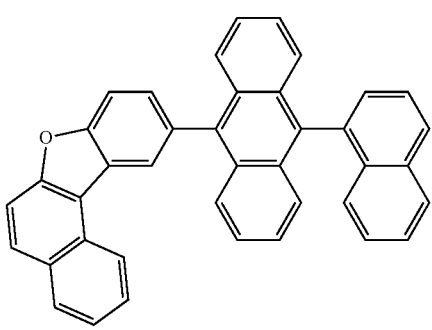

-continued
H74
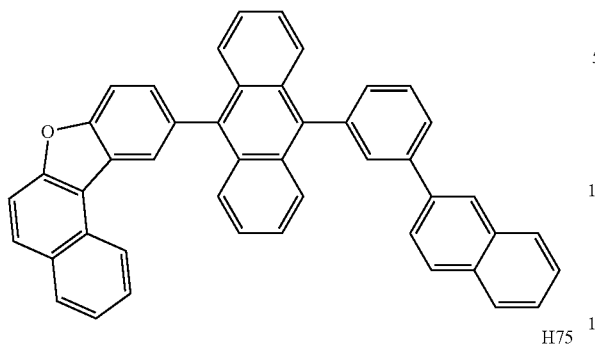
H75
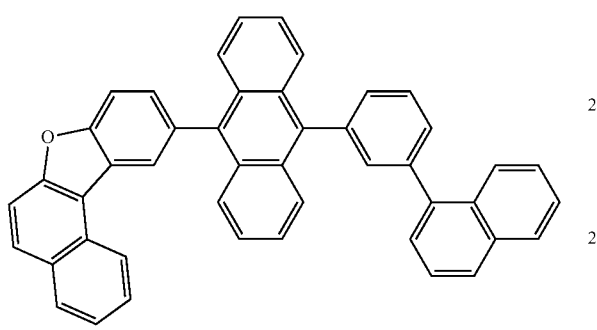
H76
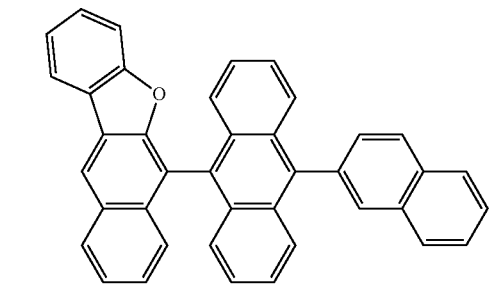
H77
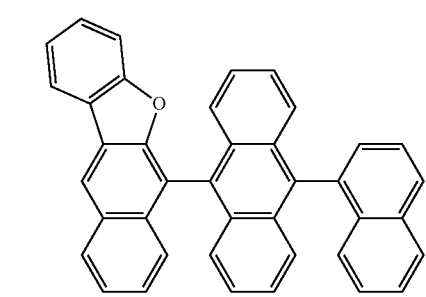
H78
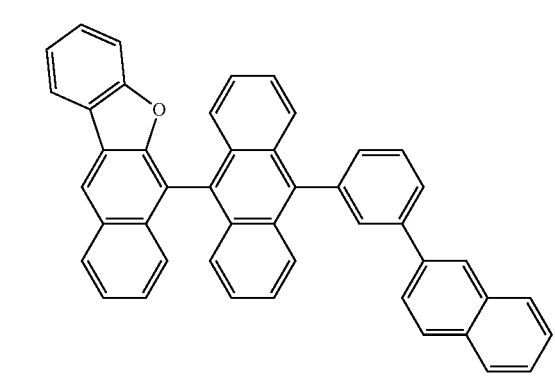
-continued
H79
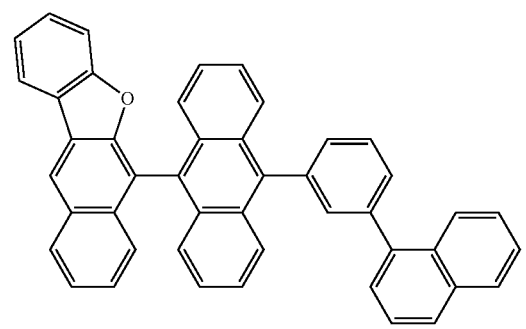
H80
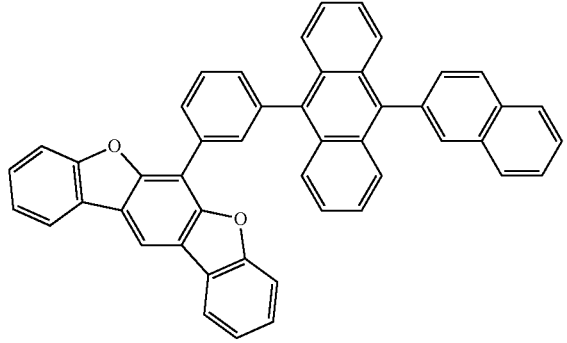
H81
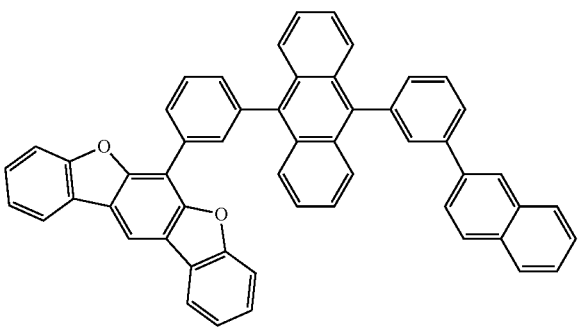
H82

-continued
H83
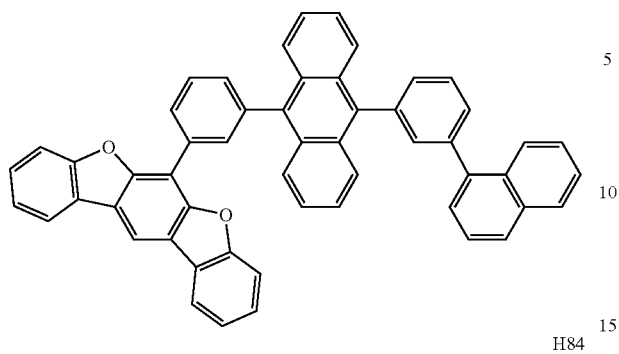
H84
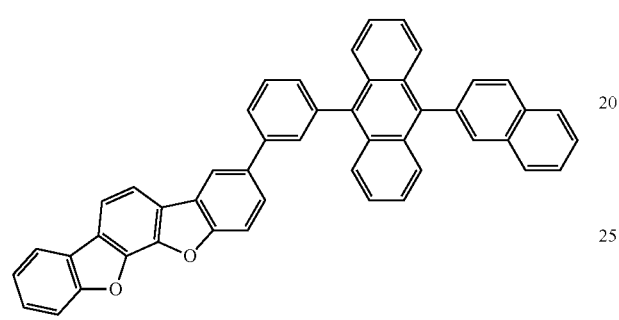
H85
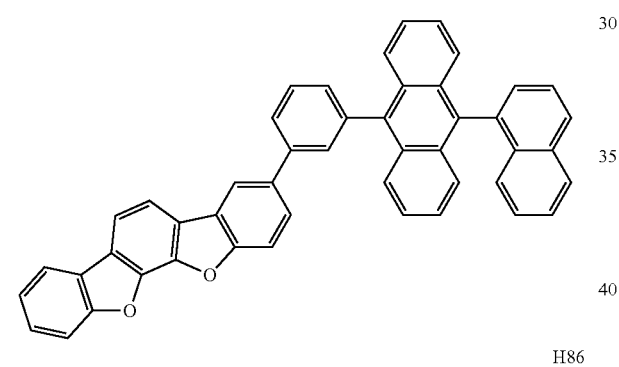
H86
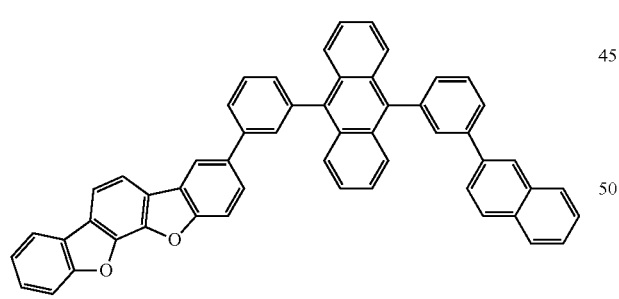
H87
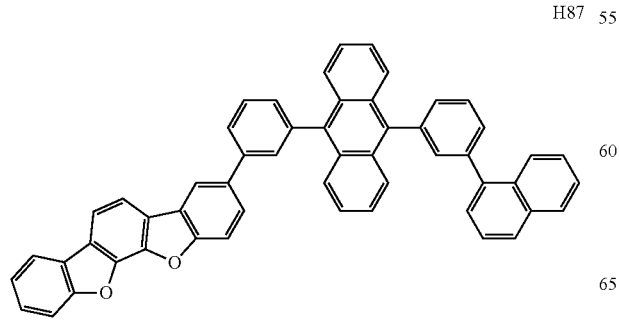
-continued
H88
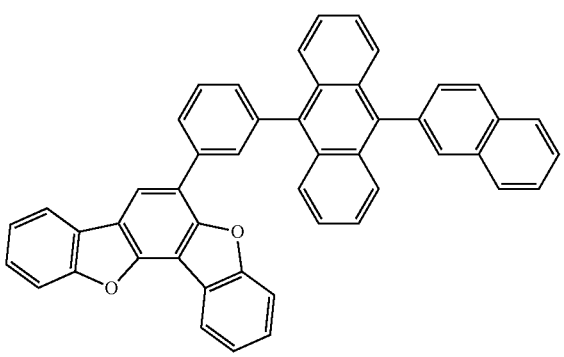
H89
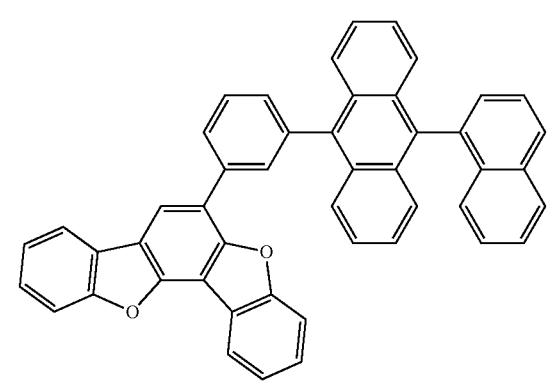
H90
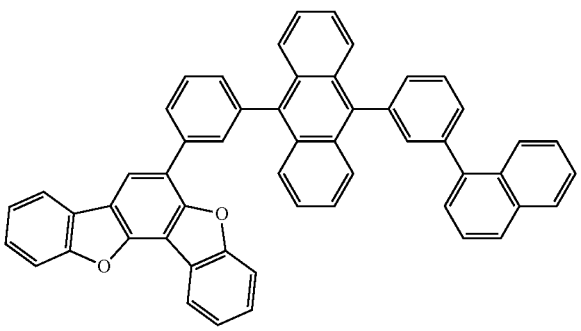
H91

H92
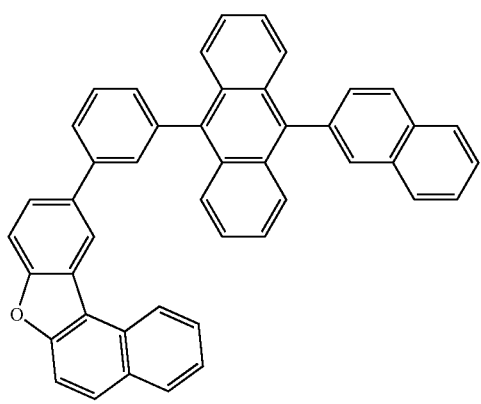
H93
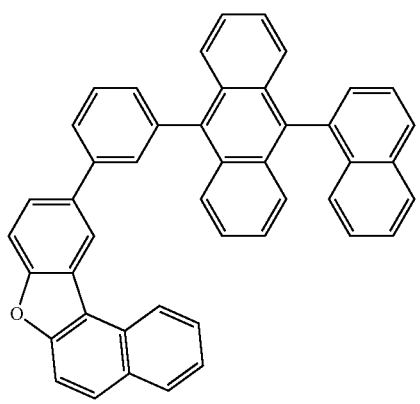
H94
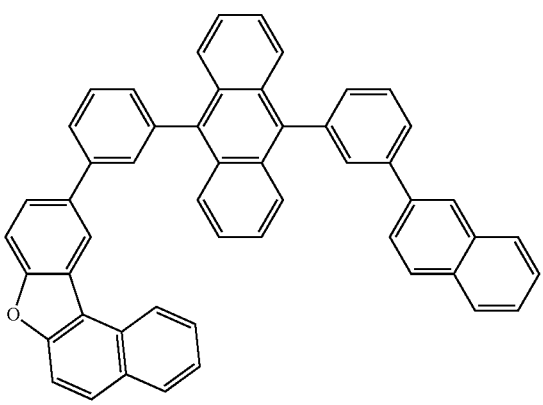
H95
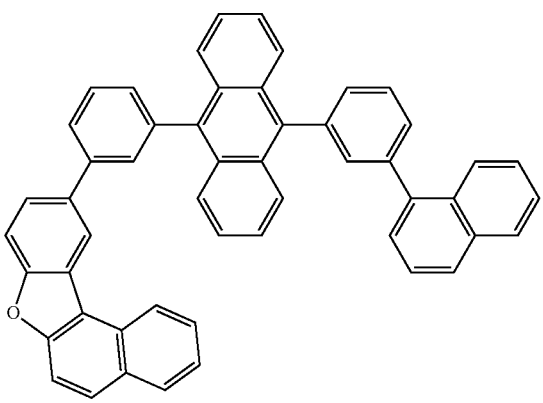
H96
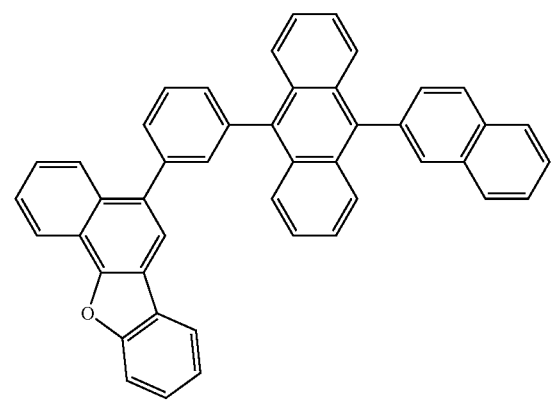
H97
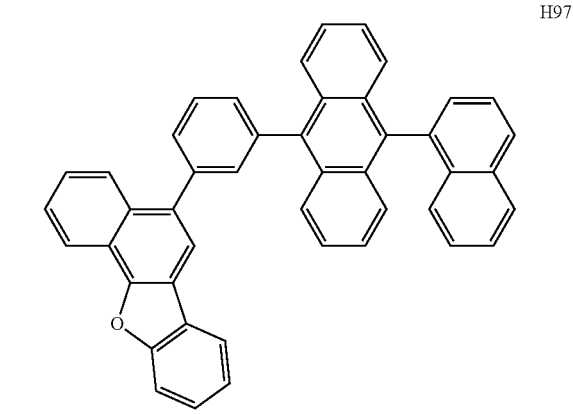
H98
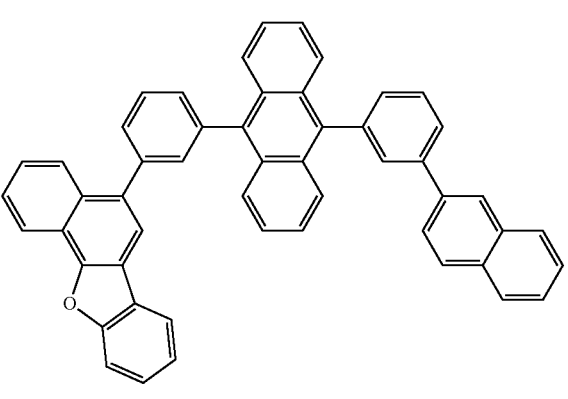
H99
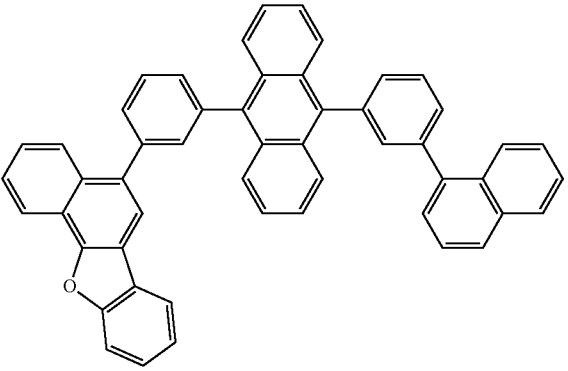

H100
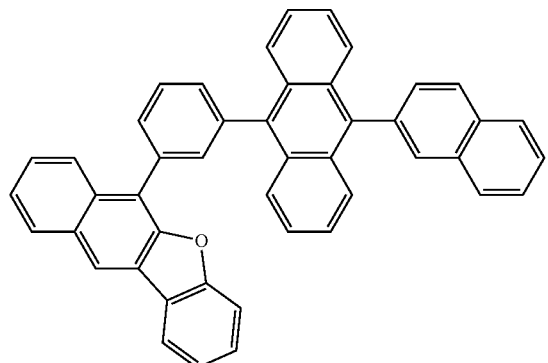
H101
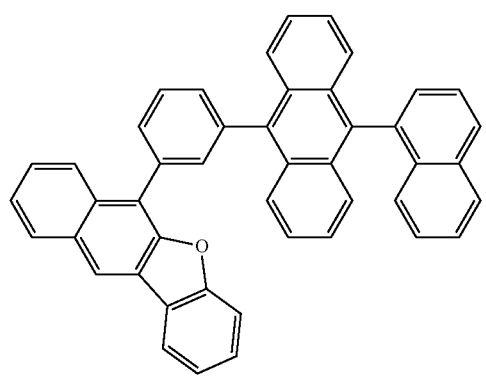
H102
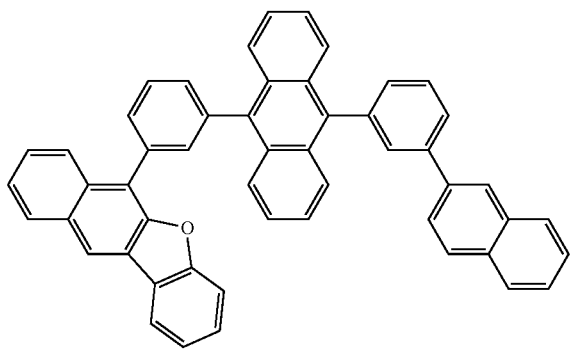
H103
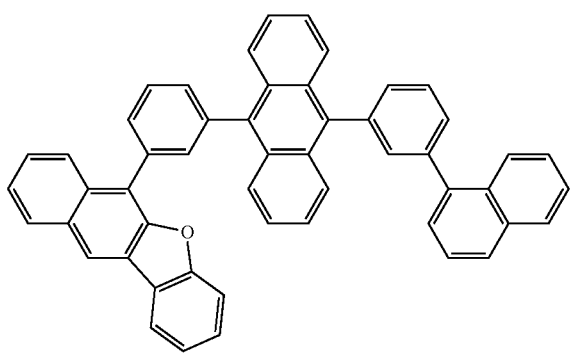
H104
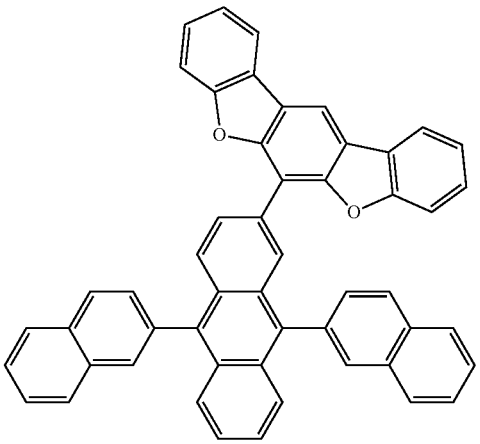
H105
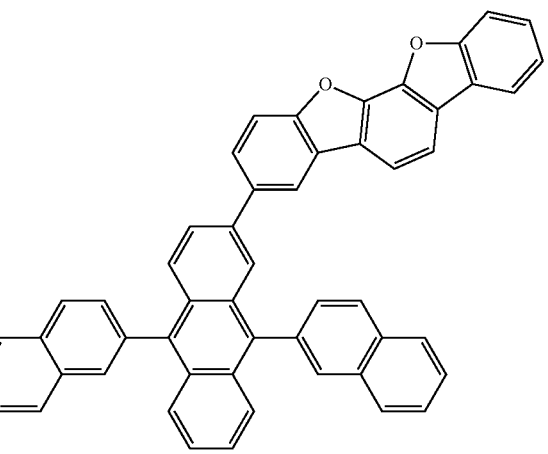
H106
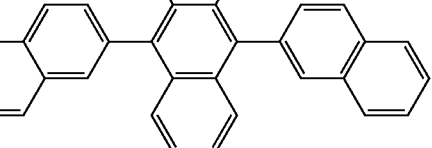

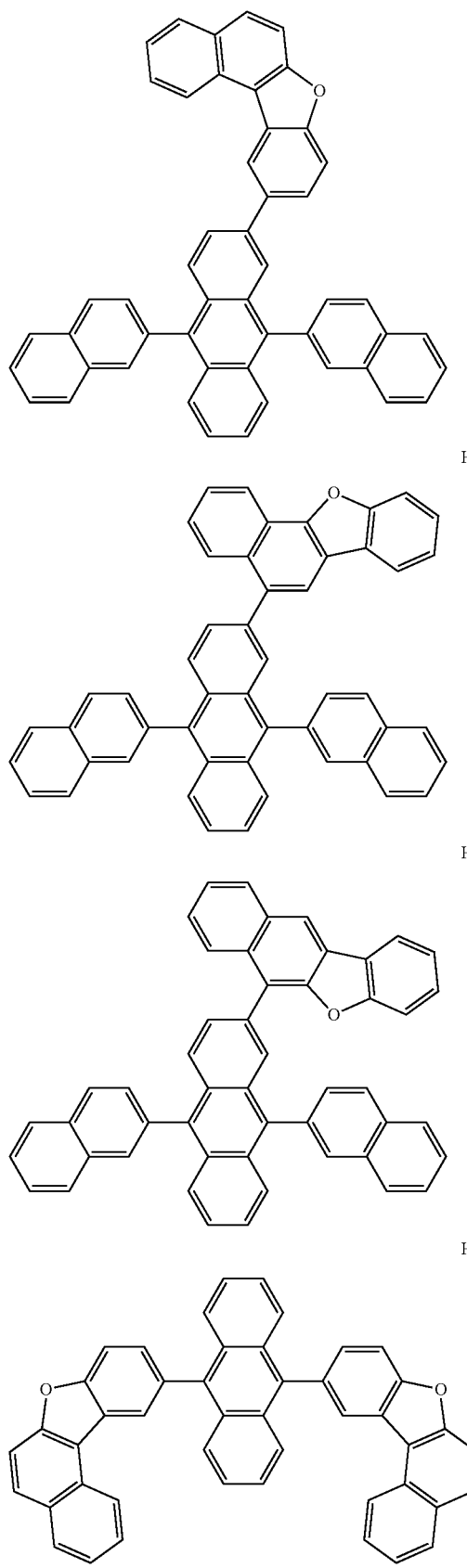
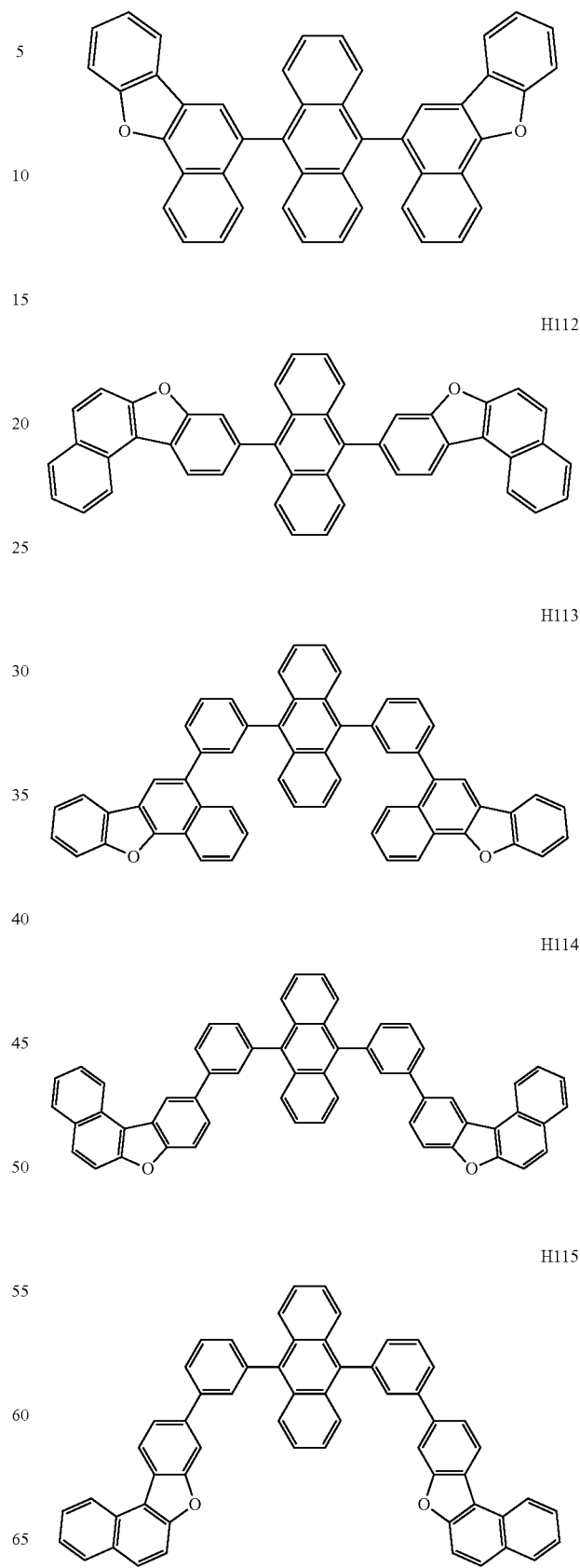

H116
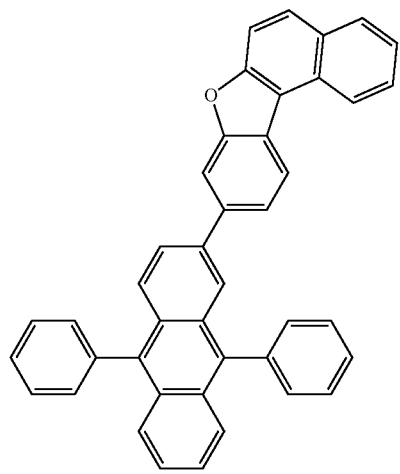
H117
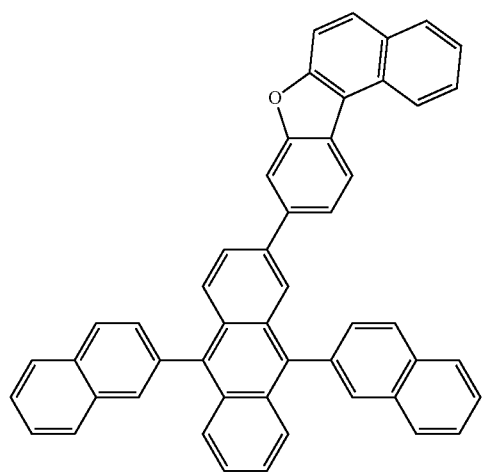
H118
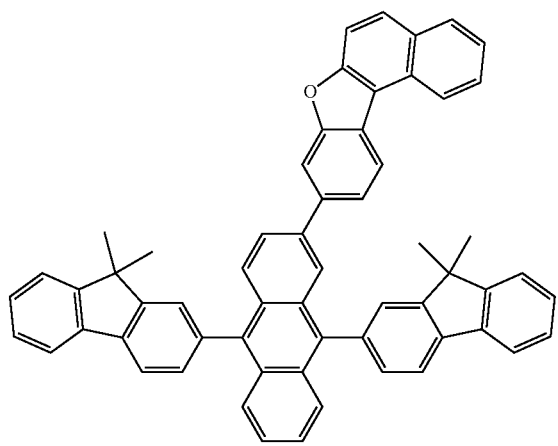
H119
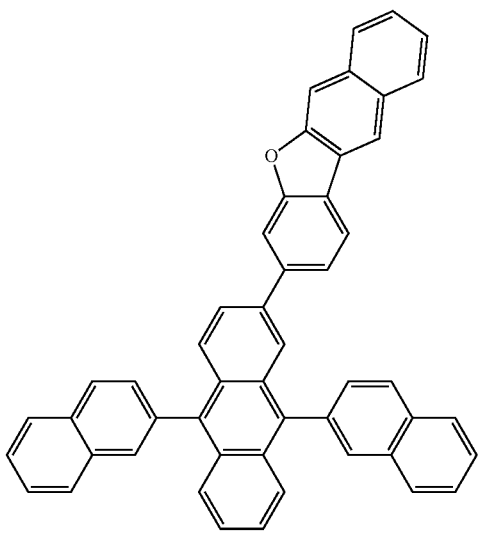
H120
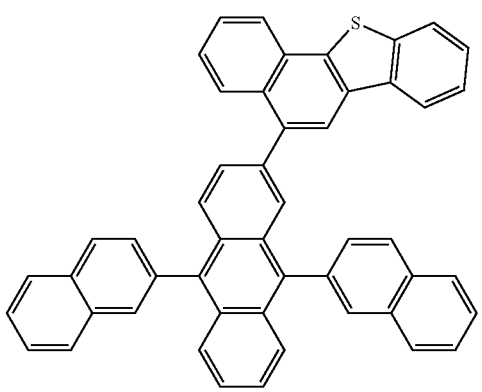
H121
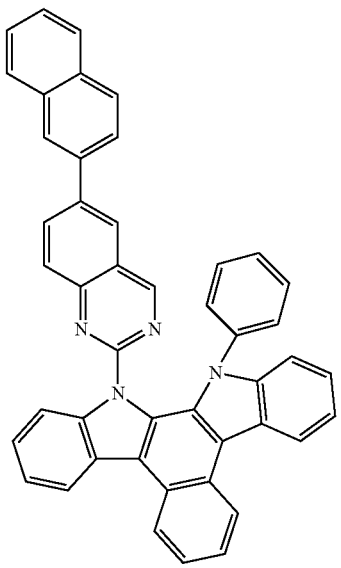

-continued

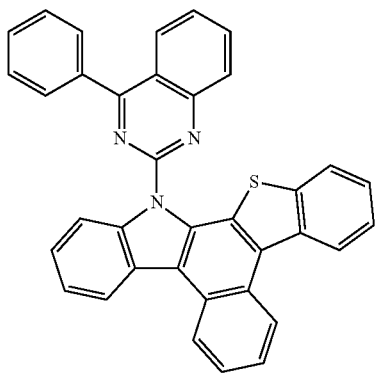

H122

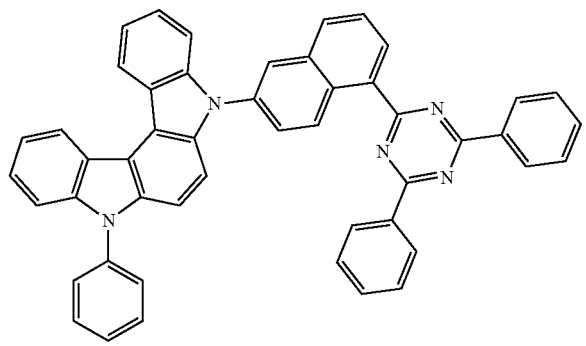

H123

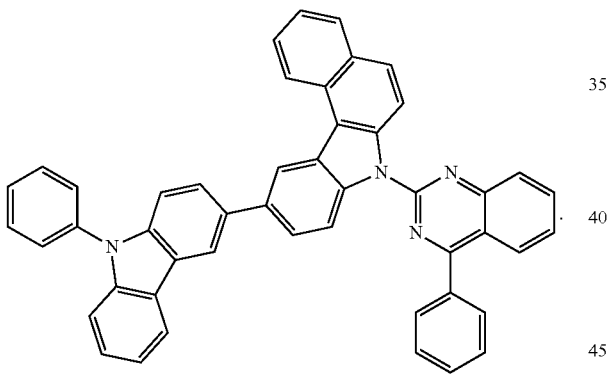

H124

Delayed Fluorescence Material

The emission layer may include a delayed fluorescence material.

The delayed fluorescence material, as described herein, may be any compound that is capable of emitting delayed fluorescence based on a delayed fluorescence emission mechanism.

The delayed fluorescence material included in the emission layer may act as a host or a dopant depending on the type or kind of other materials included in the emission layer.

In an embodiment, a difference between a triplet energy level (eV) of the delayed fluorescence material and a singlet energy level (eV) of the delayed fluorescence material may be equal to or greater than 0 eV and equal to or less than 0.5 eV. When the difference between the triplet energy level (eV) of the delayed fluorescence material and the singlet energy level (eV) of the delayed fluorescence material is with the ranges above, up-conversion in which the delayed fluorescence materials transfer from the triplet state to the singlet state may effectively occur, and thus, the luminescence efficiency of the light-emitting device 10 may be improved.

For example, the delayed fluorescence material may include i) a material that includes at least one electron donor (for example, a π electron-rich $C_3$-$C_{60}$ cyclic group, such as a carbazole group) and at least one electron acceptor (for example, a sulfoxide group, a cyano group, or a π electron-deficient nitrogen-containing $C_1$-$C_{60}$ cyclic group), or ii) a material including a $C_8$-$C_{60}$ polycyclic group in which two or more cyclic groups share a boron (B) atom and are condensed with each other (e.g., combined together with each other).

The delayed fluorescence material may include, for example, at least one of Compounds DF1 to DF9:

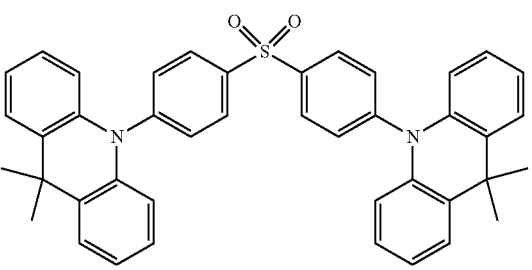

(DMAC-DPS)

DF1

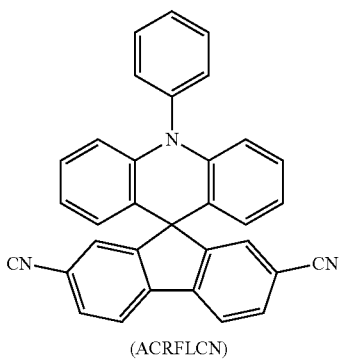

(ACRFLCN)

DF2

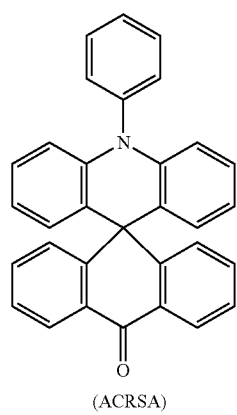

(ACRSA)

DF3

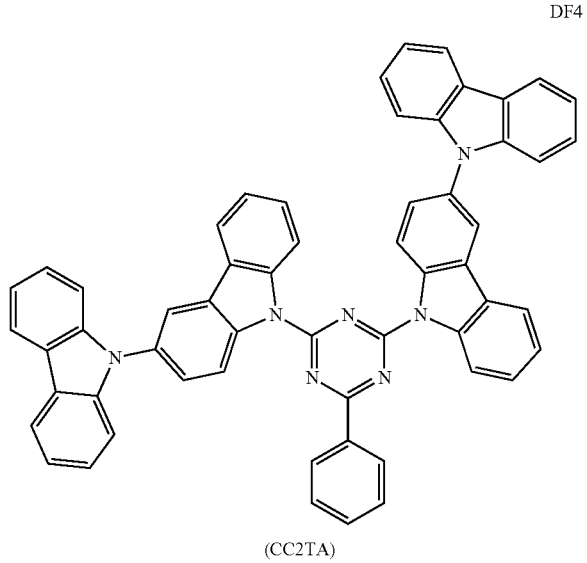

(CC2TA)

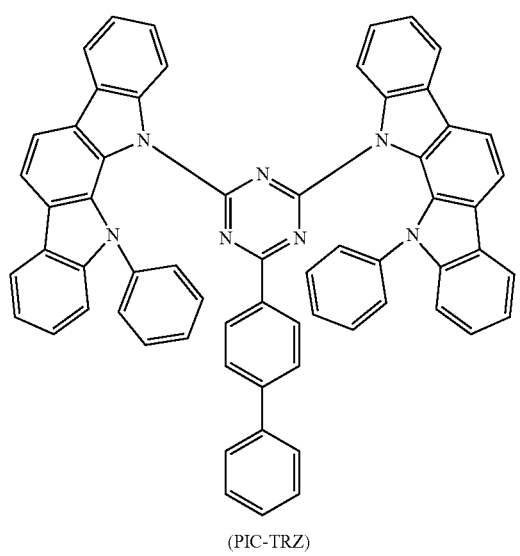

(PIC-TRZ)

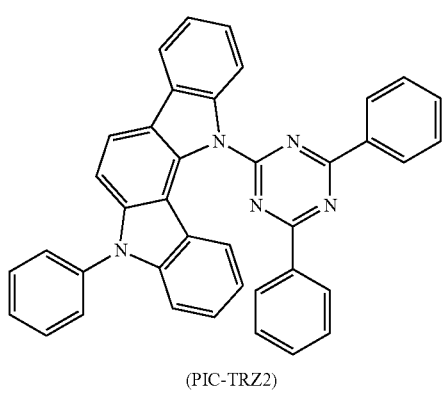

(PIC-TRZ2)

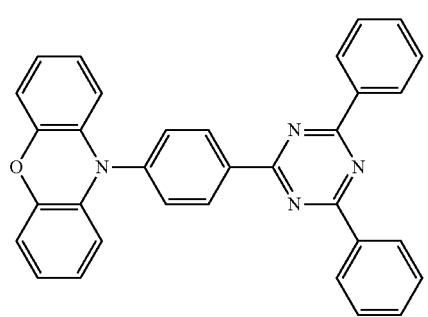

(PXZ-TRZ)

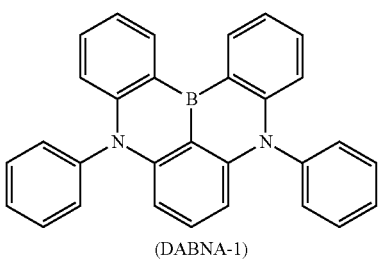

(DABNA-1)

(DABNA-2)

Quantum Dot

The emission layer may include a quantum dot.

The term "quantum dot," as used herein, refers to the crystal of a semiconductor compound, and may include any suitable material that is capable of emitting light of various suitable emission wavelengths depending on the size of the crystal.

A diameter of the quantum dot may be, for example, in a range of about 1 nm to about 10 nm.

The quantum dot may be synthesized by a wet chemical process, an organometallic chemical vapor deposition process, a molecular beam epitaxy process, and/or a process that is similar to these processes.

The wet chemical process refers to a method in which an organic solvent and a precursor material are mixed, and then, a quantum dot particle crystal is grown. When the crystal grows, the organic solvent acts as a dispersant naturally coordinated on the surface of the quantum dot crystal and controls the growth of the crystal. Accordingly, by using a process that is easily performed at low costs compared to a vapor deposition process, such as a metal organic chemical vapor deposition (MOCVD) process and a molecular beam epitaxy (MBE) process, the growth of quantum dot particles may be controlled.

The quantum dot may include: a Group II-VI semiconductor compound; a Group III-V semiconductor compound; a Group III-VI semiconductor compound; a Group I-III-VI semiconductor compound; a Group IV-VI semiconductor compound; a Group IV element or compound; or any combination thereof.

Examples of the Group II-VI semiconductor compound include: a binary compound, such as CdSe, CdTe, ZnS, ZnSe, ZnTe, ZnO, HgS, HgSe, HgTe, MgSe, and/or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and/or MgZnS; a quaternary compound, such as CdZnSeS, CdZnSeTe, CdZnSTe, CdHgSeS, CdHgSeTe, CdHgSTe, HgZnSeS, HgZnSeTe, and/or HgZnSTe; or any combination thereof.

Examples of the Group III-V semiconductor compounds include: a binary compound, such as GaN, GaP, GaAs, GaSb, AlN, AlP, AlAs, AlSb, InN, InP, InAs, and/or InSb; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, and/or GaAlNP; a quaternary compound, such as GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, and/or InAlPSb; or any combination thereof. The Group III-V semiconductor compounds may further include a Group II element. Examples of the Group III-V semiconductor compounds further including a Group II element include InZnP, InGaZnP, and InAlZnP.

Examples of the Group III-VI semiconductor compound include: a binary compound, such as GaS, GaSe, $Ga_2Se_3$, GaTe, InS, InSe, $In_2Se_3$, and/or InTe; a ternary compound, such as $InGaS_3$, and/or $InGaSe_3$; or any combination thereof.

Examples of the Groups I-III-VI semiconductor compounds include: a ternary compound, such as AgInS, $AgInS_2$, CuInS, $CuInS_2$, $CuGaO_2$, $AgGaO_2$, and/or $AgAlO_2$; or any combination thereof.

Examples of the Group IV-VI semiconductor compounds include: a binary compound, such as SnS, SnSe, SnTe, PbS, PbSe, and/or PbTe; a ternary compound, such as SnSeS, SnSeTe, SnSTe, PbSeS, PbSeTe, PbSTe, SnPbS, SnPbSe, and/or SnPbTe; a quaternary compound, such as SnPbSSe, SnPbSeTe, and/or SnPbSTe; or any combination thereof.

Examples of the Group IV element or compound include: a single element, such as Si or Ge; a binary compound, such as SiC and/or SiGe; or any combination thereof.

Each element included in the multi-element compound such as the binary compound, a ternary compound, and a quaternary compound may be present, in a particle, at a uniform concentration or a non-uniform concentration.

In one or more embodiments, the quantum dot may have a single structure having a uniform (e.g., substantially uniform) concentration of each element included in the corresponding quantum dot or a dual structure of a core-shell. For example, the material included in the core may be different from the material included in the shell.

The shell of the quantum dot may function as a protective layer for maintaining semiconductor characteristics by preventing or reducing chemical degeneration of the core and/or may function as a charging layer for imparting electrophoretic characteristics to the quantum dot. The shell may be a single layer or a multilayer. An interface between the core and the shell may have a concentration gradient in which the concentration of elements existing in the shell decreases along a direction toward the center.

Examples of the shell of the quantum dot include a metal or non-metal oxide, a semiconductor compound, or any combination thereof. Examples of the oxide of metal or non-metal include: a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO; a ternary compound, such as $MgAl_2O_4$, $CoFe_2O_4$, $NiFe_2O_4$, and/or $CoMn_2O_4$; or any combination thereof. Examples of the semiconductor compound include: as described herein, Group II-VI semiconductor compounds; Group III-V semiconductor compounds; Group III-VI semiconductor compounds; Group I-III-VI semiconductor compounds; Group IV-VI semiconductor compounds; or any combination thereof. For example, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWFIM) of an emission wavelength spectrum of the quantum dot may be equal to or less than about 45 nm, for example, equal to or less than about 40 nm, and for example, equal to or less than about 30 nm. When the FWFIM of the emission wavelength spectrum of the quantum dot is within these ranges, color purity and/or color reproduction may be improved. In addition, light emitted through such quantum dots is irradiated in omnidirection (e.g., substantially every direction). Accordingly, a wide viewing angle may be increased.

In addition, the quantum dot may be, for example, a spherical, pyramidal, multi-arm, or cubic nanoparticle, a nanotube, a nanowire, a nanofiber, and/or nanoplate particle.

By adjusting the size of the quantum dot, the energy band gap may also be adjusted, thereby obtaining light of various suitable wavelengths in the quantum dot emission layer. Therefore, by using quantum dots of different sizes, a light-emitting device that emits light of various suitable wavelengths may be implemented. In more detail, the size of the quantum dot may be selected to emit red, green, and/or blue light. In addition, the size of the quantum dot may be adjusted such that light of various suitable colors are combined to emit white light.

Electron Transport Region in Interlayer 130

The electron transport region may have: i) a single-layered structure including (e.g., consisting of) a single layer including (e.g., consisting of) a single material, ii) a single-layered structure including (e.g., consisting of) a single layer including (e.g., consisting of) a plurality of different materials, or iii) a multi-layered structure including a plurality of layers including different materials.

The electron transport region may include a buffer layer, a hole blocking layer, an electron control layer, an electron transport layer, an electron injection layer, or any combination thereof.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, in each structure, layers are sequentially stacked on the emission layer.

The electron transport region (for example, the buffer layer, the hole blocking layer, the electron control layer, or the electron transport layer in the electron transport region) may include a metal-free compound including at least one π electron-deficient nitrogen-containing $C_1$-$C_{60}$ cyclic group.

In an embodiment, the electron transport region may include a compound represented by Formula 601:

$$[Ar_{601}]_{xe11}-[(L_{601})_{xe1}-R_{601}]_{xe21}$$ Formula 601 wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$carbocyclic group unsubstituted or substituted with at least one $R_{10a}$, a $C_1$-$C_{60}$ heterocyclic group unsubstituted or substituted with at least one $R_{10a}$, —Si($Q_{601}$)($Q_{602}$)($Q_{603}$), —C(=O)($Q_{601}$), —S(=O)$_2$($Q_{601}$), or —P(=O)($Q_{601}$)($Q_{602}$), $Q_{601}$ to $Q_{603}$ may each be the same as described in connection with $Q_1$, xe21 may be 1, 2, 3, 4, or 5, and at least one of $Ar_{601}$, $L_{601}$ and $R_{601}$ may each independently be a π electron-deficient nitrogen-containing $C_1$-$C_{60}$ cyclic group unsubstituted or substituted with at least one $R_{10a}$.

In one or more embodiments, when xe11 in Formula 601 is 2 or more, two or more of $Ar_{601}$(s) may be linked to each other via a single bond.

In one or more embodiments, $Ar_{601}$ in Formula 601 may be a substituted or unsubstituted anthracene group.

In one or more embodiments, the electron transport region may include a compound represented by Formula 601-1:

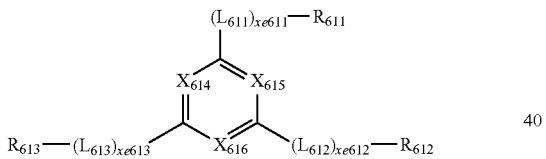

Formula 601-1 wherein, in Formula 601-1, $X_{614}$ may be N or C($R_{614}$), $X_{615}$ may be N or C($R_{615}$), $X_{616}$ may be N or C($R_{616}$), and at least one of $X_{614}$ to $X_{616}$ may be N, $L_{611}$ to $L_{613}$ may each be the same as described in connection with $L_{601}$, xe611 to xe613 may each be the same as described in connection with xe1, $R_{611}$ to $R_{613}$ may each be the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$carbocyclic group unsubstituted or substituted with at least one $R_{10a}$, or a $C_1$-$C_{60}$ heterocyclic group unsubstituted or substituted with at least one $R_{10a}$.

For example, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), Alq$_3$, BAlq, TAZ, NTAZ, or any combination thereof:

ET1

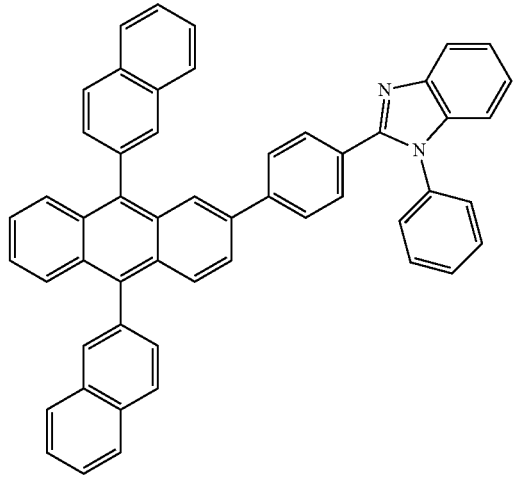

ET2

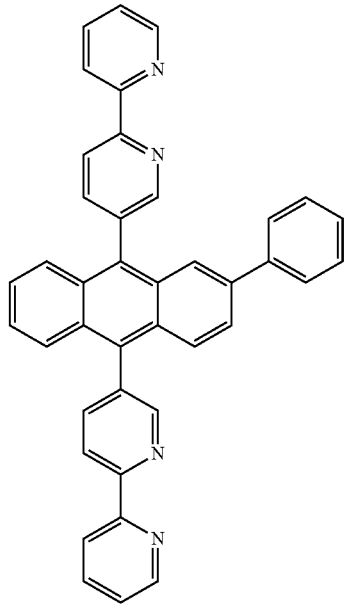

ET3

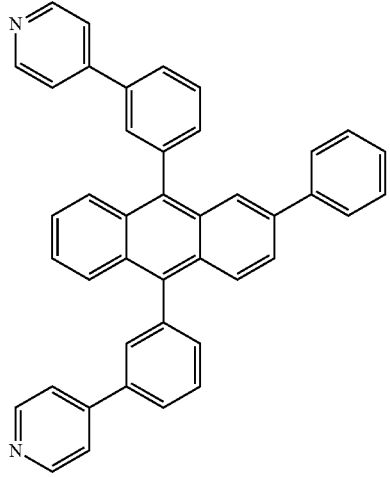

ET4
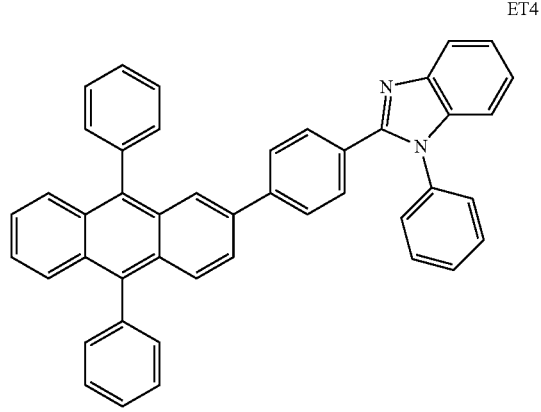
ET5
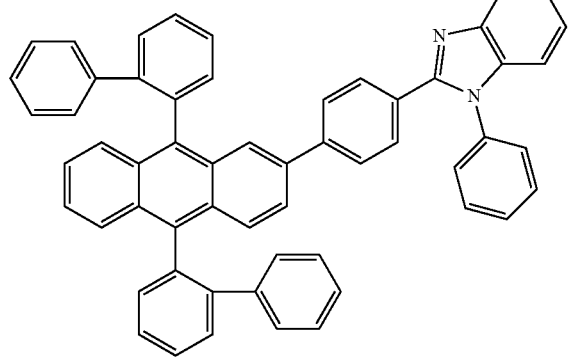
ET6
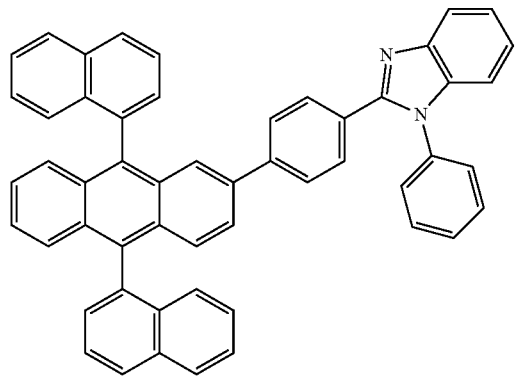
ET7
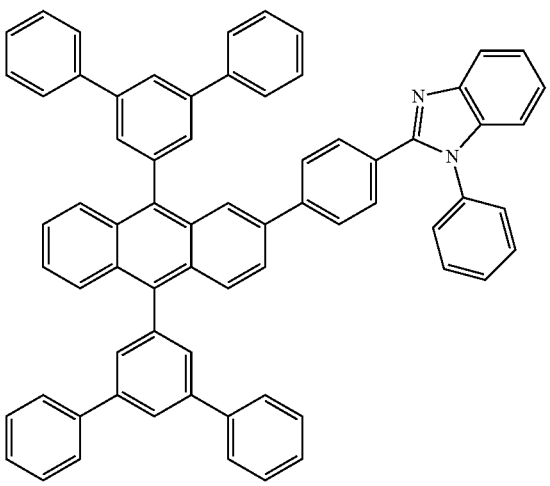
ET8
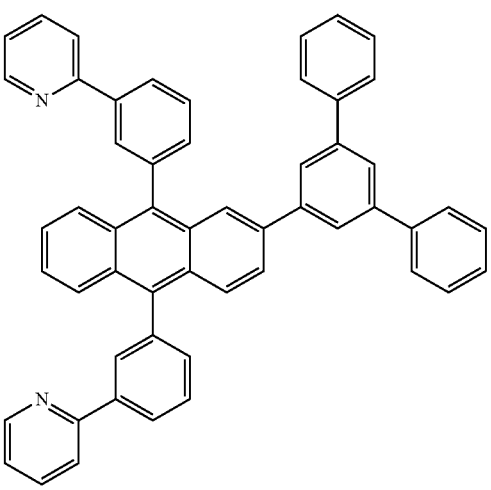
ET9
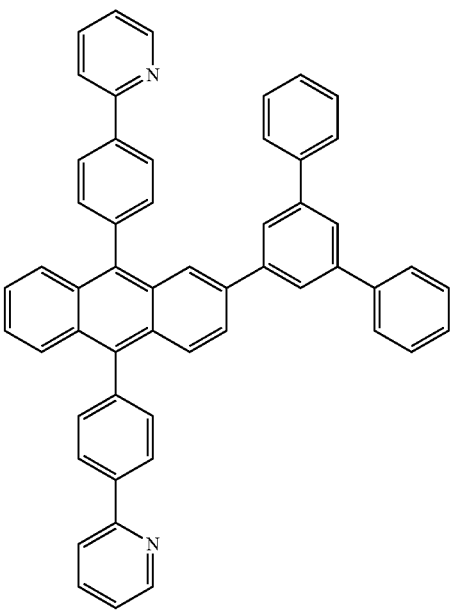

ET10
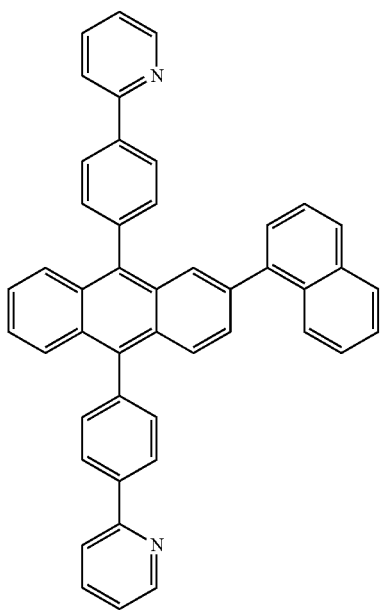
ET11
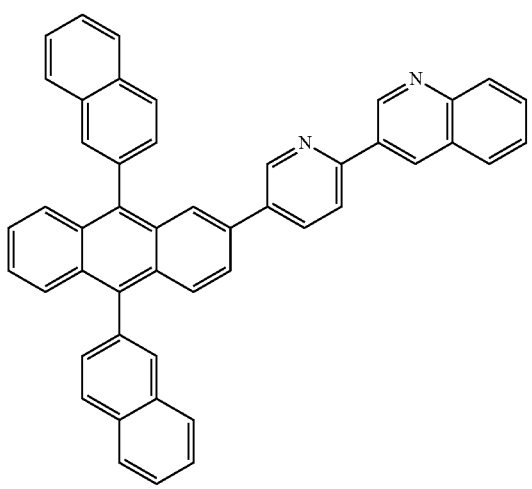
ET12
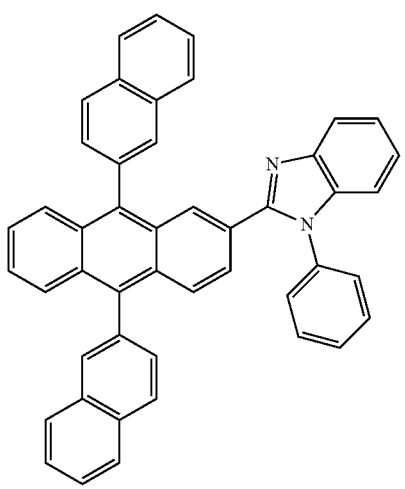
ET13
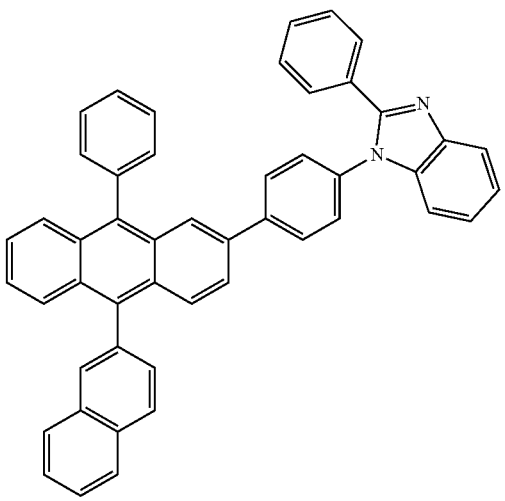
ET14
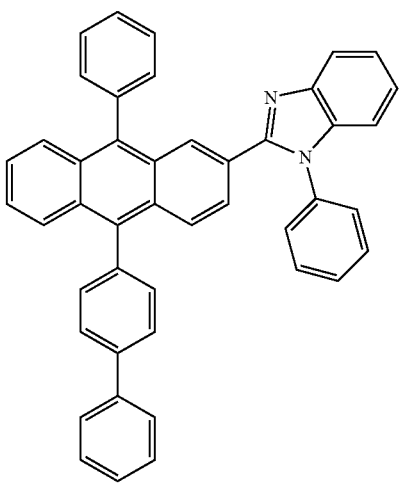
ET15
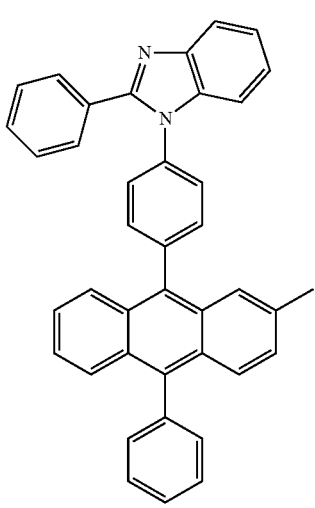

ET16
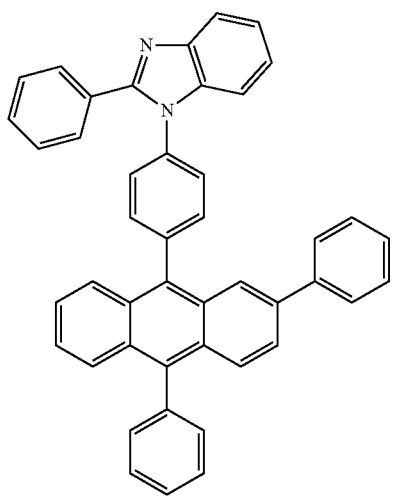
ET19
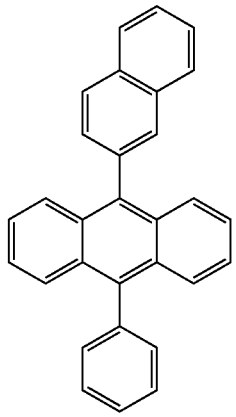
ET17
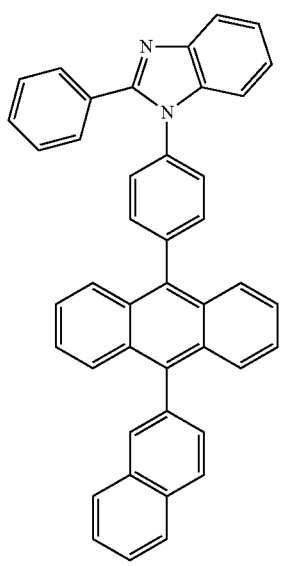
ET20
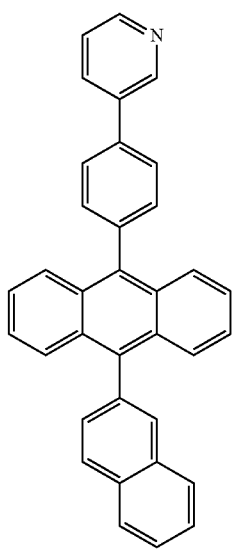
ET18
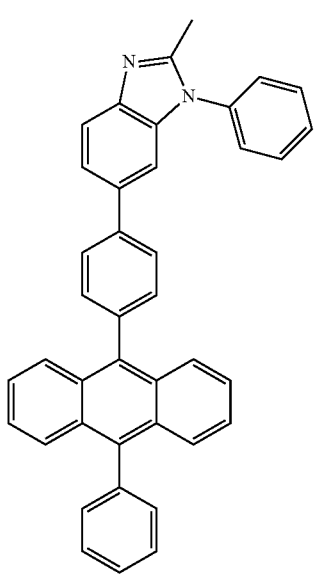
ET21
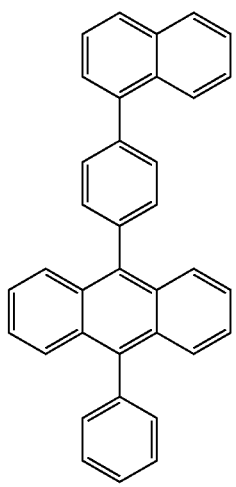

ET22
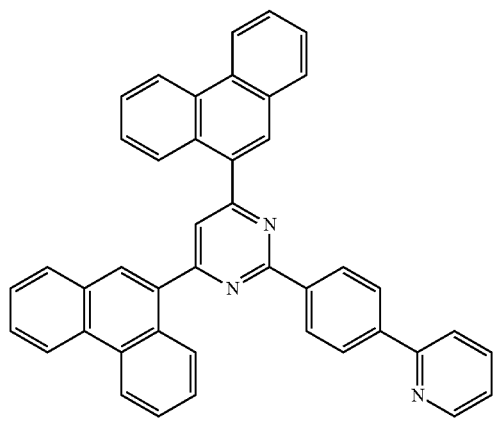
ET25
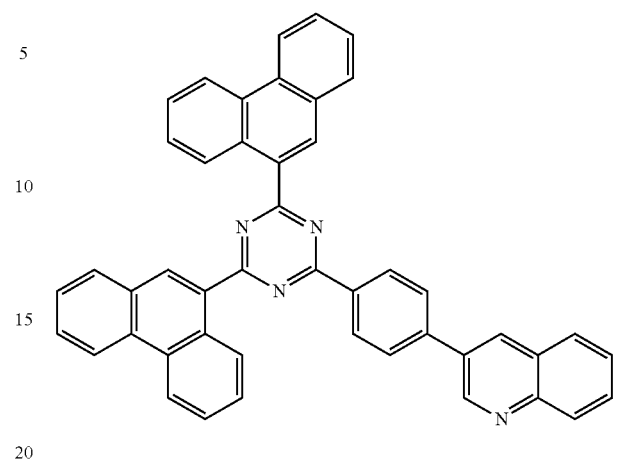
ET23
ET26
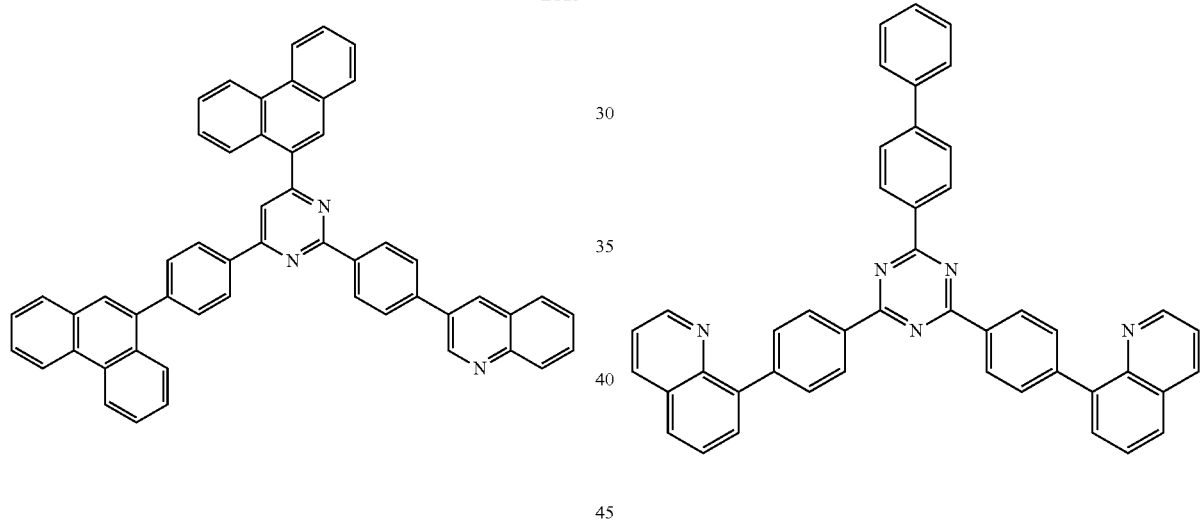
ET24
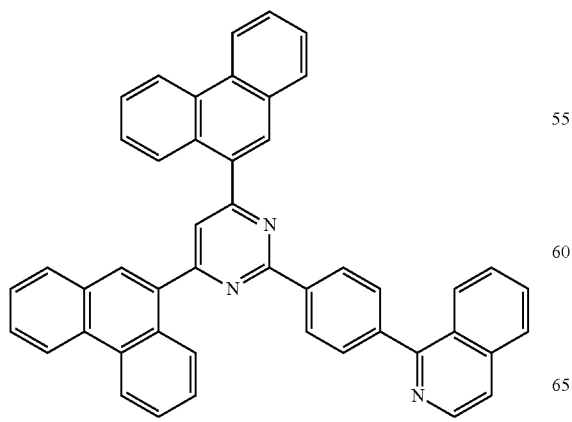
ET27
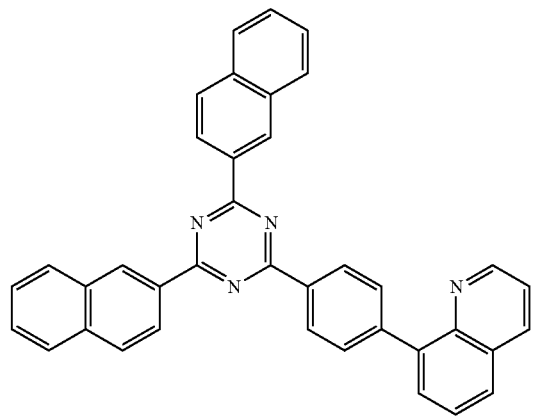

ET28
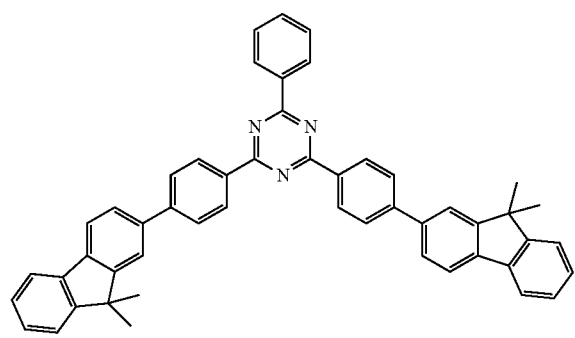
ET29
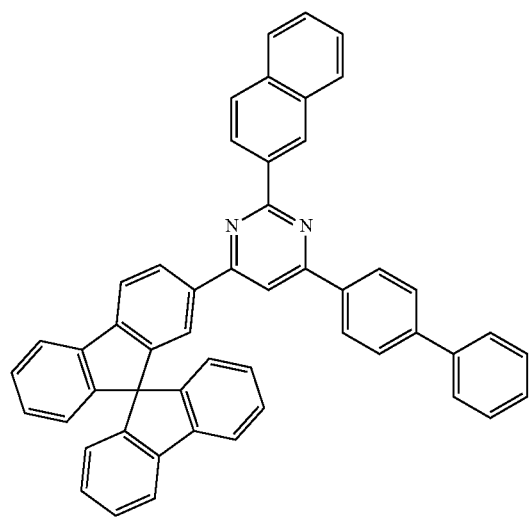
ET30
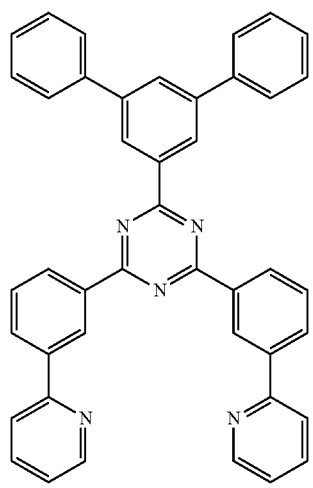
ET31
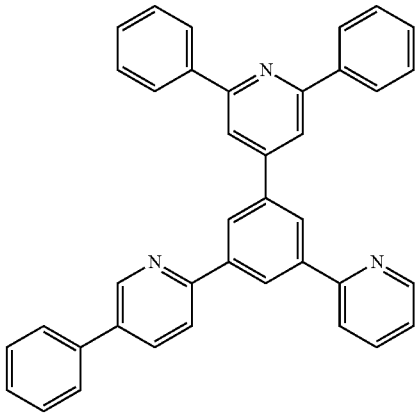
ET32
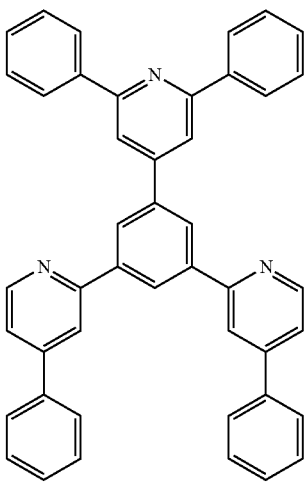
ET33
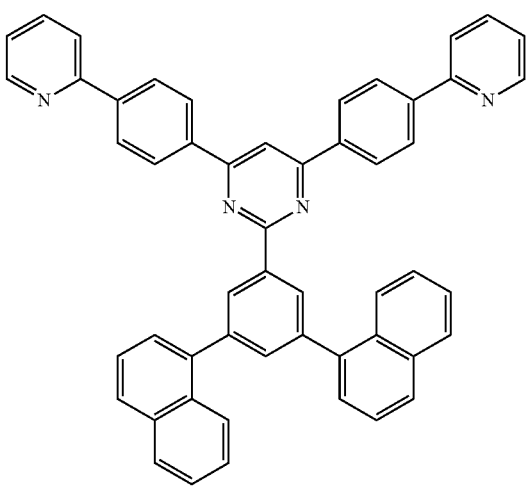

ET34
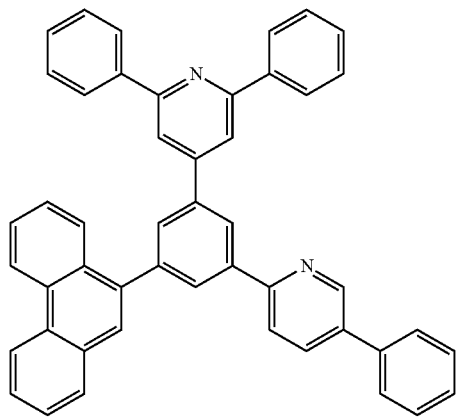
ET38
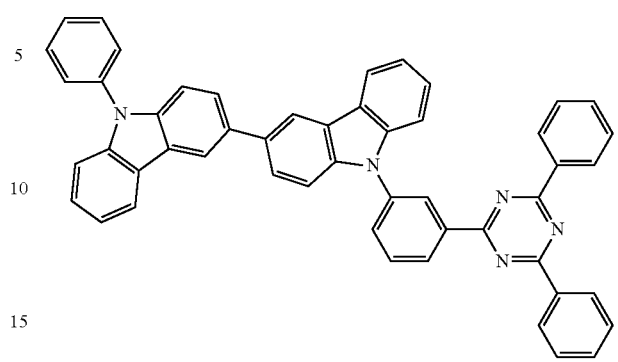
ET35
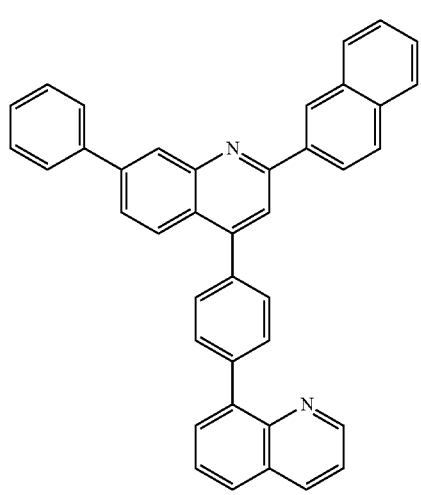
ET39
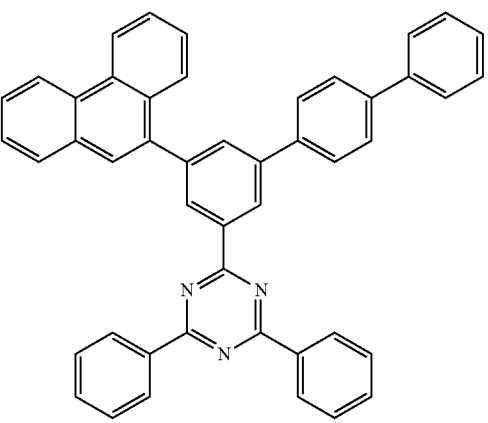
ET36
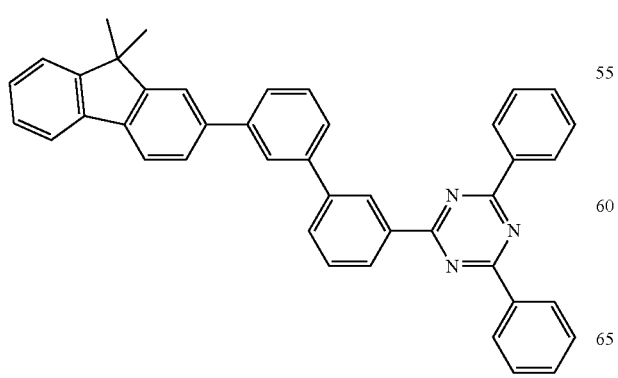
ET37
ET40
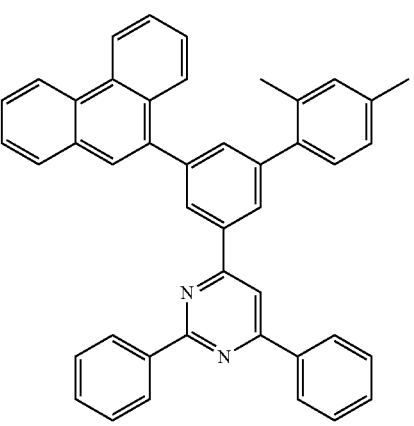

ET41
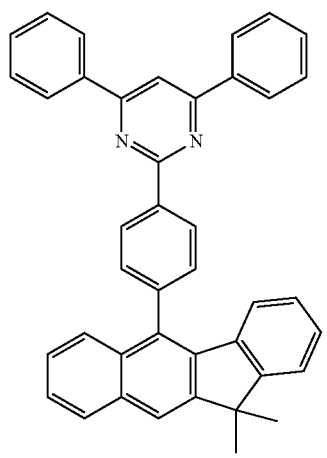
ET42
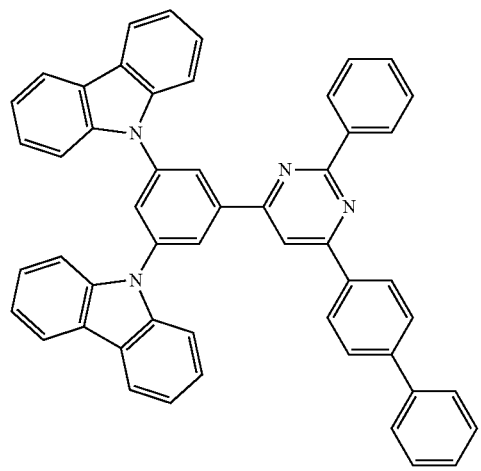
ET43
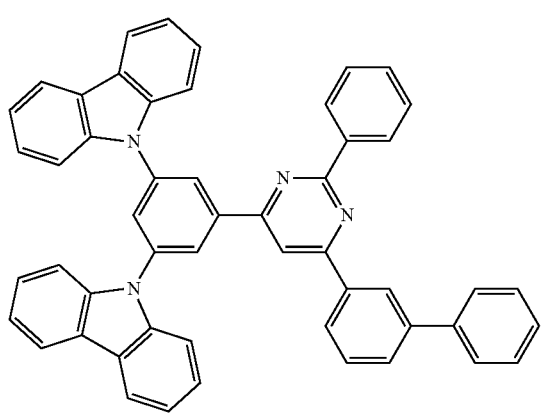
ET44
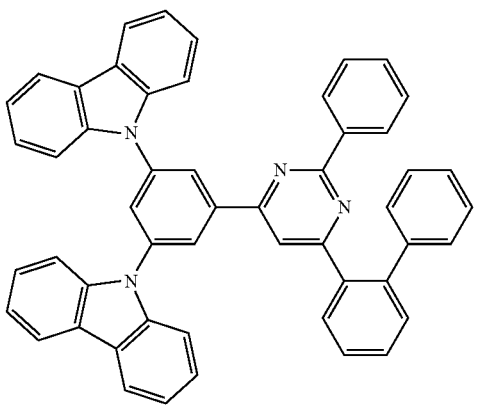
ET45
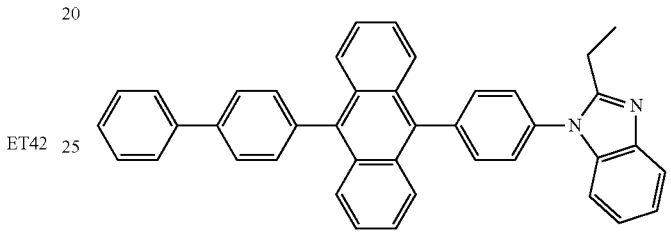
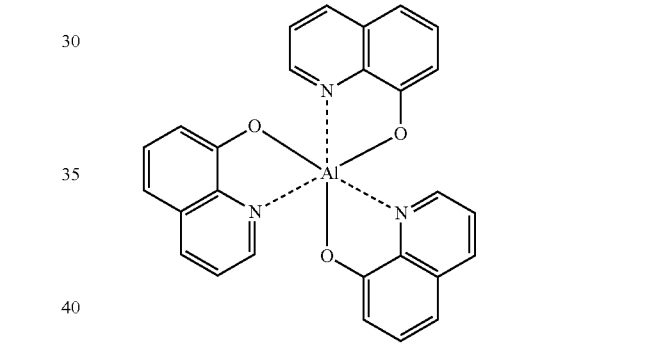
Alq3
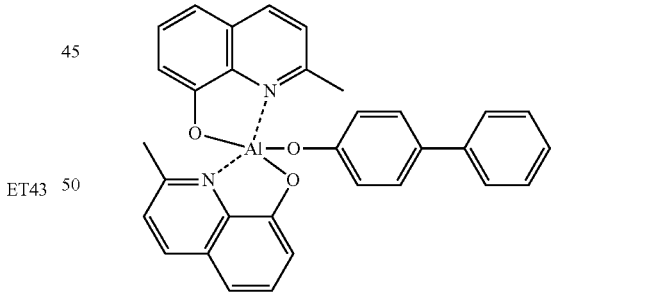
BAlq
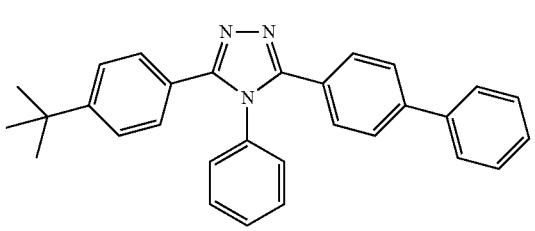
TAZ

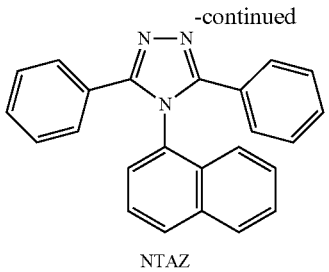

NTAZ

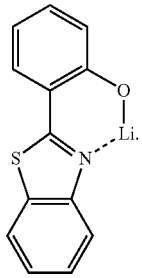

ET-D2

A thickness of the electron transport region may be in a range of about 160 Å to about 5,000 Å, for example, about 100 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be in a range of about 20 Å to about 1,000 Å, for example, about 30 Å to about 300 Å, and a thickness of the electron transport layer may be in a range of about 100 Å to about 1,000 Å, for example, about 150 Å to about 500 Å. When the thickness of the buffer layer, the hole blocking layer, the electron control layer, the electron transport layer, and/or the electron transport layer are within these ranges, suitable or satisfactory hole transporting characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth-metal complex, or any combination thereof. A metal ion of the alkali metal complex may be a Li ion, a Na ion, a K ion, a Rb ion, or a Cs ion, and a metal ion of the alkaline earth-metal complex may be a Be ion, a Mg ion, a Ca ion, a Sr ion, or a Ba ion. A ligand coordinated with the metal ion of the alkali metal complex or the alkaline earth-metal complex may be a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, a cyclopentadiene, or any combination thereof.

For example, the metal-containing material may include a Li complex. The Li complex may include, for example, Compound ET-D1 (LiQ) or ET-D2:

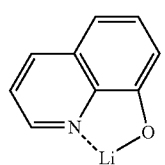

ET-D1

The electron transport region may include an electron injection layer that facilitates the injection of electrons from the second electrode 150. The electron injection layer may directly contact the second electrode 150.

The electron injection layer may have: i) a single-layered structure including (e.g., consisting of) a single layer including (e.g., consisting of) a single material, ii) a single-layered structure including (e.g., consisting of) a single layer including (e.g., consisting of) a plurality of different materials, or iii) a multi-layered structure including a plurality of layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may include oxides and halides (for example, fluorides, chlorides, bromides, and/or iodides) of the alkali metal, the alkaline earth metal, and the rare earth metal, telluride, or any combination thereof.

The alkali metal-containing compound may include alkali metal oxides, such as $Li_2O$, $Cs_2O$, and/or $K_2O$, and alkali metal halides, such as LiF, NaF, CsF, KF, LiI, NaI, CsI, and/or KI, or any combination thereof. The alkaline earth metal-containing compound may include an alkaline earth metal compound, such as BaO, SrO, CaO, $Ba_xSr_{1-x}O$ (x is a real number that satisfies the condition of 0<x<1), and/or $Ba_xCa_{1-x}O$ (x is a real number that satisfies the condition of 0<x<1). The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. For example, the rare earth metal-containing compound may include lanthanide metal telluride. Examples of the lanthanide metal telluride include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii) as a ligand linked to the metal ion, for example, hydroxyquinoline, hydroxyan isoquinoline, hydroxybenzoquinoline, hydroxyacridine, hydroxyphenanthridine, hydroxyphenyloxazole, hydroxyphenylthiazole, hydroxydiphenyloxadiazole, hydroxydiphenylthiadiazole, hydroxyphenylpyridine, hydroxyphenyl benzimidazole, hydroxyphenylbenzothiazole, bipyridine, phenanthroline, cyclopentadiene, or any combination thereof.

The electron injection layer may include (e.g., consist of) an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof, or may further include an organic material (for example, a compound represented by Formula 601).

In an embodiment, the electron injection layer may include (e.g., consist of) i) an alkali metal-containing compound (for example, an alkali metal halide), or ii) a) an alkali metal-containing compound (for example, an alkali metal halide); and b) alkali metal, alkaline earth metal, rare earth metal, or any combination thereof. In one or more embodiments, the electron injection layer may include a KI:Yb co-deposited layer and/or a RbI:Yb co-deposited layer.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within these ranges, suitable or satisfactory electron injection characteristics may be obtained without a substantial increase in driving voltage.

Second Electrode 150

The second electrode 150 may be on the interlayer 130 having such a structure. The second electrode 150 may be a cathode, which is an electron injection electrode, and as a material for forming the second electrode 150, a metal, an alloy, an electrically conductive compound, or any combination thereof, each having a low work function, may be used.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure or a multi-layered structure including two or more layers.

Capping Layer

A first capping layer may be outside the first electrode 110, and/or a second capping layer may be outside the second electrode 150. In more detail, the light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

Light generated in the emission layer of the interlayer 130 of the light-emitting device 10 may be extracted toward the outside through the first electrode 110, which is a semi-transmissive electrode or a transmissive electrode, and the first capping layer, and light generated in the emission layer of the interlayer 130 of the light-emitting device 10 may be extracted toward the outside through the second electrode 150, which is a semi-transmissive electrode or a transmissive electrode, and the second capping layer.

The first capping layer and the second capping layer may increase external luminescence efficiency according to the principle of constructive interference. Accordingly, the light extraction efficiency of the light-emitting device 10 is increased, so that the luminescence efficiency of the light-emitting device 10 may be improved.

Each of the first capping layer and the second capping layer may include a material having a refractive index of equal to or greater than 1.6 (at a wavelength of 589 nm).

The first capping layer and the second capping layer may each independently include an organic capping layer including an organic material, an inorganic capping layer including an inorganic material, and/or a composite capping layer including an organic material and an inorganic material.

At least one selected from the first capping layer and the second capping layer may each independently include a carbocyclic compound, a heterocyclic compound, an amine group-containing compound, a porphyrine derivative, a phthalocyanine derivative, a naphthalocyanine derivative, an alkali metal complex, an alkaline earth-metal complex, or a combination thereof. The carbocyclic compound, the heterocyclic compound, and the amine group-containing compound may be optionally substituted with a substituent containing O, N, S, Se, Si, F, Cl, Br, I, or any combination thereof.

In an embodiment, at least one of the first capping layer and the second capping layer may each independently include an amine group-containing compound.

In one or more embodiments, at least one selected from the first capping layer and second capping layer may each independently include a compound represented by Formula 201, a compound represented by Formula 202, or any combination thereof.

In one or more embodiments, at least one selected from the first capping layer and the second capping layer may each independently include one of Compounds HT28 to HT33, one of Compounds CP1 to CP6, β-NPB, or any combination thereof:

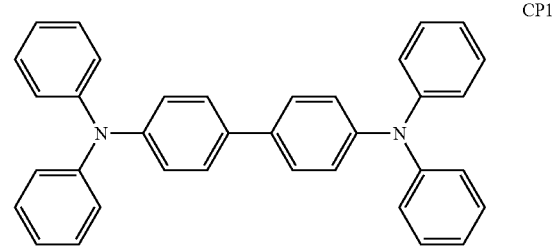

CP1

CP2

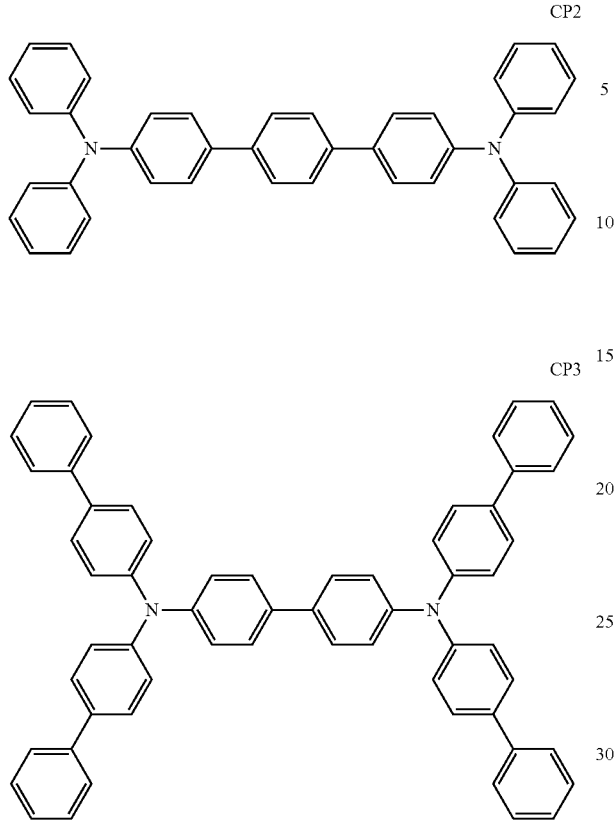

CP3

CP4

CP5

CP6

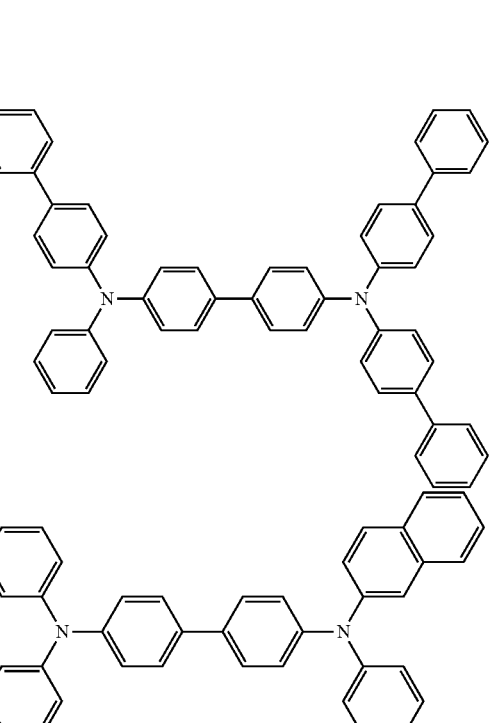

β-NPB

Electronic Apparatus

The light-emitting device may be included in various suitable electronic apparatuses. For example, the electronic apparatus including the light-emitting device may be a light-emitting apparatus, an authentication apparatus, and/or the like.

The electronic apparatus (for example, light-emitting apparatus) may further include, in addition to the light-emitting device, i) a color filter, ii) a color conversion layer, or iii) a color filter and a color conversion layer. The color filter and/or the color conversion layer may be in at least one traveling direction of light emitted from the light-emitting device. For example, light emitted from the light-emitting device may be blue light and/or white light. The light-emitting device may be the same as described above. In an embodiment, the color conversion layer may include quantum dots. The quantum dots may be the same as described elsewhere in the present specification.

The electronic apparatus may include a first substrate. The first substrate may include a plurality of subpixel areas, the color filter may include a plurality of color filter areas respectively corresponding to the plurality of subpixel areas, and the color conversion layer may include a plurality of color conversion areas respectively corresponding to the subpixel areas.

A pixel-defining film may be between the plurality of subpixel areas to define each of the subpixel areas.

The color filter may further include the color filter areas and a light-blocking pattern between adjacent color filter areas of the color filter areas, and the color conversion layer may further include the color conversion areas and a light-blocking pattern between adjacent color conversion areas of the color conversion areas.

The color filter areas (or, a plurality of color conversion areas) may include: a first area that emits a first-color light; a second area that emits a second-color light; and/or a third area that emits a third-color light, and the first-color light, the second-color light, and/or the third-color light may have different maximum luminescence wavelengths from one another. For example, the first color light may be red light, the second color light may be green light, and the third color light may be blue light. For example, the color filter areas (or the color conversion areas) may include quantum dots. In more detail, the first area may include red quantum dots, the second area may include green quantum dots, and the third area may not include quantum dots. The quantum dots may be the same as described elsewhere in the present specification. Each of the first area, the second area, and/or the third area may further include a scatterer.

For example, the light-emitting device may emit first light, the first area may absorb the first light to emit a first first-color light, the second area may absorb the first light to emit a second first-color light, and the third area may absorb the first light to emit a third first-color light. In this regard, the first first-color light, the second first-color light, and the third first-color light may have different maximum emission wavelengths from one another. In more detail, the first light may be blue light, the first first-color light may be red light, the second first-color light may be green light, and the third first-color light may be blue light.

The electronic apparatus may further include a thin-film transistor in addition to the light-emitting device as described above. The thin-film transistor may include a source electrode, a drain electrode, and an activation layer, wherein any one selected from the source electrode and the drain electrode may be electrically coupled to any one selected from the first electrode and the second electrode of the light-emitting device.

The thin-film transistor may further include a gate electrode, a gate insulation layer, and/or the like.

The active layer may include crystalline silicon, amorphous silicon, organic semiconductor, oxide semiconductor, and/or the like.

The electronic apparatus may further include a sealing portion for sealing the light-emitting device. The sealing portion may be between the color filter and/or the color conversion layer and the light-emitting device. The sealing portion allows light from the light-emitting device 10 to be extracted to the outside, while concurrently (e.g., simultaneously) preventing or reducing penetration of ambient air and/or moisture into the light-emitting device 10. The sealing portion may be a sealing substrate including a transparent glass substrate and/or a plastic substrate. The sealing portion may be a thin-film encapsulation layer including at least one layer of an organic layer and/or an inorganic layer. When the sealing portion is a thin-film encapsulation layer, the electronic apparatus may be flexible.

On the sealing portion, in addition to the color filter and/or the color conversion layer, various suitable functional layers may be further arranged according to the use of the electronic device. The functional layers may include a touch screen layer, a polarizing layer, and/or the like. The touch screen layer may be a pressure-sensitive touch screen layer, a capacitive touch screen layer, and/or an infrared touch screen layer. The authentication apparatus may be, for example, a biometric authentication apparatus for authenticating an individual by using biometric information of a biometric body (for example, a fingertip, a pupil, and/or the like).

The authentication apparatus may further include, in addition to the light-emitting device, a biometric information collector.

The electronic apparatus may be applied to various suitable displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement apparatuses, pulse wave measurement apparatuses, electrocardiogram displays, ultrasonic diagnostic apparatuses, and/or endoscope displays), fish finders, various suitable measuring instruments, meters (for example, meters for a vehicle, an aircraft, and/or a vessel), projectors, and/or the like.

Figure 2:
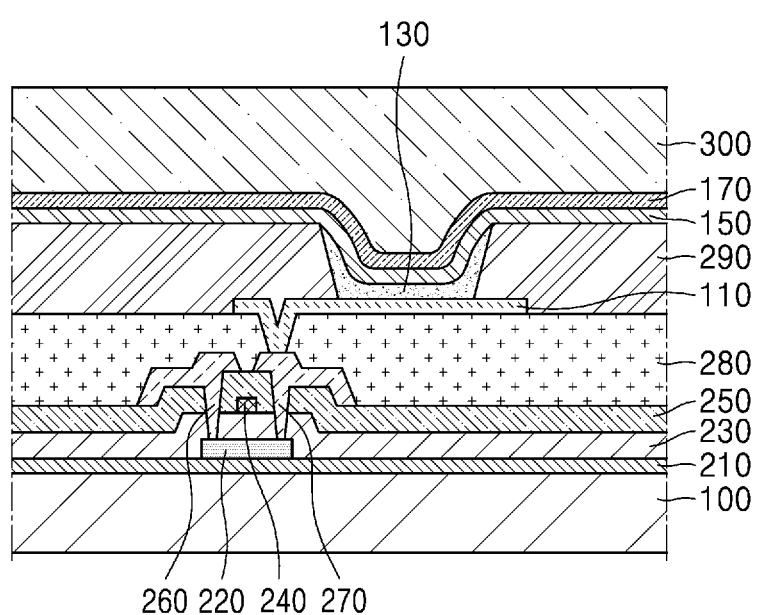
FIG. 2 is a schematic cross-sectional view of a light-emitting apparatus according to an embodiment.
Figure 3:
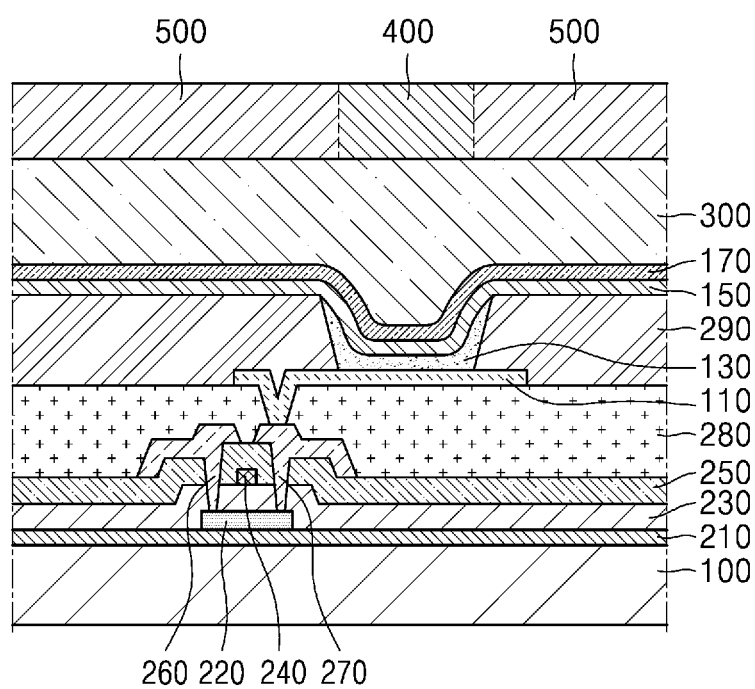
FIG. 3 is a schematic cross-sectional view of a light-emitting apparatus according to another embodiment.

Description of FIGS. 2 and 3

FIG. 2 is a cross-sectional view showing a light-emitting apparatus according to an embodiment of the present disclosure.

The light-emitting apparatus of FIG. 2 includes a substrate 100, a thin-film transistor (TFT), a light-emitting device, and an encapsulation portion 300 that seals light-emitting device.

The substrate 100 may be a flexible substrate, a glass substrate, and/or a metal substrate. A buffer layer 210 may be on the substrate 100. The buffer layer 210 prevents or reduces the penetration of impurities through the substrate 100 and may provide a flat surface on the substrate 100.

A TFT may be on the buffer layer 210. The TFT may include an activation layer 220, a gate electrode 240, a source electrode 260, and a drain electrode 270.

The activation layer 220 may include an inorganic semiconductor such as silicon and/or polysilicon, an organic semiconductor, and/or an oxide semiconductor, and may include a source region, a drain region and a channel region.

A gate insulating film 230 for insulating the activation layer 220 from the gate electrode 240 may be on the activation layer 220, and the gate electrode 240 may be on the gate insulating film 230.

An interlayer insulating film 250 may be on the gate electrode 240. The interlayer insulating film 250 is between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be on the interlayer insulating film 250. The interlayer insulating film 250 and the gate insulating film 230 may be formed to expose the source region and the drain region of the activation layer 220, and the source electrode 260 and the drain electrode 270 may be in contact (e.g., physical contact) with the exposed portions of the source region and the drain region of the activation layer 220.

The TFT may be electrically coupled to the light-emitting device to drive the light-emitting device, and is covered by a passivation layer 280. The passivation layer 280 may include an inorganic insulating film, an organic insulating film, or a combination thereof. The light-emitting device may be provided on the passivation layer 280. The light-emitting device includes the first electrode 110, the interlayer 130, and the second electrode 150.

The first electrode 110 may be on the passivation layer 280. The passivation layer 280 does not completely cover the drain electrode 270 and exposes a portion of the drain electrode 270, and the first electrode 110 may be coupled to the exposed portion of the drain electrode 270.

A pixel defining layer 290 including an insulating material may be on the first electrode 110. The pixel defining layer 290 may expose a certain region of the first electrode 110, and the interlayer 130 may be formed in the exposed region of the first electrode 110. The pixel defining layer 290 may be a polyimide and/or polyacryl-based organic film. In one or more embodiments, at least some layers of the interlayer 130 may extend beyond the upper portion of the pixel defining layer 290 and may thus be in the form of a common layer.

The second electrode 150 may be on the interlayer 130, and a capping layer 170 may be additionally formed on the second electrode 150. The capping layer 170 may cover the second electrode 150.

The encapsulation portion 300 may be on the capping layer 170. The encapsulation portion 300 may be on a light-emitting device and protects the light-emitting device from moisture and/or oxygen. The encapsulation portion 300 may include: an inorganic film including silicon nitride (SiNx), silicon oxide (SiOx), indium tin oxide, indium zinc oxide, or a combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate or polyacrylic acid), an epoxy-based resin (for example, aliphatic glycidyl ether (AGE)), or a combination thereof; or a combination of an inorganic film and an organic film.

FIG. 3 is a cross-sectional view showing a light-emitting apparatus according to another embodiment of the present disclosure.

The light-emitting apparatus of FIG. 3 is substantially the same as the light-emitting apparatus of FIG. 2, except that a light-blocking pattern 500 and a functional region 400 are additionally on the encapsulation portion 300. The functional region 400 may be i) a color filter area, ii) a color conversion area, or iii) a combination of the color filter area and the color conversion area. In an embodiment, the light-emitting device included in the light-emitting apparatus of FIG. 3 may be a tandem light-emitting device.

Preparation Method

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, the emission layer, and layers constituting the electron transport region are formed by vacuum deposition, the deposition may be performed at a deposition temperature of about 100° C. to about 500° C., a vacuum degree of about $10^{t8}$ torr to about $10^{t3}$ torr, and a deposition speed of about 0.01 Å/sec to about 100 Å/sec by taking into account a material to be included in a layer to be formed and the structure of a layer to be formed.

Definition of at Least Some of the Terms

The term "$C_3$-$C_{60}$ carbocyclic group," as used herein, refers to a cyclic group that consists of carbon only and has three to sixty carbon atoms, and the term "$C_1$-$C_{60}$ heterocyclic group," as used herein, refers to a cyclic group that has one to sixty carbon atoms and further includes, in addition to carbon, a heteroatom. The $C_3$-$C_{60}$ carbocyclic group and the $C_1$-$C_{60}$ heterocyclic group may each be a monocyclic group that consists of one ring or a polycyclic group in which two or more rings are condensed with each other (e.g., combined together with each other). For example, the number of ring-forming atoms of the $C_1$-$C_{60}$ heterocyclic group may be from 3 to 61.

The term "cyclic group," as used herein, includes the $C_3$-$C_{60}$ carbocyclic group and the $C_1$-$C_{60}$ heterocyclic group.

The term "π electron-rich $C_3$-$C_{60}$ cyclic group," as used herein, refers to a cyclic group that has three to sixty carbon atoms and does not include *—N=*' as a ring-forming moiety, and the term "π electron-deficient nitrogen-containing $C_1$-$C_{60}$ cyclic group," as used herein, refers to a heterocyclic group that has one to sixty carbon atoms and includes *—N=*' as a ring-forming moiety.

For example, the $C_3$-$C_{60}$ carbocyclic group may be i) a group T1 or ii) a condensed cyclic group in which two or more groups T1 are condensed with (e.g., combined together with) each other (for example, a cyclopentadiene group, an adamantane group, a norbornane group, a benzene group, a pentalene group, a naphthalene group, an azulene group, an indacene group, acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be i) a group T2, ii) a condensed cyclic group in which two or more groups T2 are condensed with (e.g., combined together with) each other, or iii) a condensed cyclic group in which at least one group T2 and at least one group T1 are condensed with (e.g., combined together with) each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothieno dibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, or an azadibenzofuran group), the π electron-rich $C_3$-$C_{60}$ cyclic group may be i) a group T1, ii) a condensed cyclic group in which two or more groups T1 are condensed with (e.g., combined together with) each other, iii) a group T3, iv) a condensed cyclic group in which two or more groups T3 are condensed with (e.g., combined together with) each other, or v) a condensed cyclic group in which at least one group T3 and at least one group T1 are condensed with (e.g., combined together with) each other (for example, a $C_3$-$C_{60}$ carbocyclic group, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, or a benzothienodibenzothiophene group), the π electron-deficient nitrogen-containing $C_1$-$C_{60}$ cyclic group may be i) a group T4, ii) a condensed cyclic group in which two or more groups T4 are condensed with (e.g., combined together with) each other, iii) a condensed cyclic group in which at least one group T4 and at least one group T1 are condensed with (e.g., combined together with) each other, iv) a condensed cyclic group in which at least one group T4 and at least one group T3 are condensed with (e.g., combined together with) each other, or v) a condensed cyclic group in which at least one group T4, at least one group T1, and at least one group T3 are condensed with (e.g., combined together with) each other (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, or an azadibenzofuran group), the group T1 may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane group (or, a bicyclo[2.2.1]heptane group), a norbornene group, a bicyclo[1.1.1]pentane group, a bicyclo[2.1.1]hexane group, a bicyclo[2.2.2]octane group, or a benzene group, the group T2 may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group, the group T3 may be a furan group, a thiophene group, a 1H-pyrrole group, a silole group, or a borole group, and the group T4 may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group," "the $C_3$-$C_{60}$ carbocyclic group," "the $C_1$-$C_{60}$ heterocyclic group," "the π electron-rich $C_3$-$C_{60}$ cyclic group," or "the π electron-deficient nitrogen-containing $C_1$-$C_{60}$ cyclic group," as used herein, refer to a group that is condensed with (e.g., combined together with) a cyclic group, a monovalent group, a polyvalent group (for example, a divalent group, a trivalent group, a tetravalent group, or the like), according to the structure of a formula described with corresponding terms. For example, "a benzene group" may be a benzo group, a phenyl group, a phenylene group, or the like, which may be easily understand by one of ordinary skill in the art according to the structure of a formula including the "benzene group."

For example, examples of the monovalent $C_3$-$C_{60}$ carbocyclic group and the monovalent $C_1$-$C_{60}$ heterocyclic group may each include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the monovalent $C_1$-$C_{60}$ heterocyclic group include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group," as used herein, refers to a linear or branched aliphatic hydrocarbon monovalent group having 1 to 60 carbon atoms, and examples thereof are a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a monovalent hydrocarbon group having at least one carbon-carbon double bond at a main chain (e.g., in the middle) or at a terminal end (e.g., the terminus) of a $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a monovalent hydrocarbon group having at least one carbon-carbon triple bond at a main chain (e.g., in the middle) or at a terminal end (e.g., the terminus) of a $C_2$-$C_{60}$ alkyl group, and examples thereof include an ethynyl group, and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —O$A_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon cyclic group having 3 to 10 carbon atoms, and examples thereof are a cyclopropyl group, a cyclobutyl group, a cyclopentyl group, a cyclohexyl group, a cycloheptyl group, a cyclooctyl group, an adamantanyl group, a norbornanyl group (or a bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent cyclic group that further includes, in addition to a carbon atom, at least one heteroatom as a ring-forming atom and has 1 to 10 carbon atoms, and examples thereof are a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent cyclic group that has 3 to 10 carbon atoms and at least one carbon-carbon double bond in the ring thereof and no aromaticity (e.g., is not aromatic), and non-limiting examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent cyclic group that has, in addition to a carbon atom, at least one heteroatom as a ring-forming atom, 1 to 10 carbon atoms, and at least one carbon-carbon double bond in the cyclic structure thereof. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and the term "$C_6$-$C_{60}$ arylene group," as used herein, refers to a divalent group having a carbocyclic aromatic system having 6 to 60 carbon atoms. Examples of the $C_6$-$C_{60}$ aryl group include a fluorenyl group, a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the two or more rings may be condensed to each other (e.g., combined together with each other).

The term "$C_1$-$C_{60}$ heteroaryl group," as used herein, refers to a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group," as used herein, refers to a divalent group having a heterocyclic aromatic system that has, in addition to a carbon atom, at least one heteroatom as a ring-forming atom, and 1 to 60 carbon atoms. Examples of the $C_1$-$C_{60}$ heteroaryl group include a carbazolyl group, a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the two or more rings may be condensed with each other (e.g., combined together with each other).

The term "monovalent non-aromatic condensed polycyclic group," as used herein, refers to a monovalent group (for example, having 8 to 60 carbon atoms) having two or more rings condensed with each other (e.g., combined together with each other), only carbon atoms as ring-forming atoms, and no aromaticity in its entire molecular structure (e.g., is not aromatic when considered as a whole). Examples of the monovalent non-aromatic condensed polycyclic group include an indenyl group, a fluorenyl group, a spiro-bifluorenyl group, a benzofluorenyl group, an indenophenanthrenyl group, and an indenoanthracenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together with each other), at least one heteroatom other than carbon atoms, as a ring-forming atom, and no aromaticity in its entire molecular structure (e.g., is not aromatic when considered as a whole). Examples of the monovalent non-aromatic condensed heteropolycyclic group include a pyrrolyl group, a thiophenyl group, a furanyl group, an indolyl group, a benzoindolyl group, a naphthoindolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic condensed heteropolycyclic group," as used herein, refers to a divalent group having substantially the same structure as the monovalent non-aromatic condensed heteropolycyclic group.

The term "$C_6$-$C_{60}$ aryloxy group," as used herein, refers to —$OA_{102}$ (wherein $A_{102}$ is the $C_6$-$C_{60}$ aryl group), and the term "$C_6$-$C_{60}$ arylthio group," as used herein, refers to —$SA_{103}$ (wherein $A_{103}$ is the $C_6$-$C_{60}$ aryl group).

The term "$R_{10a}$," as used herein, may refer to:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof, or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

In the present specification, $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

The term "heteroatom," as used herein, refers to any atom other than a carbon atom. Examples of the heteroatom are O, S, N, P, Si, B, Ge, Se, and any combination thereof.

The term "Ph," as used herein, refers to a phenyl group, the term "Me," as used herein, refers to a methyl group, the term "Et," as used herein, refers to an ethyl group, the term "ter-Bu" or "Bu$^t$," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a substituted phenyl group having, as a substituent, a $C_6$-$C_{60}$ aryl group substituted with a $C_6$-$C_{60}$ aryl group.

* and *', as used herein, unless defined otherwise, each refer to a binding site to a neighboring atom in a corresponding formula.

Hereinafter, a compound according to embodiments and a light-emitting device according to embodiments will be described in more detail with reference to Synthesis Examples and Examples. The wording "B was used instead of A" used in describing Synthesis Examples refers to that an identical molar equivalent of B was used in place of A.

EXAMPLES

Synthesis Example 1: Synthesis of Compound 1

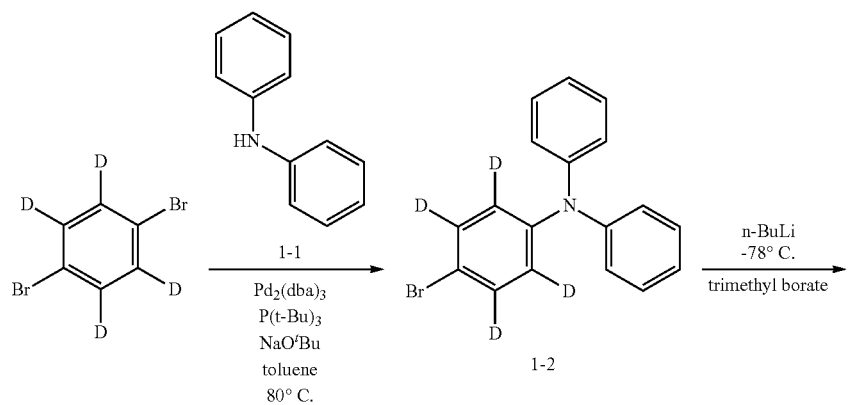

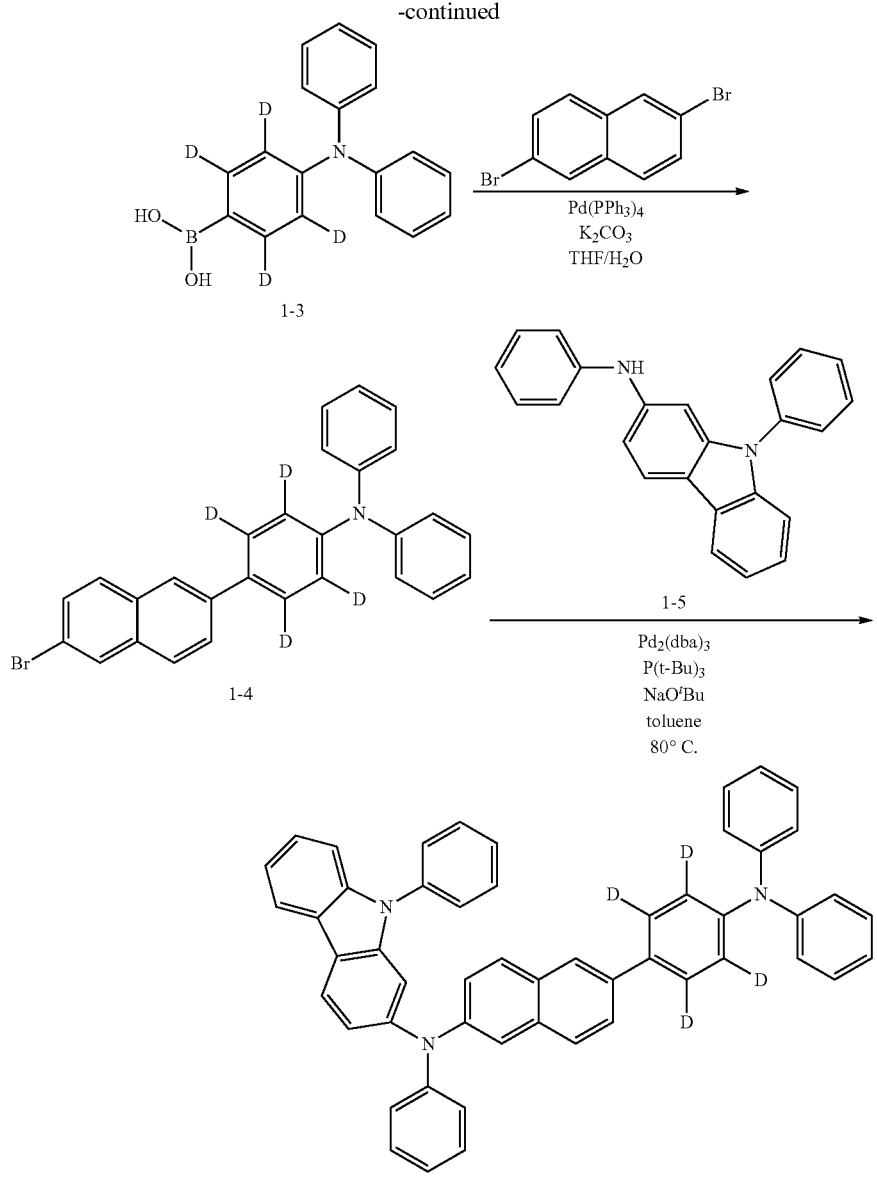

Synthesis of Intermediate 1-1

Iodobenzene (2.04 g), aniline (1.39 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 1-1 (1.18 g, yield: 70%).

Synthesis of Intermediate 1-2

1,4-dibromobenzene-2,3,5,6-d4 (2.39 g), Intermediate 1-1 (1.69 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 1-2 (2.24 g, yield: 70%).

Synthesis of Intermediate 1-3

Intermediate 1-2 (3.28 g) was dissolved in THF (50 ml), and 2.5 M n-BuLi (4.8 ml) was added dropwise thereto at a temperature of −78° C. The resultant reaction solution was stirred at a temperature of −78° C. for 1 hour, and trimethyl borate (1.04 g) was added thereto and stirred for 12 hours. The reaction was terminated by using water, and an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 1-3 (1.74 g, yield: 60%).

Synthesis of Intermediate 1-4

Intermediate 1-3 (2.93 g), Pd(PPh$_3$)$_4$ (0.56 g), K$_2$CO$_3$ (3.45 g), and 2,6-dibromonaphthalene (2.85 g) were dissolved in THF/H$_2$O (100 ml/25 ml) and stirred at a temperature of 80° C. for 12 hours. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 1-4 (2.86 g, yield: 63%).

Synthesis of Intermediate 1-5

4-bromo-1,1'-biphenyl (2.33 g), aniline (1.39 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 1-5 (2.33 g, yield: 70%).

Synthesis of Compound 1

Intermediate 1-4 (4.54 g) and Intermediate 1-5 (3.34 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by decompression was separated and purified by using column chromatography, thereby obtaining Compound 1 (4.59 g, yield: 65%).

Synthesis Example 2: Synthesis of Compound 6

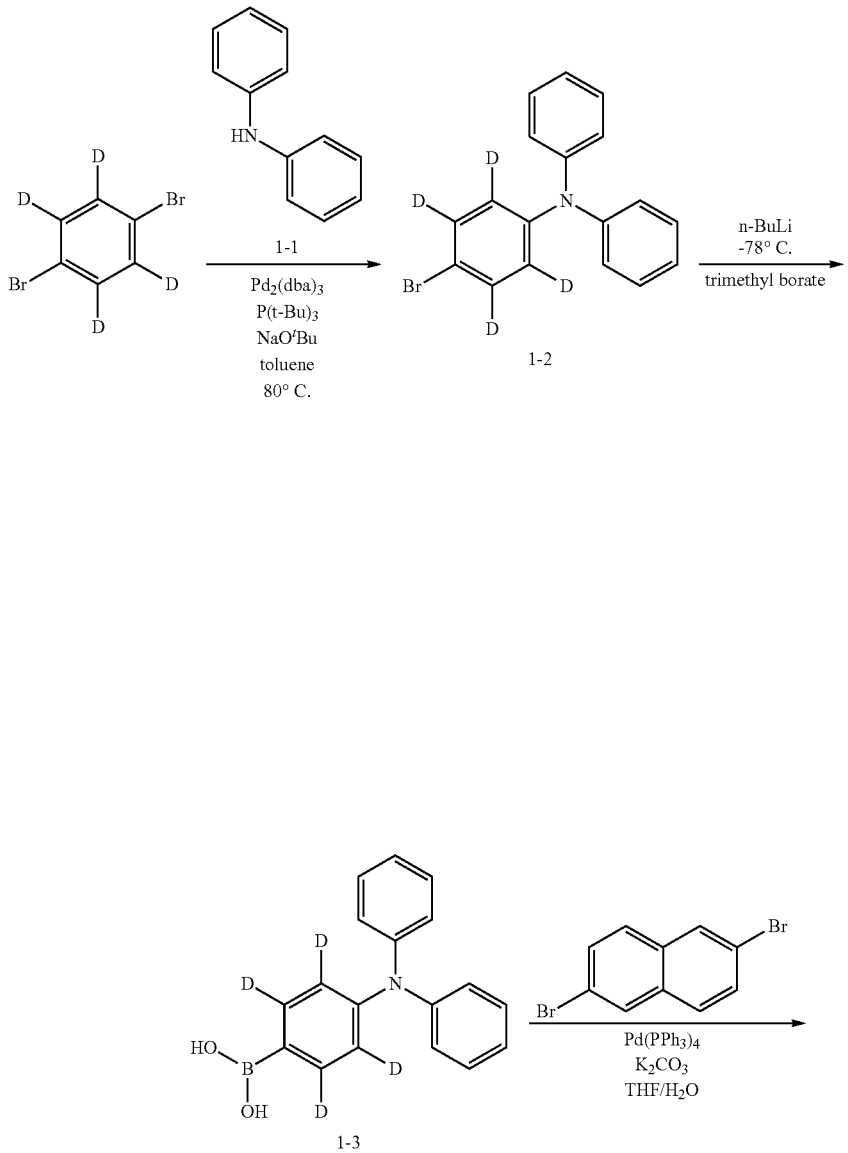

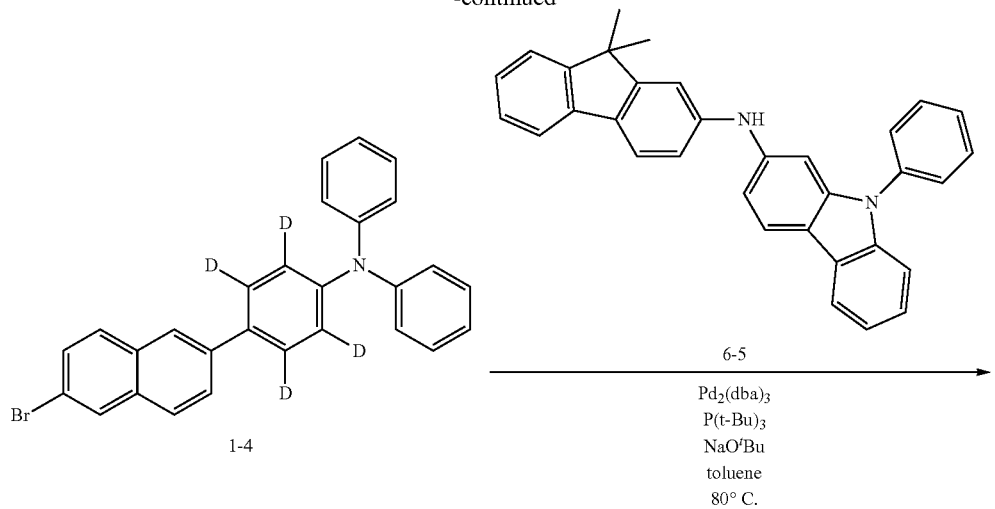

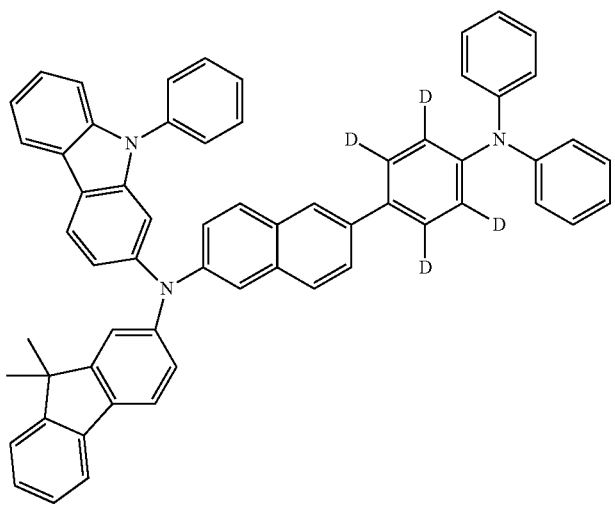

6

Synthesis of Intermediate 6-5

2-bromo-9-phenyl-9H-carbazole (3.22 g), 9,9-dimethyl-9H-fluoren-2-amine (2.09 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 6-5 (2.74 g, yield: 61%).

Synthesis of Compound 6

Intermediate 1-4 (4.54 g) and Intermediate 6-5 (4.50 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Compound 6 (4.12 g, yield: 50%).

Synthesis Example 3: Synthesis of Compound 13
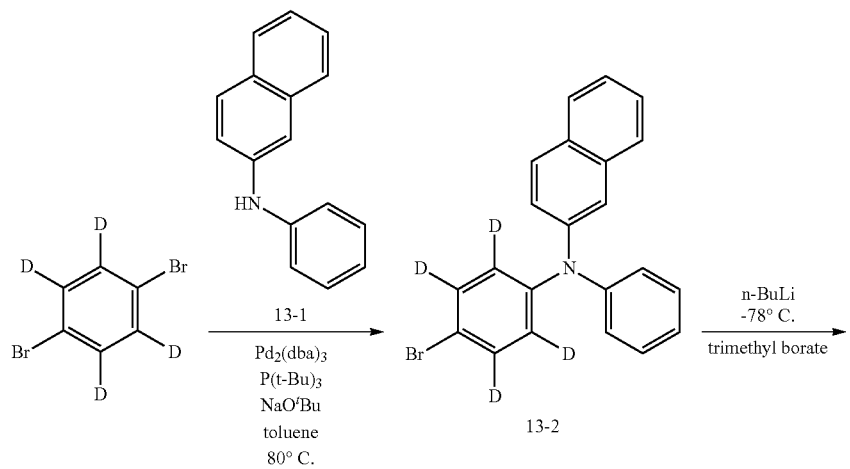
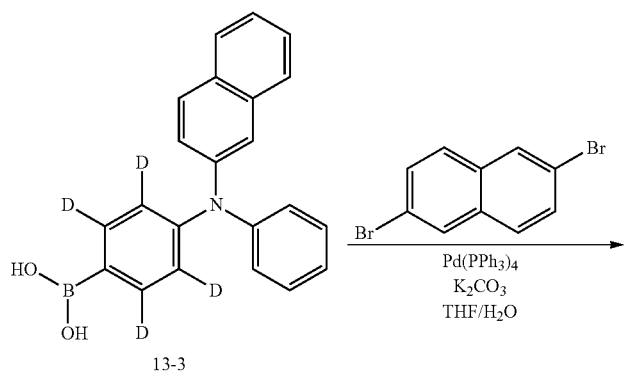
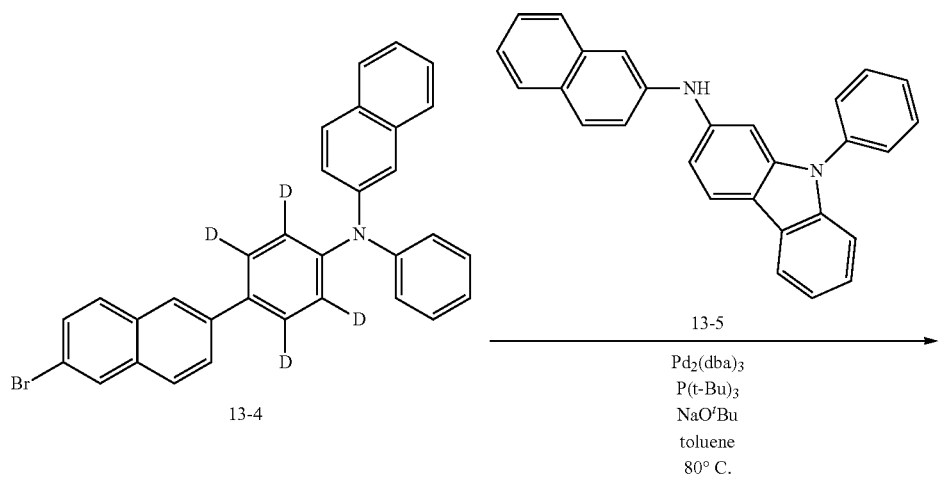

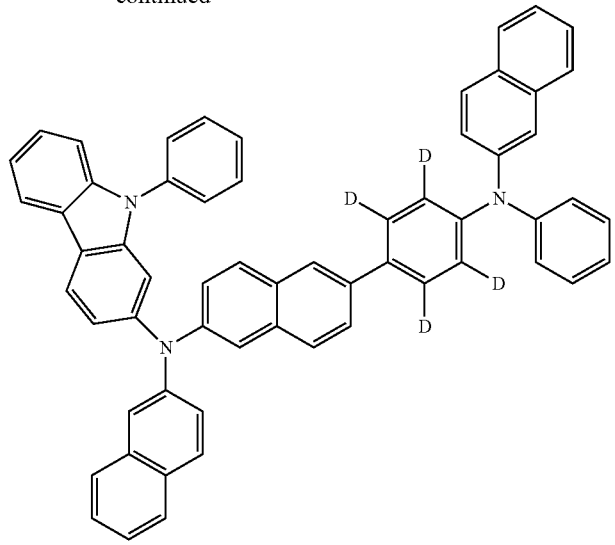

13

Synthesis of Intermediate 13-1

Intermediate 13-1 (1.51 g, yield: 69%) was obtained in substantially the same manner as in the synthesis of Intermediate 1-1, except that 2-bromonaphthalene was used instead of iodobenzene.

Synthesis of Intermediate 13-2

Intermediate 13-2 (2.64 g, yield: 70%) was obtained in substantially the same manner as in the synthesis of Intermediate 1-2, except that Intermediate 13-1 was used instead of Intermediate 1-1.

Synthesis of Intermediate 13-3

Intermediate 13-3 (2.40 g, yield: 70%) was obtained in substantially the same manner as in the synthesis of Intermediate 1-3, except that Intermediate 13-2 was used instead of Intermediate 1-2.

Synthesis of Intermediate 13-4

Intermediate 13-4 (4.03 g, yield: 80%) was obtained in substantially the same manner as in the synthesis of Intermediate 1-4, except that Intermediate 13-3 was used instead of Intermediate 1-3.

Synthesis of Intermediate 13-5

2-bromo-9-phenyl-9H-carbazole (3.22 g), naphthalen-2-amine (1.43 g), $Pd_2(dba)_3$ (0.46 g), $P(t-Bu)_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 13-5 (3.07 g, yield: 80%).

Synthesis of Compound 13

Compound 13 (4.36 g, yield: 54%) was obtained in substantially the same manner as in the synthesis of Compound 1, except that Intermediates 13-4 and 13-5 were used instead of Intermediates 1-4 and 1-5, respectively.

Synthesis Example 4: Synthesis of Compound 17

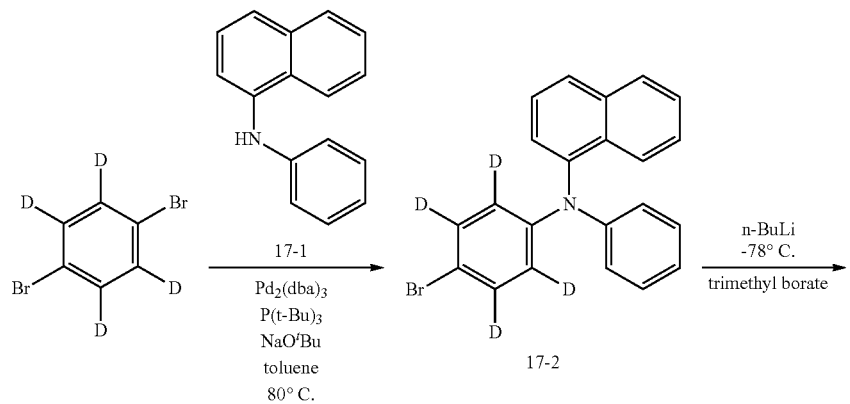

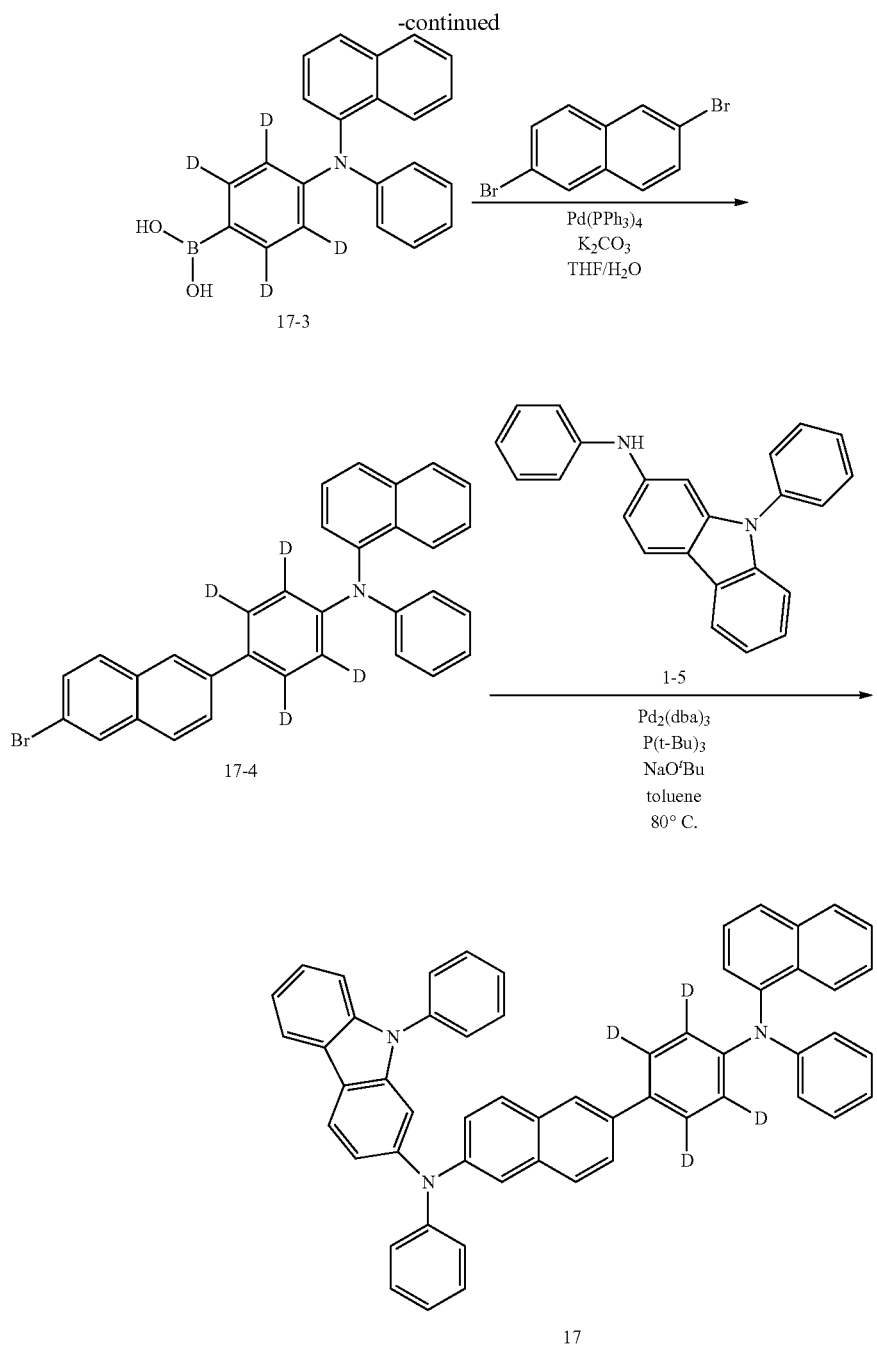

Synthesis of Intermediate 17-1

Intermediate 17-1 (1.51 g, yield: 69%) was obtained in substantially the same manner as in the synthesis of Intermediate 1-1, except that 1-bromonaphthalene was used instead of iodobenzene.

Synthesis of Intermediate 17-2

Intermediate 17-2 (2.64 g, yield: 71%) was obtained in substantially the same manner as in the synthesis of Intermediate 1-2, except that Intermediate 17-1 was used instead of Intermediate 1-1.

Synthesis of Intermediate 17-3

Intermediate 17-3 (2.40 g, yield: 70%) was obtained in substantially the same manner as in the synthesis of Intermediate 1-3, except that Intermediate 17-2 was used instead of Intermediate 1-2.

Synthesis of Intermediate 17-4

Intermediate 17-4 (3.78 g, yield: 75%) was obtained in substantially the same manner as in the synthesis of Intermediate 1-4, except that Intermediate 17-3 was used instead of Intermediate 1-3.

Synthesis of Compound 17

Compound 17 (3.70 g, yield: 49%) was obtained in substantially the same manner as in the synthesis of Compound 1, except that Intermediates 17-4 and 1-5 were used instead of Intermediates 1-4 and 1-5, respectively.

Synthesis Example 5: Synthesis of Compound 37
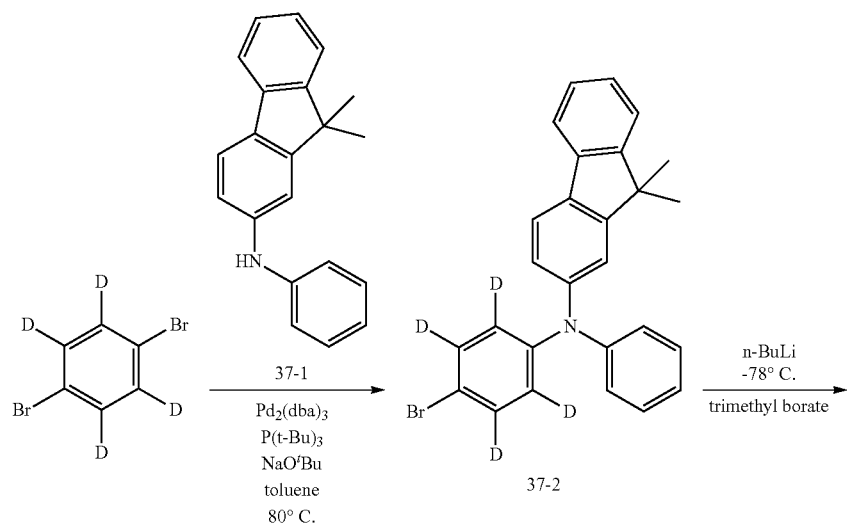
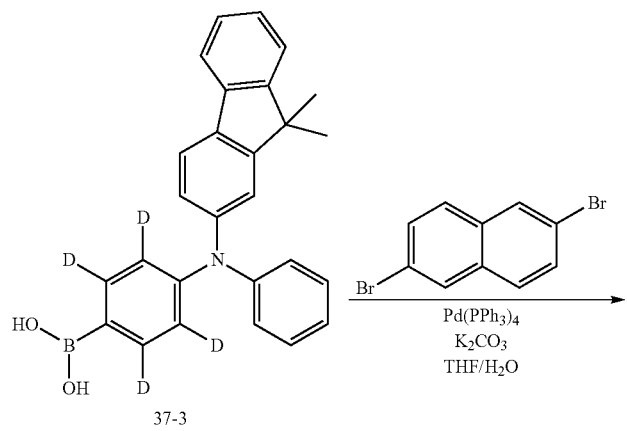
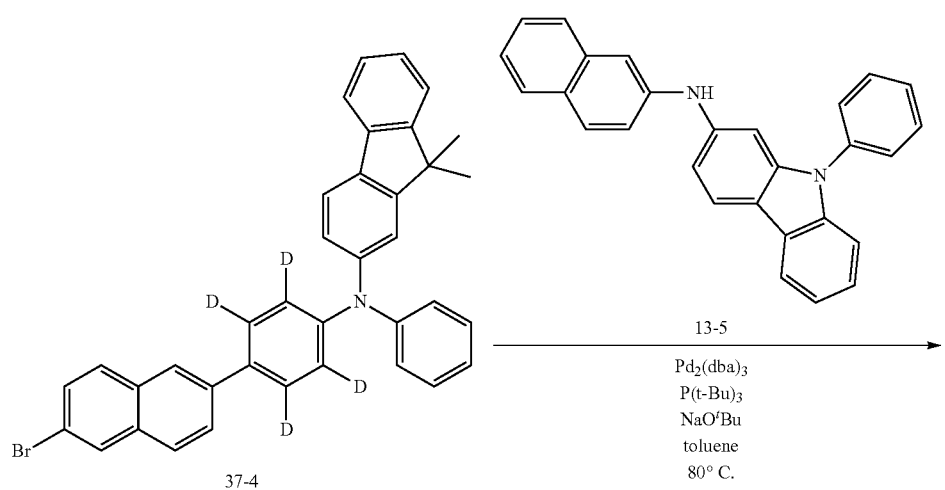

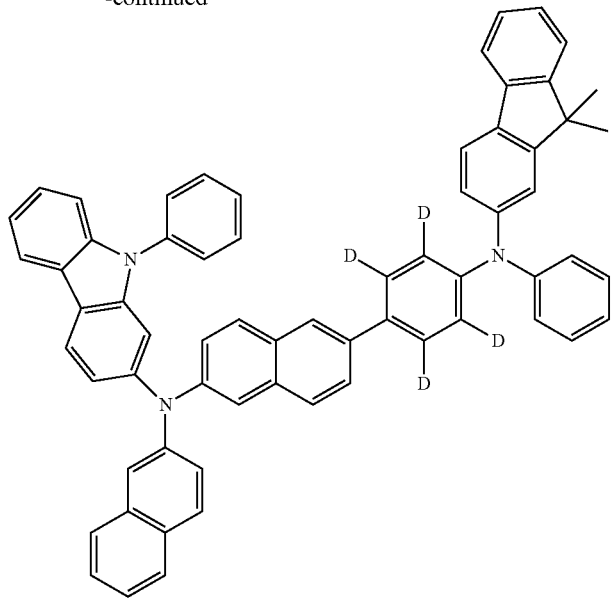

37

Synthesis of Intermediate 37-1

Intermediate 37-1 (2.30 g, yield: 81%) was obtained in substantially the same manner as in the synthesis of Intermediate 1-1, except that 9,9-dimethyl-9H-fluoren-2-amine was used instead of iodobenzene.

Synthesis of Intermediate 37-2

Intermediate 37-2 (3.10 g, yield: 70%) was obtained in substantially the same manner as in the synthesis of Intermediate 1-2, except that Intermediate 37-1 was used instead of Intermediate 1-1.

Synthesis of Intermediate 37-3

Intermediate 37-3 (2.40 g, yield: 70%) was obtained in substantially the same manner as in the synthesis of Intermediate 1-3, except that Intermediate 37-2 was used instead of Intermediate 1-2.

Synthesis of Intermediate 37-4

Intermediate 37-4 (3.99 g, yield: 70%) was obtained in substantially the same manner as in the synthesis of Intermediate 1-4, except that Intermediate 37-3 was used instead of Intermediate 1-3.

Synthesis of Compound 37

Compound 37 (4.89 g, yield: 56%) was obtained in substantially the same manner as in the synthesis of Compound 1, except that Intermediates 37-4 and 13-5 were used instead of Intermediates 1-4 and 1-5, respectively.

Synthesis Example 5: Synthesis of Compound 41

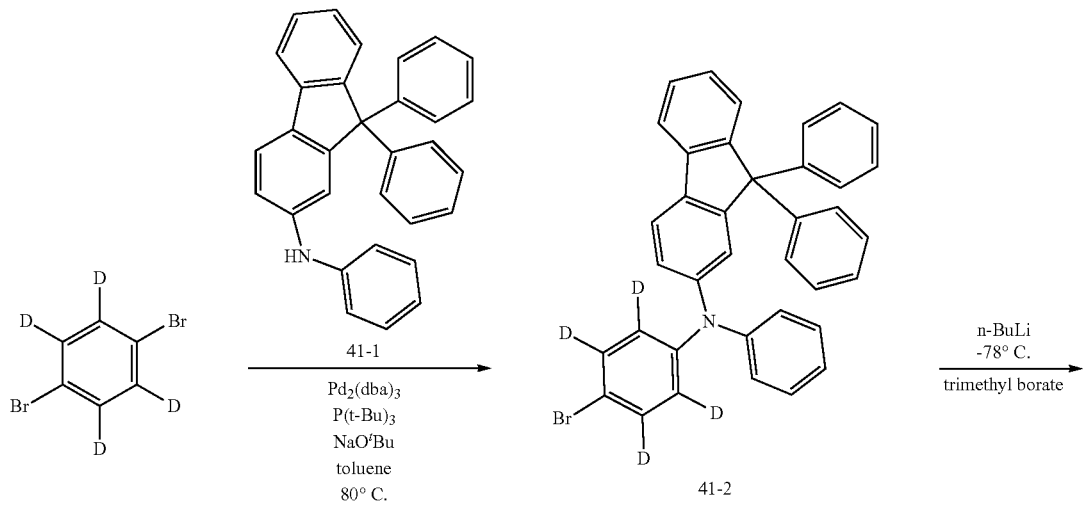

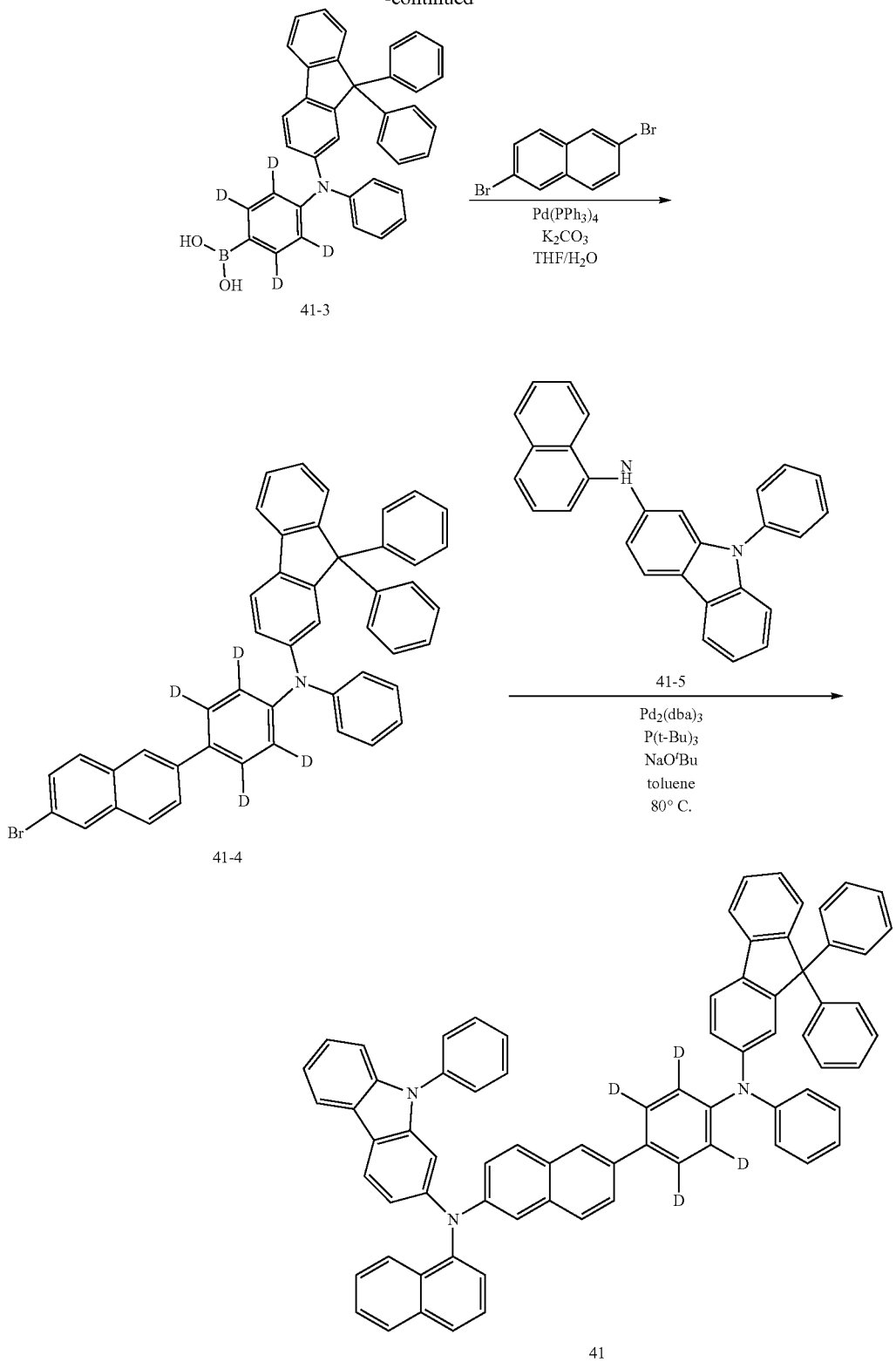

Synthesis of Intermediate 41-1

Intermediate 41-1 (2.58 g, yield: 65%) was obtained in substantially the same manner as in the synthesis of Intermediate 1-1, except that 2-bromo-9,9-diphenyl-9H-fluorene was used instead of iodobenzene.

Synthesis of Intermediate 41-2

Intermediate 41-2 (4.37 g, yield: 77%) was obtained in substantially the same manner as in the synthesis of Intermediate 1-2, except that Intermediate 41-1 was used instead of Intermediate 1-1.

Synthesis of Intermediate 41-3

Intermediate 41-3 (3.46 g, yield: 65%) was obtained in substantially the same manner as in the synthesis of Intermediate 1-3, except that Intermediate 41-2 was used instead of Intermediate 1-2.

Synthesis of Intermediate 41-4

Intermediate 41-4 (4.23 g, yield: 63%) was obtained in substantially the same manner as in the synthesis of Intermediate 1-4, except that Intermediate 41-3 was used instead of Intermediate 1-3.

Synthesis of Intermediate 41-5

2-bromo-9-phenyl-9H-carbazole (3.22 g), naphthalen-1-amine (1.43 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 41-5 (2.68 g, yield: 70%).

Synthesis of Compound 41

Compound 41 (5.08 g, yield: 51%) was obtained in substantially the same manner as in the synthesis of Compound 1, except that Intermediates 41-4 and 41-5 were used instead of Intermediates 1-4 and 1-5, respectively.

Synthesis Example 7: Synthesis of Compound 50

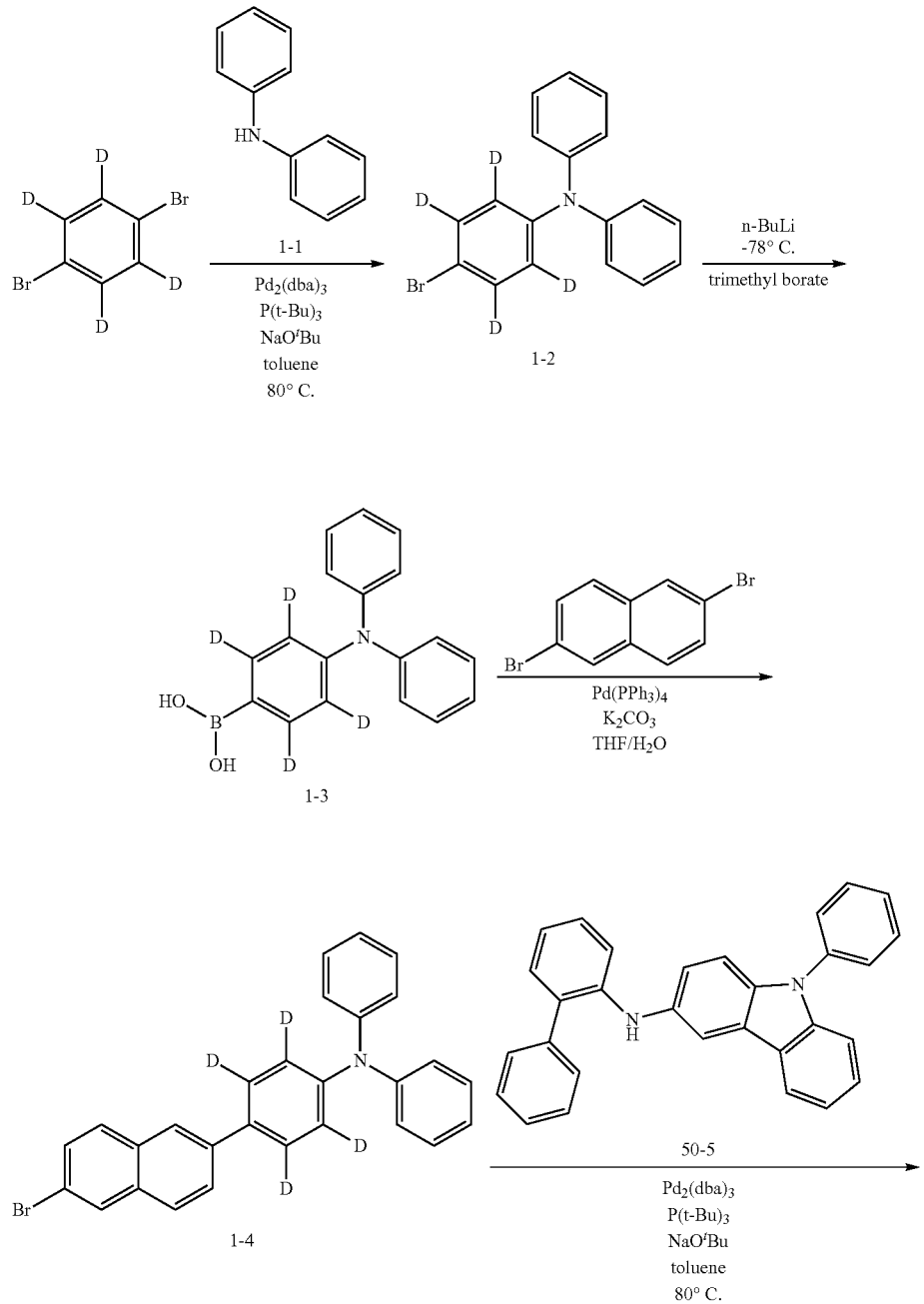

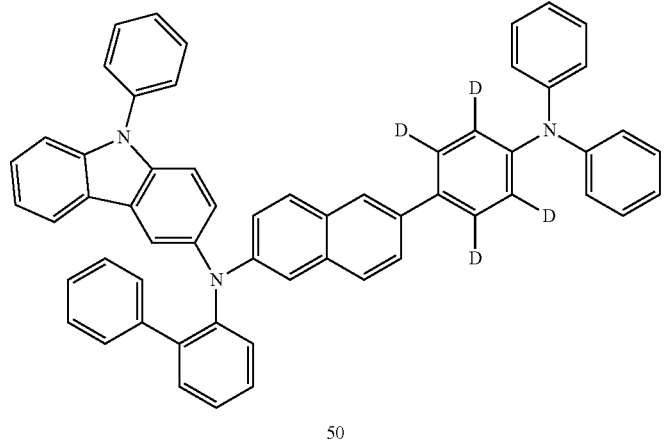

50

Synthesis of Intermediate 50-5

3-bromo-9-phenyl-9H-carbazole (3.22 g), [1,1'-biphenyl]-2-amine (1.69 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 50-5 (2.66 g, yield: 65%).

Synthesis of Compound 50

Compound 50 (4.78 g, yield: 61%) was obtained in substantially the same manner as in the synthesis of Compound 1, except that Intermediate 50-5 was used instead of Intermediate 1-5.

Synthesis Example 8: Synthesis of Compound 62

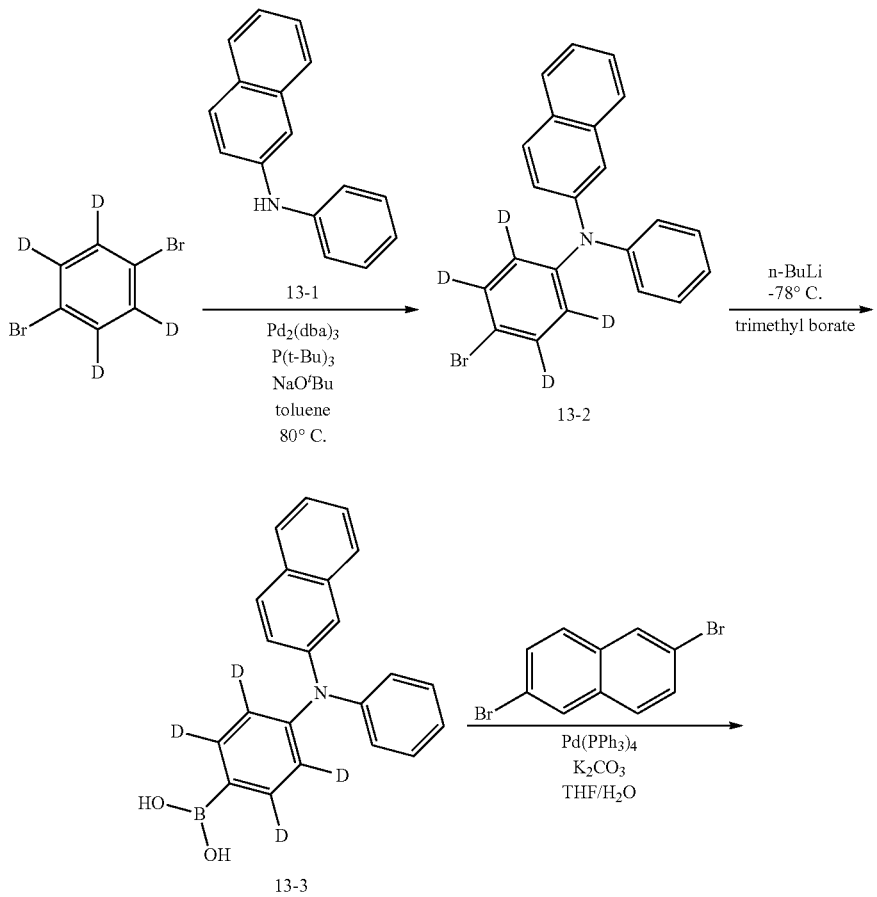

-continued

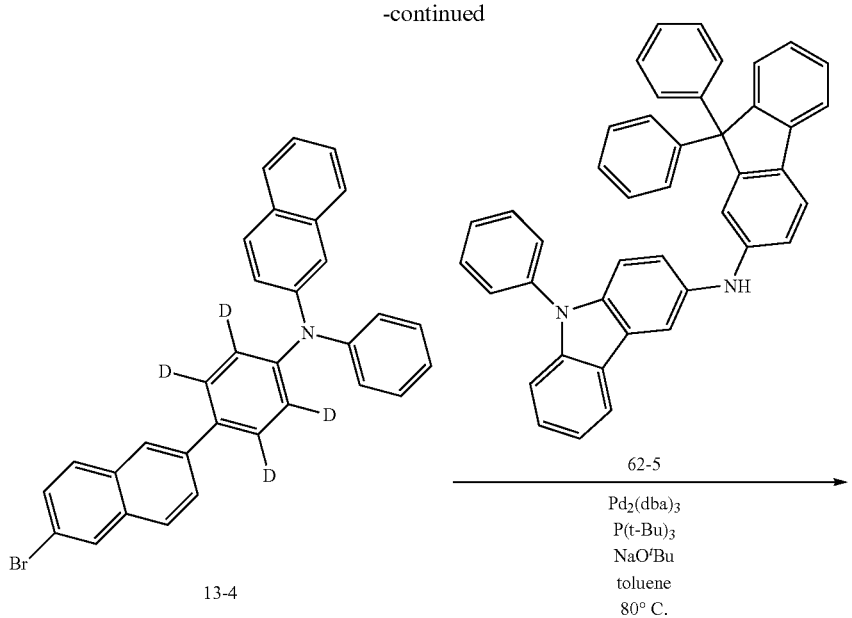

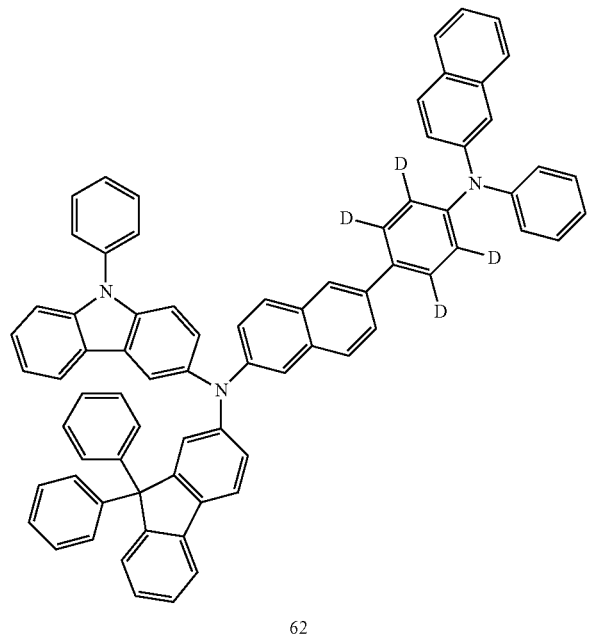

Synthesis of Intermediate 62-5

2-bromo-9-phenyl-9H-carbazole (3.22 g), 9,9-diphenyl-9H-fluoren-2-amine (3.33 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 62-5 (3.78 g, yield: 66%).

Synthesis of Compound 62

Compound 62 (5.08 g, yield: 51%) was obtained in substantially the same manner as in the synthesis of Compound 1, except that Intermediates 13-4 and 62-5 were used instead of Intermediates 1-4 and 1-5, respectively.

Synthesis Example 9: Synthesis of Compound 84
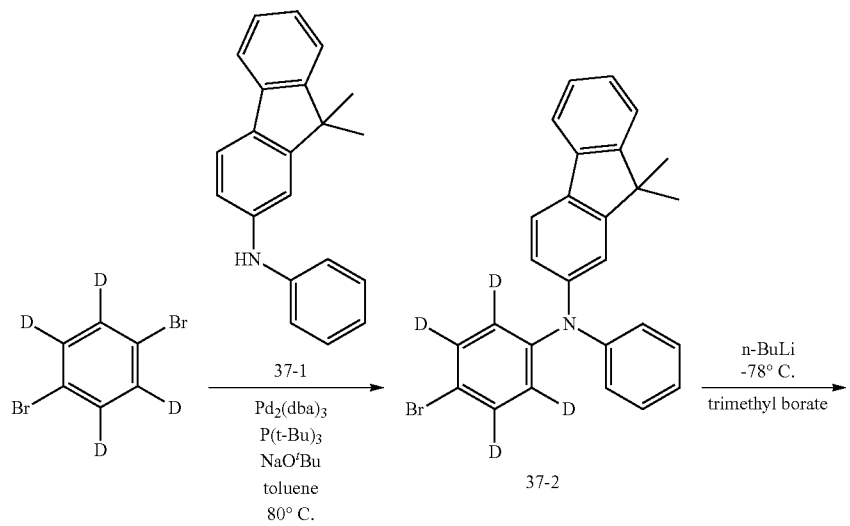
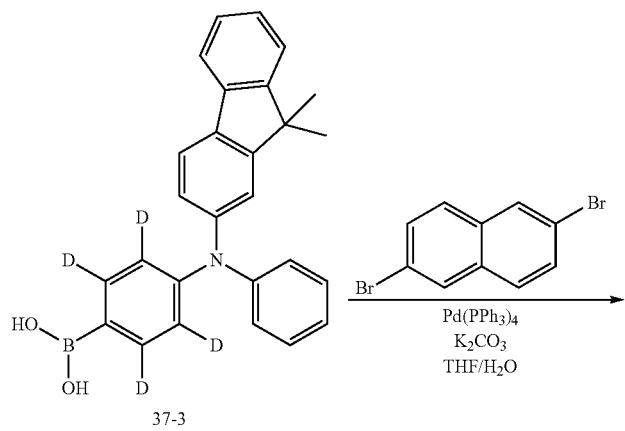
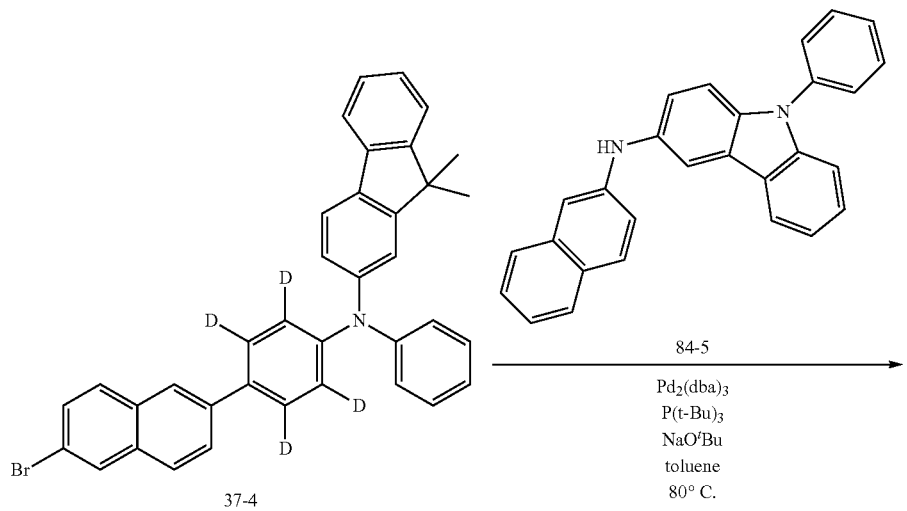

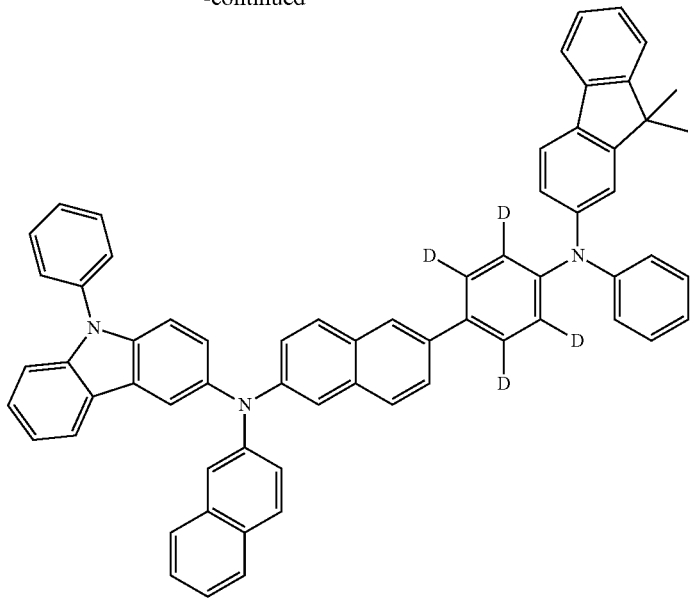

84

Synthesis of Intermediate 84-5

2-bromo-9-phenyl-9H-carbazole (3.22 g), naphthalen-2-amine (1.43 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 84-5 (2.68 g, yield: 70%).

Synthesis of Compound 84

Compound 84 (5.50 g, yield: 63%) was obtained in substantially the same manner as in the synthesis of Compound 1, except that Intermediates 37-4 and 84-5 were used instead of Intermediates 1-4 and 1-5, respectively.

Synthesis Example 10: Synthesis of Compound 95

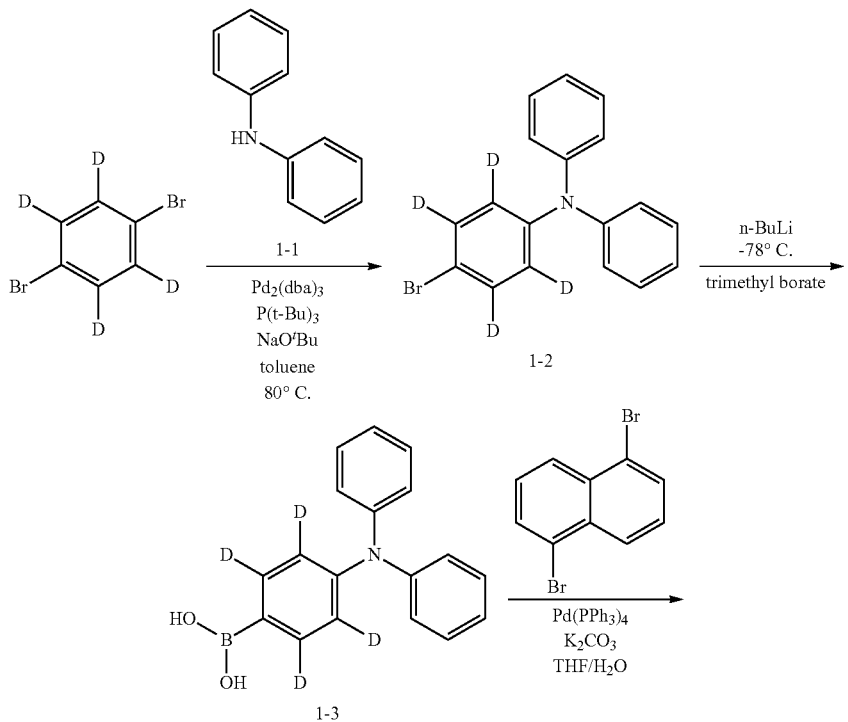

-continued

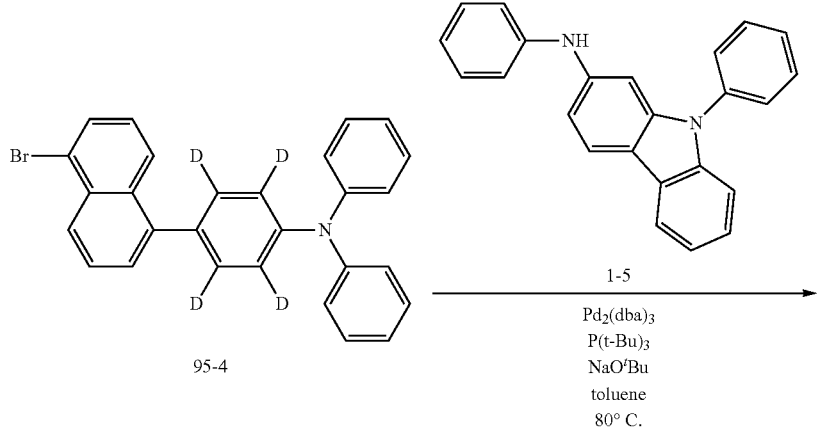

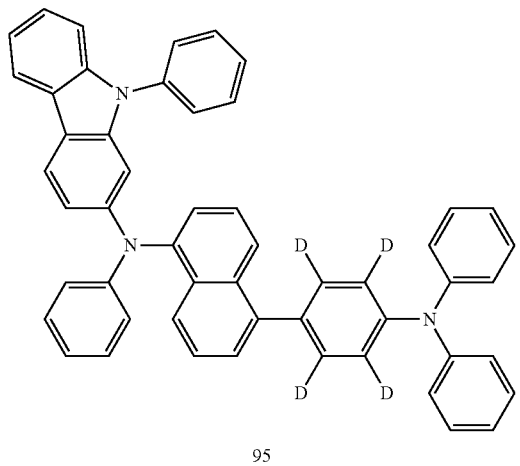

Synthesis of Intermediate 95-4

Intermediate 1-3 (2.93 g), Pd(PPh₃)₄ (0.56 g), K₂CO₃ (3.45 g), and 1,5-dibromonaphthalene (2.85 g) were dissolved in THF/H₂O (100 ml/25 ml) and stirred at a temperature of 80° C. for 12 hours. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 95-4 (2.86 g, yield: 63%).

Synthesis of Compound 95

Compound 95 (5.44 g, yield: 77%) was obtained in substantially the same manner as in the synthesis of Compound 1, except that Intermediate 95-4 was used instead of Intermediate 1-4.

Synthesis Example 11: Synthesis of Compound 115

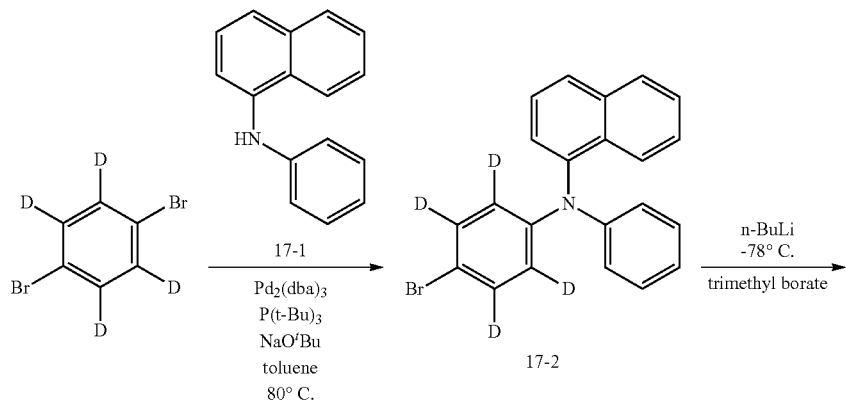

-continued

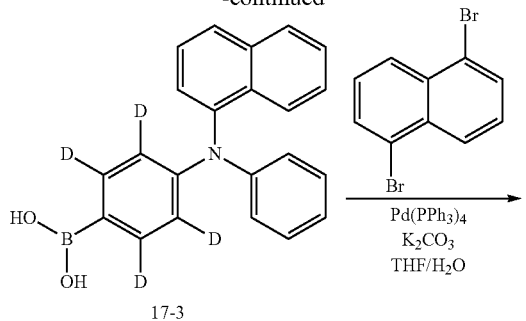
17-3

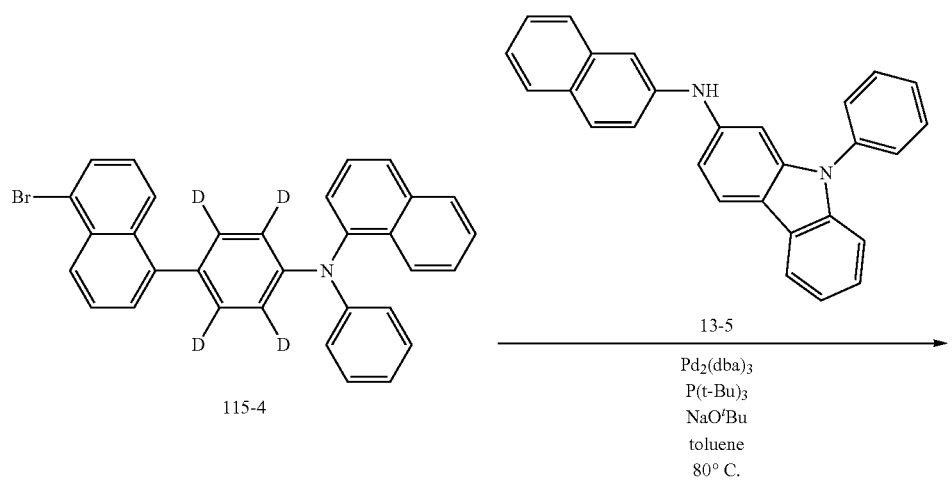
115-4     13-5

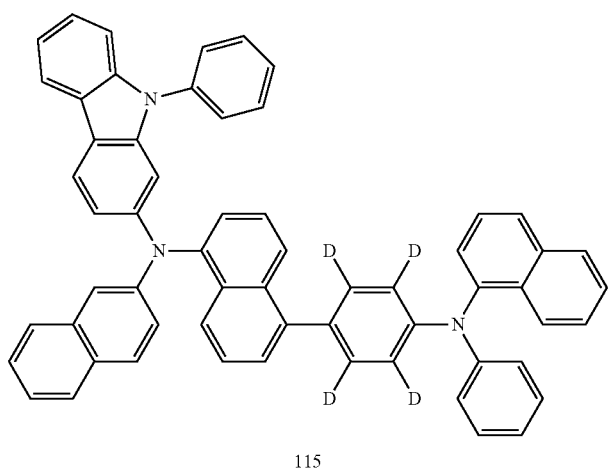
115

Synthesis of Intermediate 115-4

Intermediate 115-4 (2.77 g, yield: 55%) was obtained in substantially the same manner as in the synthesis of Intermediate 1-4, except that 1,5-dibromonaphthalene and Intermediate 17-3 were used instead of 2,6-dibromonaphthalene and Intermediate 1-3, respectively.

Synthesis of Compound 115

Compound 115 (5.25 g, yield: 65%) was obtained in substantially the same manner as in the synthesis of Compound 1, except that Intermediates 115-4 and 13-5 were used instead of Intermediates 1-4 and 1-5, respectively.

Synthesis Example 12: Synthesis of Compound 119
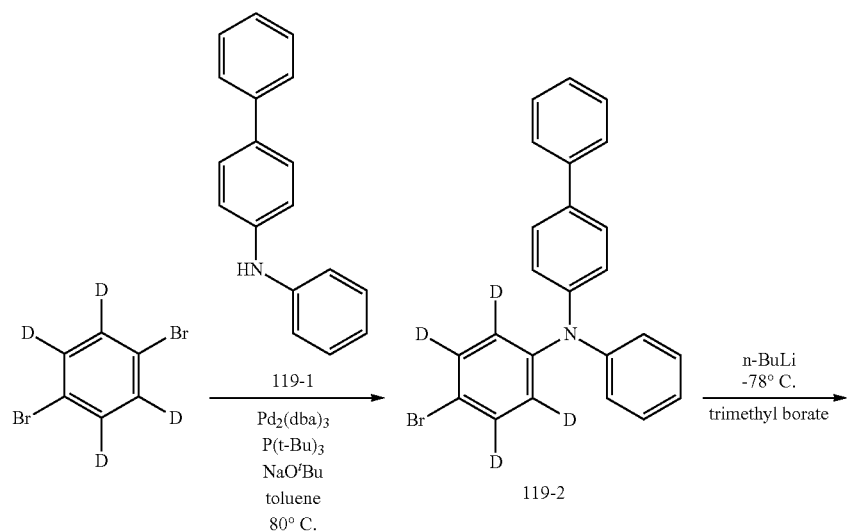
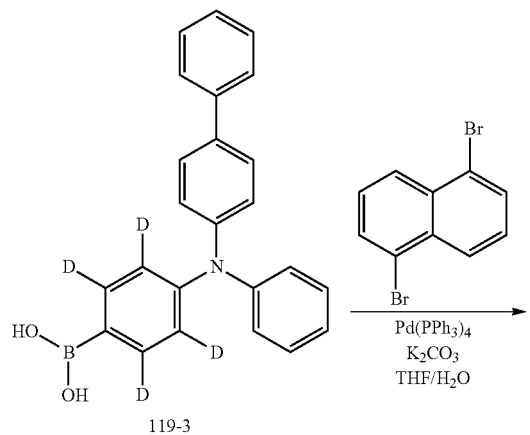
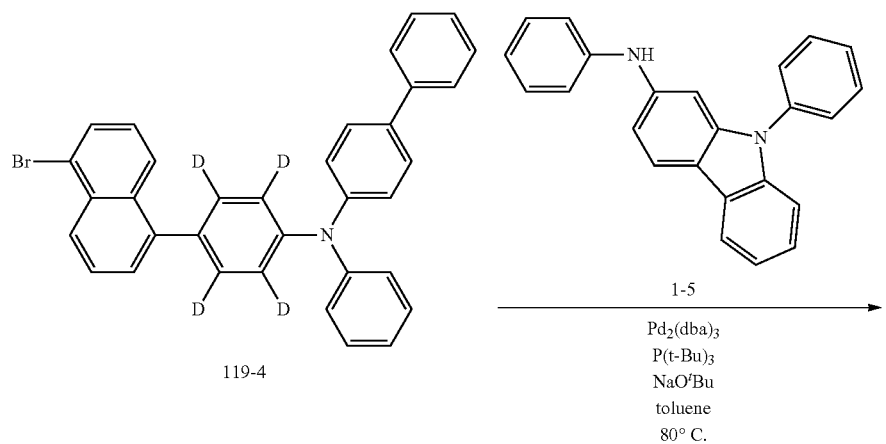

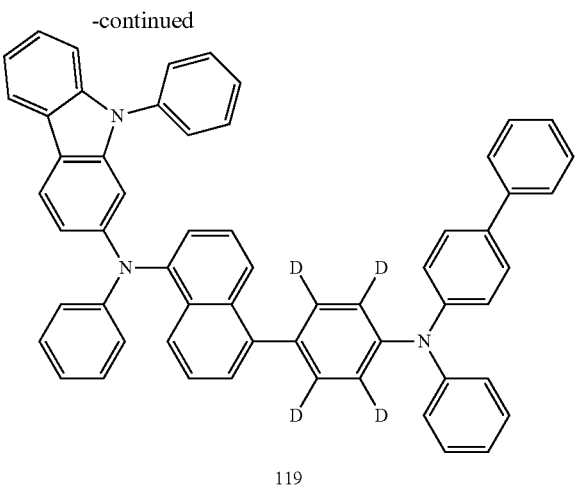

119

Synthesis of Intermediate 119-1

Intermediate 119-1 (1.96 g, yield: 80%) was obtained in substantially the same manner as in the synthesis of Intermediate 1-1, except that 4-bromo-1,1'-biphenyl was used instead of iodobenzene.

Synthesis of Intermediate 119-2

Intermediate 119-2 (3.03 g, yield: 76%) was obtained in substantially the same manner as in the synthesis of Intermediate 1-2, except that Intermediate 119-1 was used instead of Intermediate 1-1.

Synthesis of Intermediate 119-3

Intermediate 119-3 (2.95 g, yield: 80%) was obtained in substantially the same manner as in the synthesis of Intermediate 1-3, except that Intermediate 119-2 was used instead of Intermediate 1-2.

Synthesis of Intermediate 119-4

Intermediate 119-4 (3.92 g, yield: 73%) was obtained in substantially the same manner as in the synthesis of Intermediate 1-4, except that 1,5-dibromonaphthalene and Intermediate 119-3 were used instead of 2,6-dibromonaphthalene and Intermediate 1-3, respectively.

Synthesis of Compound 119

Compound 119 (4.93 g, yield: 63%) was obtained in substantially the same manner as in the synthesis of Compound 1, except that Intermediate 119-4 was used instead of Intermediate 1-4.

Synthesis Example 13: Synthesis of Compound 150

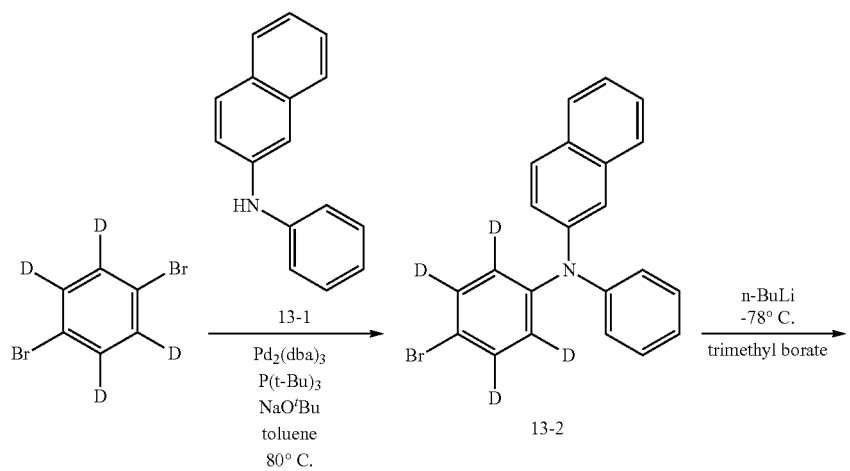

-continued

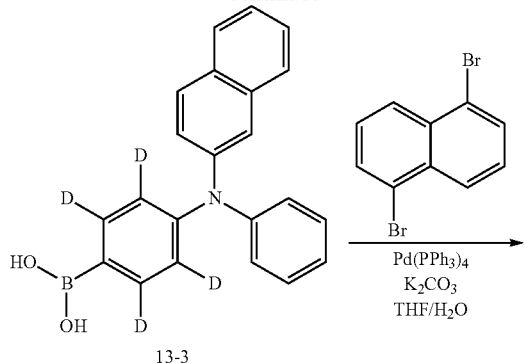

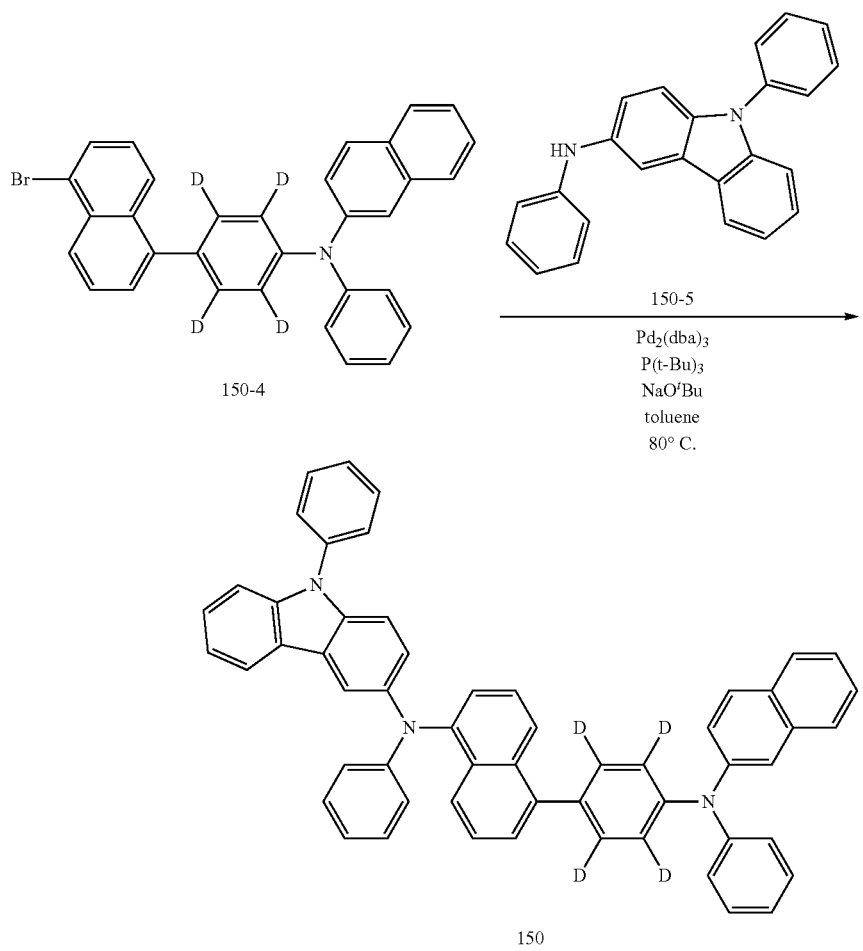

Synthesis of Intermediate 150-4

Intermediate 150-4 (3.27 g, yield: 65%) was obtained in substantially the same manner as in the synthesis of Intermediate 1-4, except that 1,5-dibromonaphthalene and Intermediate 13-3 were used instead of 2,6-dibromonaphthalene and Intermediate 1-3, respectively.

Synthesis of Intermediate 150-5

2-bromo-9-phenyl-9H-carbazole (3.22 g), aniline (1.38 g), Pd$_2$(dba)$_3$ (0.46 g), P(t-Bu)$_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 150-5 (2.50 g, yield: 75%).

Synthesis of Compound 150

Compound 150 (5.37 g, yield: 71%) was obtained in substantially the same manner as in the synthesis of Compound 1, except that Intermediates 150-4 and 150-5 were used instead of Intermediates 1-4 and 1-5, respectively.

Synthesis Example 14: Synthesis of Compound 166
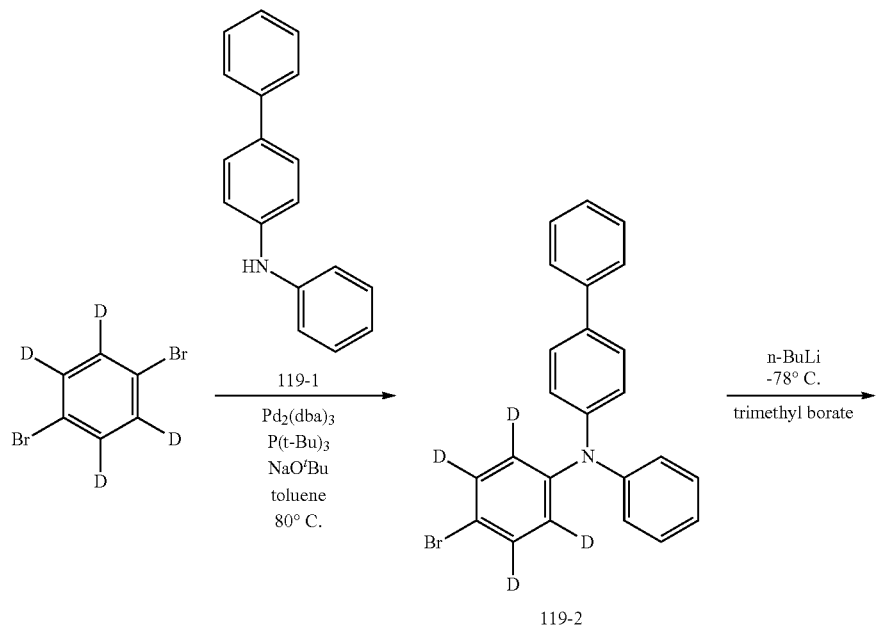
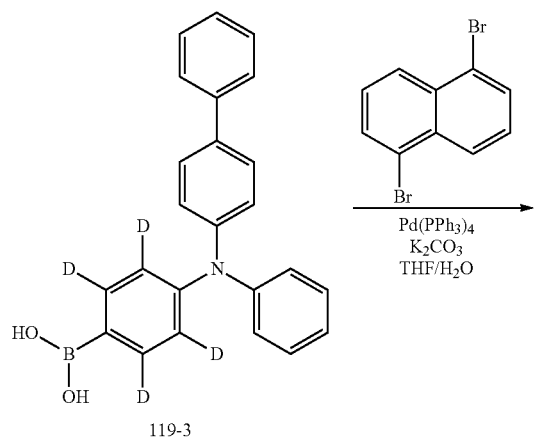
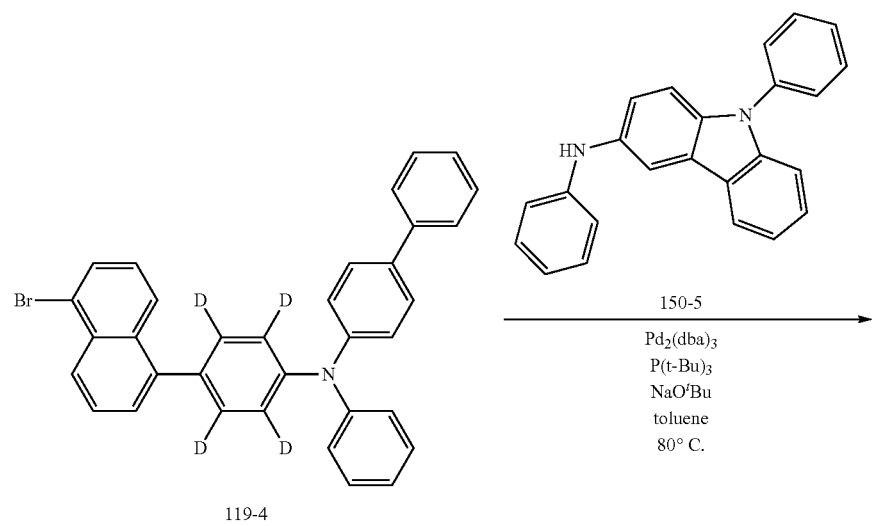

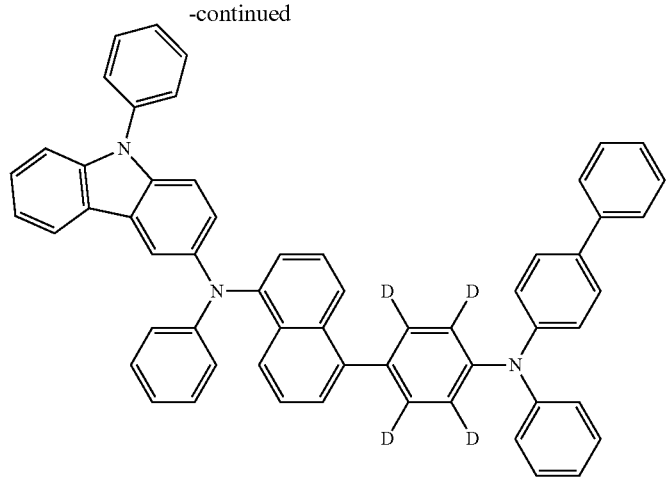
166
Synthesis of Compound 166
Compound 166 (5.56 g, yield: 71%) was obtained in substantially the same manner as in the synthesis of Compound 1, except that Intermediates 119-4 and 150-5 were used instead of Intermediates 1-4 and 1-5, respectively.
Synthesis Example 15: Synthesis of Compound 177
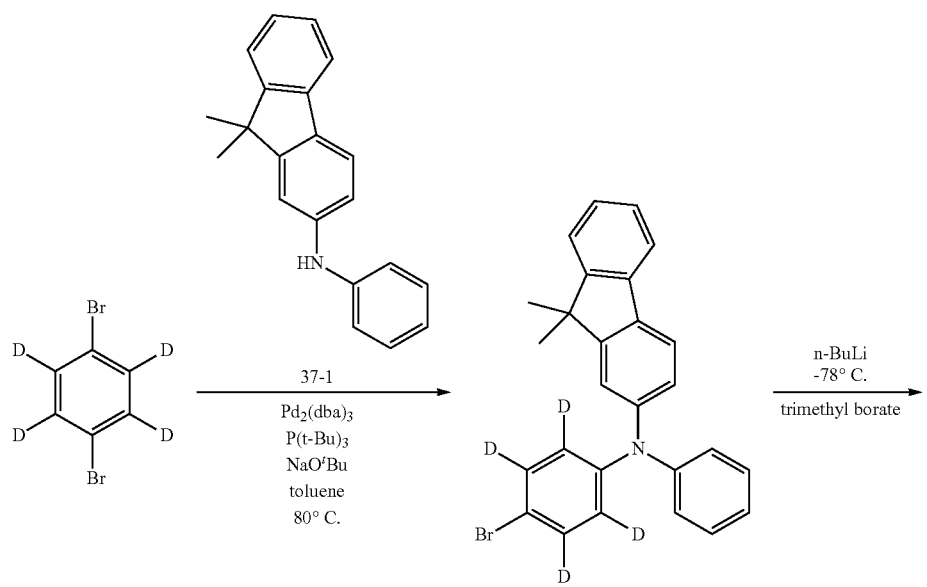

-continued
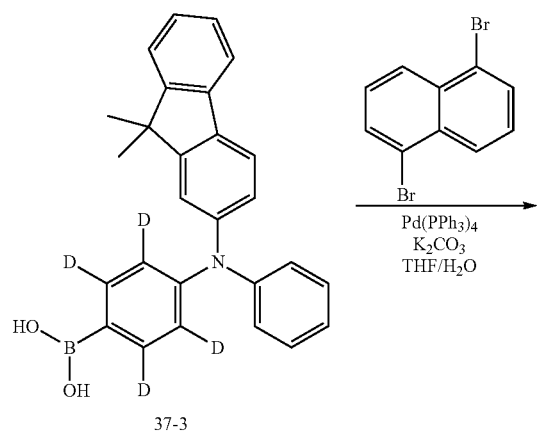
37-3
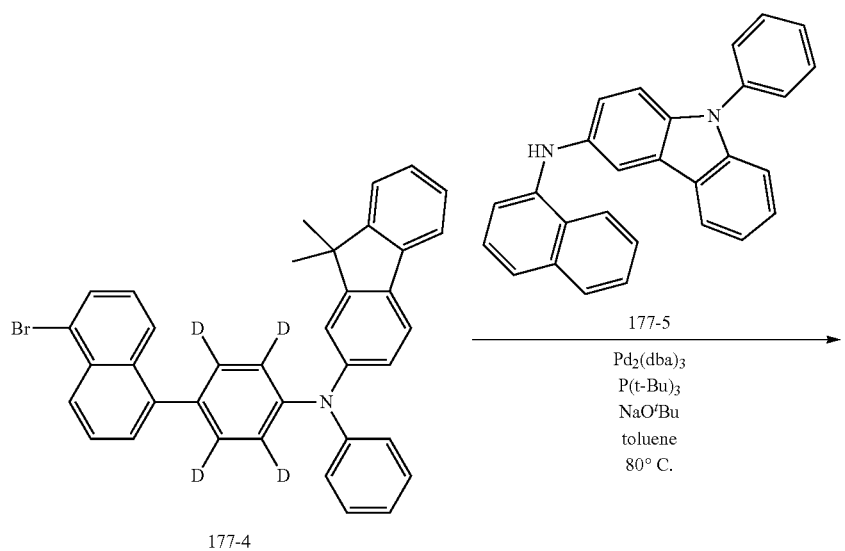
177-4
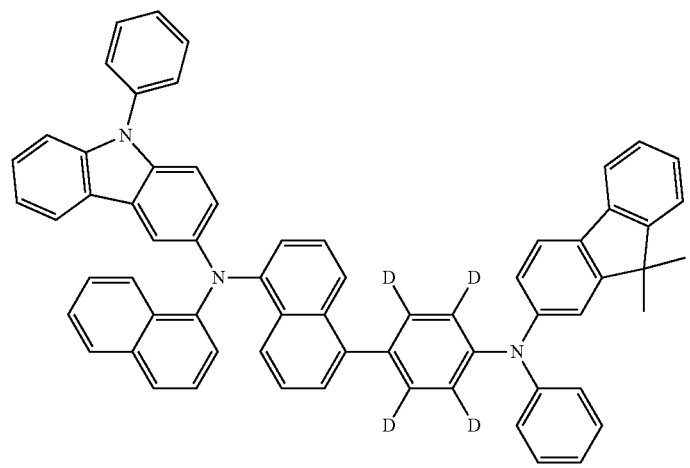
177

Synthesis of Intermediate 177-4

Intermediate 177-4 (3.64 g, yield: 64%) was obtained in substantially the same manner as in the synthesis of Intermediate 1-4, except that 1,5-dibromonaphthalene and Intermediate 37-3 were used instead of 2,6-dibromonaphthalene and Intermediate 1-3, respectively.

Synthesis of Intermediate 177-5

2-bromo-9-phenyl-9H-carbazole (3.22 g), 1-bromonaphthalene (2.07 g), $Pd_2(dba)_3$ (0.46 g), $P(t-Bu)_3$ (0.21 g), and NaOtBu (2.44 g) were dissolved in toluene (50 ml) and stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by distillation under reduced pressure was separated and purified by using column chromatography, thereby obtaining Intermediate 177-5 (2.41 g, yield: 61%).

Synthesis of Compound 177

Compound 177 (4.25 g, yield: 56%) was obtained in substantially the same manner as in the synthesis of Compound 1, except that Intermediates 177-4 and 177-5 were used instead of Intermediates 1-4 and 1-5, respectively.

TABLE 1

| Com- | | MS/FAB | |
|---|---|---|---|
| pound | H NMR (δ) | Calc | found |
| 1 | 8.55(d, 1H), 8.24(d, 1H), 7.94(d, 1H), 7.84 (d, 1H), 7.62-7.50 (m, 6H), 7.35-7.00 (m, 23H) | 707.32 | 706.32 |
| 6 | 8.55(d, 1H), 8.24(d, 1H), 7.94-7.84(m, 4H), 7.62-7.50 (m, 7H), 7.38-7.00 (m, 22H), 1.69 (s, 6H) | 823.39 | 822.39 |
| 13 | 8.55(d, 1H), 8.24(d, 1H), 7.94(d, 1H), 7.84-7.00 (m, 34H) | 807.36 | 806.36 |
| 17 | 8.55(d, 1H), 8.24-8.15(m, 3H), 7.94(d, 1H), 7.84-7.81(m, 2H), 7.63-7.49 (m, 10H), 7.40-7.00 (m, 18H) | 757.34 | 756.34 |
| 37 | 8.55(d, 1H), 8.24(d, 1H), 7.94-7.71(m, 6H), 7.62-7.00 (m, 30H), 1.69 (s, 6H) | 873.40 | 872.40 |
| 41 | 8.55(d, 1H), 8.24-8.15(m, 3H), 7.94-7.81 (m, 5H), 7.62-7.49 (m, 11H), 7.40-7.00 (m, 27H) | 997.43 | 996.43 |
| 50 | 8.55(d, 1H), 8.10(d, 1H), 7.94(d, 1H), 7.84(d, 1H), 7.62-7.00(m, 34H), | 783.36 | 782.36 |
| 62 | 8.55(d, 1H), 7.94-7.71(m, 6H), 7.62-7.00(m, 40H), | 997.43 | 996.43 |
| 84 | 8.55(d, 1H), 7.94-7.71(m, 6H), 7.62-7.00(m, 30H), 1.69 (s, 6H) | 873.40 | 872.40 |
| 95 | 8.61 (d, 1H), 8.55(d, 1H), 8.47(d, 1H), 8.24(d, 1H), 8.16(d, 1H), 7.94(d, 1H), 7.77(t, 1H), 7.62-7.45 (m, 7H), 7.35-7.00 (m, 19H) | 707.32 | 706.32 |
| 115 | 8.61 (d, 1H), 8.55(d, 1H), 8.47(d, 1H), 8.24 8.15(m, 4H), 7.94(d, 1H), 7.78-7.00(m, 29H) | 807.36 | 806.36 |
| 119 | 8.61 (d, 1H), 8.55(d, 1H), 8.47(d, 1H), 8.24(d, 1H), 8.16(d, 1H), 7.94(d, 1H), 7.77-7.75(m, 3H), 7.62-7.00(m, 28H) | 783.36 | 782.36 |
| 150 | 8.61(d, 1H), 8.47(d, 1H), 8.19-8.16(m, 2H), 8.01(s, 1H), 7.90(d, 1H), 7.77-7.40(m, 16H), 7.20-7.24(m, 5H), 7.11-7.00(m, 7H), 6.48(d, 1H) | 757.34 | 756.34 |
| 166 | 8.61(d, 1H), 8.47(d, 1H), 8.19-8.16(m, 2H), 8.01(s, 1H), 7.90(d, 1H), 7.77-7.75(m, 3H), 7.62-7.37(m, 16H), 7.24-7.20(m, 3H), 7.08-7.00(m, 6H), 6.48(d, 1H) | 783.36 | 782.36 |
| 177 | 8.61(d, 1H), 8.47(d, 1H), 8.22-8.15(m, 4H), 8.01(s, 1H), 7.90(m, 5H), 7.62-7.16(m, 21H), 7.08-7.00(m, 3H), 6.48(d, 1H), 1.69 (s, 6H) | 873.40 | 872.40 |

Comparative Example 1

As an anode, a Corning 15 $\Omega/cm^2$ (1,200 Å) ITO glass substrate was cut to a size of 50 mm×50 mm×0.7 mm, sonicated with isopropyl alcohol and pure water each for 5 minutes, and then cleaned by exposure to ultraviolet rays and ozone for 30 minutes. The ITO glass substrate was provided to a vacuum deposition apparatus.

2-TNATA was vacuum-deposited on the ITO anode formed on the glass substrate to form a hole injection layer having a thickness of 600 Å, and then, 4,4'-bis[N-(1-naphthyl)-N-phenylamino]biphenyl (NPB) was vacuum deposited on the hole injection layer to form a hole transport layer having a thickness of 300 Å.

10-di(naphthalene-2-yl)anthracene (DNA, host) and 4,4'-bis[2-(4-(N,N'-diphenylamino)phenyl)vinyl]biphenyl (DPAVBi, dopant) were co-deposited on the hole transport layer to a weight ratio of 98:2 to form an emission layer having a thickness of 300 Å.

Subsequently, $Alq_3$ was deposited on the emission layer to form an electron transport layer having a thickness of 300 Å, LiF was deposited on the electron transport layer to form an electron injection layer having a thickness of 10 Å, and Al was vacuum-deposited on the electron injection layer to form a LiF/Al electrode having a thickness of 3,000 Å, thereby completing the manufacture of a light-emitting device.

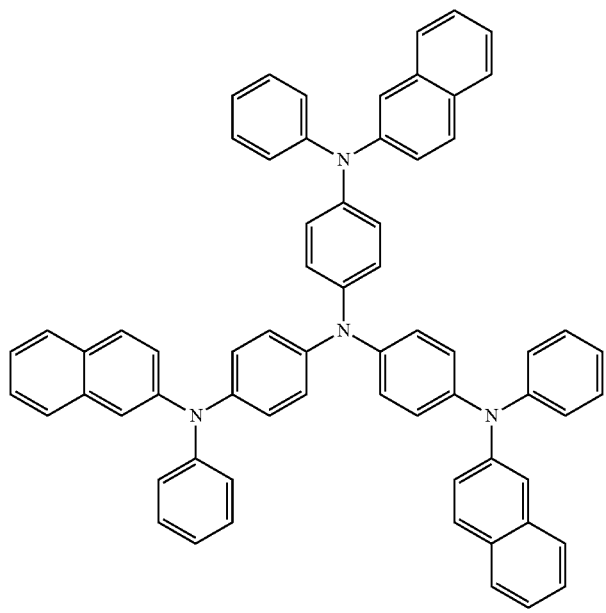
2-TNATA
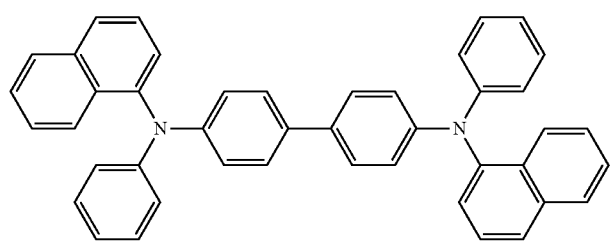
NPB
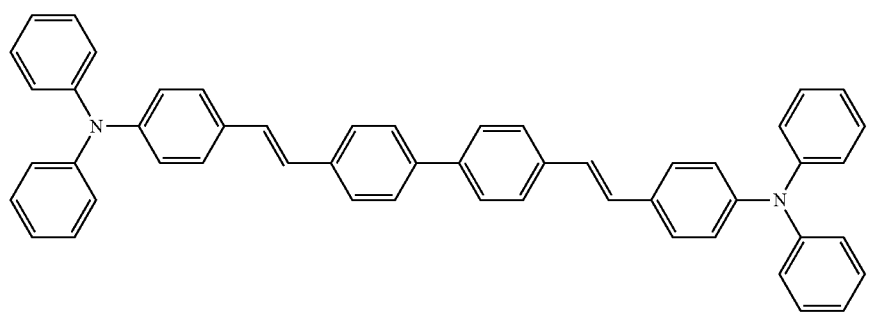
DPAVBi
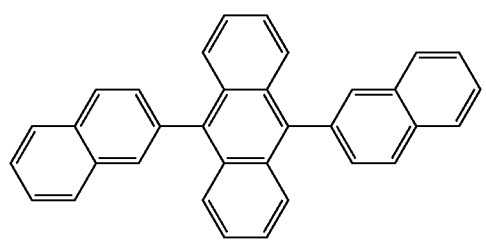
DNA

Examples 1 to 15 and Comparative Examples 2 to 9

Light-emitting devices were manufactured in substantially the same manner as in Comparative Example 1, except that compounds shown in Table 2 were each used instead of NPB in forming a hole transport layer.

Evaluation Example 1

To evaluate characteristics of the light-emitting devices manufactured according to Examples 1 to 15 and Comparative Examples 1 to 9, the driving voltage at the current density of 05 mA/cm$^2$, luminescence efficiency, and maximum external quantum efficiency (EQE) thereof were measured. The driving voltage of each light-emitting device was measured using a source meter (Keithley Instrument Inc., 2400 series), and the maximum external quantum efficiency was measured using the external quantum efficiency measurement apparatus C9920-2-12 of Hamamatsu Photonics Inc. In evaluating the maximum external quantum efficiency, the luminance/current density was measured using a luminance meter that was calibrated for wavelength sensitivity, and the maximum external quantum efficiency was converted by assuming an angular luminance distribution (Lambertian) which introduced a perfect reflecting diffuser. Table 2 below shows the evaluation results of the characteristics of the light-emitting devices.

TABLE 2

| | Hole transport material | Driving voltage (V) | Emission efficiency (cd/A) | Maximum EQE (%) | Emission color | Half lifespan (hr @100 mA/cm$^2$) |
|---|---|---|---|---|---|---|
| Example 1 | Compound 1 | 4.21 | 6.45 | 20.4 | Blue | 495 |
| Example 2 | Compound 6 | 4.33 | 6.52 | 20.6 | Blue | 510 |
| Example 3 | Compound 13 | 4.27 | 6.13 | 19.8 | Blue | 550 |
| Example 4 | Compound 17 | 4.35 | 6.15 | 19.8 | Blue | 605 |
| Example 5 | Compound 37 | 4.33 | 6.32 | 20.3 | Blue | 510 |
| Example 6 | Compound 41 | 4.21 | 6.16 | 19.9 | Blue | 550 |
| Example 7 | Compound 50 | 4.28 | 6.32 | 20.5 | Blue | 520 |
| Example 8 | Compound 62 | 4.19 | 6.45 | 20.8 | Blue | 562 |
| Example 9 | Compound 84 | 4.18 | 6.44 | 21.0 | Blue | 600 |
| Example 10 | Compound 95 | 4.32 | 6.45 | 21.1 | Blue | 510 |
| Example 11 | Compound 115 | 4.36 | 6.33 | 20.4 | Blue | 547 |
| Example 12 | Compound 119 | 4.25 | 6.50 | 20.9 | Blue | 570 |
| Example 13 | Compound 150 | 4.34 | 6.33 | 19.9 | Blue | 588 |
| Example 14 | Compound 166 | 4.44 | 6.12 | 19.5 | Blue | 587 |
| Example 15 | Compound 177 | 4.39 | 6.29 | 20.4 | Blue | 565 |
| Comparative Example 1 | NPB | 7.01 | 5.29 | 17.6 | Blue | 258 |
| Comparative Example 2 | Compound A | 3.77 | 5.81 | 18.7 | Blue | 420 |
| Comparative Example 3 | Compound B | 4.51 | 5.77 | 15.4 | Blue | 130 |
| Comparative Example 4 | Compound C | 4.71 | 5.65 | 15.7 | Blue | 160 |
| Comparative Example 5 | Compound D | 3.79 | 5.73 | 18.9 | Blue | 435 |
| Comparative Example 6 | Compoud E | 3.94 | 5.67 | 18.8 | Blue | 448 |
| Comparative Example 7 | Compound F | 4.22 | 5.99 | 18.1 | Blue | 392 |
| Comparative Example 8 | Compound G | 4.13 | 5.78 | 18.3 | Blue | 430 |
| Comparative Example 9 | Compound H | 4.05 | 5.77 | 17.9 | Blue | 386 |

TABLE 2-continued
| Hole transport material | Driving voltage (V) | Emission efficiency (cd/A) | Maximum EQE (%) | Emission color | Half lifespan (hr @100 mA/cm$^2$) |
|---|---|---|---|---|---|
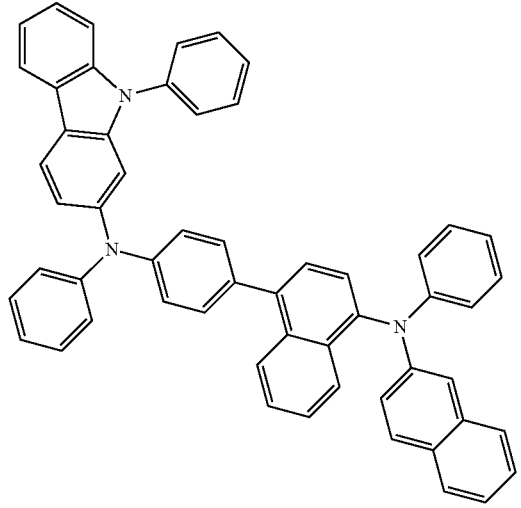
A
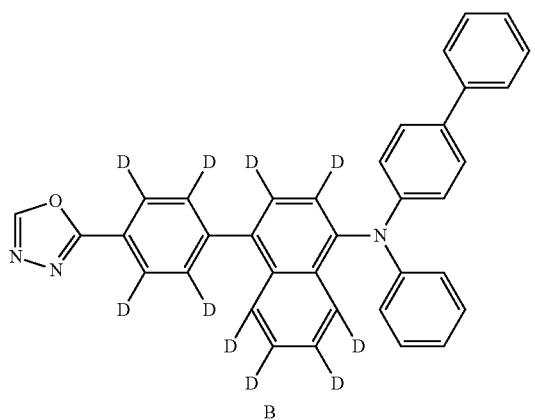
B
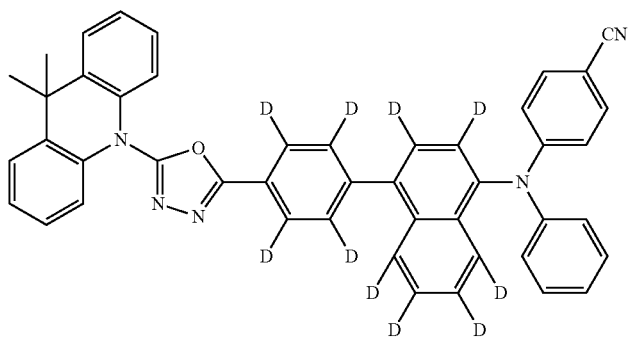
C TABLE 2-continued
| Hole transport material | Driving voltage (V) | Emission efficiency (cd/A) | Maximum EQE (%) | Emission color | Half lifespan (hr @100 mA/cm$^2$) |
| --- | --- | --- | --- | --- | --- |
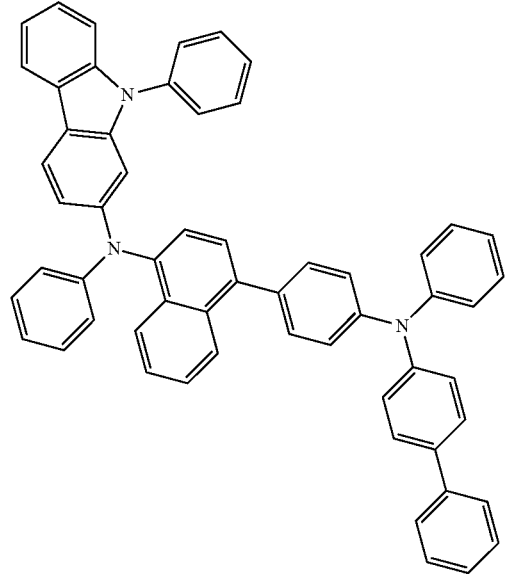
D
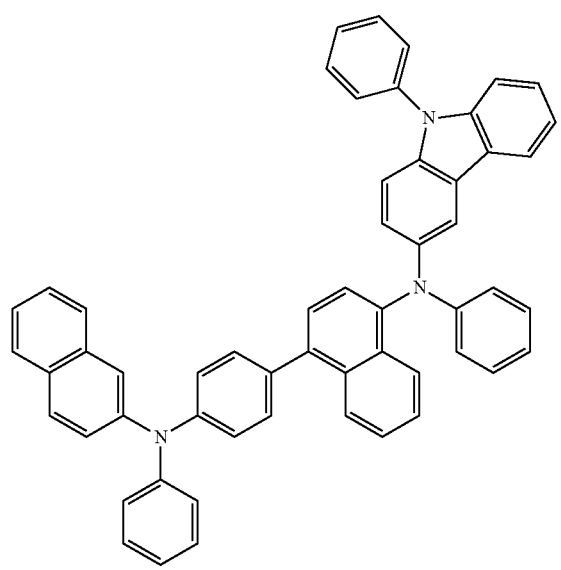
E TABLE 2-continued
| Hole transport material | Driving voltage (V) | Emission efficiency (cd/A) | Maximum EQE (%) | Emission color | Half lifespan (hr @100 mA/cm²) |
|---|---|---|---|---|---|
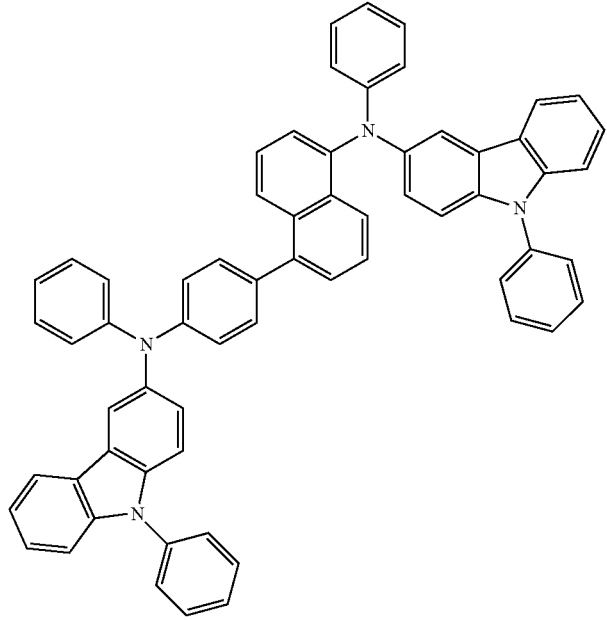
F
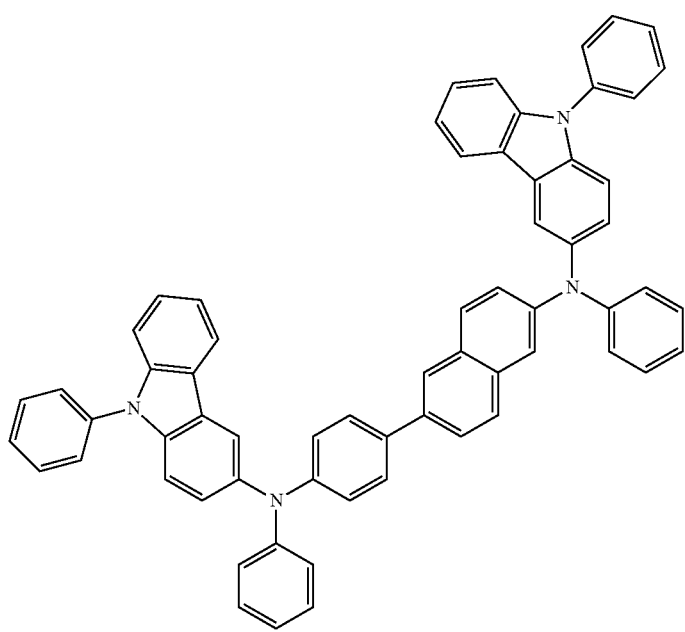
G TABLE 2-continued

| Hole transport material | Driving voltage (V) | Emission efficiency (cd/A) | Maximum EQE (%) | Emission color | Half lifespan (hr @100 mA/cm$^2$) |
| --- | --- | --- | --- | --- | --- |

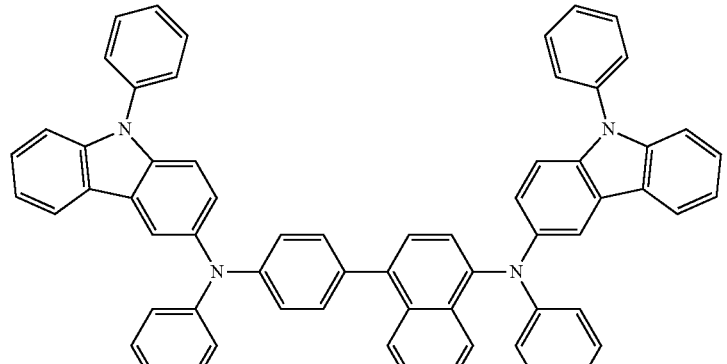

H

Referring to Table 2, it can be seen that the light-emitting devices of Examples 1 to 15 had excellent driving voltage and excellent luminescence efficiency EQE compared to the light-emitting devices of Comparative Examples 1 to 9.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the present disclosure as defined by the following claims, and equivalents thereof.

What is claimed is:

1. An arylamine compound represented by Formula 1:

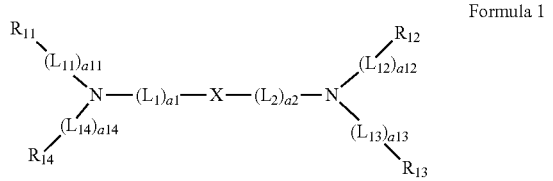

Formula 1

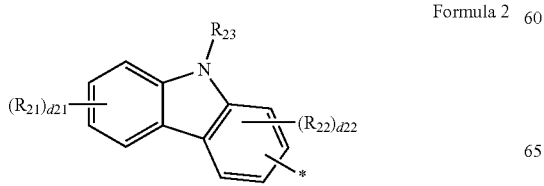

Formula 2

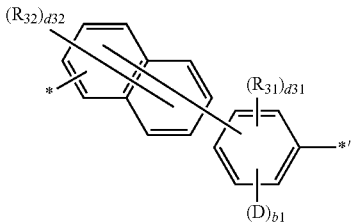

Formula 3 wherein, in Formula 1, $L_1$, $L_2$, and $L_{11}$ to $L_{14}$ are each independently selected from a single bond, a $C_5$-$C_{60}$ carbocyclic group unsubstituted or substituted with at least one $R_{10a}$, and a $C_1$-$C_{60}$ heterocyclic group unsubstituted or substituted with at least one $R_{10a}$, a1, a2, and a11 to a14 are each independently an integer from 1 to 3, $R_{11}$ to $R_{14}$ are each independently selected from a group represented by Formula 2, a $C_1$-$C_{60}$ alkyl group unsubstituted or substituted with at least one $R_{10a}$, a $C_5$-$C_{30}$ carbocyclic group unsubstituted or substituted with at least one $R_{10a}$, and a $C_2$-$C_{30}$ heterocyclic group unsubstituted or substituted with at least one $R_{10a}$, wherein at least one of $R_{11}$ to $R_{14}$ is a group represented by Formula 2, X is a linking group represented by Formula 3, $R_{21}$ to $R_{23}$, $R_{31}$, and $R_{32}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, or $-P(=O)(Q_1)(Q_2)$, d21 is an integer from 1 to 4, d22 is an integer from 1 to 3, d31 is an integer from 0 to 3, d32 is an integer from 1 to 6,

* in Formula 2 indicates a binding site to a neighboring atom,

D in Formula 3 is deuterium, b1 is an integer from 1 to 4, the sum of d31 and b1 is 4,

* and *' each indicate a binding site to a neighboring atom, $R_{10a}$ is:

deuterium, $-F$, $-Cl$, $-Br$, $-I$, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, $-F$, $-Cl$, $-Br$, $-I$, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, $-Si(Q_{11})(Q_{12})(Q_{13})$, $-N(Q_{11})(Q_{12})$, $-B(Q_{11})(Q_{12})$, $-C(=O)(Q_{11})$, $-S(=O)_2(Q_{11})$, $-P(=O)(Q_{11})(Q_{12})$, or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, $-F$, $-Cl$, $-Br$, $-I$, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, $-Si(Q_{21})(Q_{22})(Q_{23})$, $-N(Q_{21})(Q_{22})$, $-B(Q_{21})(Q_{22})$, $-C(=O)(Q_{21})$, $-S(=O)_2(Q_{21})$, $-P(=O)(Q_{21})(Q_{22})$, or any combination thereof, or $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, or $-P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ are each independently: hydrogen; deuterium; $-F$; $-Cl$; $-Br$; $-I$; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, $-F$, a cyano group, a $C_1$-$C_{60}$ alkyl group, a $C_1$-$C_{60}$ alkoxy group, a phenyl group, a biphenyl group, or any combination thereof.

2. The arylamine compound of claim 1, wherein Formula 2 is represented by one of Formulae 2-1 to 2-4:

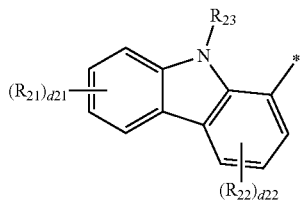

Formula 2-1

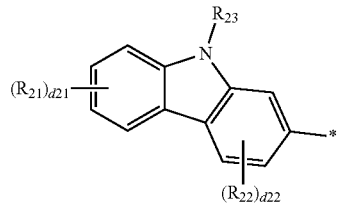

Formula 2-2

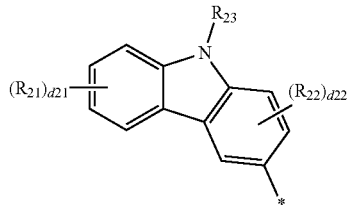

Formula 2-3

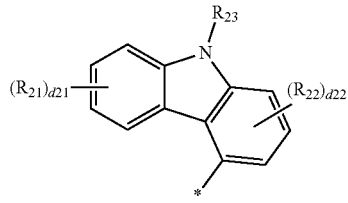

Formula 2-4 wherein, in Formulae 2-1 to 2-4, $R_{21}$ to $R_{23}$, d21, and d22 are each the same as described in claim 1, and * indicates a binding site to a neighboring atom.

3. The arylamine compound of claim 1, wherein:

$R_{11}$ is a group represented by Formula 2;

$R_{12}$ is a group represented by Formula 2;

$R_{11}$ and $R_{12}$ are each a group represented by Formula 2;

$R_{11}$ and $R_{14}$ are each a group represented by Formula 2;

$R_{11}$, $R_{12}$, and $R_{14}$ are each a group represented by Formula 2;

$R_{11}$, $R_{12}$, and $R_{13}$ are each a group represented by Formula 2; or $R_{11}$, $R_{12}$, $R_{13}$, and $R_{14}$ are each a group represented by Formula 2.

4. The arylamine compound of claim 1, wherein:

$R_{11}$ is a group represented by Formula 2; or $R_{12}$ is a group represented by Formula 2.

5. The arylamine compound of claim 1, wherein $L_1$, $L_2$, and $L_{11}$ to $L_{14}$ are each independently:

a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-a fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$, and $R_{10a}$ is the same as described in claim 1.

6. The arylamine compound of claim 1, wherein $L_1$, $L_2$, and $L_{11}$ to $L_{14}$ are each independently selected from a single bond and groups represented by Formulae 10-1 to 10-41:

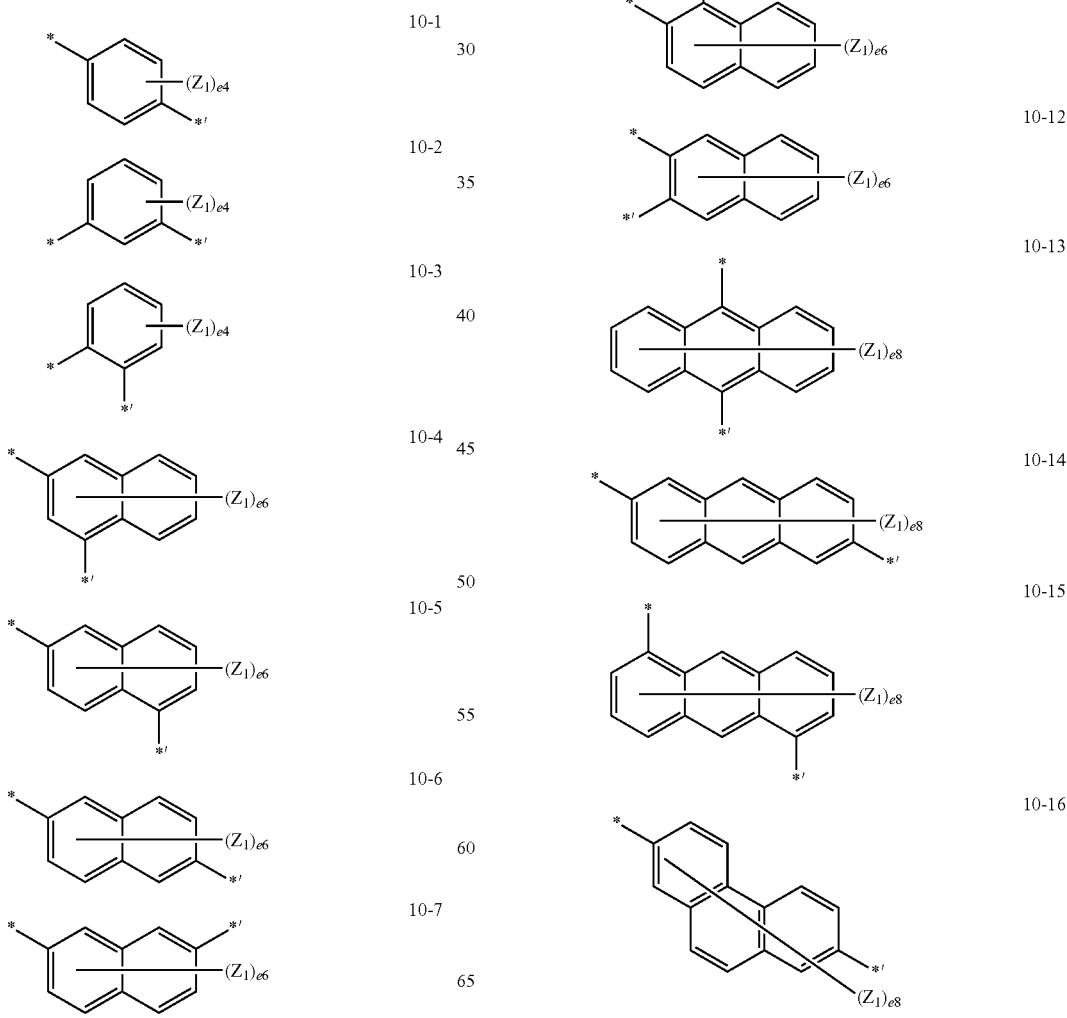

10-17
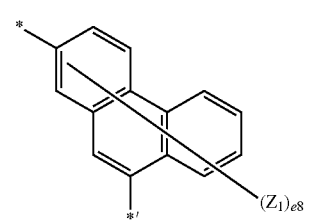
10-18
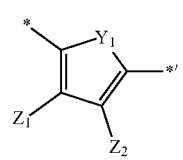
10-19
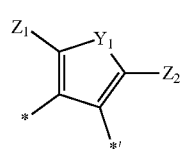
10-20
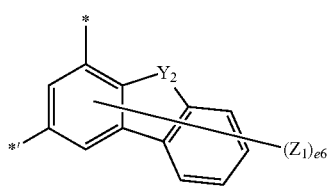
10-21
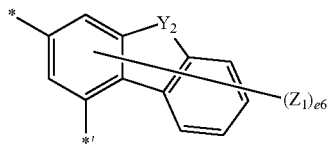
10-22
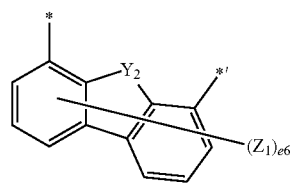
10-23
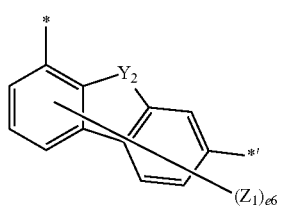
10-25
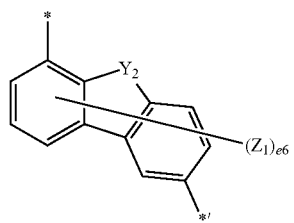
10-26
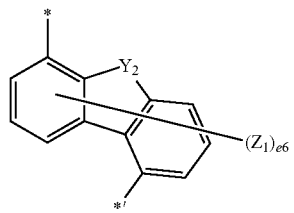
10-27
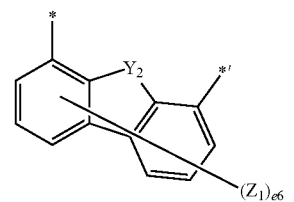
10-28
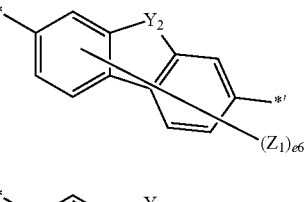
10-29
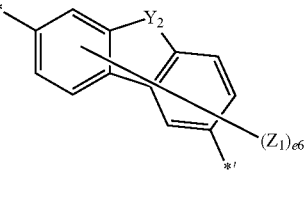
10-30
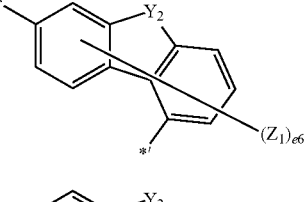
10-31
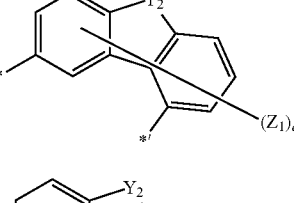
10-24
10-32

-continued 10-33

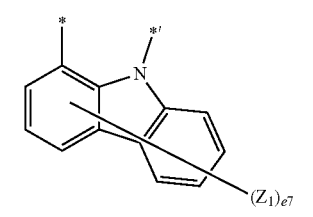

10-34

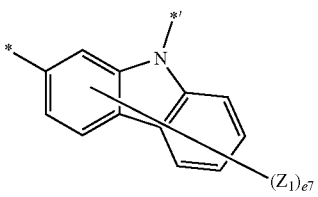

10-35

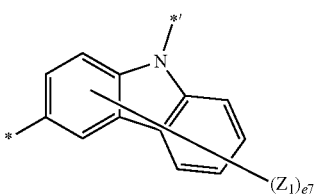

10-36

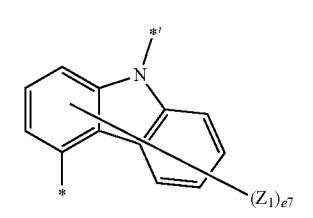

10-37

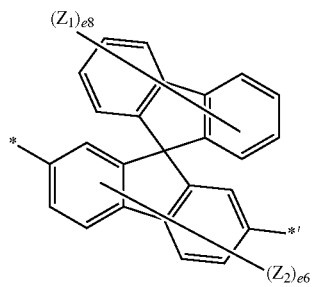

10-38

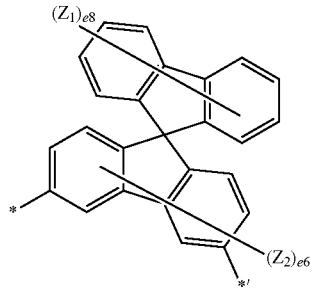

-continued 10-39

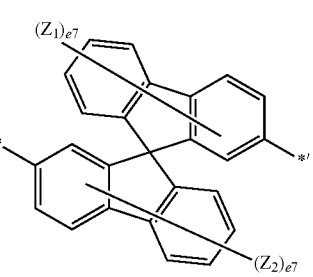

10-40

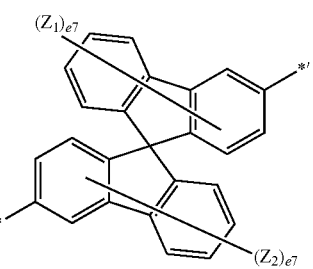

10-41

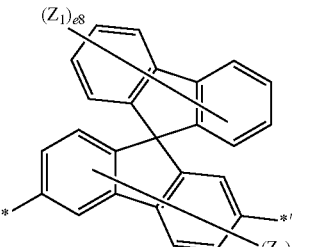

wherein, in Formulae 10-1 to 10-41, $Y_1$ is selected from O and S, $Y_2$ is selected from O, S, N($Z_3$), and C($Z_3$)($Z_4$), $Z_1$ to $Z_4$ are each the same as described in connection with $R_{21}$ in claim 1, e4 is an integer from 1 to 4, e6 is an integer from 1 to 6, e7 is an integer from 1 to 7, e8 is an integer from 1 to 8, and

* and *' each indicate a binding site to a neighboring atom.

7. The arylamine compound of claim 1, wherein $L_1$ and $L_2$ are each a single bond, and a1 and a2 are each 1.

8. The arylamine compound of claim 1, wherein a11 to a14 are each independently 0 or 1.

9. The arylamine compound of claim 1, wherein Formula 3 is represented by one of Formulae 3-1 to 3-14:

3-1

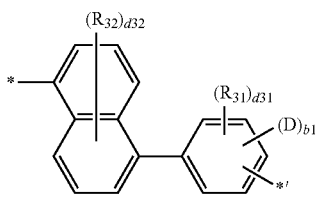

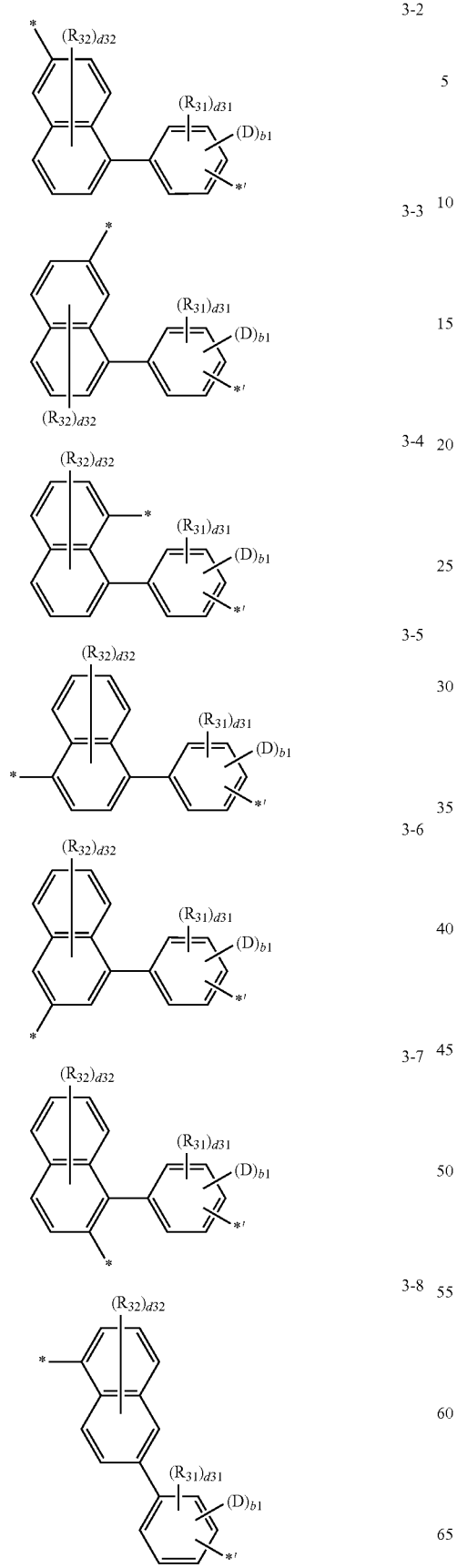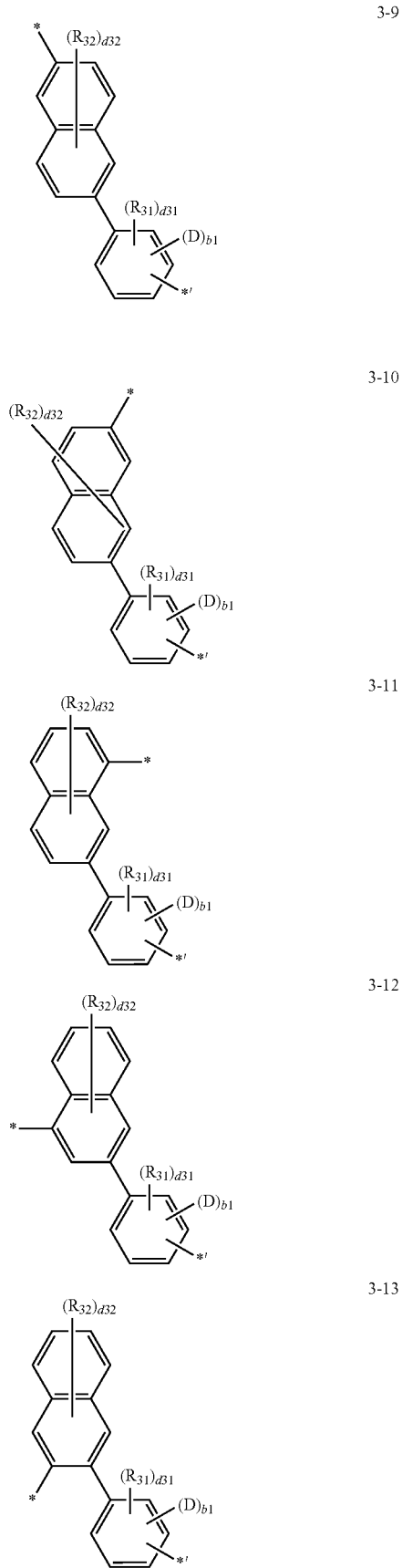

3-14
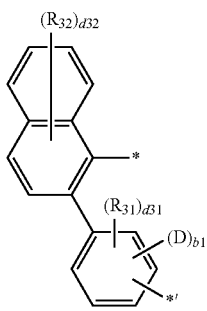
wherein, in Formulae 3-1 to 3-14, $R_{31}$, $R_{32}$, d31, d32, and b1 are each the same as described in claim 1, and * and *' each indicate a binding site to a neighboring atom.
10. The arylamine compound of claim 1, wherein Formula 3 is represented by one of Formulae 4-1 to 4-14:
4-1
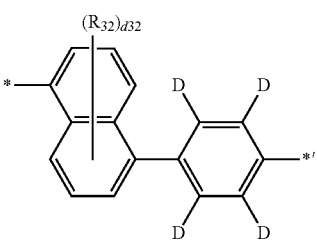
4-2
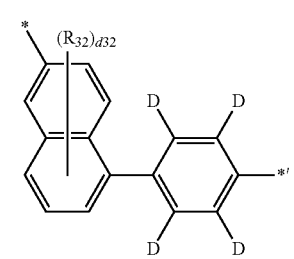
4-3
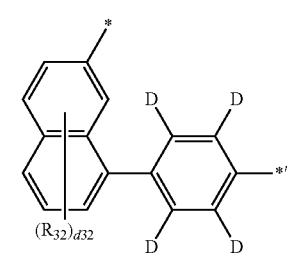
4-4
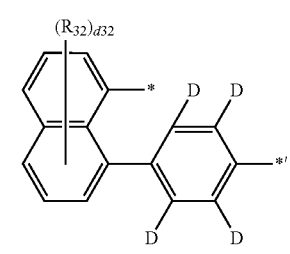
4-5
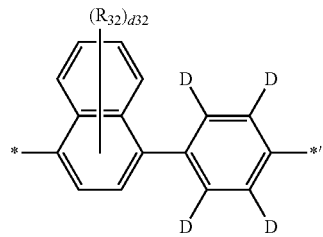
4-6
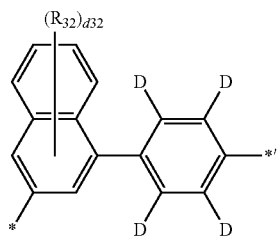
4-7
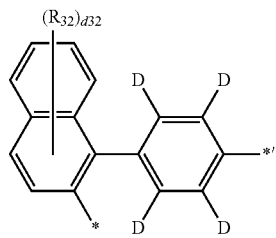
4-8
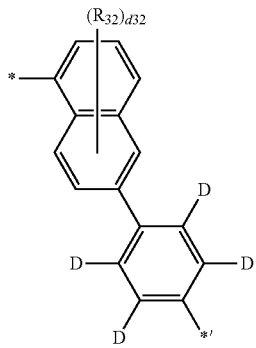
4-9
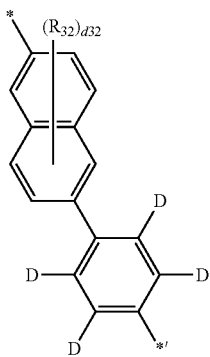

4-10
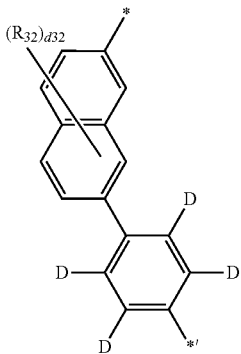

4-11
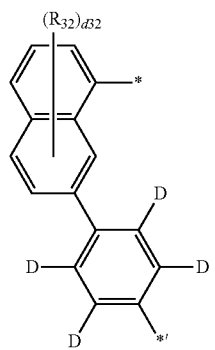

4-12
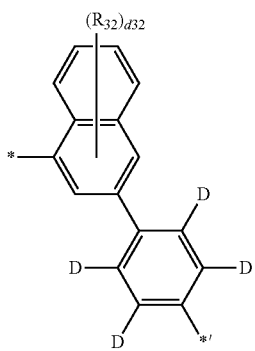

4-13
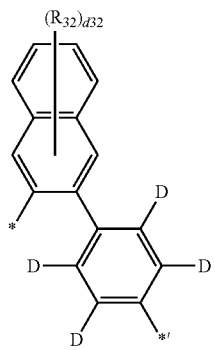

4-14
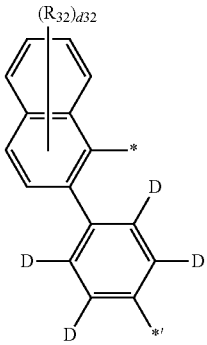

wherein, in Formulae 4-1 to 4-14, $R_{32}$ and d32 are each the same as described in claim 1, and * and *' each indicate a binding site to a neighboring atom.

11. The arylamine compound of claim 1, wherein $R_{11}$ to $R_{14}$ are each independently selected from: a group represented by Formula 2; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, a naphthacenyl group, a picenyl group, a hexacenyl group, a pentaphenyl group, a rubicenyl group, a coronenyl group, an ovalenyl group, a naphthopyrrolyl group, a naphthofuranyl group, a naphthothiophenyl group, a naphthosilolyl group, a benzofurocarbazolyl group, a benzothienocarbazolyl group, a benzosilolocarbazolyl group, a triindolophenyl group, a pyrrolophenanthrenyl group, a furanophenanthrenelenyl group, a thienophenanthrenyl group, a benzonaphthofuranyl group, a benzonaphthothiophenyl group, an (indolo) phenanthrenyl group, a (benzofurano) phenanthrenyl group, and a (benzothieno) phenanthrenyl group, each unsubstituted or substituted with at least one selected from deuterium, —F, —Cl, —Br, —I, cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, a naphthacenyl group, a picenyl group, a hexacenyl group, a pentaphenyl group, a rubicenyl group, a coronenyl group, an ovalenyl group, a naphthopyrrolyl group, a naphthofuranyl group, a naphthothiophenyl group, a naphthosilolyl group, a benzofurocarbazolyl group, a benzothienocarbazolyl group, a benzosilolocarbazolyl group, a triindolophenyl group, a pyrrolophenanthrenyl group, a furanophenanthrenelenyl group, a thienophenanthrenyl group, a benzonaphthofuranyl group, a benzonaphthothiophenyl group, an (indolo) phenanthrenyl group, a (benzofurano) phenanthrenyl group, and a (benzothieno) phenanthrenyl group, wherein at least one of $R_{11}$ to $R_{14}$ is a group represented by Formula 2.

12. The arylamine compound of claim 1, wherein $R_{21}$ to $R_{23}$, $R_{31}$, and $R_{32}$ are each independently selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazino group, a hydrazono group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, and an azadibenzosilolyl group, each unsubstituted or substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, an azadibenzosilolyl group, $-Si(Q_{31})(Q_{32})(Q_{33})$, $-N(Q_{31})(Q_{32})$, $-B(Q_{31})(Q_{32})$, $-P(Q_{31})(Q_{32})$, $-C(=O)(Q_{31})$, $-S(=O)_2(Q_{31})$, and $-P(=O)(Q_{31})(Q_{32})$; and $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$, and $Q_1$ to $Q_3$ and $Q_{31}$ to $Q_{33}$ are each independently selected from:

$-CH_3$, $-CD_3$, $-CD_2H$, $-CDH_2$, $-CH_2CH_3$, $-CH_2CD_3$, $-CH_2CD_2H$, $-CH_2CDH_2$, $-CHDCH_3$, $-CHDCD_2H$, $-CHDCDH_2$, $-CHDCD_3$, $-CD_2CD_3$, $-CD_2CD_2H$, and $-CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, and a triazinyl group, each unsubstituted or substituted with at least one selected from deuterium, a $C_1$-$C_{10}$ alkyl group, a phenyl group, a biphenyl group, a pyridinyl group, a pyrimidinyl group, a pyridazinyl group, a pyrazinyl group, and a triazinyl group.

13. The arylamine compound of claim 1, wherein b1 in Formula 3 is 4.

14. The arylamine compound of claim 1, wherein Formula 1 is represented by Formula 1-1 or 1-2:

Formula 1-1

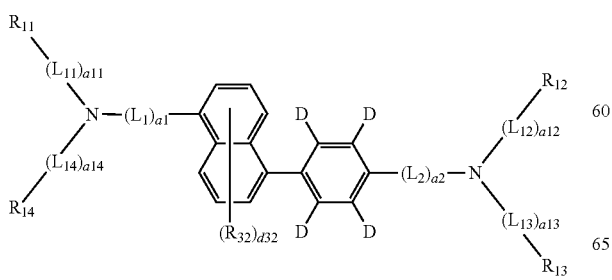

-continued

Formula 1-2

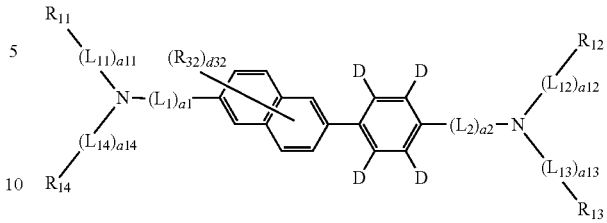

wherein, in Formulae 1-1 and 1-2, $L_1$, $L_2$, $L_{11}$ to $L_{14}$, a1, a2, a11 to a14, $R_{11}$ to $R_{14}$, $R_{32}$, and d32 are each the same as described in claim 1.

15. The arylamine compound of claim 1, wherein the arylamine compound is one of Compounds 1 to 228:

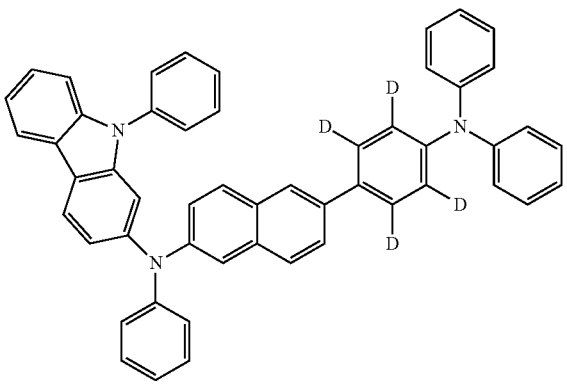

1

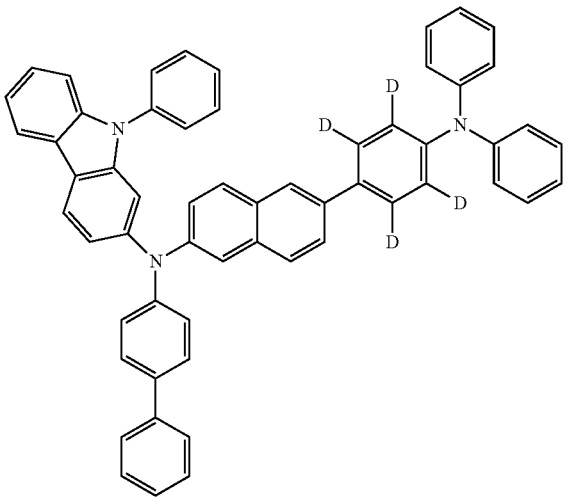

2

-continued
3
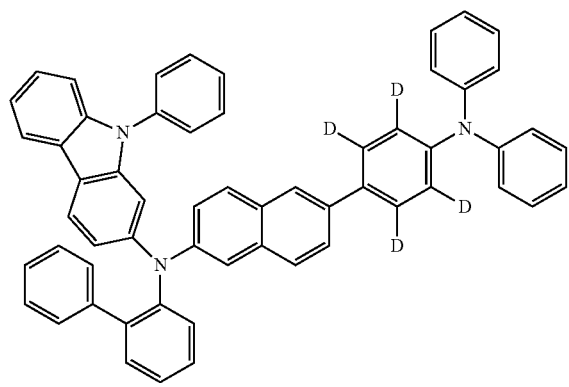
4
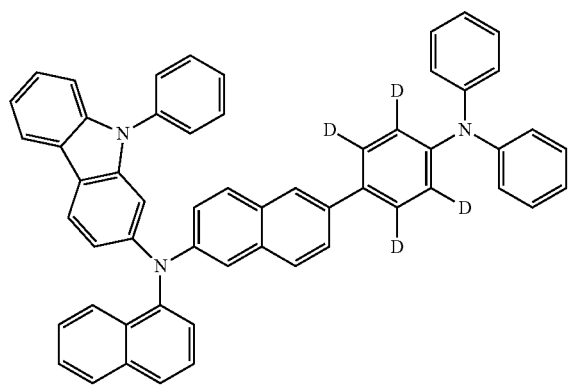
5
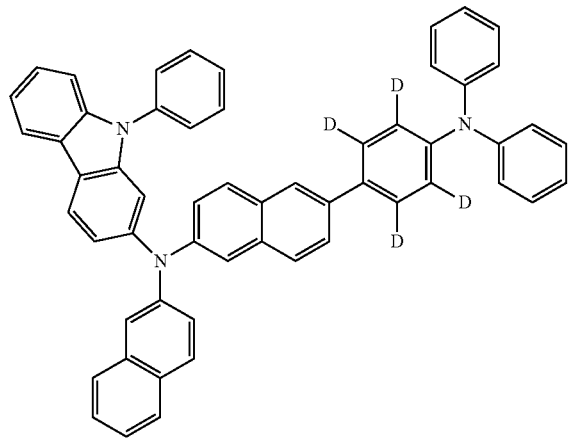
-continued
6
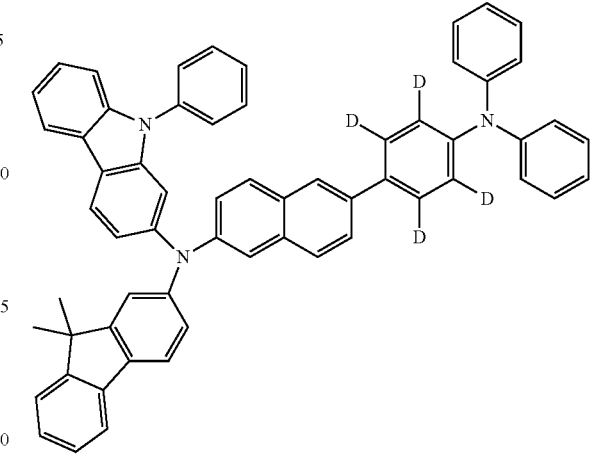
7
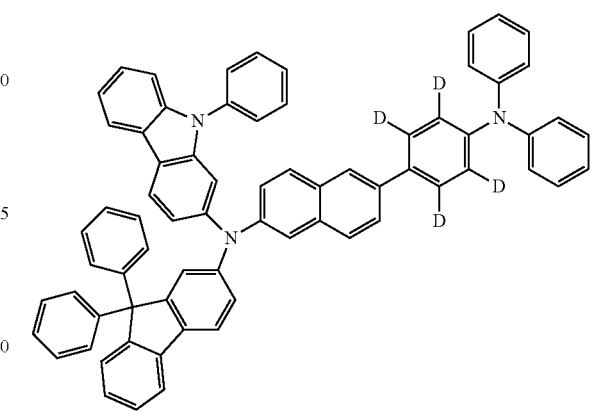
8
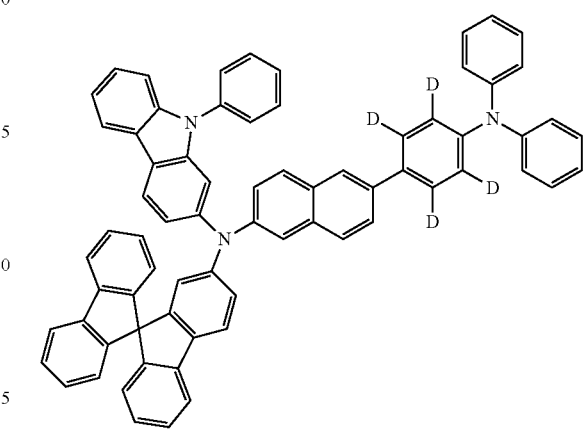

9
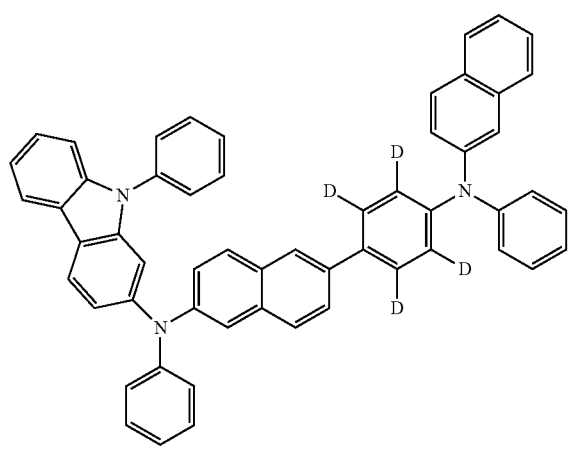
10
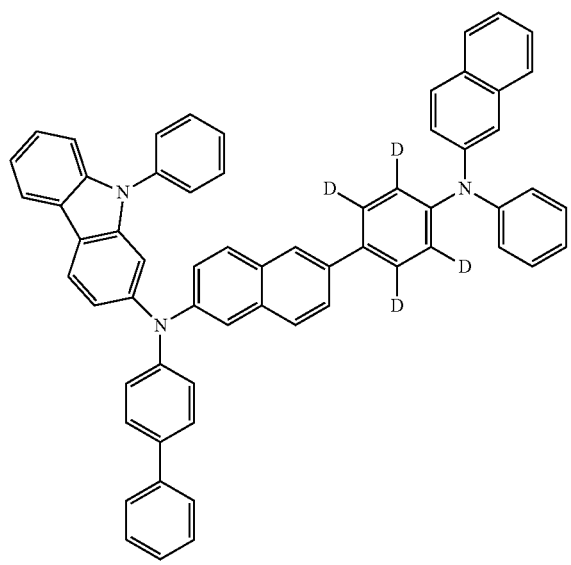
11
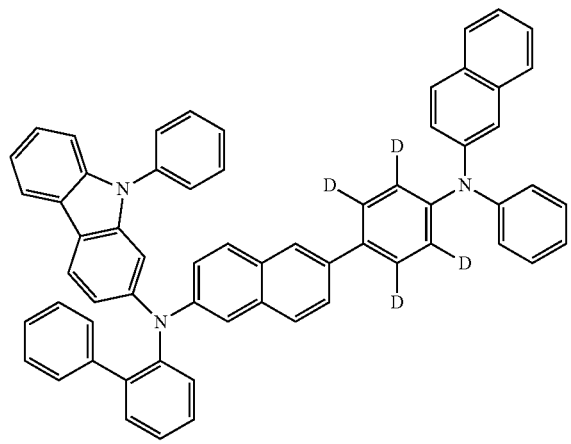
12
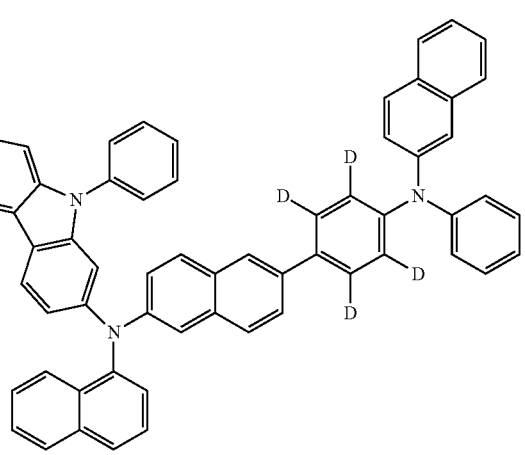
13
14
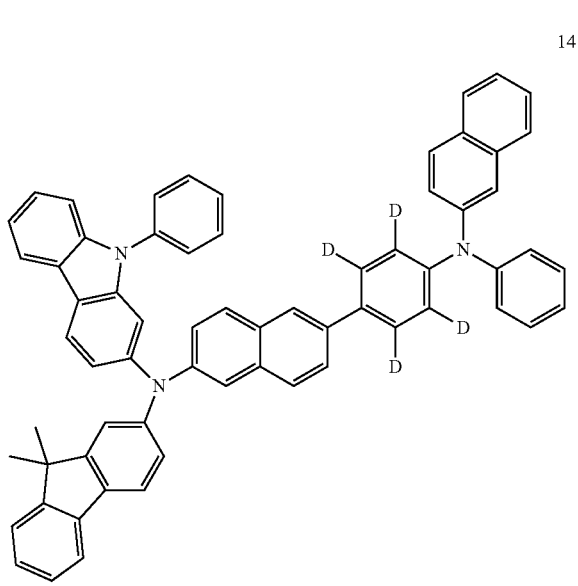

15
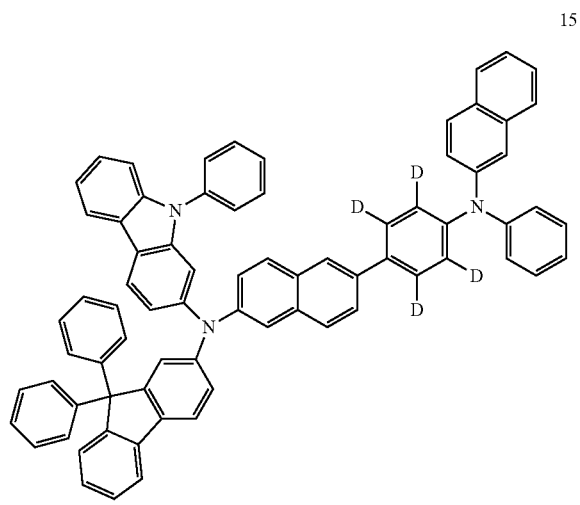
16
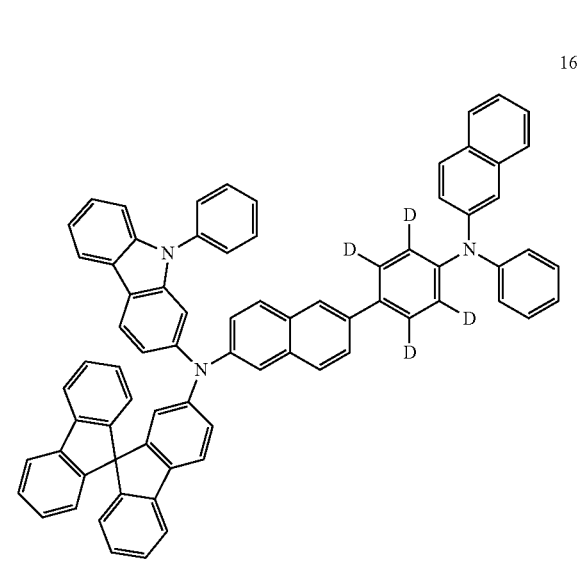
17
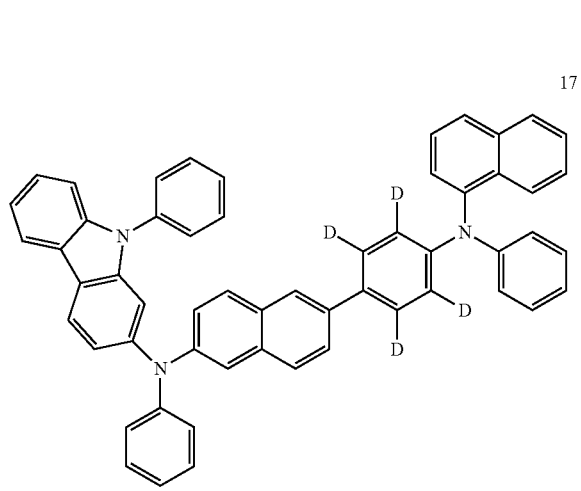
18
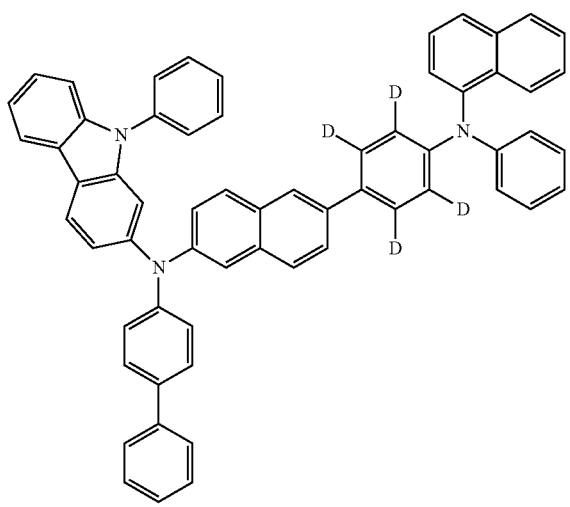
19
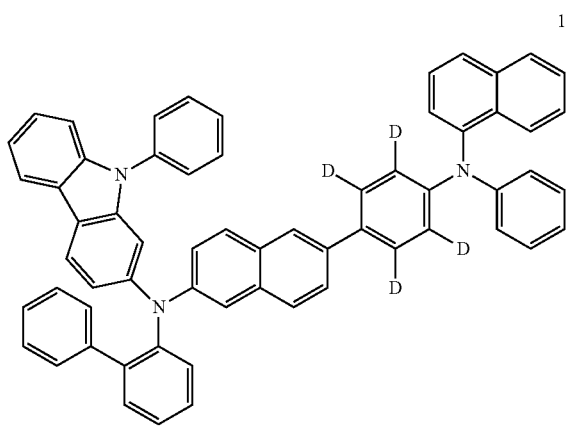
20
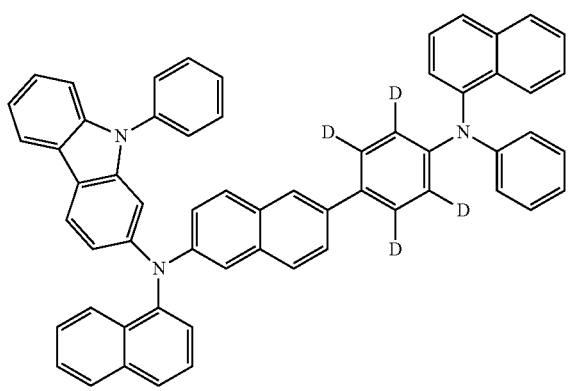

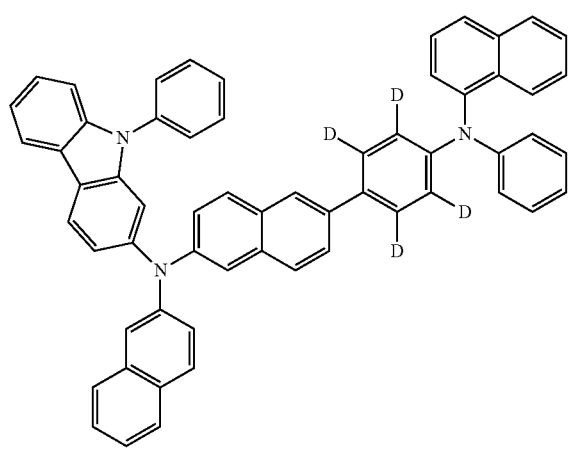
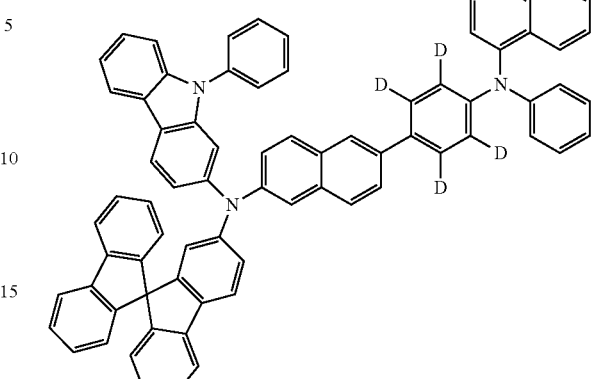
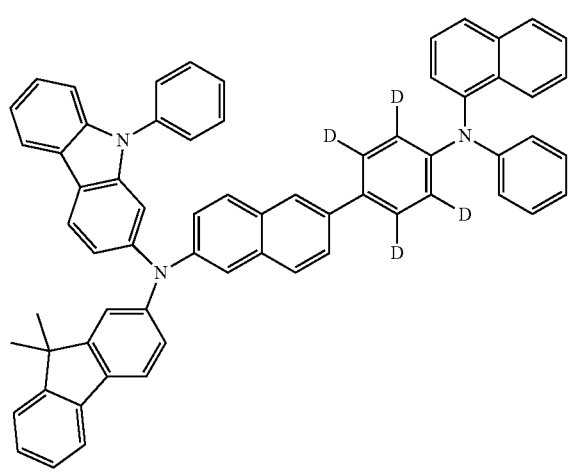
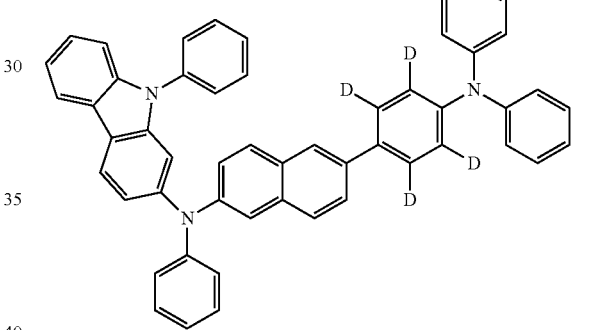
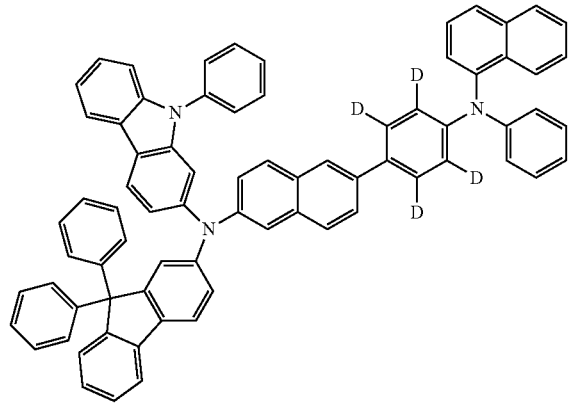
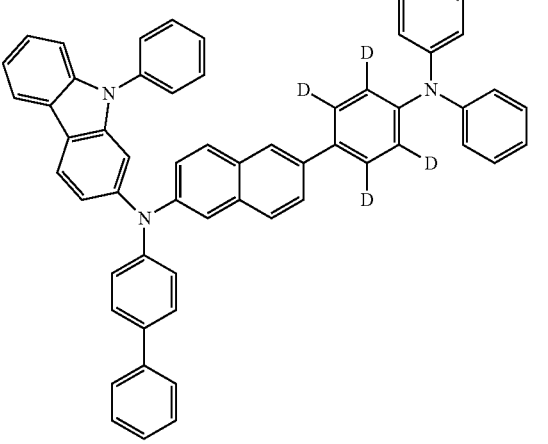

27
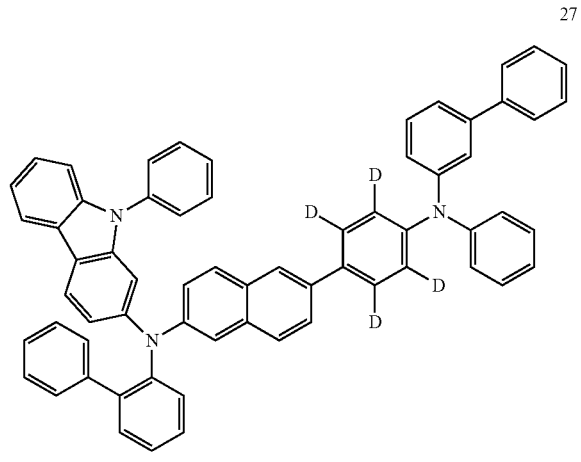
28
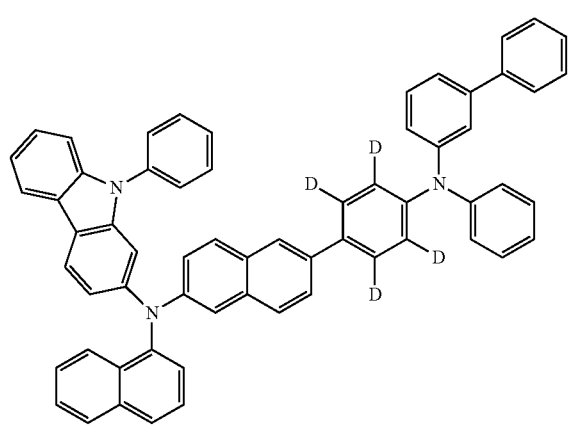
29
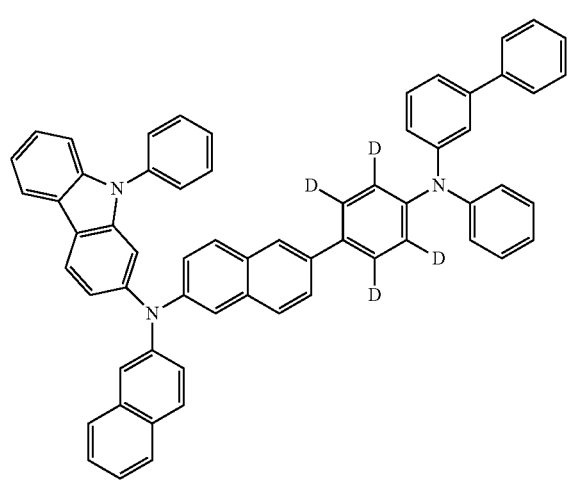
30
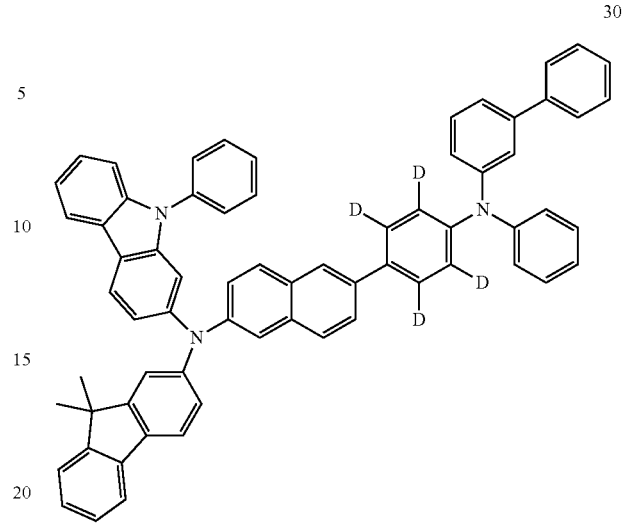
31
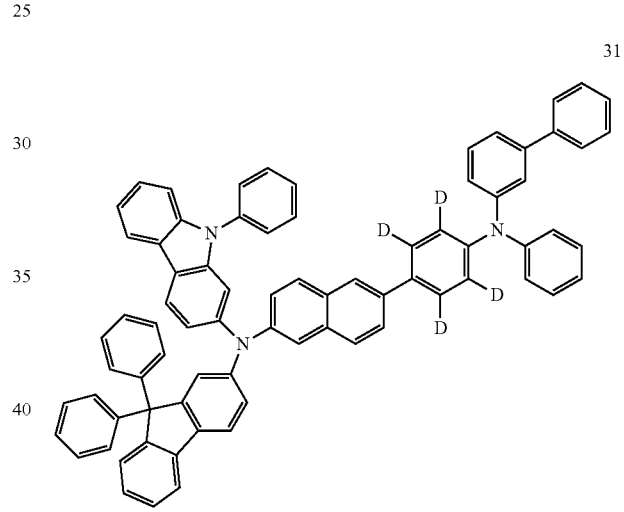
32
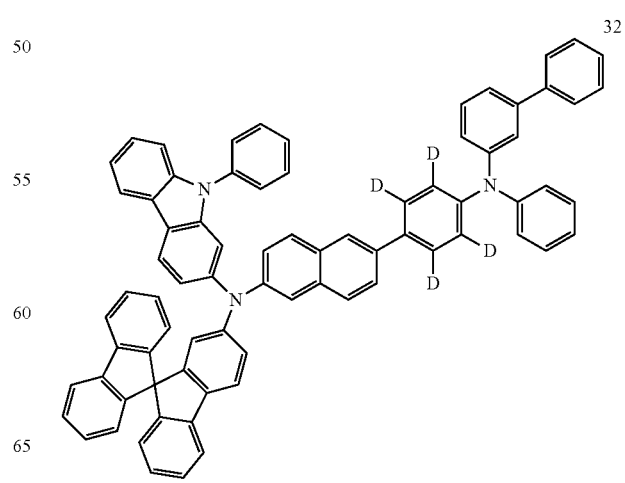

33
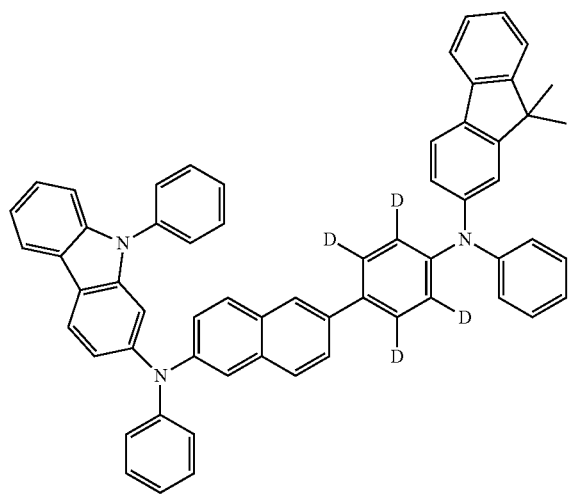
34
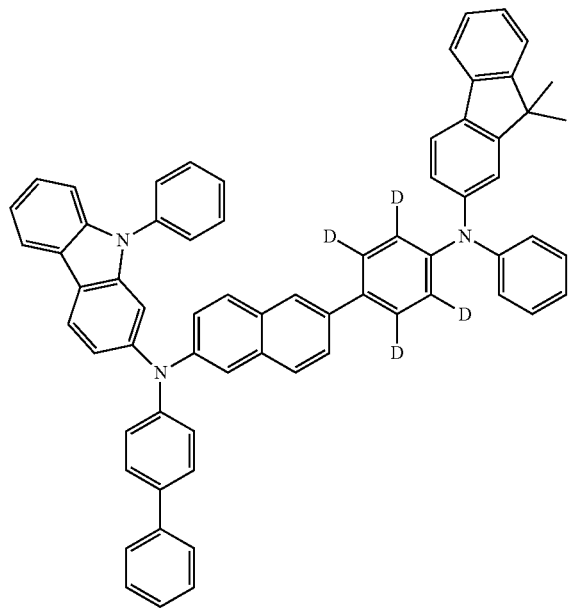
35
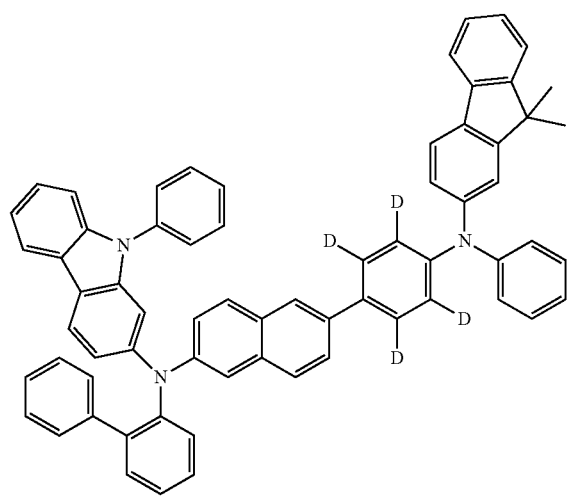
36
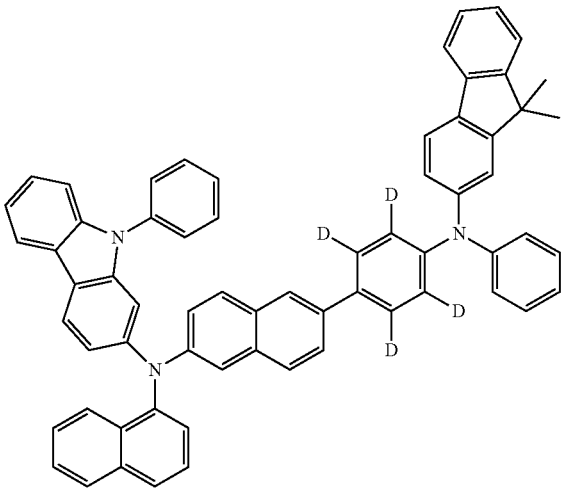
37
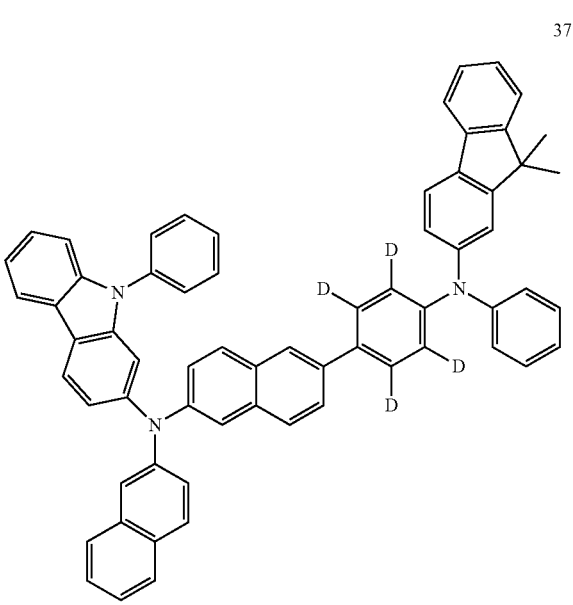
38
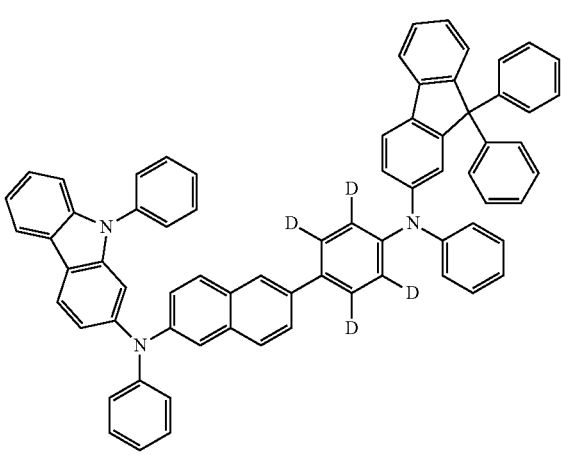

39
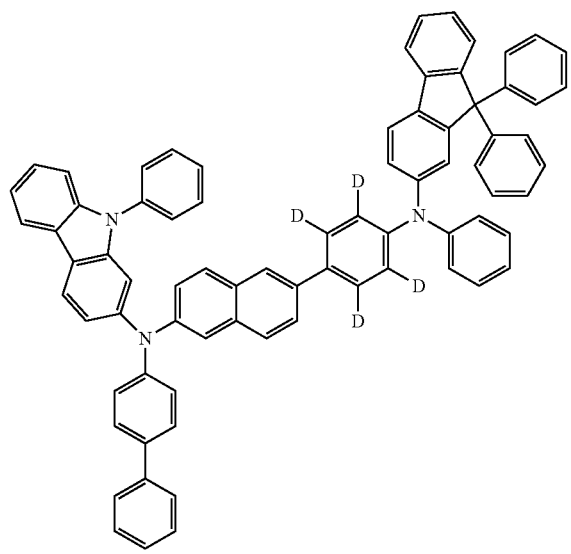
40
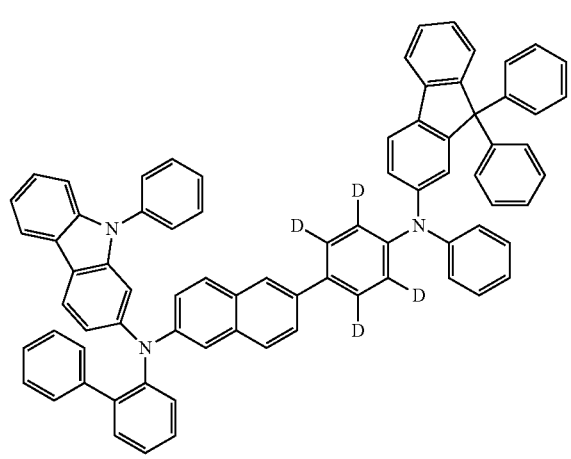
41
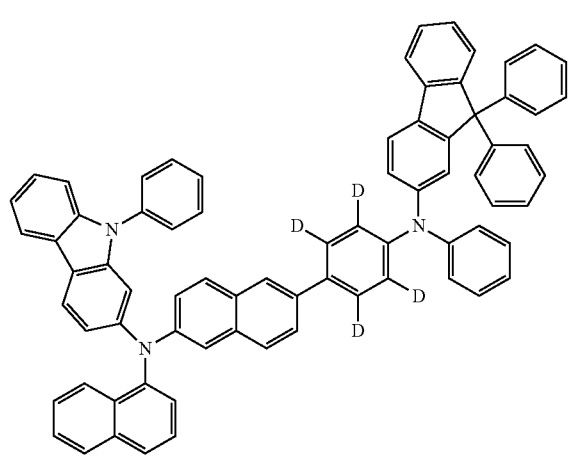
42
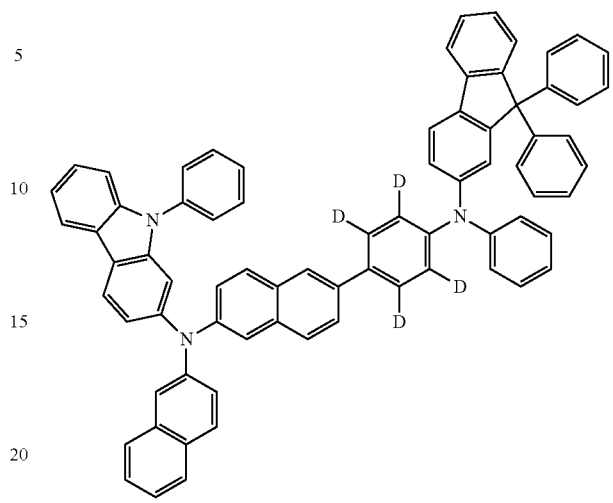
43
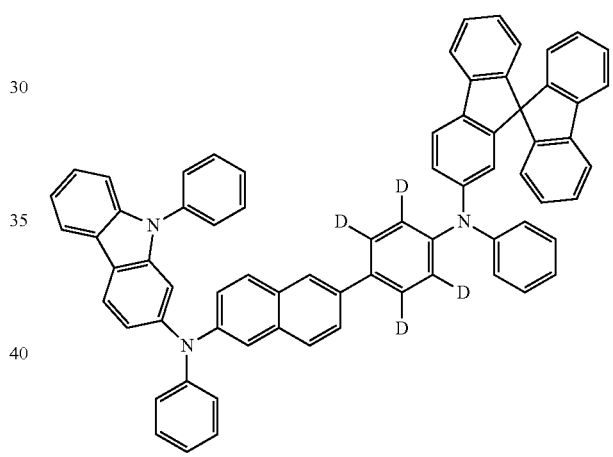
44

45
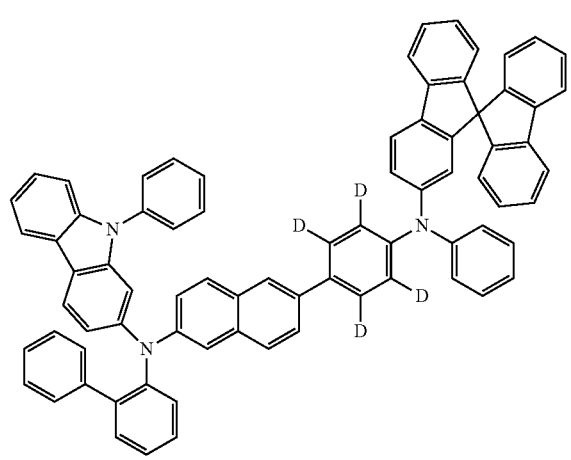
46
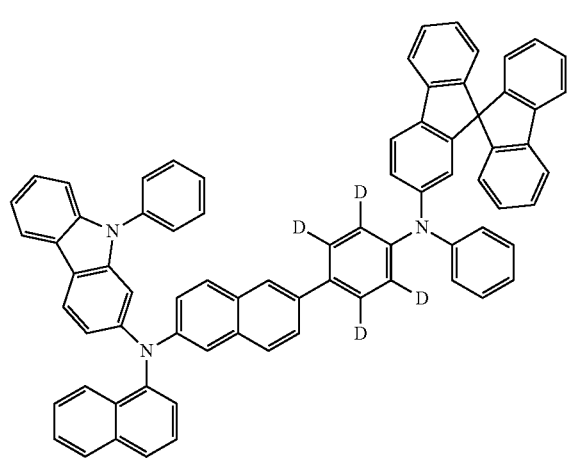
47
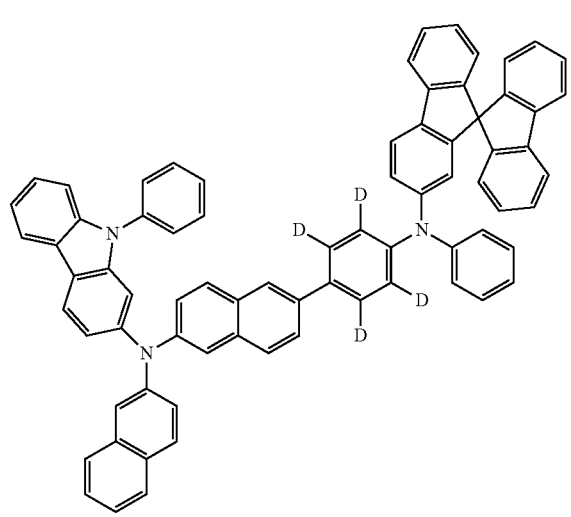
48
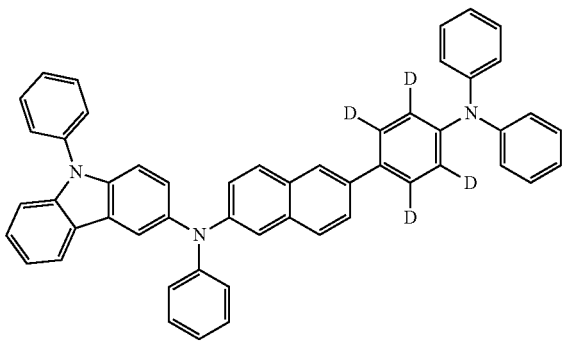
49
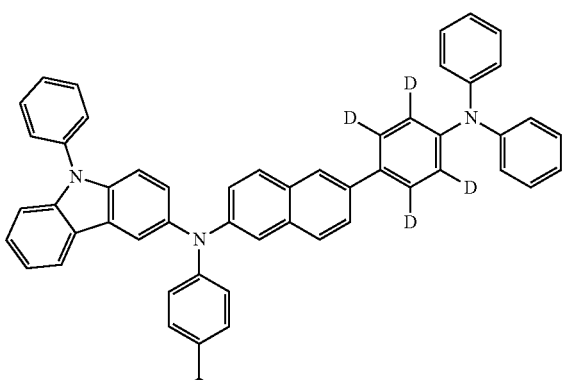
50
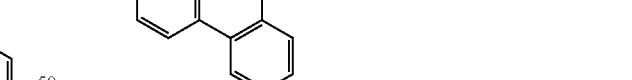
51
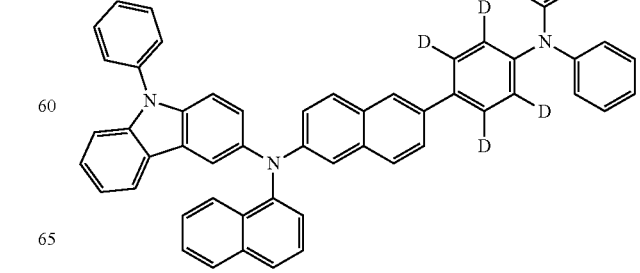

52
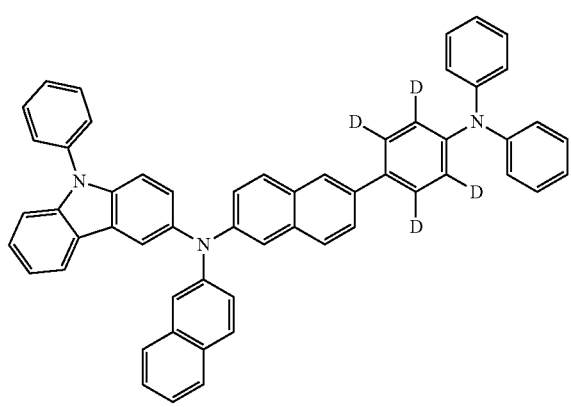
53
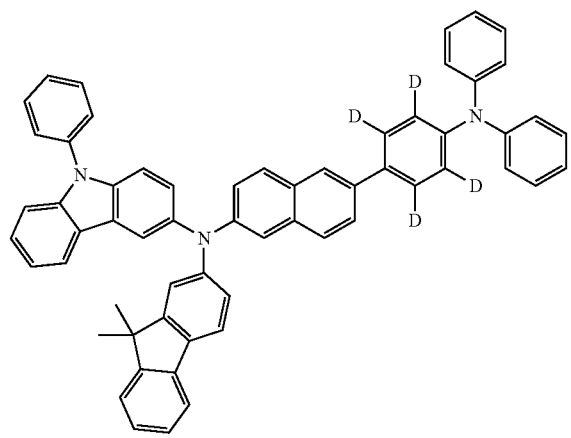
54
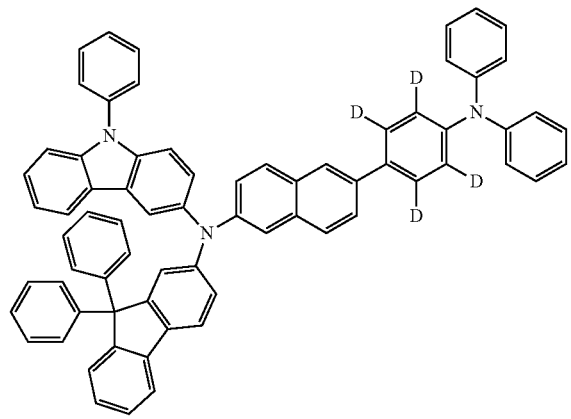
55
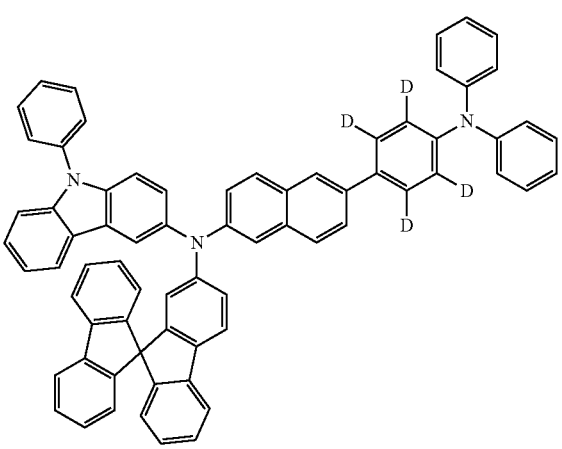
56
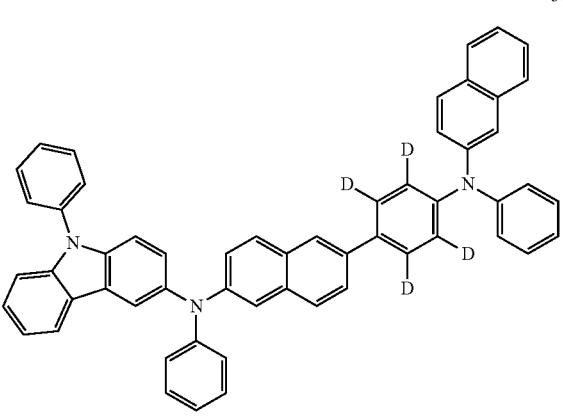
57
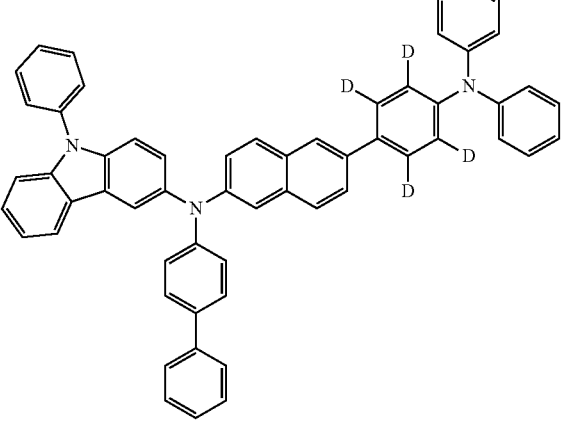

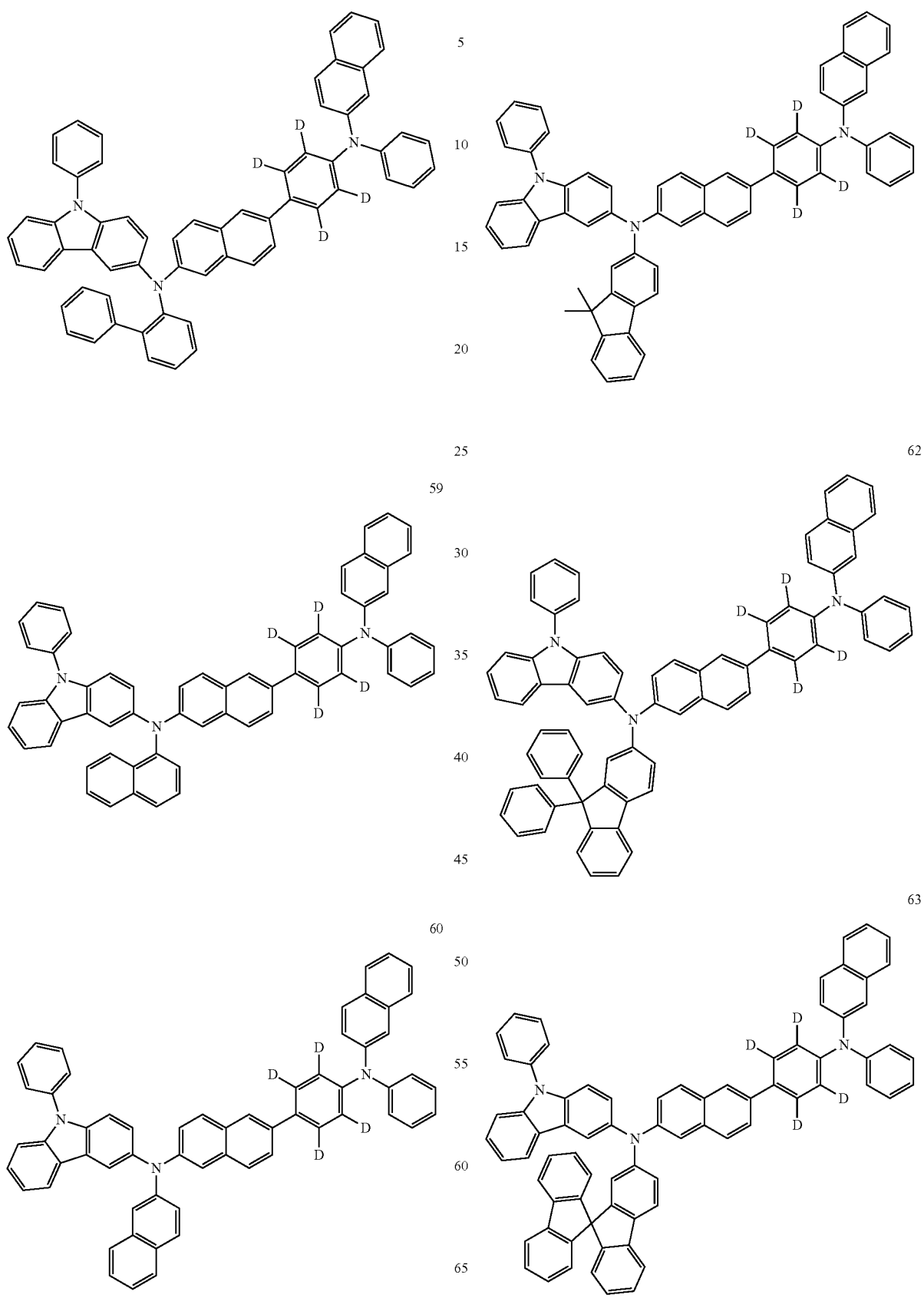

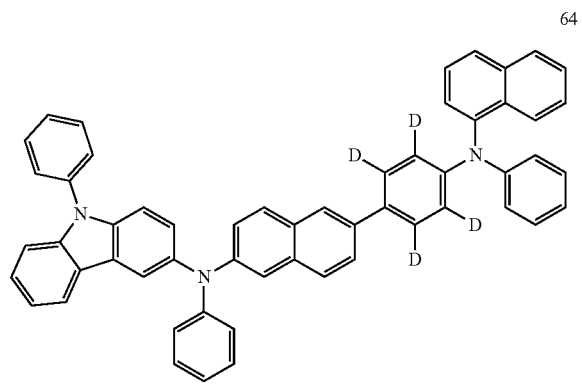
64
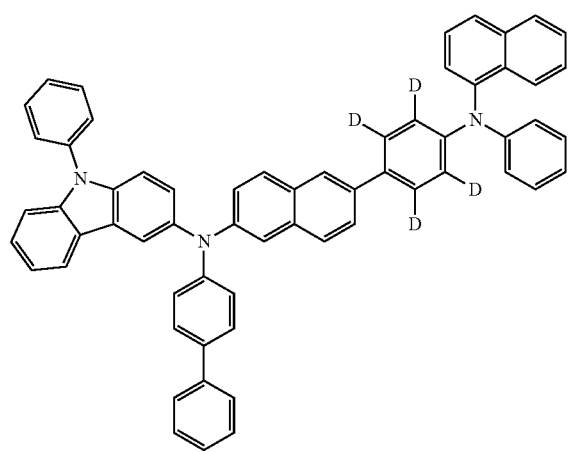
65
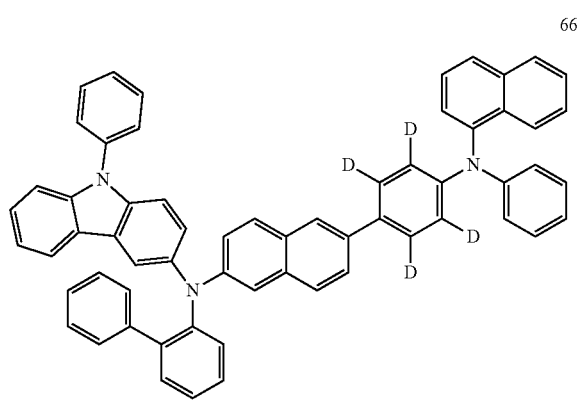
66
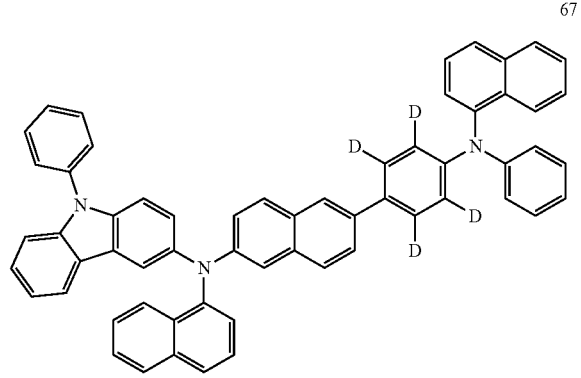
67
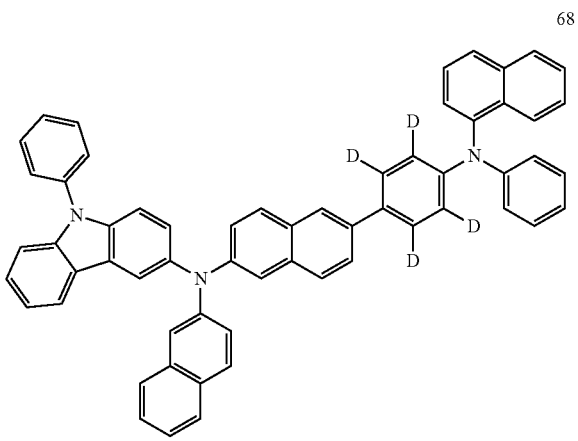
68
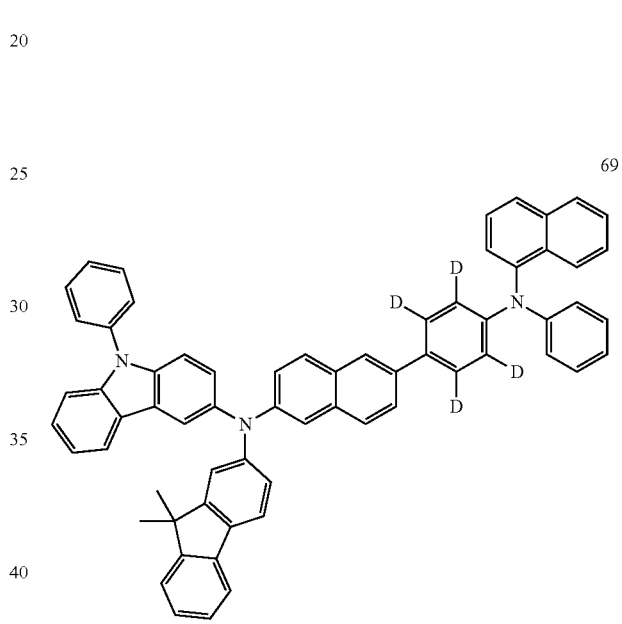
69
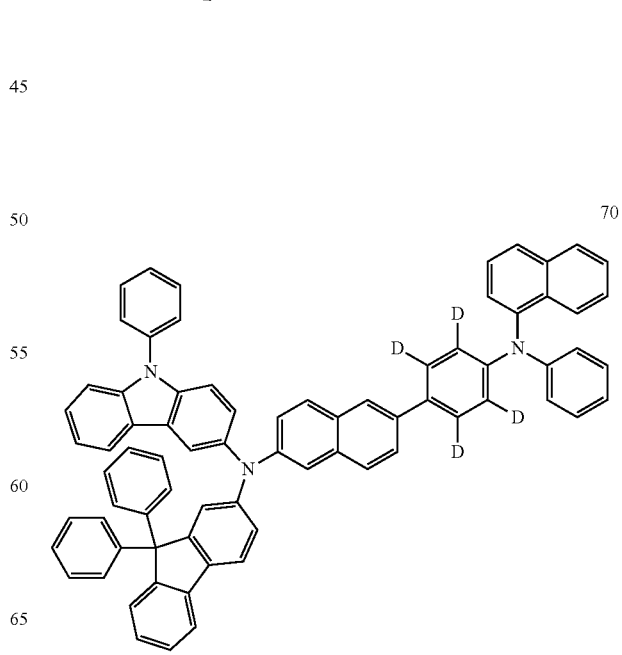
70

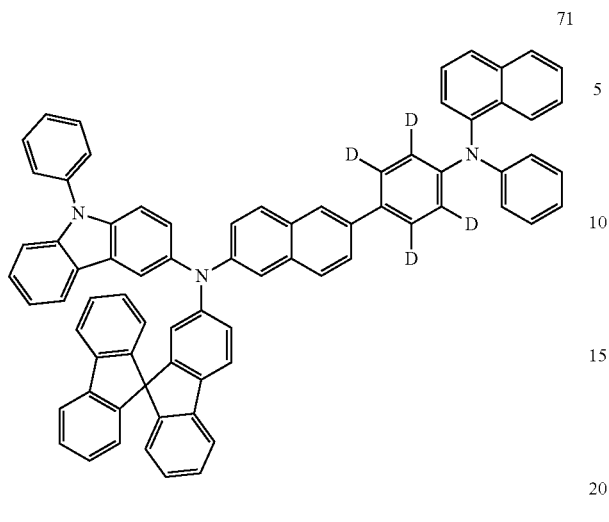
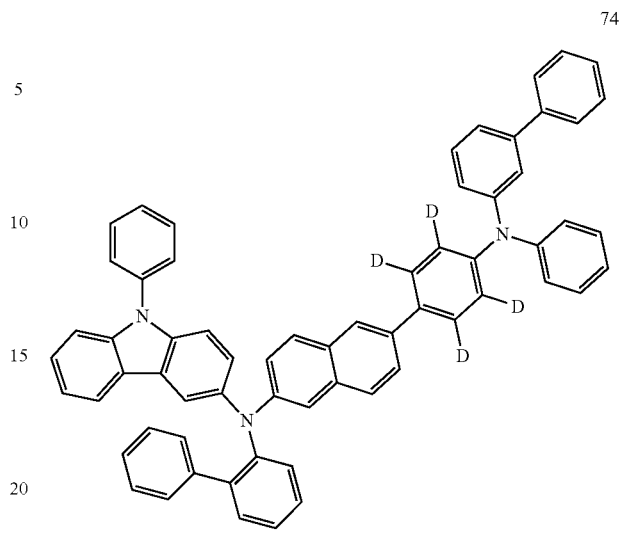
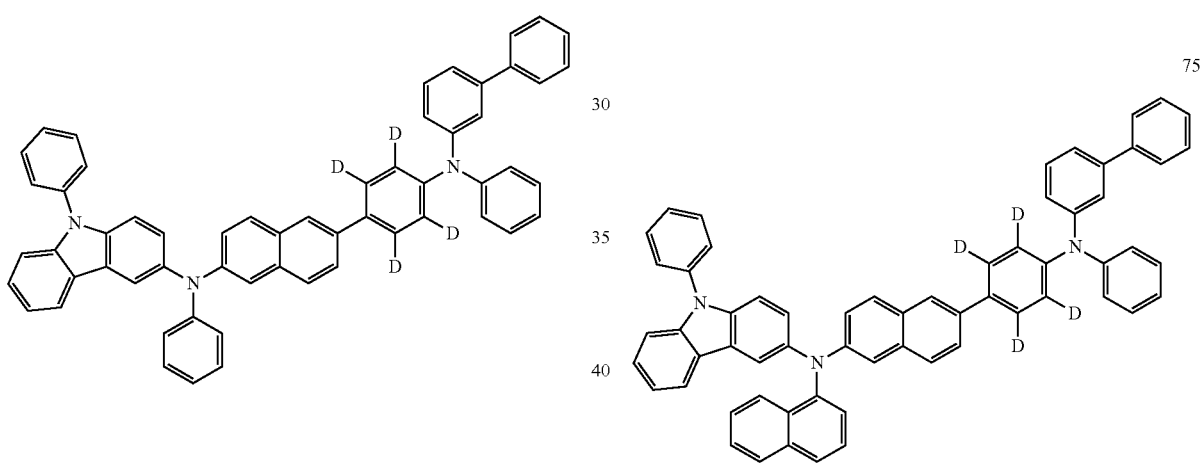
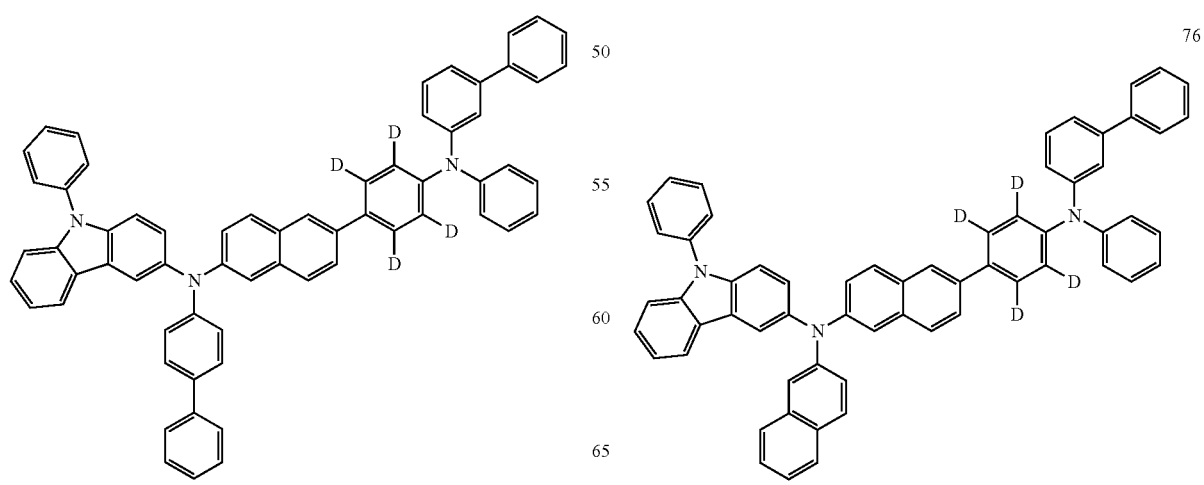

77
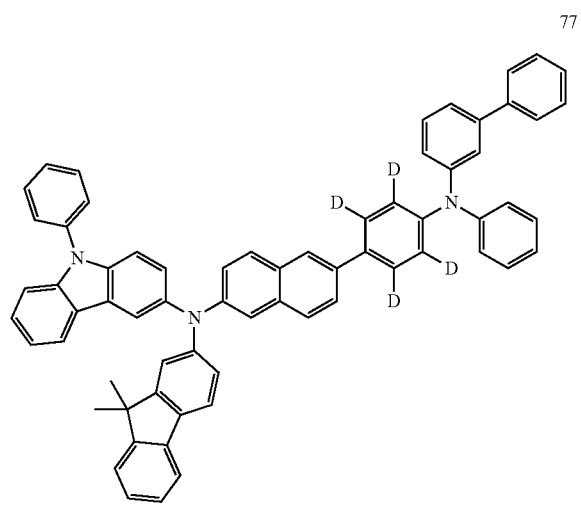
78
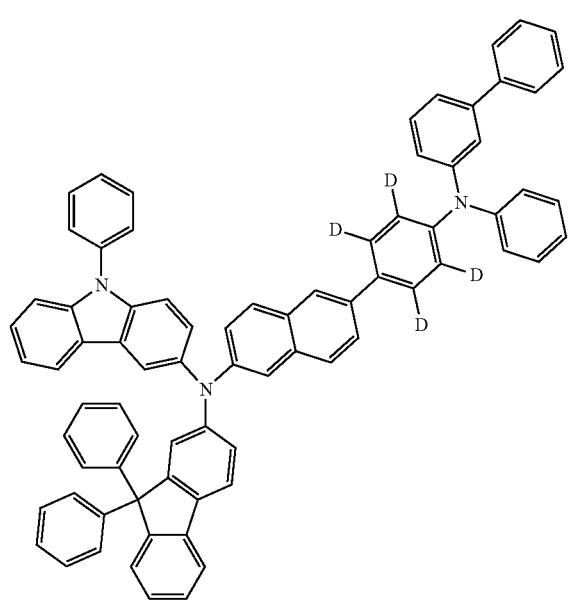
79
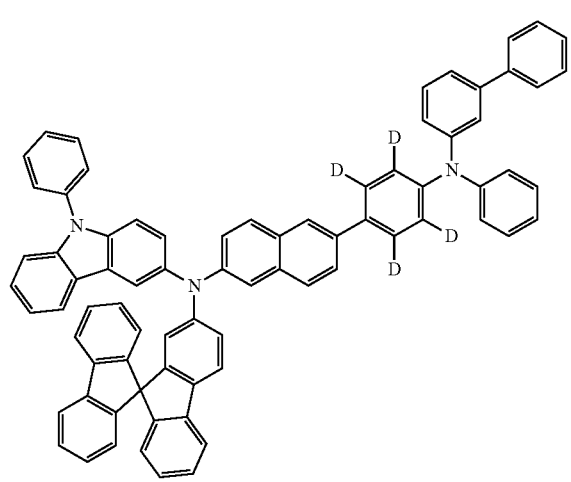
80
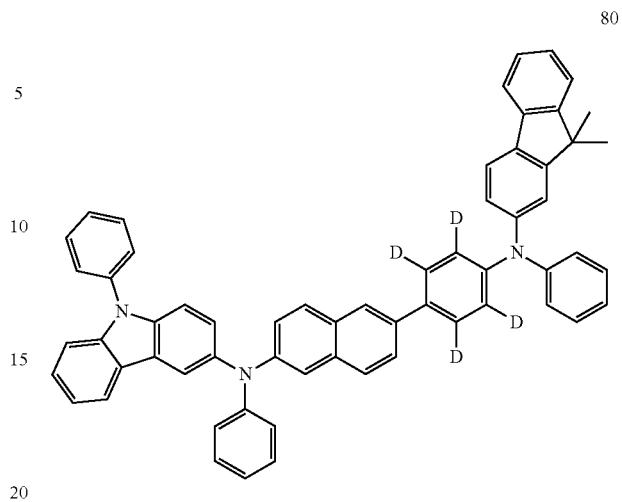
81
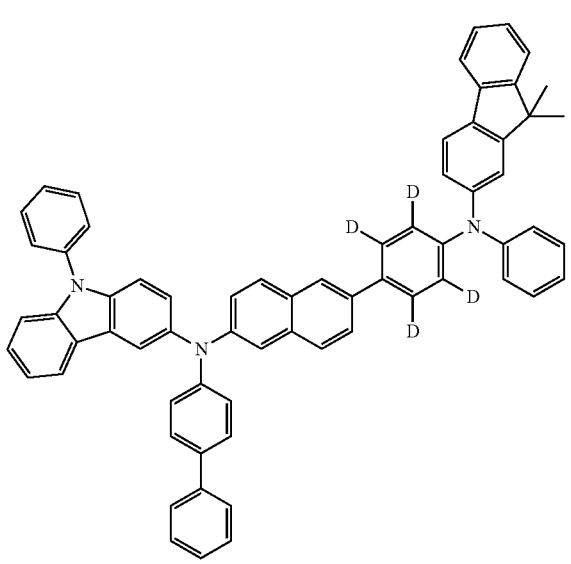
82
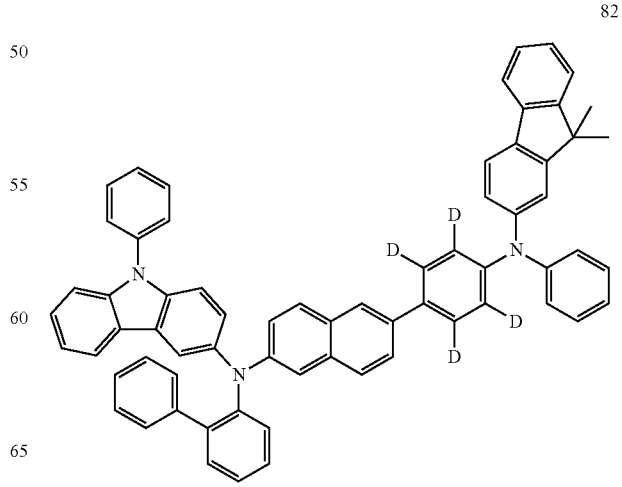

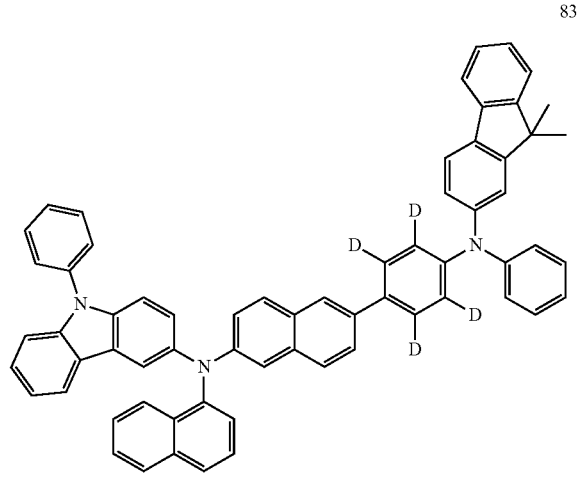
83
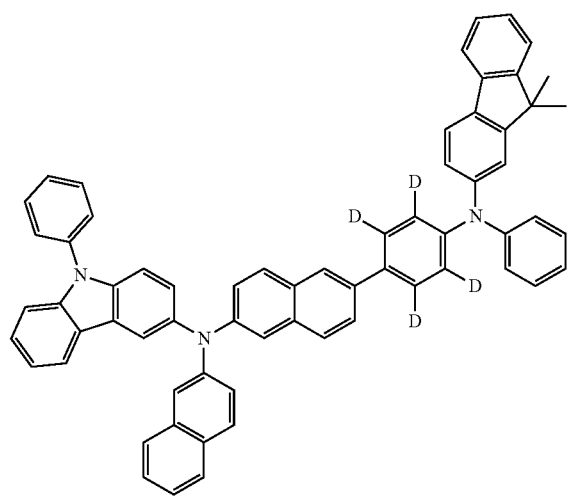
84
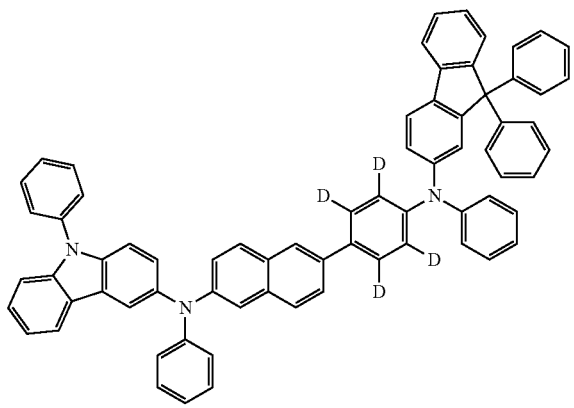
85
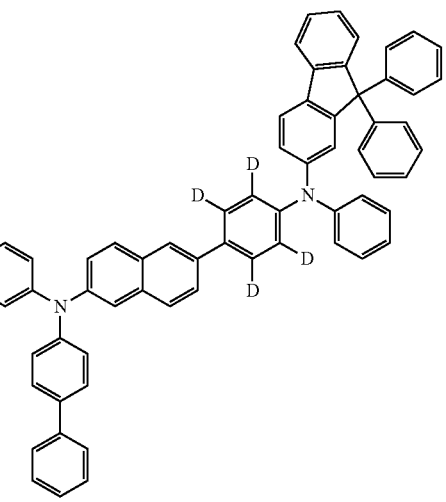
86
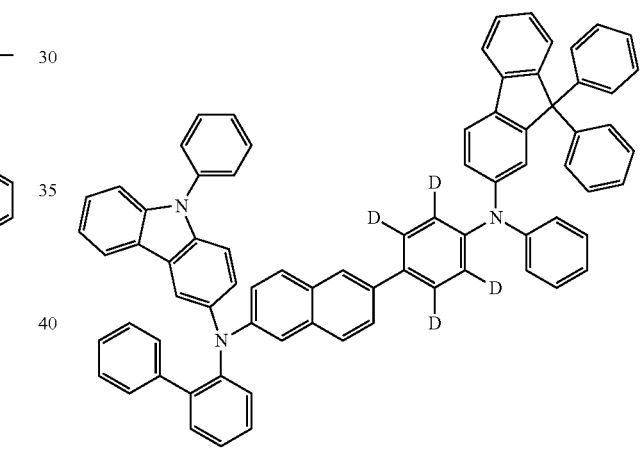
87
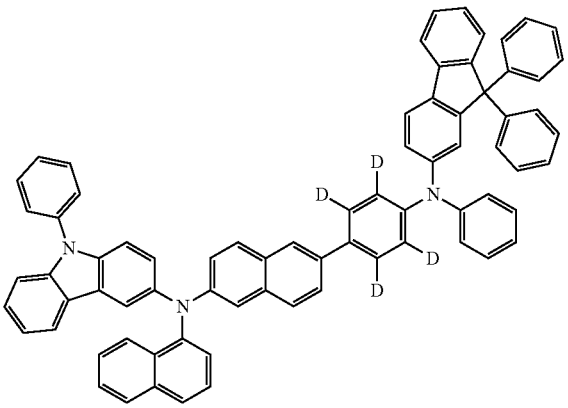
88

89
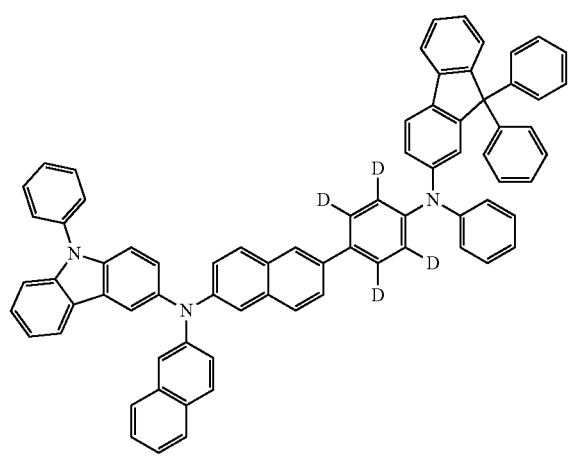
92
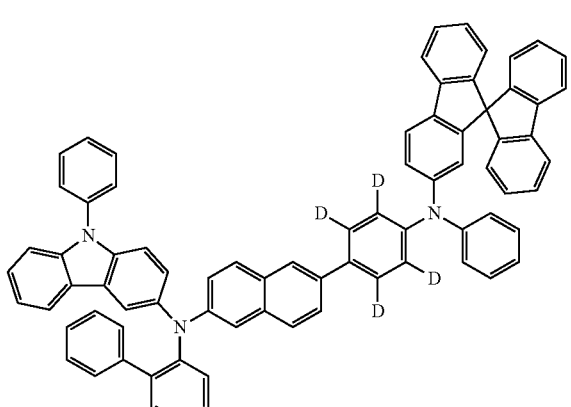
90
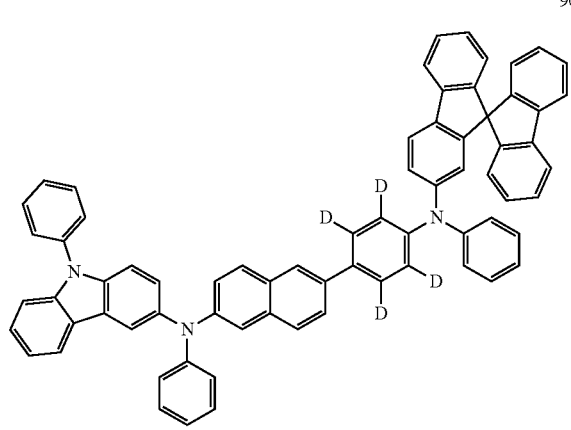
93
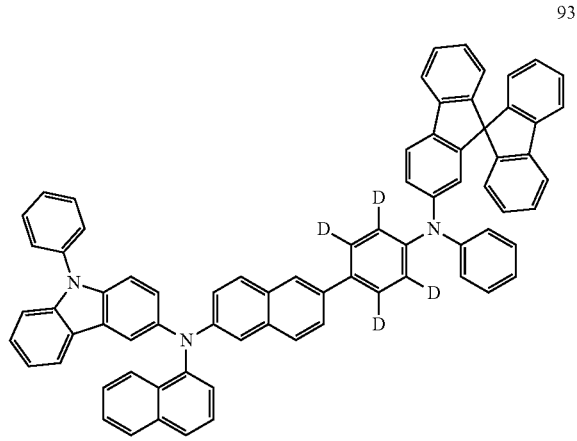
91
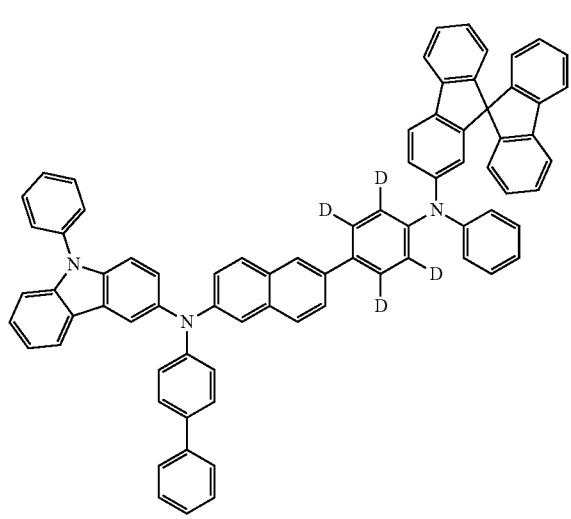
94
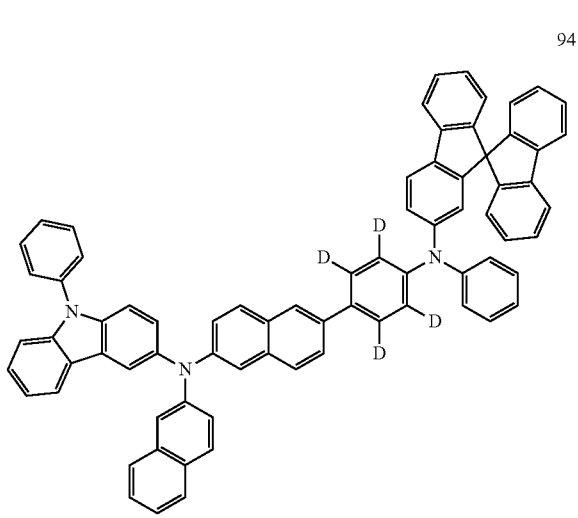

295
-continued
95
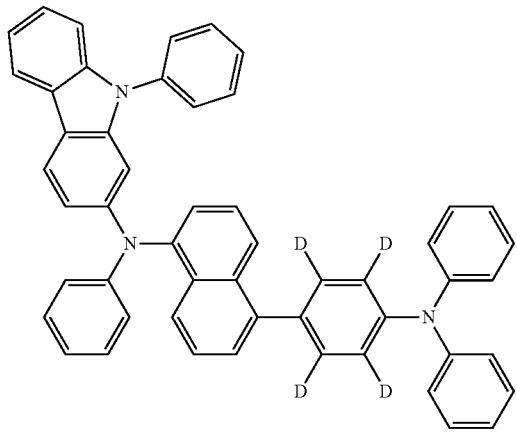
96
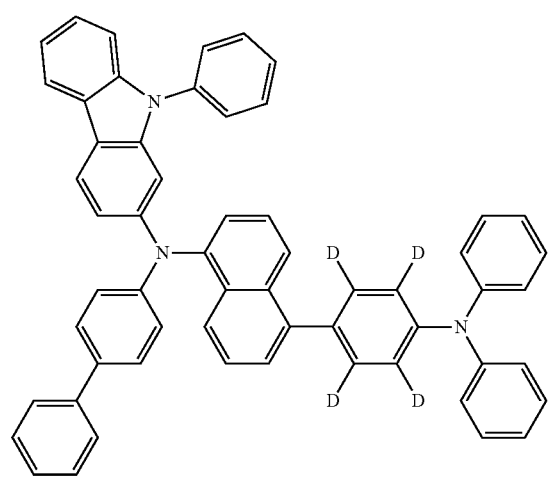
97
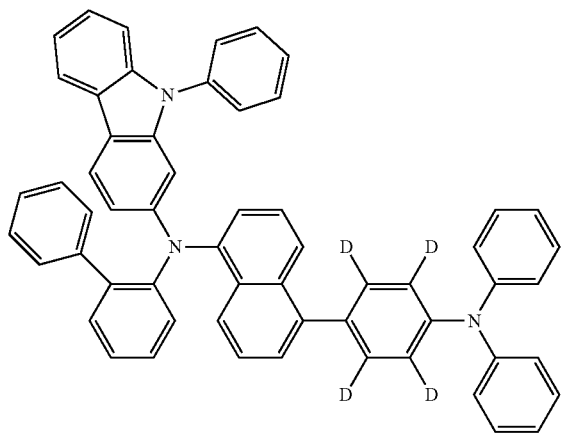
296
-continued
98
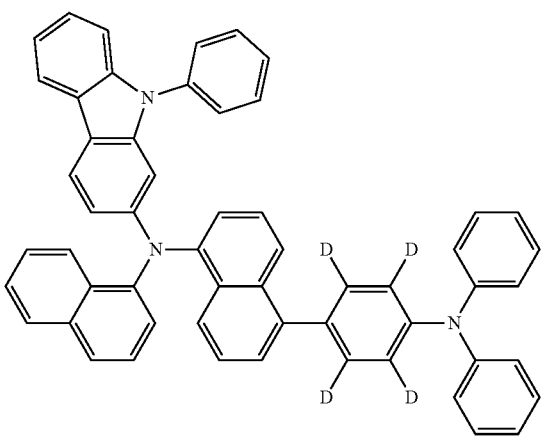
99
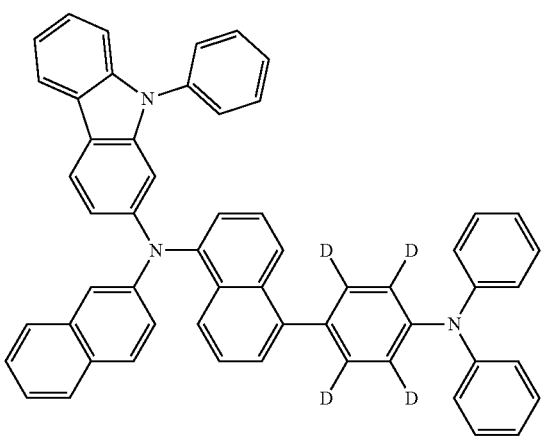
100
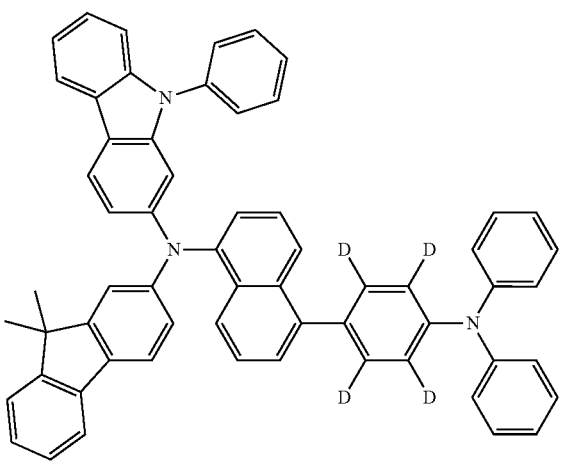

101
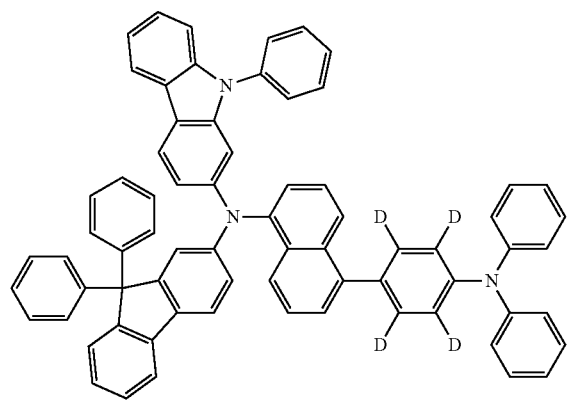
102
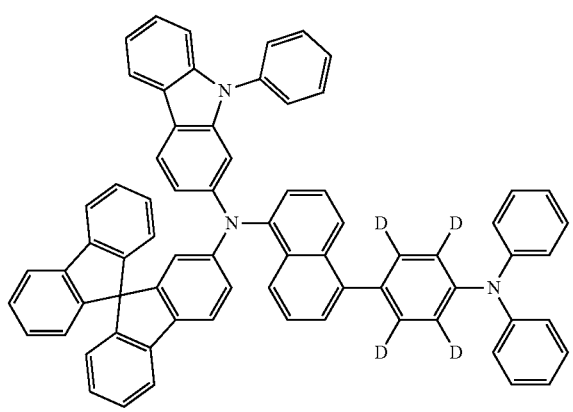
103
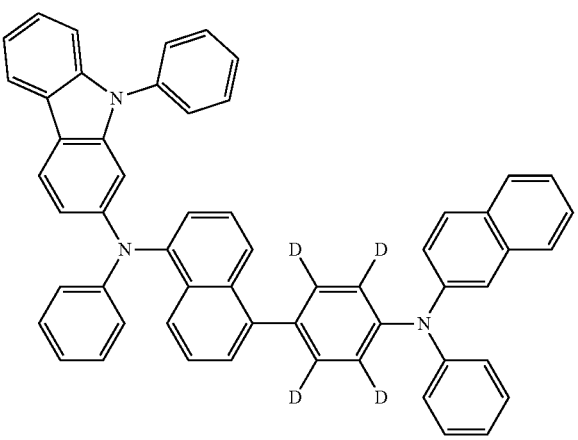
104
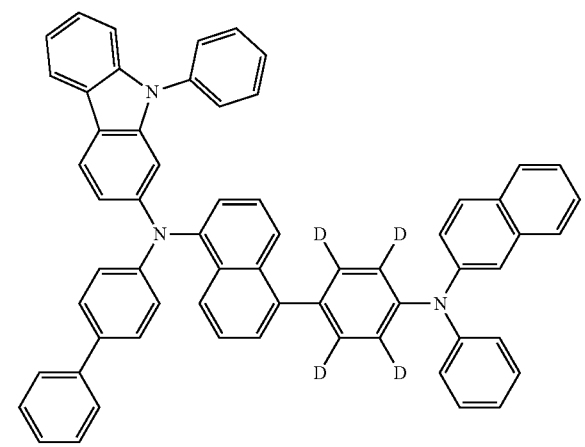
105
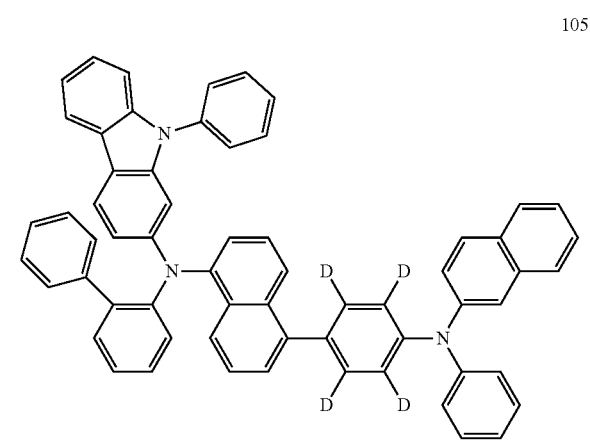
106
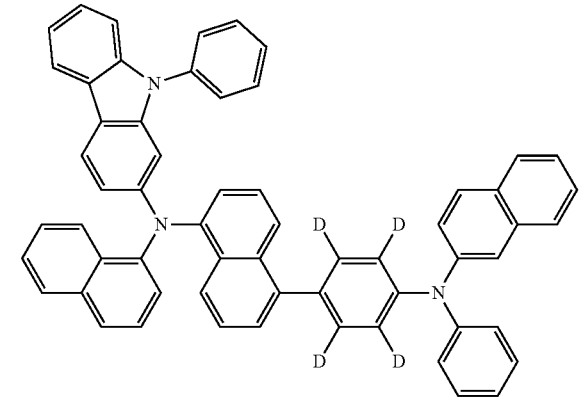

299
-continued
107
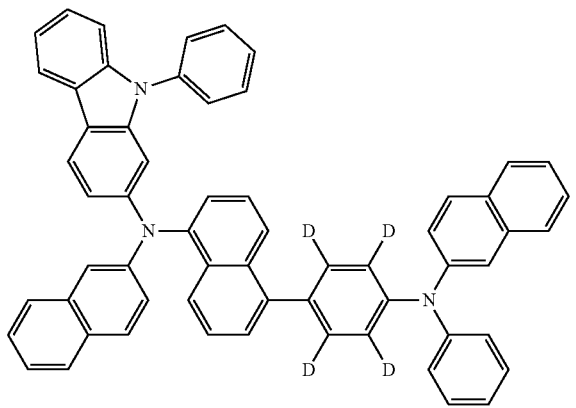
108
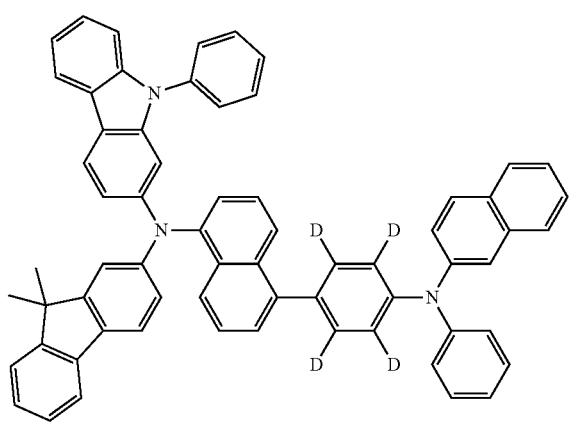
109
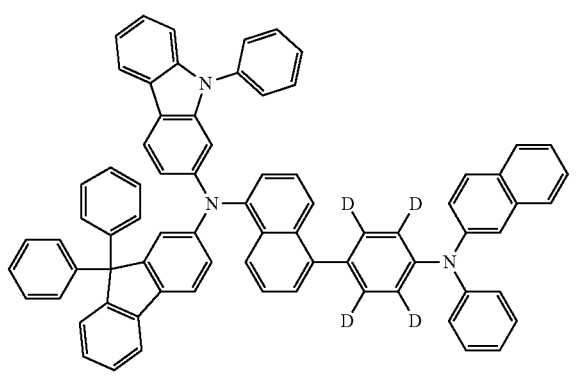
110
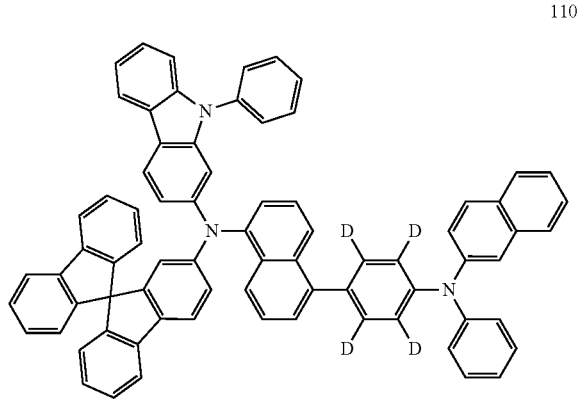
300
-continued
111
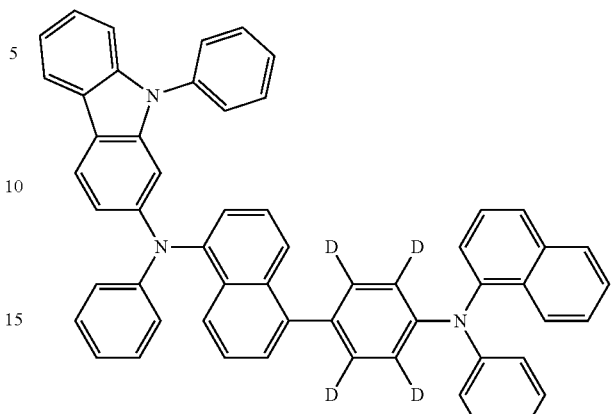
112
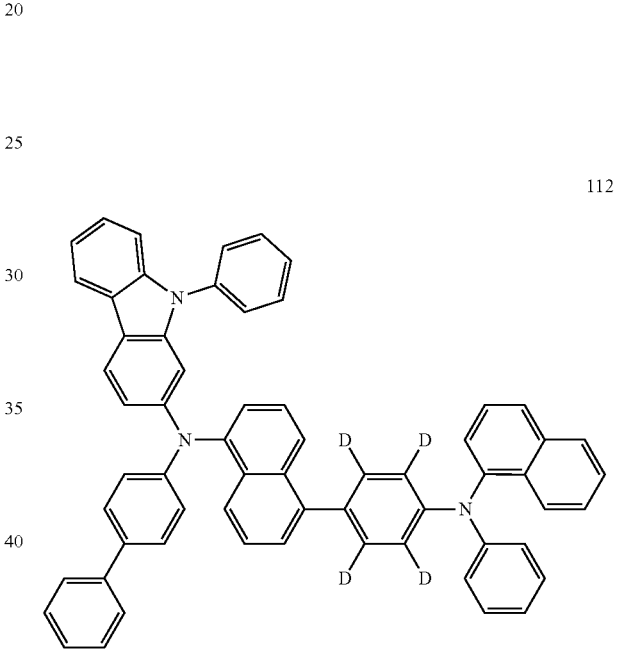
113
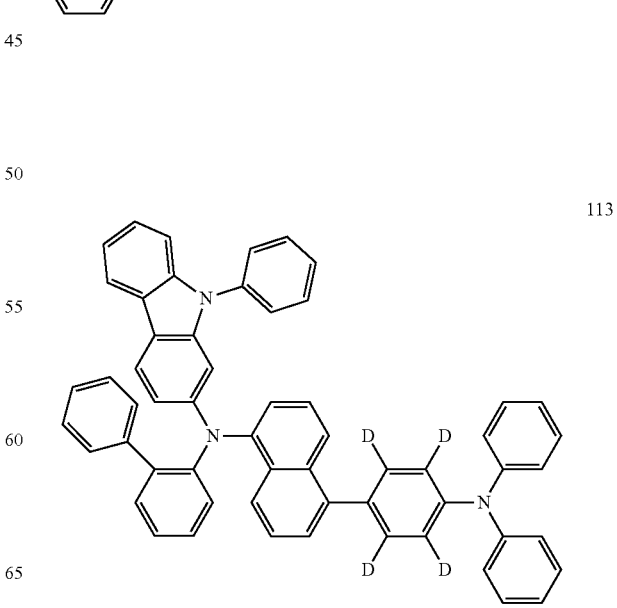

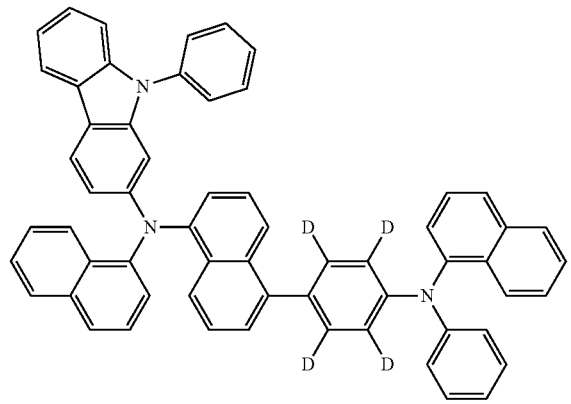
114
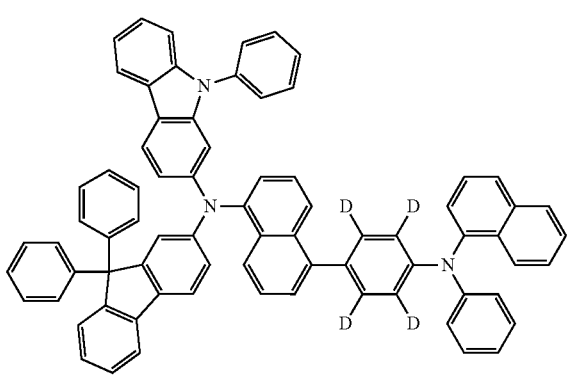
117
115
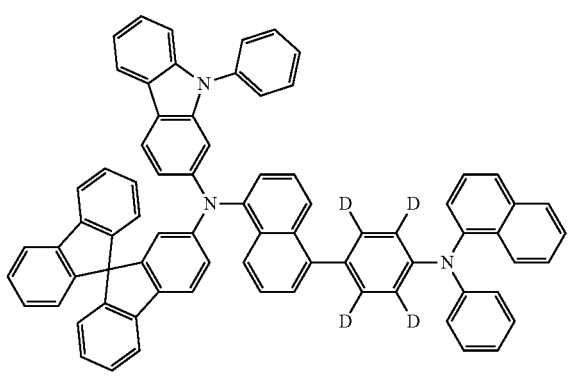
118
116
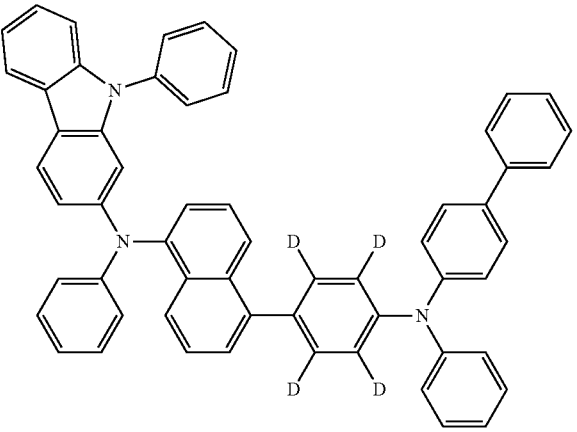
119

120
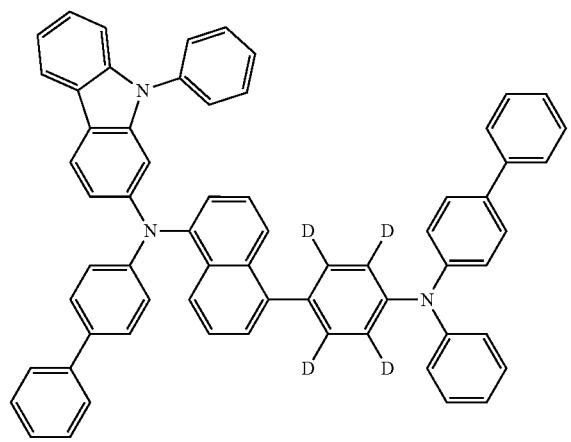
121
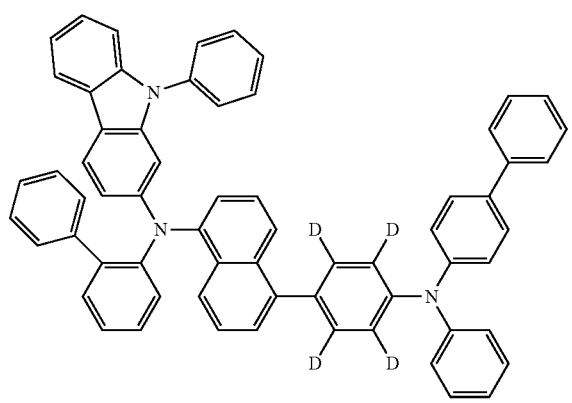
122
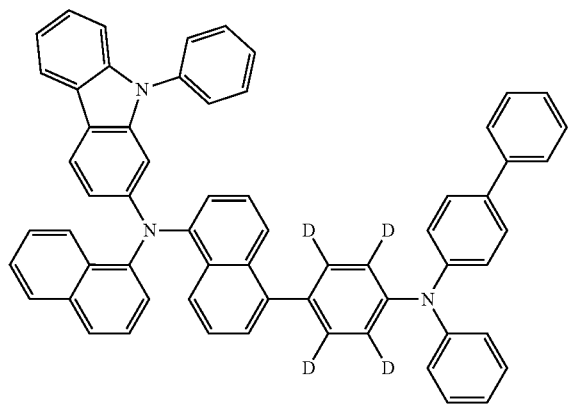
123
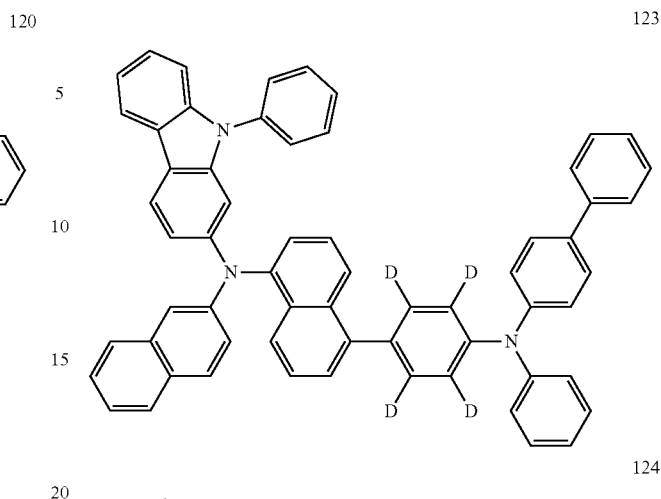
124
125
126
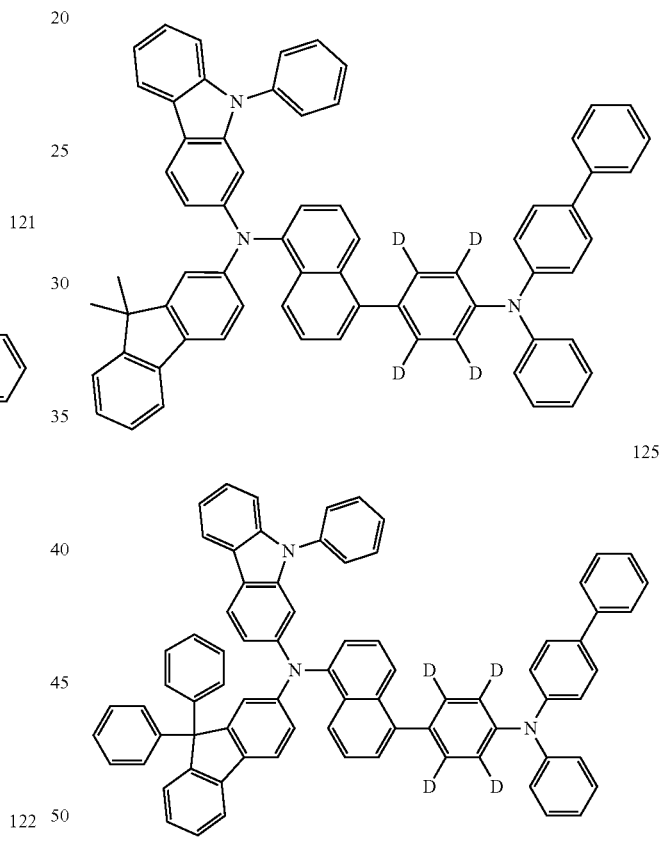
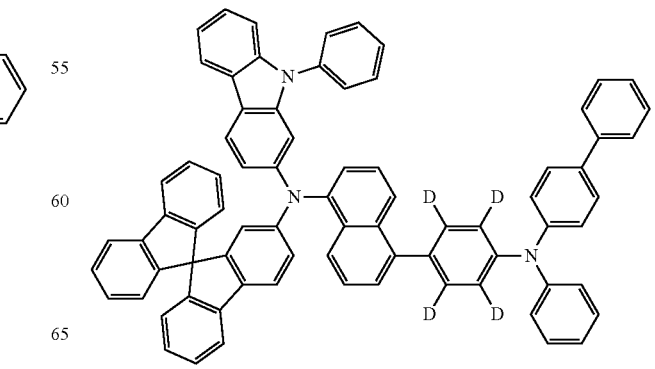

305
-continued
127
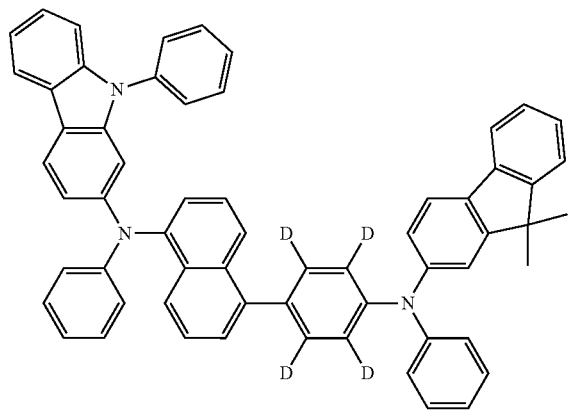
128
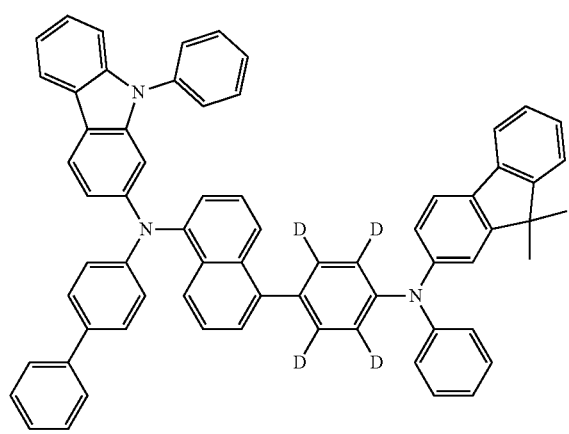
129
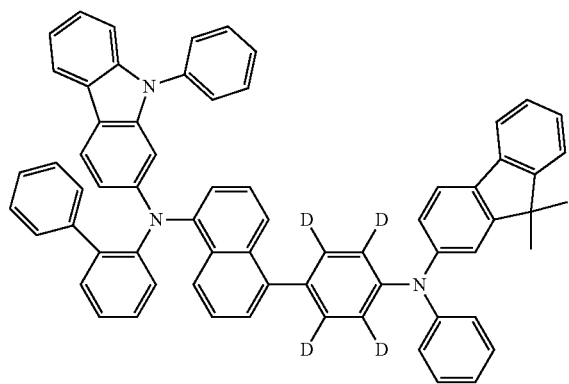
306
-continued
130
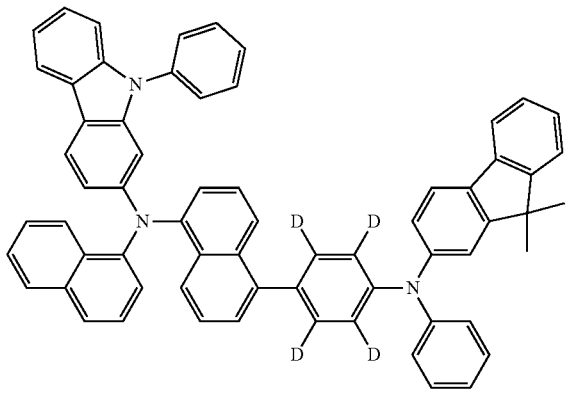
131
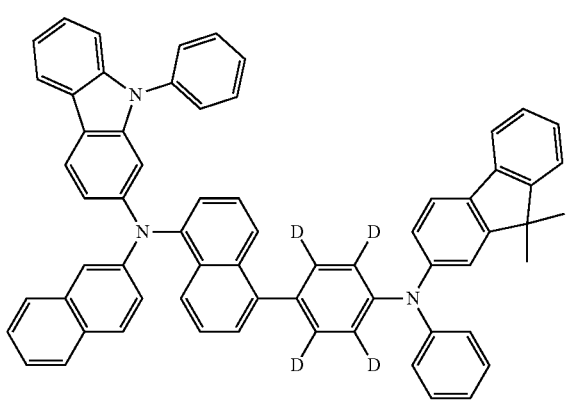
132
133
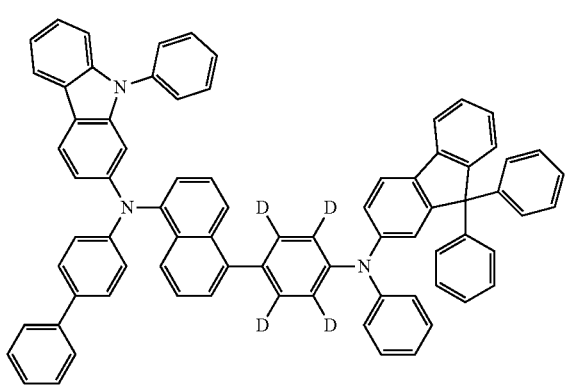

134
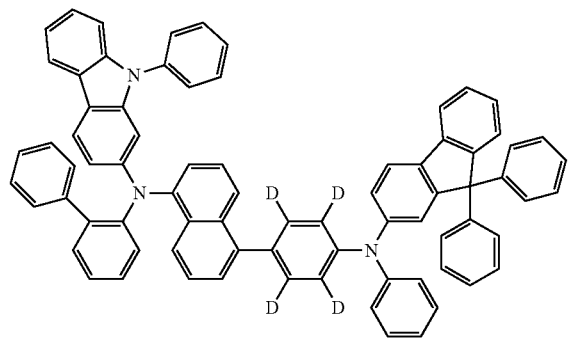
138
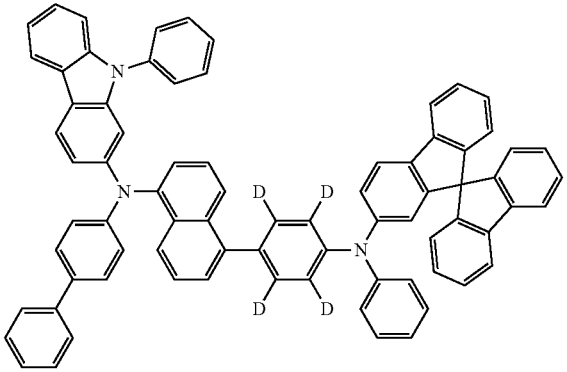
135
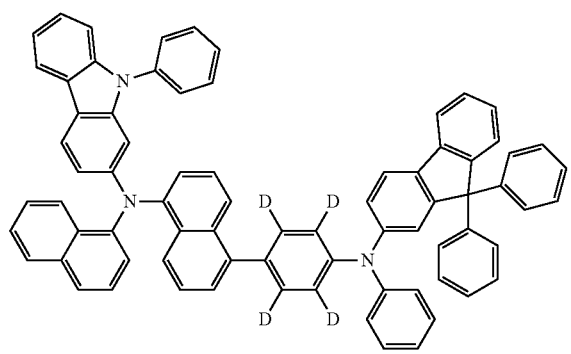
139
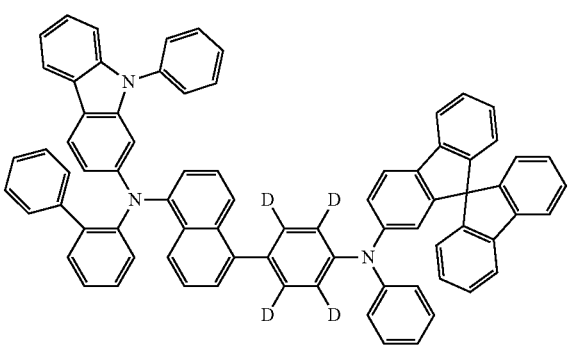
136
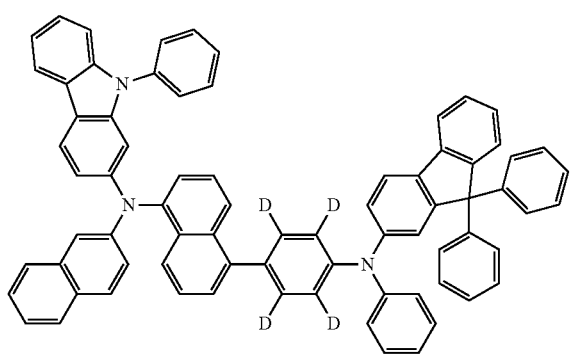
140
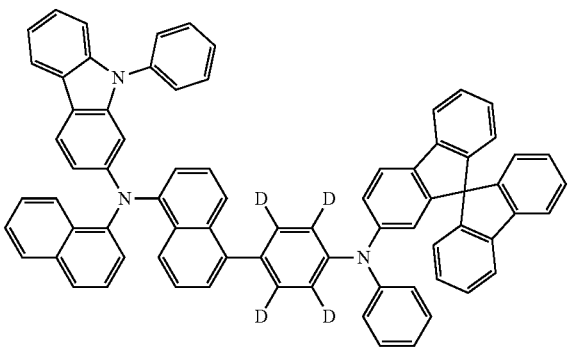
137
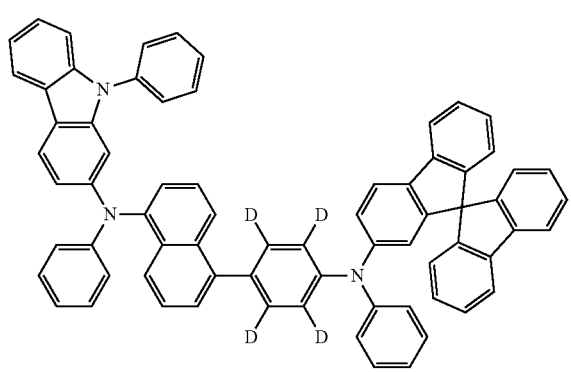
141
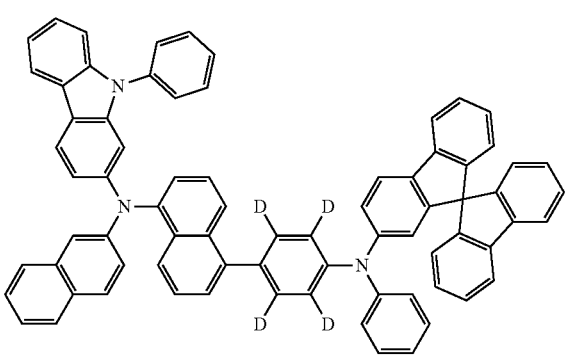

142
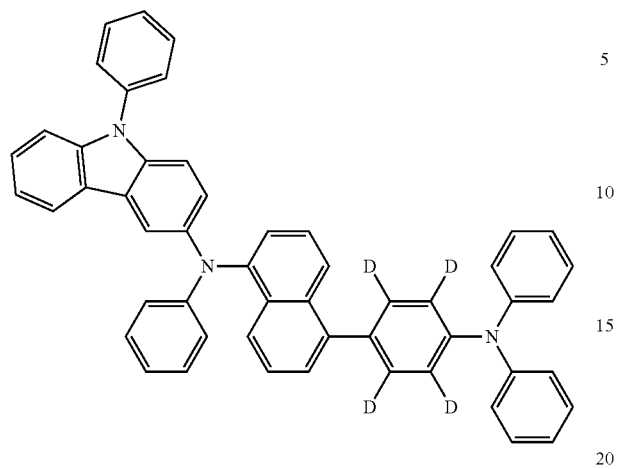
143
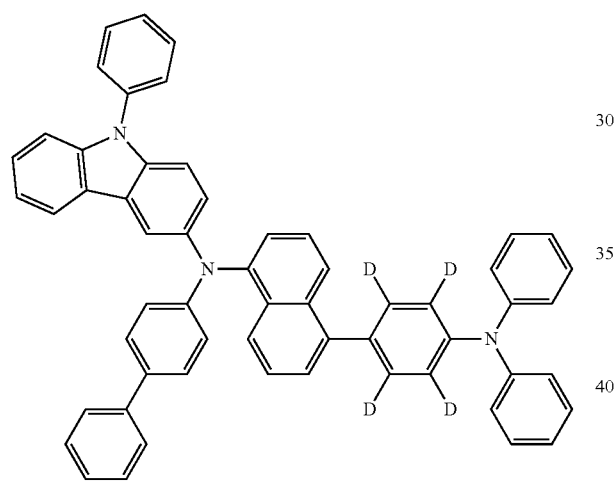
144
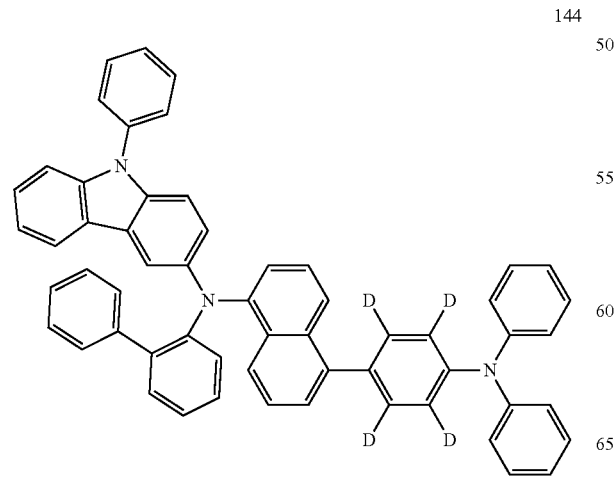
-continued
145
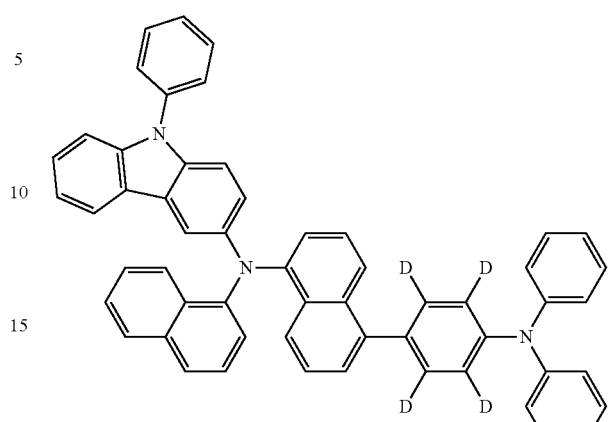
146
147
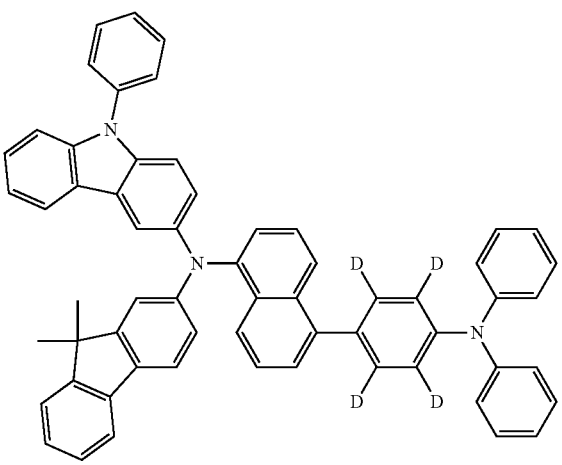

148 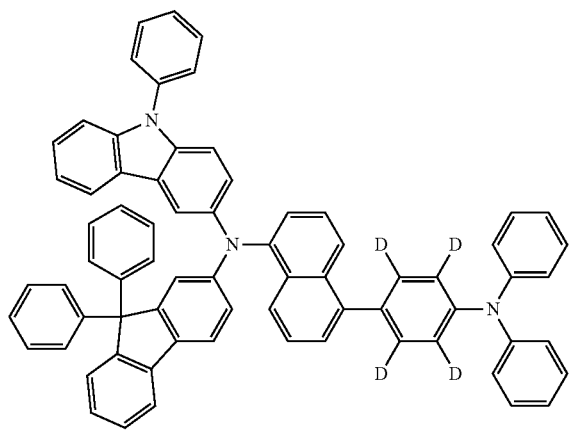
149 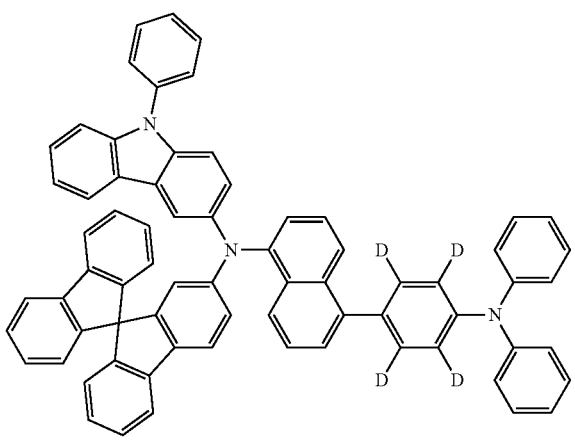
150 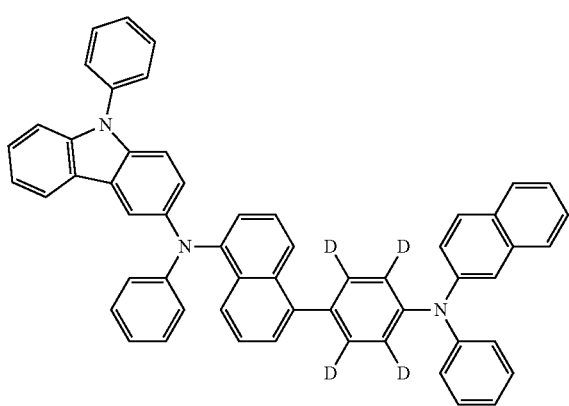
151 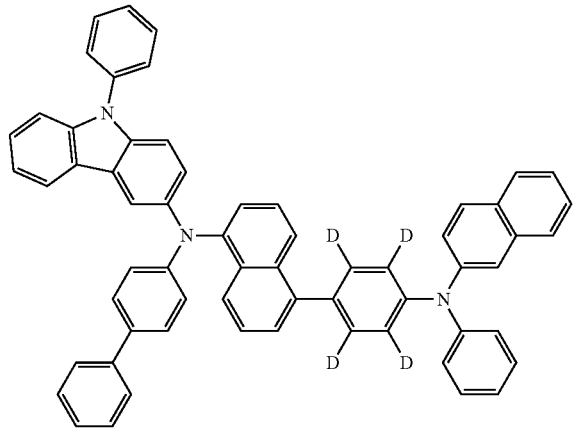
152 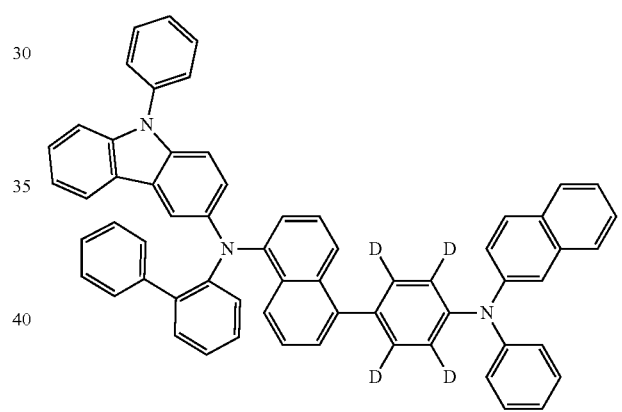
153 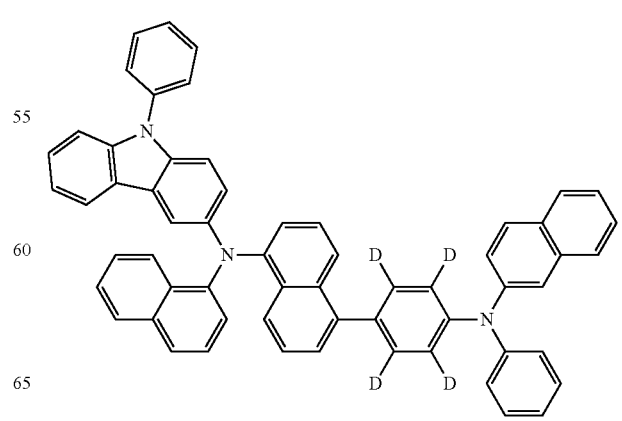

154
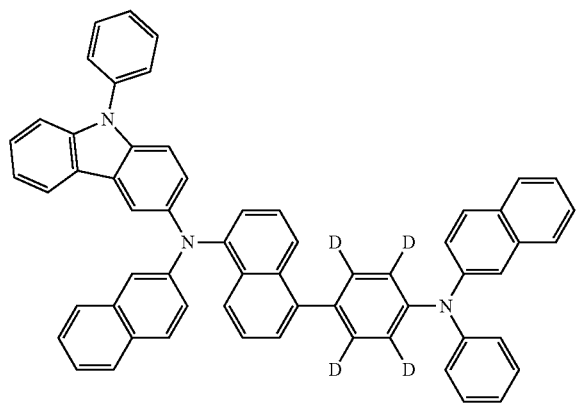
155
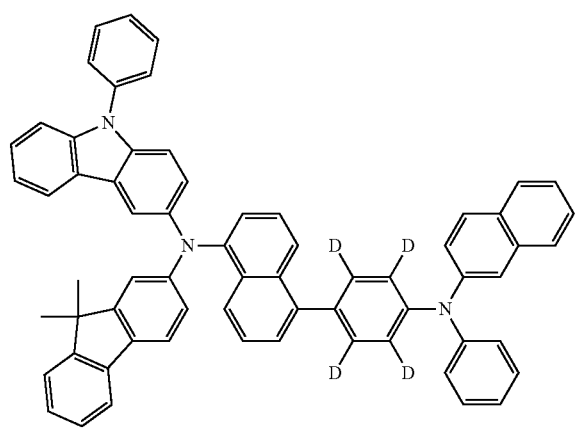
156
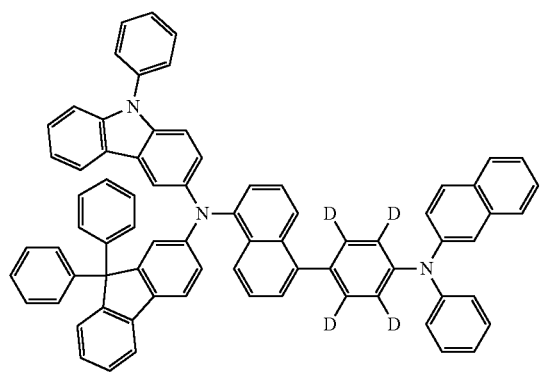
157
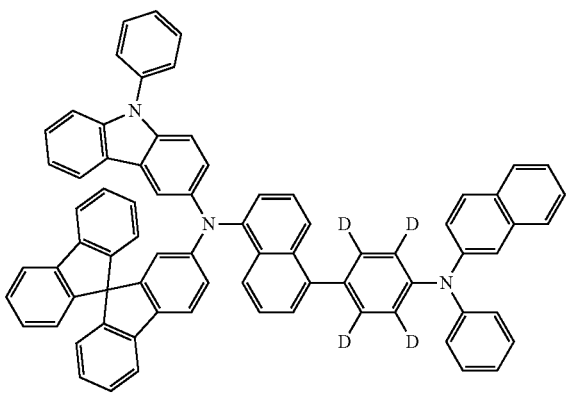
158
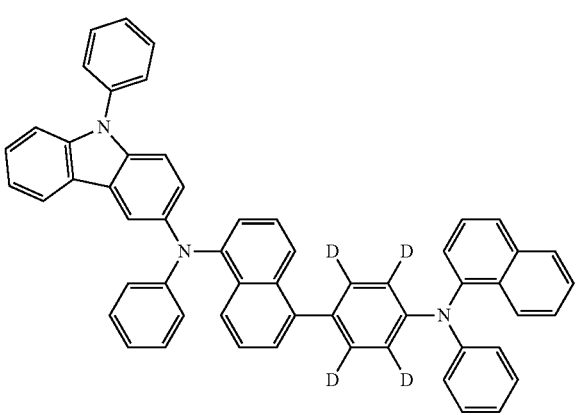
159
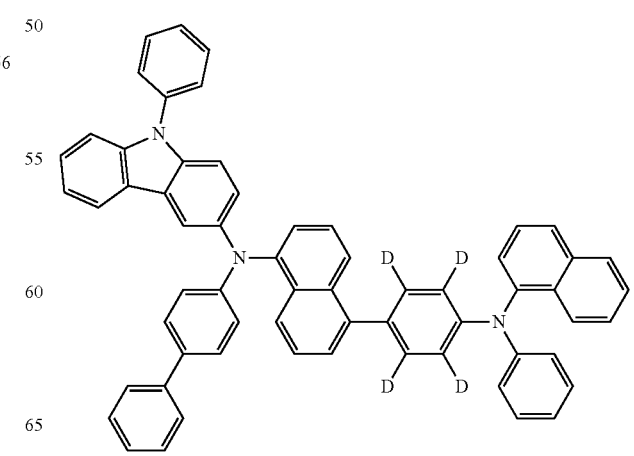

160
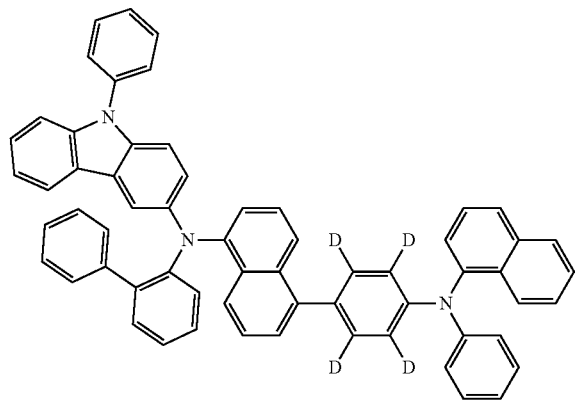
163
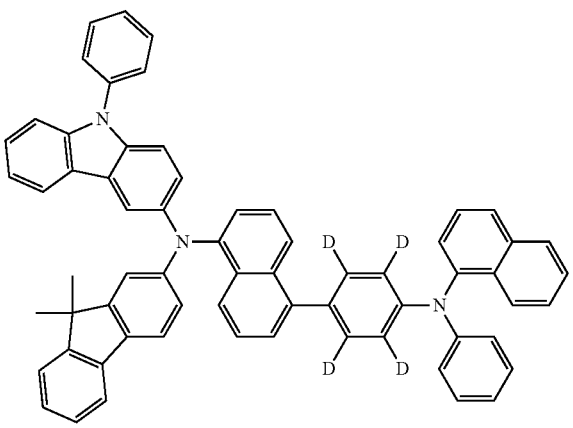
161
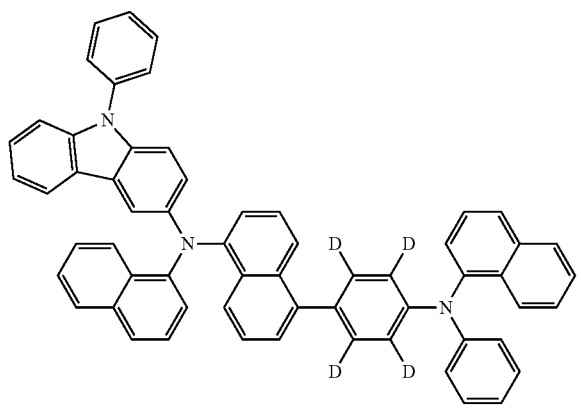
164
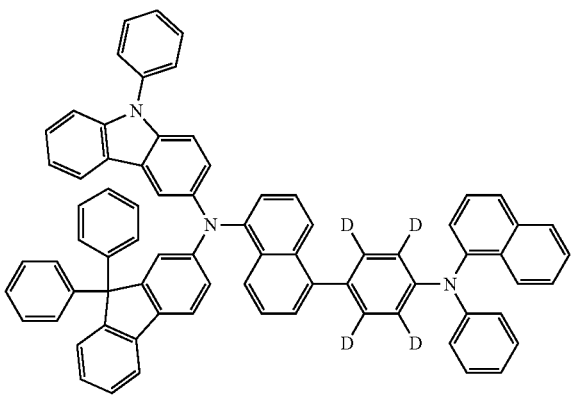
162
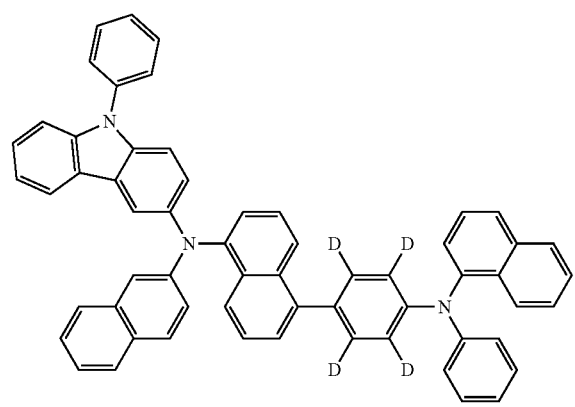
165
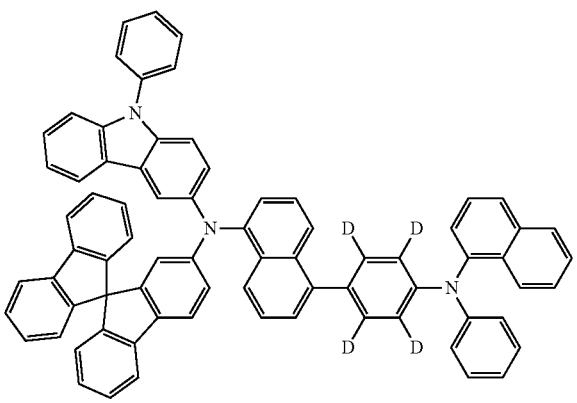

317
-continued
166
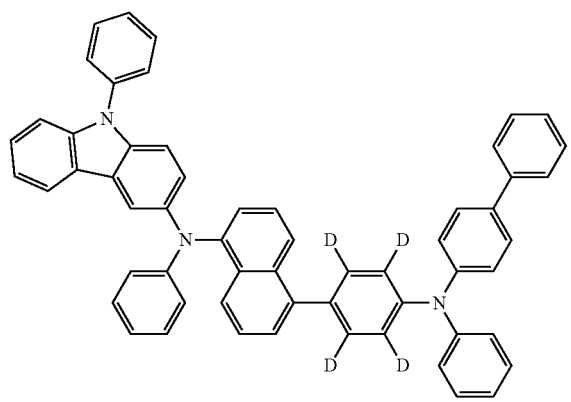
167
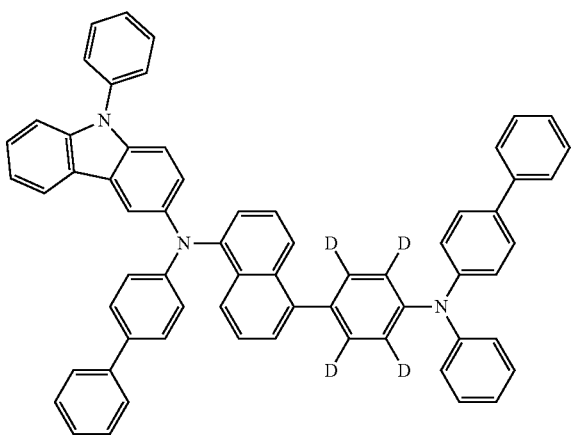
168
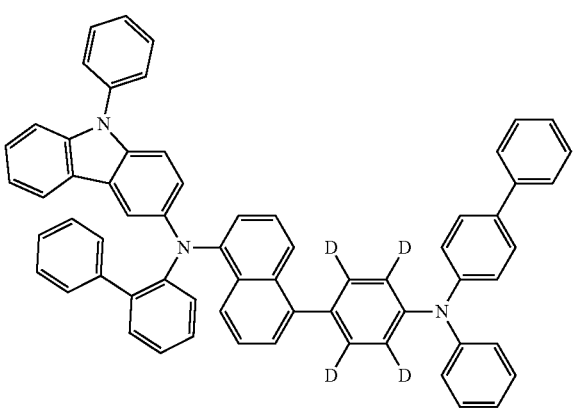
318
-continued
169
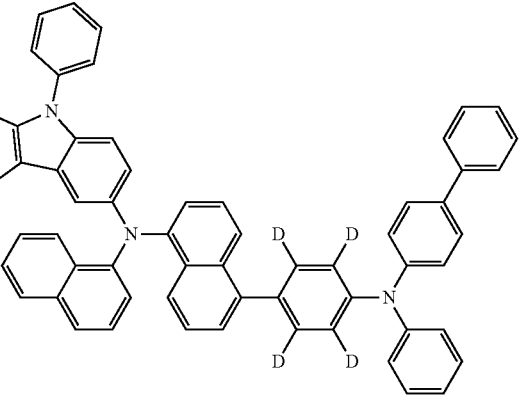
170
171
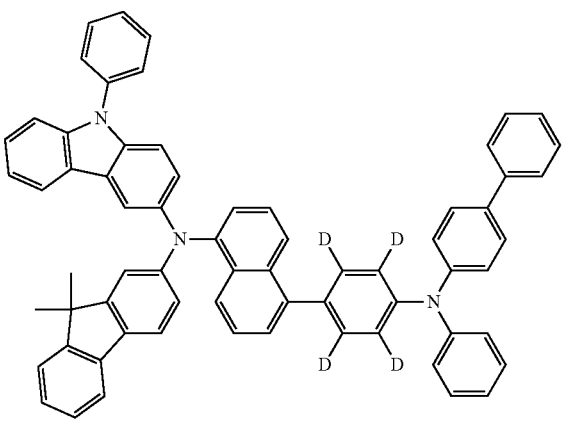

319
-continued
172
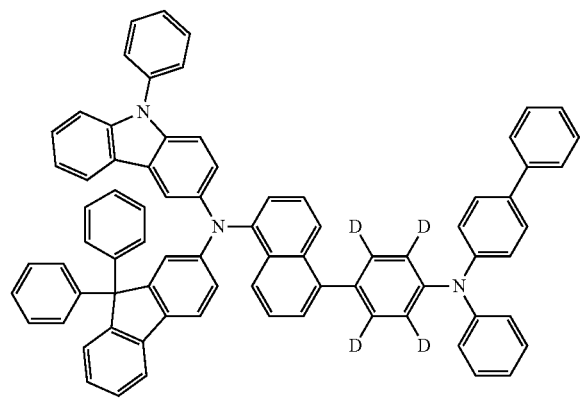
173
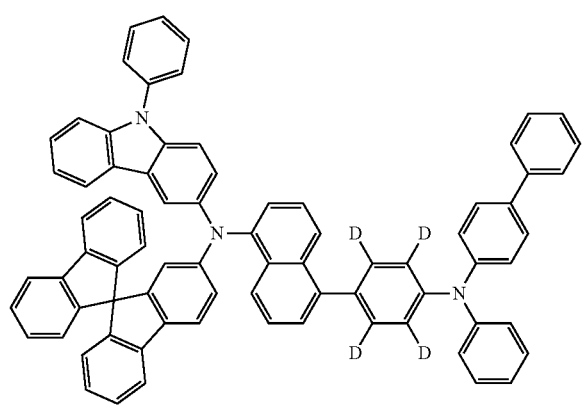
174
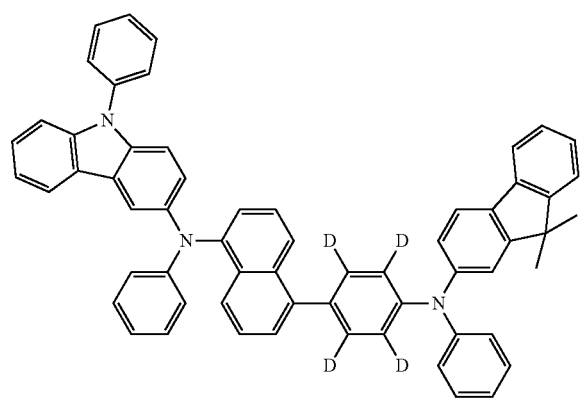
320
-continued
175
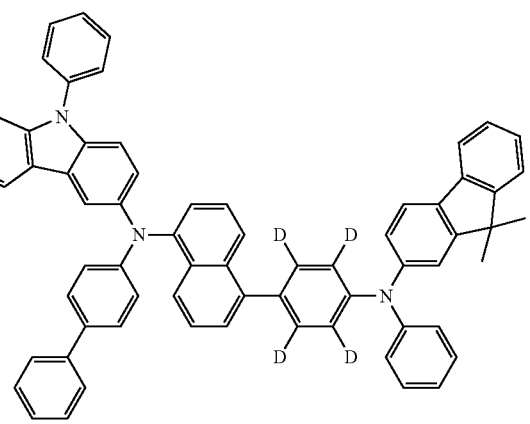
176
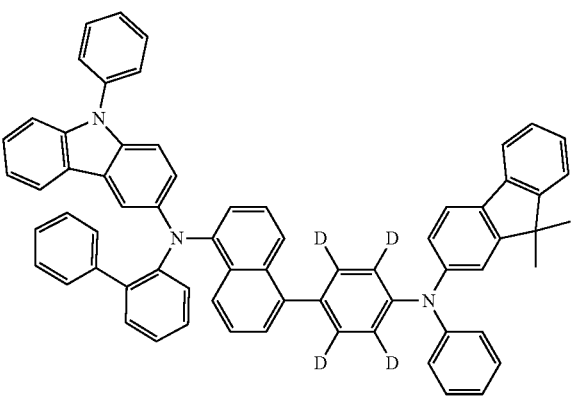
177
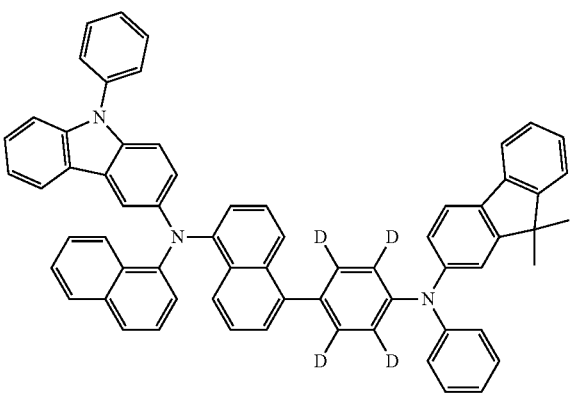

178
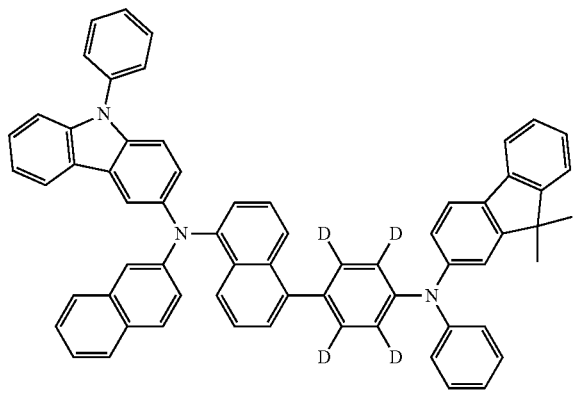
179
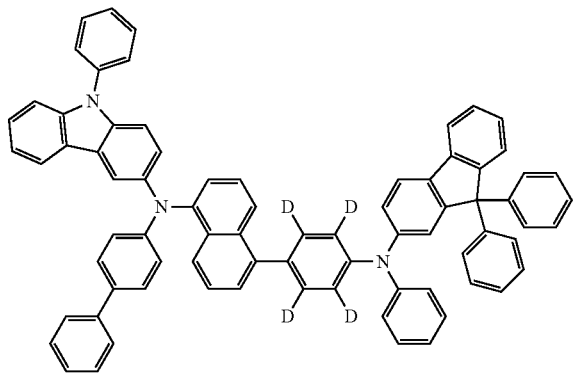
180
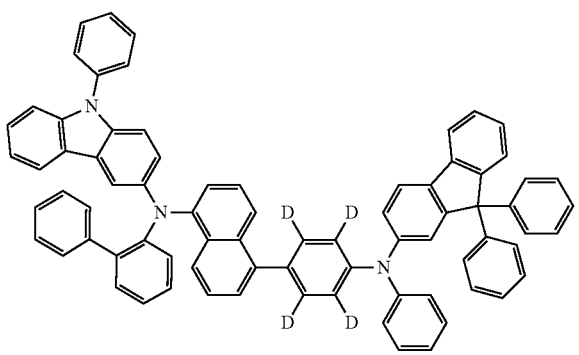
181
182
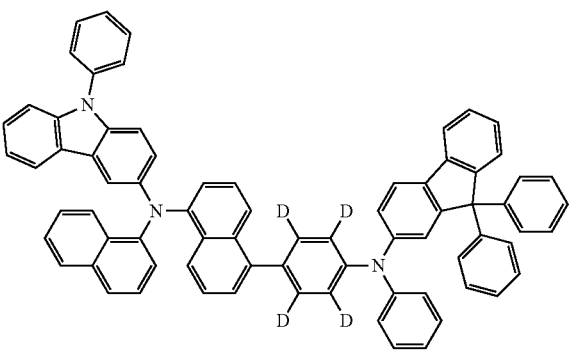
183
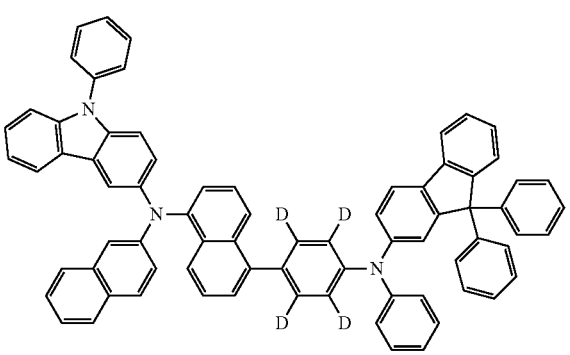
184
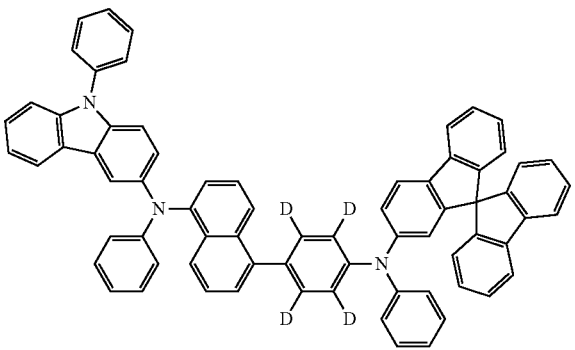
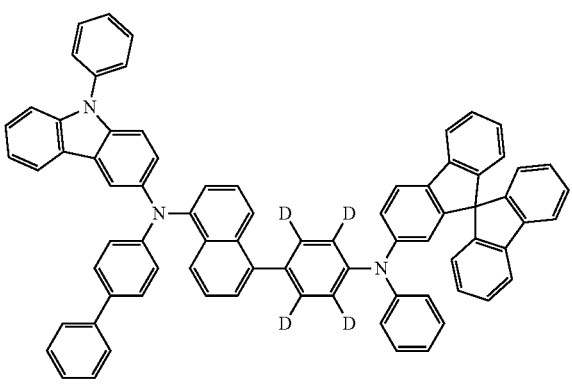

185
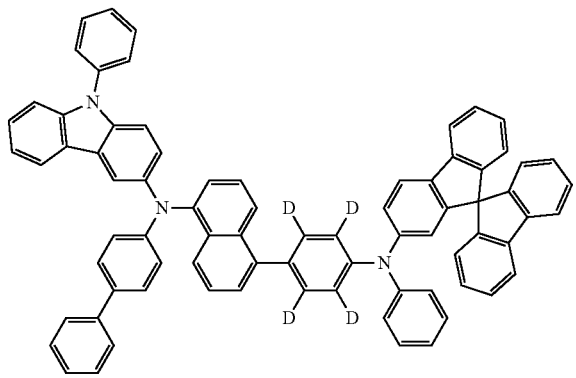
186
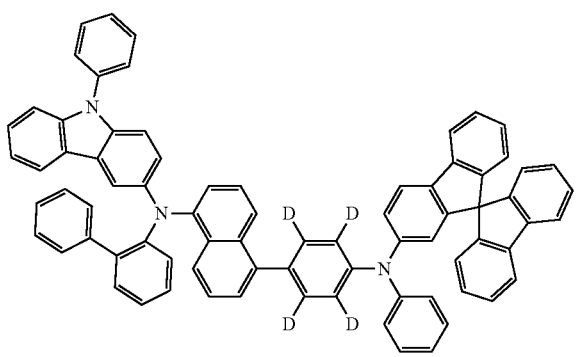
187
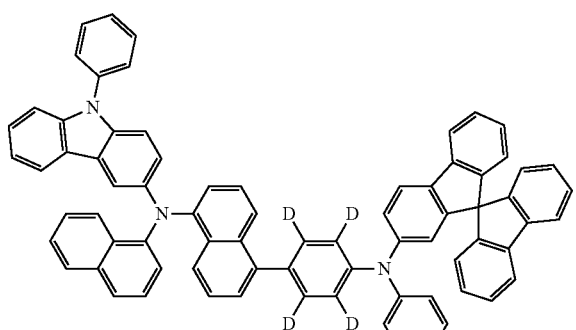
188
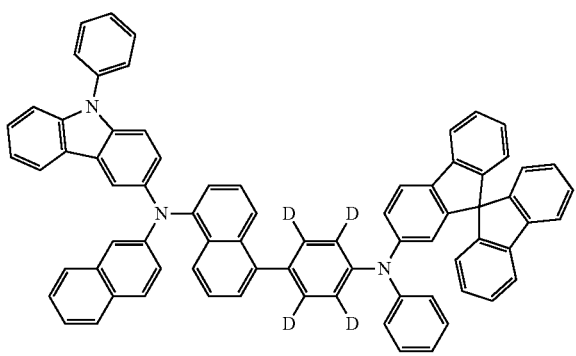
189
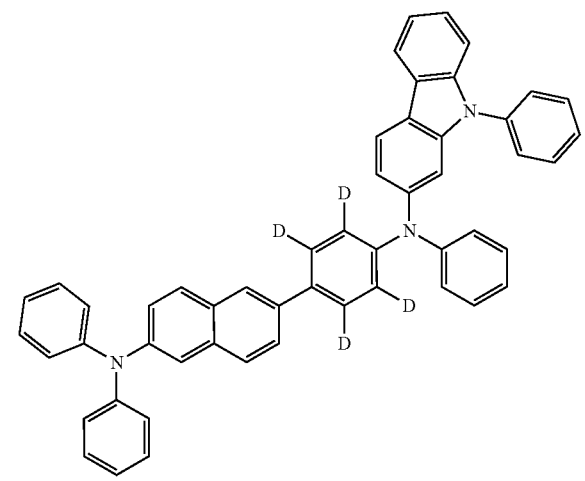
190
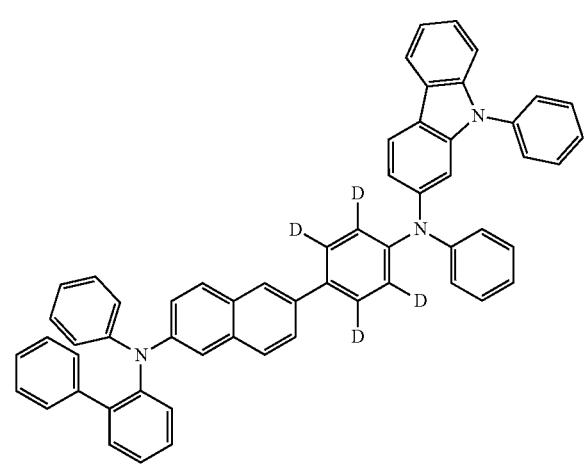
191

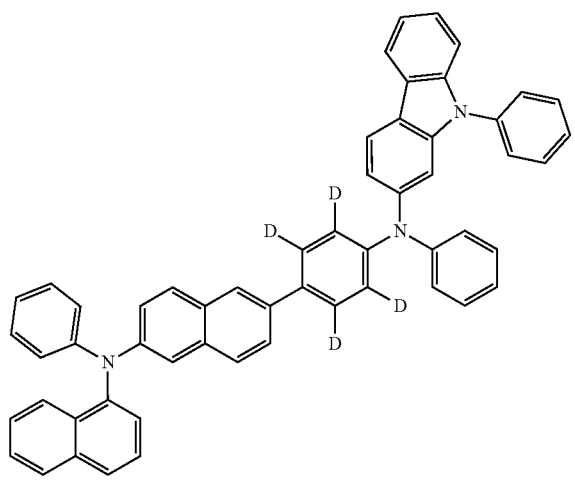
192
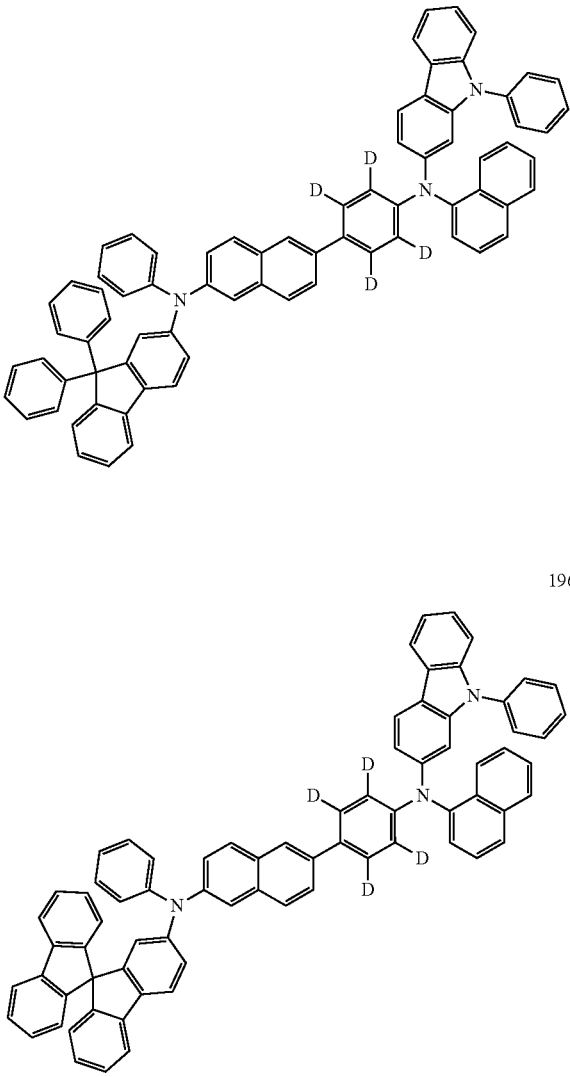
195
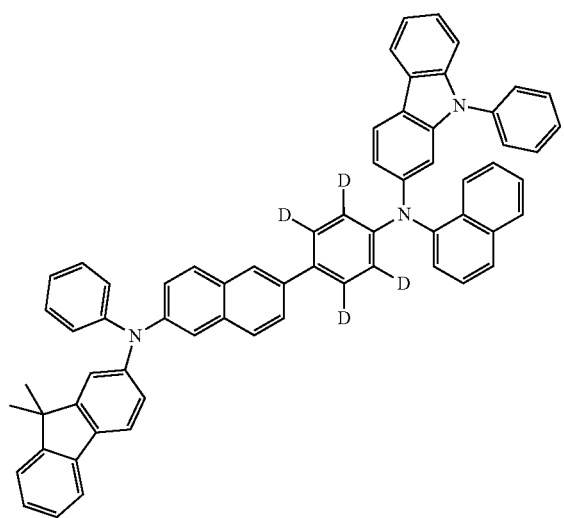
193
194
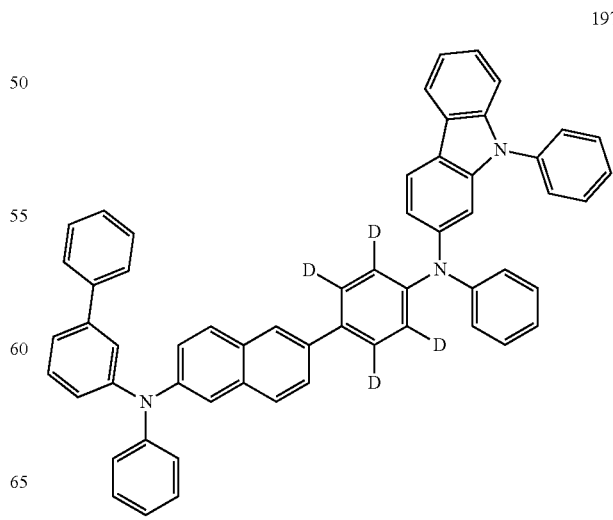
196
197

198
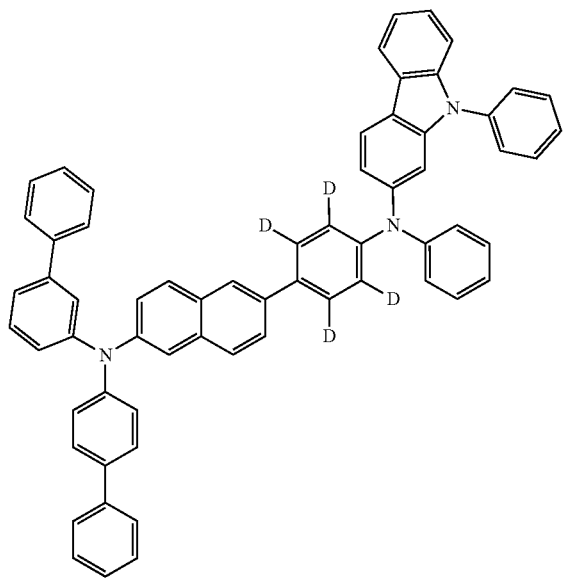
199
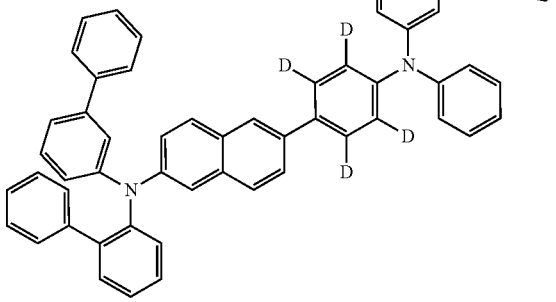
200
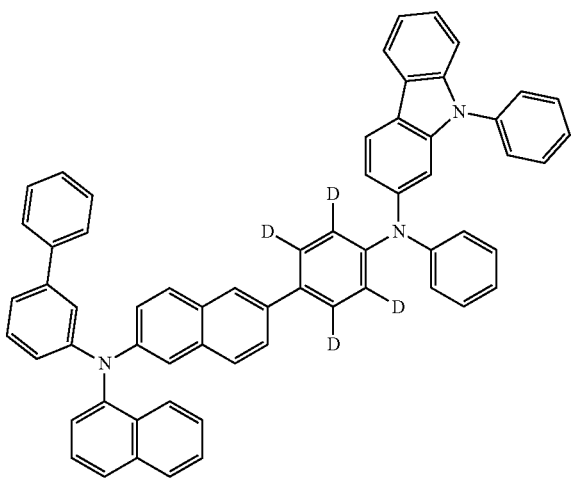
201
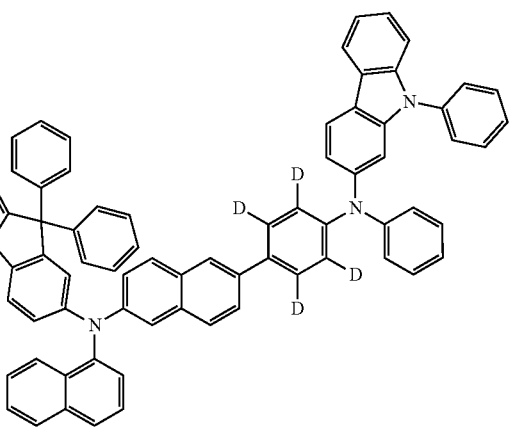
202
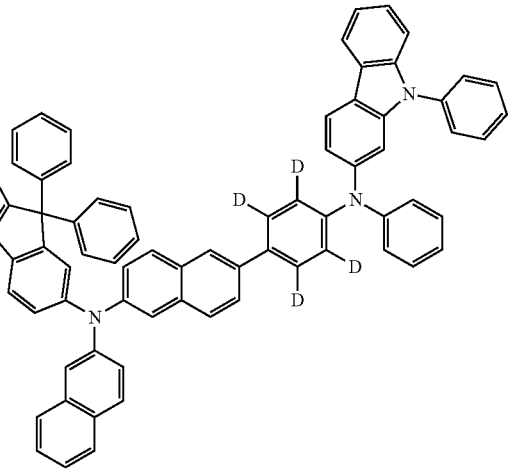
203
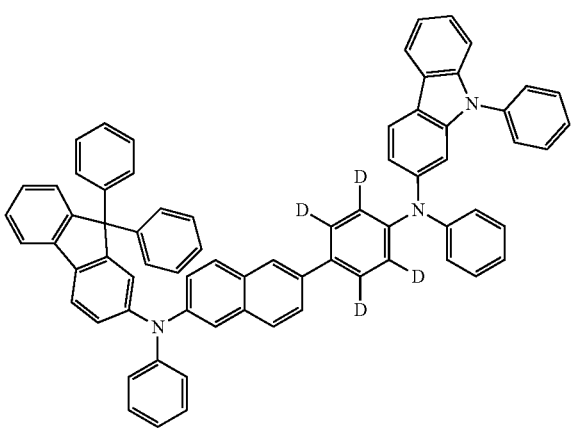

329
-continued
204
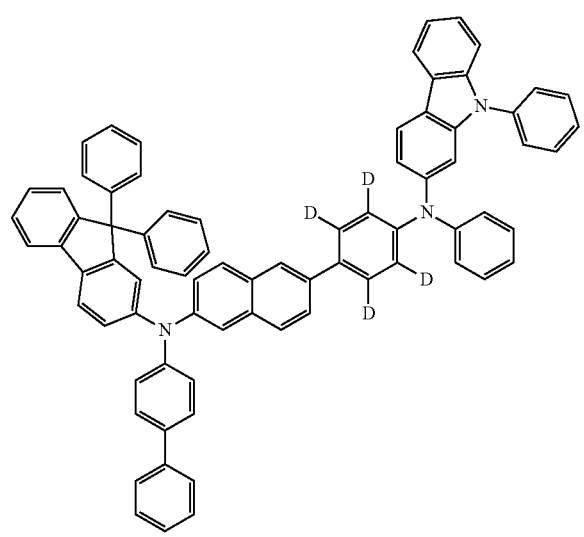
205
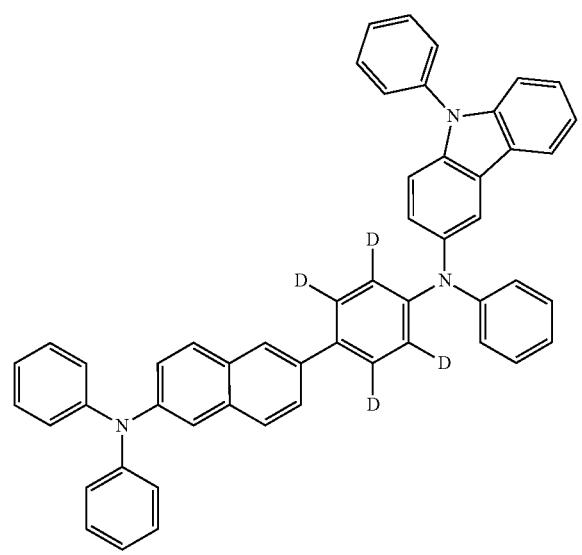
330
-continued
206
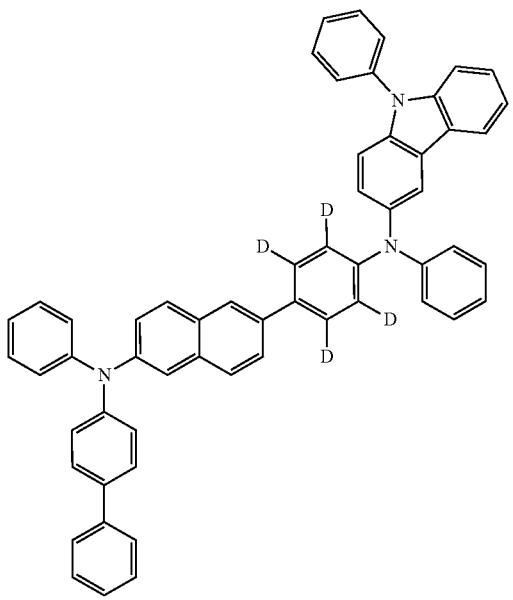
207
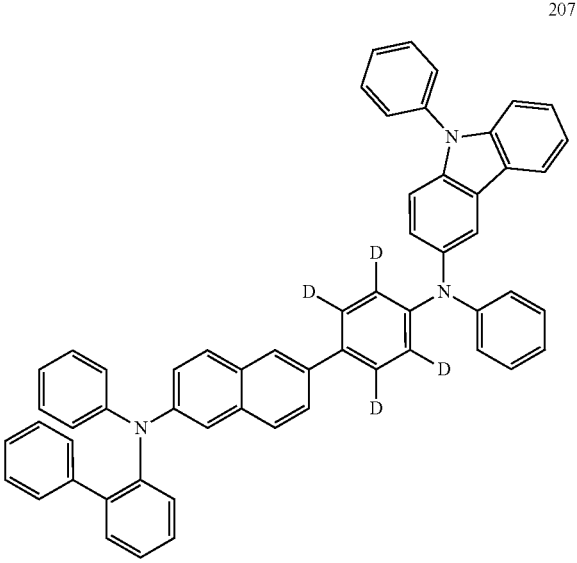

331
-continued
208
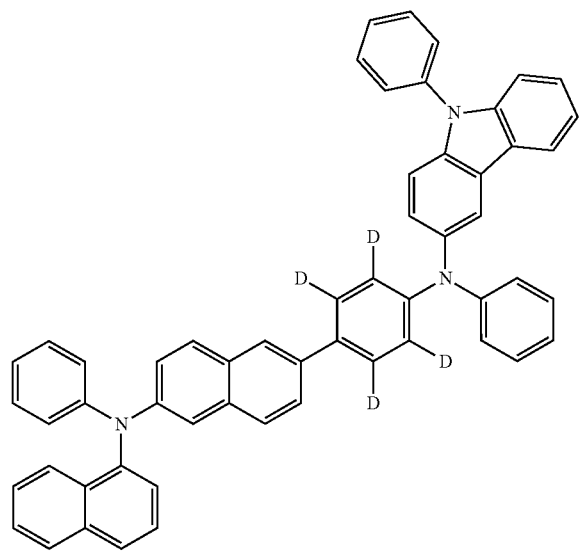
209
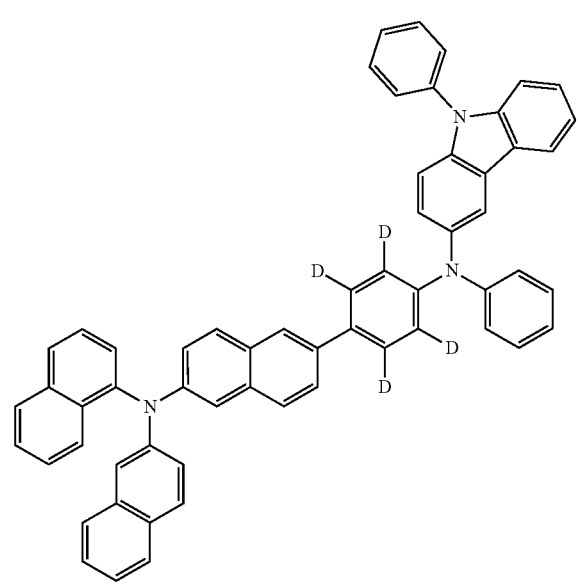
332
-continued
210
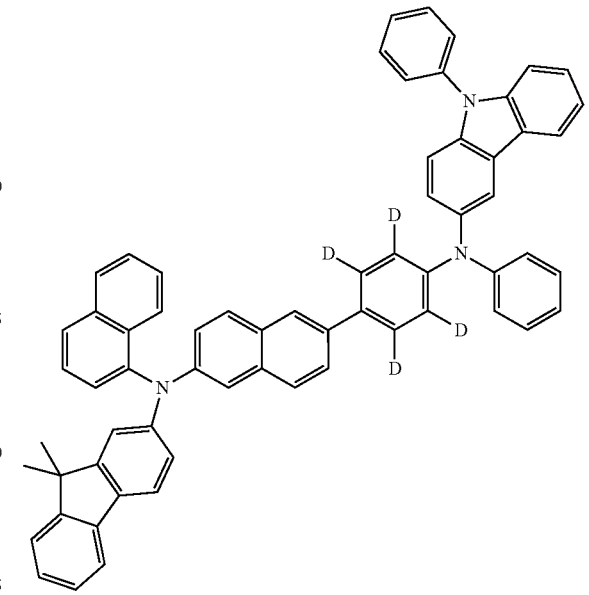
211

212
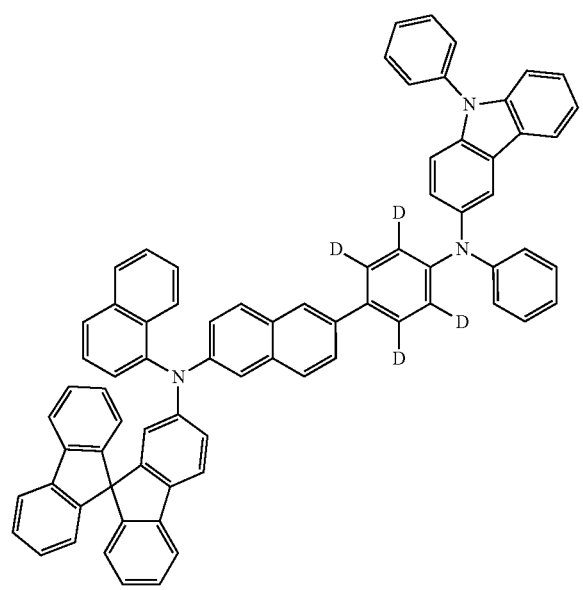
213
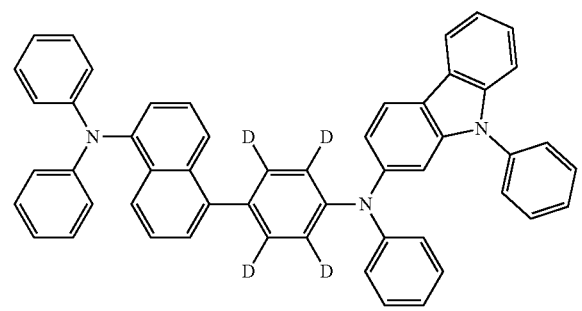
214
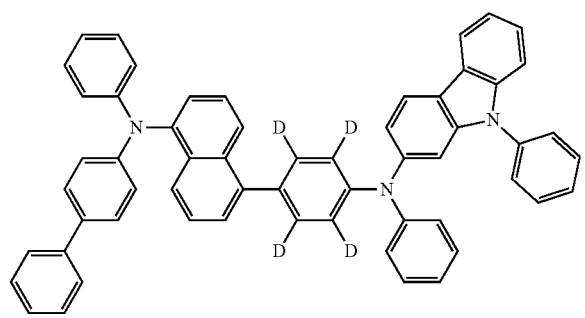
215
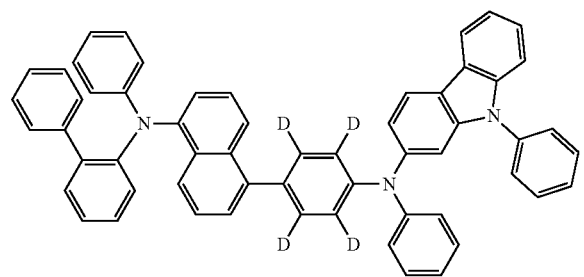
216
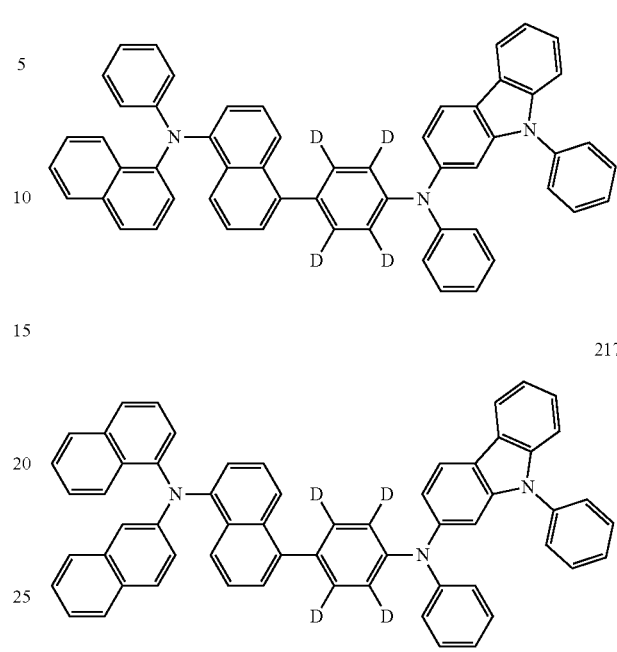
217
218
219
220
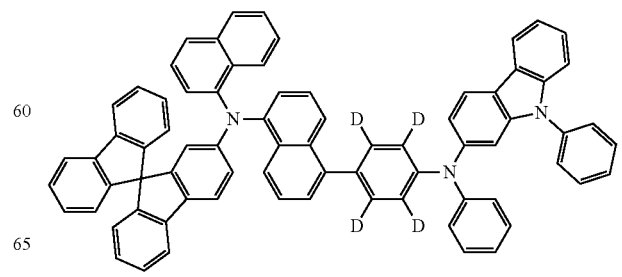

221
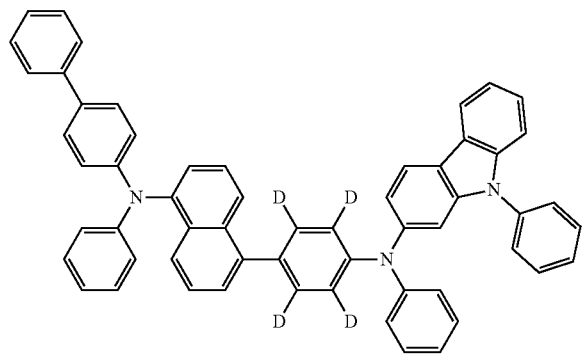
222
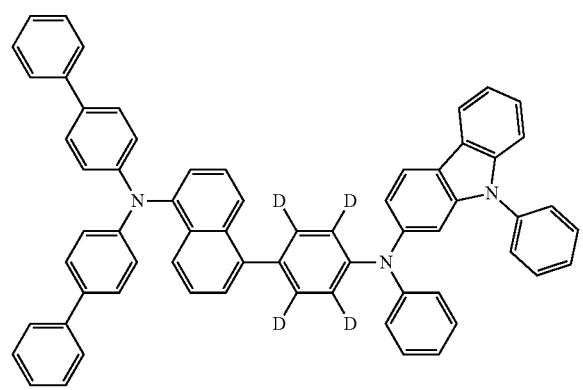
223
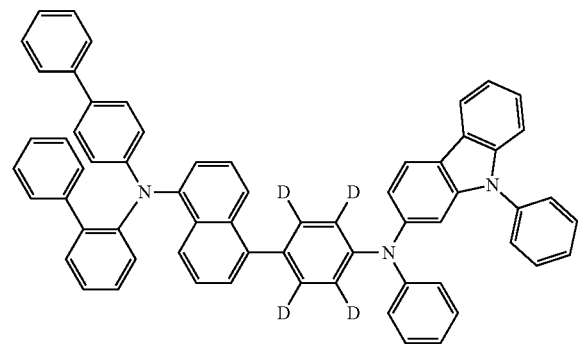
224
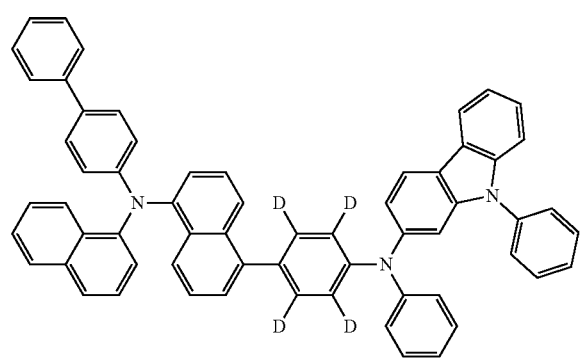
225
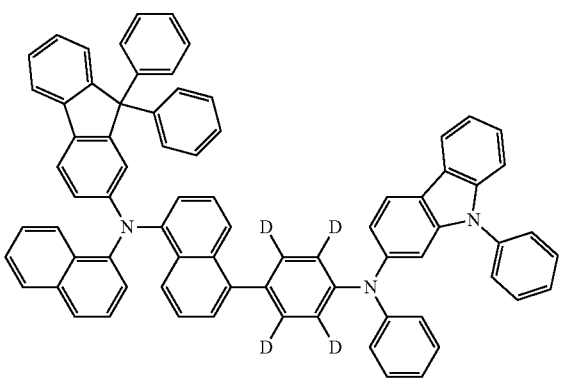
226
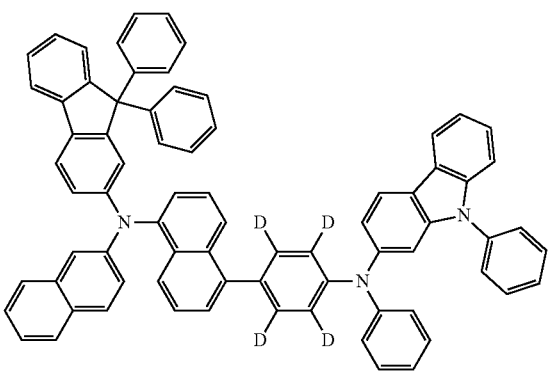
227
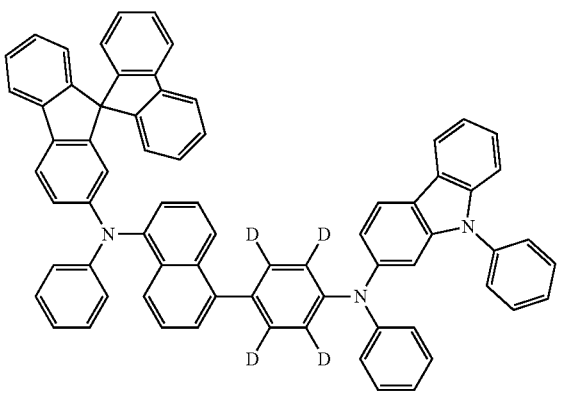

228
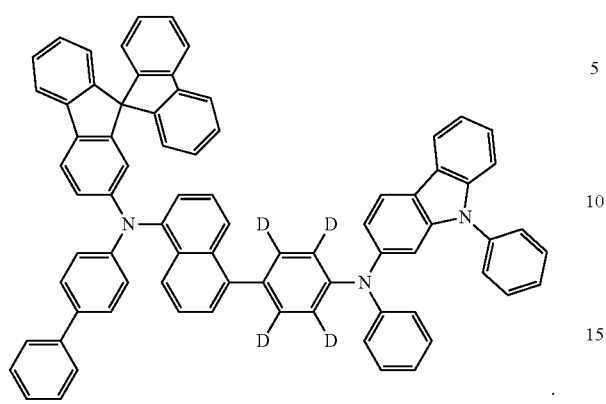
* * * * *